US012577311B2

(12) United States Patent
Marasco et al.

(10) Patent No.: US 12,577,311 B2
(45) Date of Patent: Mar. 17, 2026

(54) CHIMERIC ANTIGEN RECEPTOR FACTORIES AND METHODS OF USE THEREOF

(71) Applicant: Dana-Farber Cancer Institute, Inc., Boston, MA (US)

(72) Inventors: Wayne A. Marasco, Brookline, MA (US); Quan Karen Zhu, Southborough, MA (US); Yufei Wang, Brookline, MA (US); Matthew Chang, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 998 days.

(21) Appl. No.: 17/298,271

(22) PCT Filed: Dec. 2, 2019

(86) PCT No.: PCT/US2019/064032
§ 371 (c)(1),
(2) Date: May 28, 2021

(87) PCT Pub. No.: WO2020/113224
PCT Pub. Date: Jun. 4, 2020

(65) Prior Publication Data
US 2022/0047634 A1      Feb. 17, 2022

Related U.S. Application Data

(60) Provisional application No. 62/773,885, filed on Nov. 30, 2018, provisional application No. 62/826,462, filed on Mar. 29, 2019.

(51) Int. Cl.
| | |
|---|---|
| *A61P 35/00* | (2006.01) |
| *A61K 40/11* | (2025.01) |
| *A61K 40/31* | (2025.01) |
| *A61K 40/42* | (2025.01) |
| *C07K 16/28* | (2006.01) |
| *C07K 16/30* | (2006.01) |
| *C12N 5/0783* | (2010.01) |

(52) U.S. Cl.
CPC .......... *C07K 16/2875* (2013.01); *A61K 40/11* (2025.01); *A61K 40/31* (2025.01); *A61K 40/4232* (2025.01); *A61K 40/4244* (2025.01); *A61P 35/00* (2018.01); *C07K 16/30* (2013.01); *C12N 5/0636* (2013.01); *A61K 2239/13* (2023.05); *A61K 2239/28* (2023.05); *A61K 2239/29* (2023.05); *A61K 2239/56* (2023.05)

(58) Field of Classification Search
CPC ............... C07K 16/2875; C07K 16/30; C07K 2317/31; C07K 2317/622; A61K 40/11; A61K 40/31; A61K 40/4232; A61K 2239/13; A61K 2239/28; A61K 2239/29; A61K 39/4631; A61P 35/00
See application file for complete search history.

(56) References Cited

U.S. PATENT DOCUMENTS

| | | | |
|---|---|---|---|
| 4,683,202 | A | 7/1987 | Mullis |
| 4,797,368 | A | 1/1989 | Carter et al. |
| 4,946,778 | A | 8/1990 | Ladner et al. |
| 5,091,513 | A | 2/1992 | Huston et al. |
| 5,132,405 | A | 7/1992 | Huston et al. |
| 5,139,941 | A | 8/1992 | Muzyczka et al. |
| 5,928,906 | A | 7/1999 | Hubert et al. |
| 5,994,136 | A | 11/1999 | Naldini et al. |
| 6,013,516 | A | 1/2000 | Verma et al. |
| 8,329,178 | B2 | 12/2012 | Marasco et al. |
| 8,466,263 | B2 | 6/2013 | Marasco et al. |
| 9,765,149 | B2 | 9/2017 | Silence et al. |
| 2018/0030147 | A1 | 2/2018 | Marasco |
| 2018/0111992 | A1 | 4/2018 | Fry et al. |
| 2018/0334490 | A1* | 11/2018 | Brogdon .......... C07K 14/70578 |
| 2019/0031759 | A1* | 1/2019 | Reiter ................ C07K 16/2833 |

FOREIGN PATENT DOCUMENTS

| | | | | |
|---|---|---|---|---|
| WO | WO2007065027 | A2 | 6/2007 | |
| WO | WO2009086514 | A1 | 7/2009 | |
| WO | WO-2011139375 | A1 * | 11/2011 | ............. C07K 16/40 |
| WO | WO2013123061 | A1 | 8/2013 | |
| WO | WO2013166500 | A1 | 11/2013 | |
| WO | WO2016057488 | A1 | 4/2016 | |
| WO | WO2016100980 | A1 | 6/2016 | |
| WO | WO2016100985 | A2 | 6/2016 | |
| WO | WO2016178779 | A1 | 11/2016 | |
| WO | WO2017075537 | A1 | 5/2017 | |

(Continued)

OTHER PUBLICATIONS

Adam P. J et al., "CD70 (TNFSF7) is expressed at high prevalence in renal cell carcinomas and is rapidly internalised on antibody binding", British Journal of Cancer, Nature Publishing Group UK, London, (Aug. 7, 2006), vol. 95, No. 3, doi: 10.1038/SJ.BJC. 6603222, Issn 0007-0920, pp. 298-306, XP002440598 [Y] 1-17 * abstract * * p. 298, column l * * p. 299; figure 1 * * p. 303, column I, paragraph 1 * * p. 304; figure 6 *.

Ausubel, F. M., et al. "Current protocols in molecular biology, vol. 1 John Wiley & Sons." Inc, Brooklyn, New York 3.1 (2003): 1994-2005.

Baichwal, Vijay R., and Bill Sugden. "Vectors for gene transfer derived from animal DNA viruses: transient and stable expression of transferred genes." Gene Transfer. Boston, MA: Springer US, 1986. 117-148.

(Continued)

*Primary Examiner* — Maria G Leavitt
*Assistant Examiner* — Vyoma Shubham Tiwari
(74) *Attorney, Agent, or Firm* — Baker Donelson

(57) ABSTRACT

This invention is directed to chimeric antigen receptors and cells comprising the same, wherein the cells further secrete monoclonal antibodies locally at a tumor site.

10 Claims, 101 Drawing Sheets
Specification includes a Sequence Listing.

(56) References Cited

FOREIGN PATENT DOCUMENTS

| WO | WO2018152181 A1 | 8/2018 |
| WO | WO2018156802 A1 | 8/2018 |
| WO | WO2019178356 A1 | 9/2019 |

OTHER PUBLICATIONS

Blömer, Ulrike, et al. "Highly efficient and sustained gene transfer in adult neurons with a lentivirus vector." Journal of virology 71.9 (1997): 6641-6649.

Chen, et al. "Fusion protein linkers: property, design and functionality." Advanced drug delivery reviews 65.10 (2013): 1357-1369.

Cotten, Matt, et al. "High-efficiency receptor-mediated delivery of small and large (48 kilobase gene constructs using the endosome-disruption activity of defective or chemically inactivated adenovirus particles." Proceedings of the National Academy of Sciences 89.13 (1992): 6094-6098.

Coupar, Barbara EH, Marion E. Andrew, and David B. Boyle. "A general method for the construction of recombinant vaccinia viruses expressing multiple foreign genes." Gene 68.1 (1988): 1-10.

Curiel, David T. "High-efficiency gene transfer employing adenovirus-polylysine-DNA complexes." Natural immunity 13.2-3 (1994): 141-164.

Fesnak AD, June CH, Levine BL. Engineered T cells: the promise and challenges of cancer immunotherapy. Nat Rev Cancer. Aug. 23, 2016;16(9):566-81. doi: 10.1038/nrc.2016.97. PMID: 27550819; PMCID: PMC5543811.

Friedmann, Theodore. "Progress toward human gene therapy." Science 244.4910 (1989): 1275-1281.

GENBANK Accession No. NM_000442.5.
GENBANK Accession No. NM_000591.4.
GENBANK Accession No. NM_000610.4.
GENBANK Accession No. NM_001030288.3.
GENBANK Accession No. NM_001123041.2.
GENBANK Accession No. NM_001145873.1.
GENBANK Accession No. NM_001206609.2.
GENBANK Accession No. NM_001328609.2.
GENBANK Accession No. NM_001766.3.
GENBANK Accession No. NM_001772.
GENBANK Accession No. NM_002033.3.
GENBANK Accession No. NM_002184.4.
GENBANK Accession No. NM_014143.4.
GENBANK Accession No. NP_000433.4.
GENBANK Accession No. NP_000582.1.
GENBANK Accession No. NP_000601.3.
GENBANK Accession No. NP_001025459.1.
GENBANK Accession No. NP_001116513.2.
GENBANK Accession No. NP_001139345.1.
GENBANK Accession No. NP_001193538.1.
GENBANK Accession No. NP_001315538.1.
GENBANK Accession No. NP_001757.1.
GENBANK Accession No. NP_001763.3.
GENBANK Accession No. NP_002024.1.
GENBANK Accession No. NP_002175.2.
GENBANK Accession No. NP_054862.1.

Grabmaier, Karin, et al. "Molecular cloning and immunogenicity of renal cell carcinoma-associated antigen G250." International journal of cancer 85.6 (2000): 865-870.

Horwich, A. "Protein import into mitochondria and peroxisomes." Current Opinion in Cell Biology 2.4 (1990): 625-633.

Horwitz, Grunhaus A. "Adenoviruses as cloning vectors." Semin Virol 3 (1992): 237-252.

Huston JS, Levinson D, Mudgett-Hunter M, Tai MS, Novotný J, Margolies MN, Ridge RJ, Bruccoleri RE, Haber E, Crea R, et al. Protein engineering of antibody binding sites: recovery of specific activity in an anti-digoxin single-chain Fv analogue produced in *Escherichia coli*. Proc Natl Acad Sci U S A. Aug. 1988; 85(16):5879-83. doi: 10.1073/ pnas.85.16.5879. PMID: 3045807; PMCID: PMC281868.

International Search report for PCT/US2019/064032 mailed Jul. 15, 2020.

Joyner, Alexandra L., William C. Skarnes, and Janet Rossant. "Production of a mutation in mouse En-2 gene by homologous recombination in embryonic stem cells." Nature 338.6211 (1989): 153-156.

Kelleher, Z. T., and J. M. Vos. "Long-term episomal gene delivery in human lymphoid cells using human and avian adenoviral-assisted transfection." Biotechniques 17.6 (1994): 1110-1117.

Lamers, Cor HJ, et al. "Immune responses to transgene and retroviral vector in patients treated with ex vivo- engineered T cells." Blood, The Journal of the American Society of Hematology 117.1 (2011): 72-82.

Lamers, Cor HJ, et al. "Treatment of metastatic renal cell carcinoma with autologous T-lymphocytes genetically retargeted against carbonic anhydrase IX: first clinical experience." Journal of Clinical Oncology 24.13 (2006): e20-e22.

Laughlin, C. A., C. B. Cardellichio, and H. C. Coon. "Latent infection of KB cells with adeno-associated virus type 2." Journal of virology 60.2 (1986): 515-524.

Lebkowski, Jane S., et al. "Adeno-associated virus: a vector system for efficient introduction and integration of DNA into a variety of mammalian cell types." Molecular and cellular biology 8.10 (1988): 3988-3996.

Liao, Shu-Yuan, et al. "Identification of the MN/CA9 protein as a reliable diagnostic biomarker of clear cell carcinoma of the kidney." Cancer research 57.14 (1997): 2827-2831.

Maher, John, et al. "Human T-lymphocyte cytotoxicity and proliferation directed by a single chimeric TCRZ/CD28 receptor." Nature biotechnology 20.1 (2002): 70-75.

Mann, Richard, Richard C. Mulligan, and David Baltimore. "Construction of a retrovirus packaging mutant and its use to produce helper-free defective retrovirus." Cell 33.1 (1983): 153-159.

McLaughlin, Susan K., et al. "Adeno-associated virus general transduction vectors: analysis of proviral structures." Journal of virology 62.6 (1988): 1963-1973.

Miller, A. D. "Retroviral vectors." Viral expression vectors (1992): 1-24.

Naldini, Luigi, et al. "Efficient transfer, integration, and sustained long-term expression of the transgene in adult rat brains injected with a lentiviral vector." Proceedings of the National Academy of Sciences 93.21 (1996): 11382-11388.

Nicolas, Jean-François, and John LR Rubenstein. "Retroviral vectors." Vectors (1988): 493-513.

Paskind, Michael P., Robert A. Weinberg, and David Baltimore. "Dependence of Moloney murine leukemia virus production on cell growth." Virology 67.1 (1975): 242-248.

Rini, Brian I., Steven C. Campbell, and Bernard Escudier. "Renal cell carcinoma." The Lancet 373.9669 (2009): 1119-1132.

Ryan, M., Kostner, H., Gordon, K et al. Targeting pancreatic and ovarian carcinomas using the auristatin-based anti-CD70 antibody-drug conjugate SGN-75. Br J Cancer 103, 676-684 (2010). https://doi.org/10.1038/sj.bjc.6605816.

Sambrook Joseph and David W. Russell. "Molecular cloning." A Laboratory Manual 3rd (2001).

Suarez, Eloah Rabello, et al. "Chimeric antigen receptor T cells secreting anti-PD-L1 antibodies more effectively regress renal cell carcinoma in a humanized mouse model." Oncotarget 7.23 (2016): 34341-34355. Especially abstract.

Temin, Howard M. "Retroviruses and evolution." Bioscience at the Physical Science Frontier: Proceedings of a Foundation Symposium on the 150th Anniversary of Alfred Nobel's Birth. Totowa, NJ: Humana Press, 1986.

Thomas, Kirk R., and Mario R. Capecchi. "Site-directed mutagenesis by gene targeting in mouse embryo-derived stem cells." Cell 51.3 (1987): 503-512.Mansour, et al., Nature (1988) 336, 348-352.

Tratschin, Jon-Duri, et al. "A human parvovirus, adeno-associated virus, as a eucaryotic vector: transient expression and encapsidation of the procaryotic gene for chloramphenicol acetyltransferase." Molecular and cellular biology 4.10 (1984): 2072-2081.

Written Opinion for PCT/US2019/064032 mailed Jul. 15, 2020.

(56) References Cited

OTHER PUBLICATIONS

Zufferey, Romain, et al. "Multiply attenuated lentiviral vector
achieves efficient gene delivery in vivo." Nature biotechnology 15.9
(1997): 871-875.

\* cited by examiner

2<sup>nd</sup> generation CAR-T cell factories ccRCC-Patient 9-T
primary cell line ccRCC-Patient 9-D
primary cell line

CAIX

CD70

CD70

CAIX ccRCC tumor tissue

| | CAIX | CD70 |
|---|---|---|
| Skrc-59 CAIX+ CD70+ | 2658.93 | 43.43 |
| Skrc-59 CAIX+ CD70- | 1403.36 | 3.98 |
| Skrc-59 CAIX- CD70+ | 30.37 | 132.66 |
| Skrc-59 CAIX- CD70- | 35.38 | 3.57 |

FIG. 5B

| EC$_{50}$ (ug/ml) | G36-GGGGS1-7 | 7-GGGGS1-G36 | 7-GGGGS3-G36 | G36-GGGGS5-CD27 | 7-GGGGS5-G36 | G36-hinge-7 | 7-hinge-G36 | G36 |
|---|---|---|---|---|---|---|---|---|
| | 0.7004 | 0.1093 | 0.1177 | 0.4107 | 0.09124 | 0.5921 | 0.1138 | 0.1315 |

| EC$_{50}$ (ug/ml) | G36-GGGGS1-B7 | B7-GGGGS1-G36 | B7-GGGGS3-G36 | G36-GGGGS5-CD27 | B7-GGGGS5-G36 | G36-hinge-B7 | B7-hinge-G36 | CD27 | B7 |
|---|---|---|---|---|---|---|---|---|---|
| | 0.1548 | 0.1348 | 0.1928 | 0.6188 | 0.1251 | 0.1766 | 0.2344 | 0.9166 | 0.2267 |

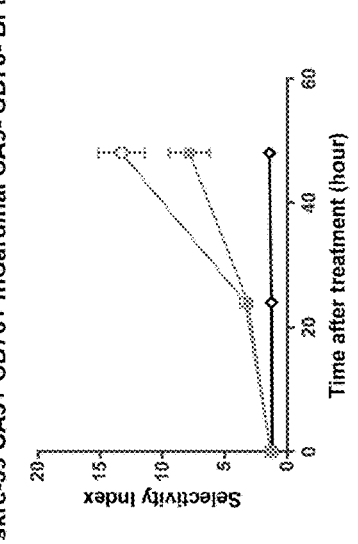
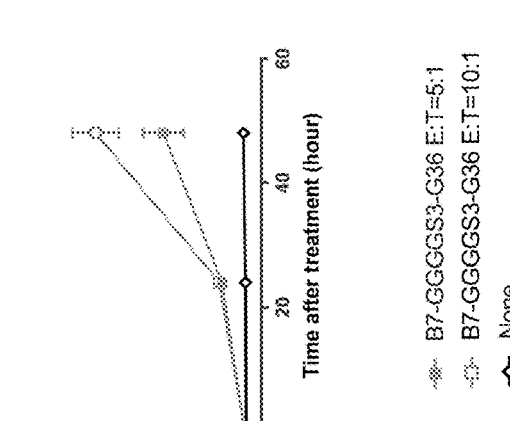
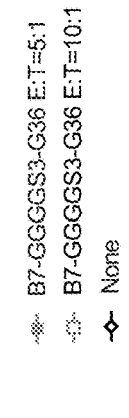
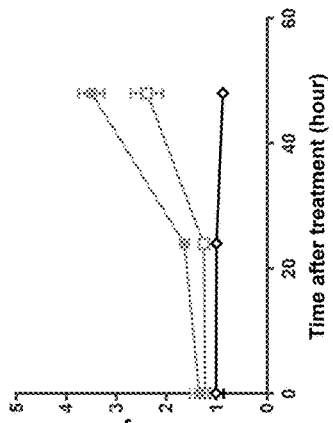
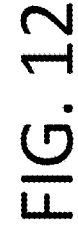
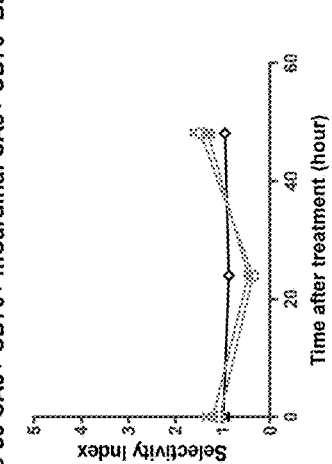
Selectivity index = BFP / mCardinal = non-target cells / target cells
FIG. 12

19 anti-CAIX ScFvs

| CAIX Abs | Affinity (KD) (nM) | Mapping* (CA-GST) (OD450) | Cross-competition Grouping | % CA Inhibition by anti-CAIX scFvFc | Internalization |
|---|---|---|---|---|---|
| G119 | 1.49 | - | 1 | 25 | +++*** |
| G10 | 1.62 | 3 | 1 | 15 | + |
| G37 | 1.89 | 3 | 1 | 40** | -*** |
| G106 | 3.20 | 2.4 | 1 | 20 | ++ |
| G36 | 3.22 | 3 | 1 | 10 | ++*** |
| G45 | 12.50 | - | 1 | - | + |
| G39 | 3.43 | 0.25 | 1 | 50** | - |
| G57 | 4.25 | - | 1 | - | - |
| G40 | 21.78 | - | 1a | 15 | - |
| G6 | 25.90 | 0.9 | 1a | 50** | - |
| G27 | 25.12 | - | 2 | - | + |
| G125 | 40.32 | - | 3 | 40** | - |
| G9 | 99.58 | 0.4 | 3 | - | - |

*All anti-CAIX antibodies recognize the CA domain but only a selected group interacts with bacterially produced CA-GST (Figure 3D &E).

**Percentage of carbonic anhydrase inhibition by CAIX antibodies was estimated from Figure 4B. The rest data are from Figure 4A.

***Internalization measured by both flow cytometry and ImageStream. + and - denotes degree of internalization as measured by regular flow cytometry (Figure 5).
doi:10.1371/journal.pone.0009625.t004

Group 1   group 1a   group 2   group 3

FIG. 16A

Group 1 | group 1a | group 2 | group 3

| | scFv-Fc | KD(nM) | Internalization | Killing activity | Sequencing validation | pHAGE | Lentivirus |
|---|---|---|---|---|---|---|---|
| 1 | G6 | 25.90 | - | ++ | ✓ | ✓ | ✓ |
| 2 | G9 | 99.58 | - | ++ | ✓ | ✓ | ✓ |
| 3 | G10 | 1.62 | + | +++ | ✓ | ✓ | ✓ |
| 4 | G17 | | | ++ | ✓ | ✓ | ✓ |
| 5 | G21 | | | +++ | ✓ | | ✓ |
| 6 | G27 | 25.12 | + | ++ | ✓ | ✓ | ✓ |
| 7 | G28 | | | ++ | ✓ | | ✓ |
| 8 | G36 | 3.22 | ++ | +++ | ✓ | ✓ | ✓ |
| 9 | G37 | 1.89 | - | ++++ | ✓ | ✓ | ✓ |
| 10 | G39 | 3.43 | + | ++++ | ✓ | ✓ | ✓ |
| 11 | G40 | 21.78 | - | +++ | ✓ | ✓ | ✓ |
| 12 | G45 | 12.50 | + | +++ | ✓ | ✓ | ✓ |
| 13 | G57 | 4.25 | - | +++ | ✓ | ✓ | ✓ |
| 14 | G62 | | | +++ | ✓ | | ✓ |
| 15 | G98 | | | +++ | ✓ | | ✓ |
| 16 | G104 | Non-binder | | + | ✓ | ✓ | ✓ |
| 17 | G106 | 3.20 | ++ | +++ | ✓ | ✓ | ✓ |
| 18 | G119 | 1.49 | +++ | +++ | ✓ | ✓ | ✓ |
| 19 | G125 | 40.32 | - | ++++ | ✓ | ✓ | ✓ |

Anti-CAIX scFvs were cloned into pHAGE vector and packaged as lentivirus. CAR T cells were generated and tested killing activity. We proved that there is correlation between affinity of scFv and killing of CART, G37, G39, G125>G10, G21, G36, G40, G45, G57, G62, G98, G106, G119>G6, G9, G17, G27, G28>G104.

FIG. 16B

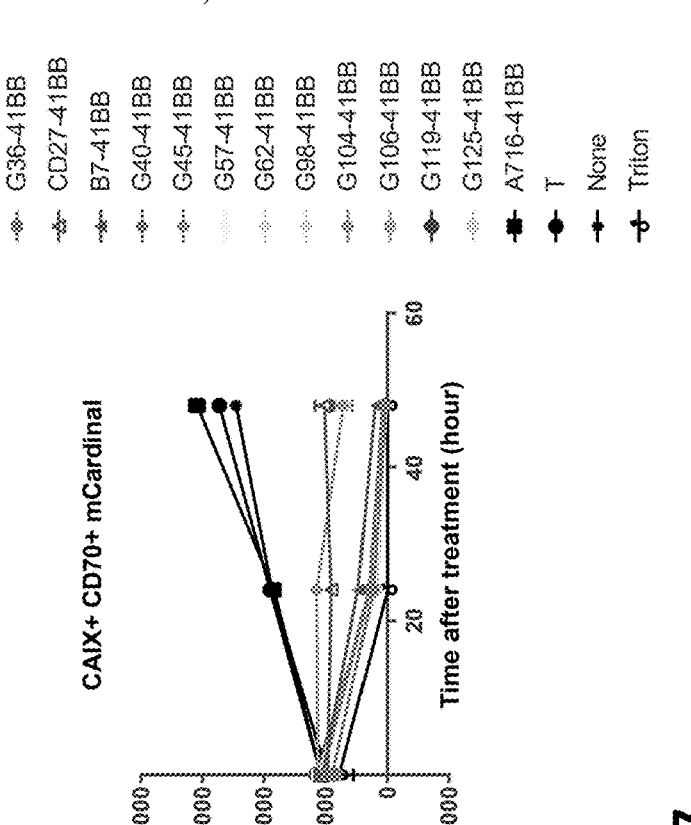
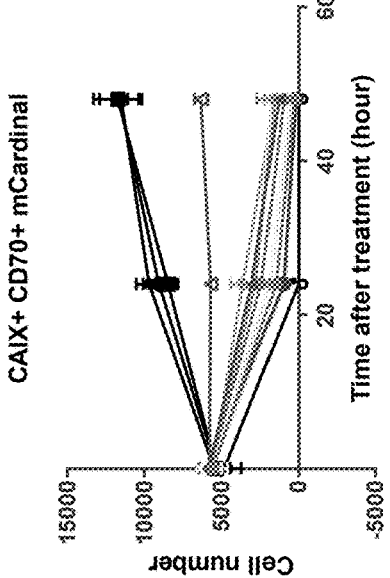
FIG. 17

| Group | Treatment | Dose |
|---|---|---|
| 1 | G36-41BB | 1.00E+06 |
| 2 | G36-41BB | 3.00E+06 |
| 3 | G36-41BB | 1.00E+07 |
| 4 | G36-CD28 | 3.00E+06 |
| 5 | G36-41BB CD4/8 (CD4:CD8 = 2:1) | 3.00E+06 |
| 6 | G36-41BB CD4/8 (CD4:CD8 = 2:1) | 1.00E+07 |
| 7 | G36-CD28-41BB | 3.00E+06 |
| 8 | G36-CD28-41BB | 1.00E+07 |
| 9 | Ctrl (untransduced T cells) | 3.00E+06 |
| 10 | Ctrl (untransduced T cells) | 1.00E+07 |
| 11 | Ctrl (untransduced T cells) (CD4:CD8 = 2:1) | 3.00E+06 |

Engraftme
nt of Week 8
tumor cell

BLI
imaging /
CART
injection

Week 9 BLI /
Bleeding

Week 10

Week 11 BLI /
Bleeding

Week 12

Week 37

FIG. 29

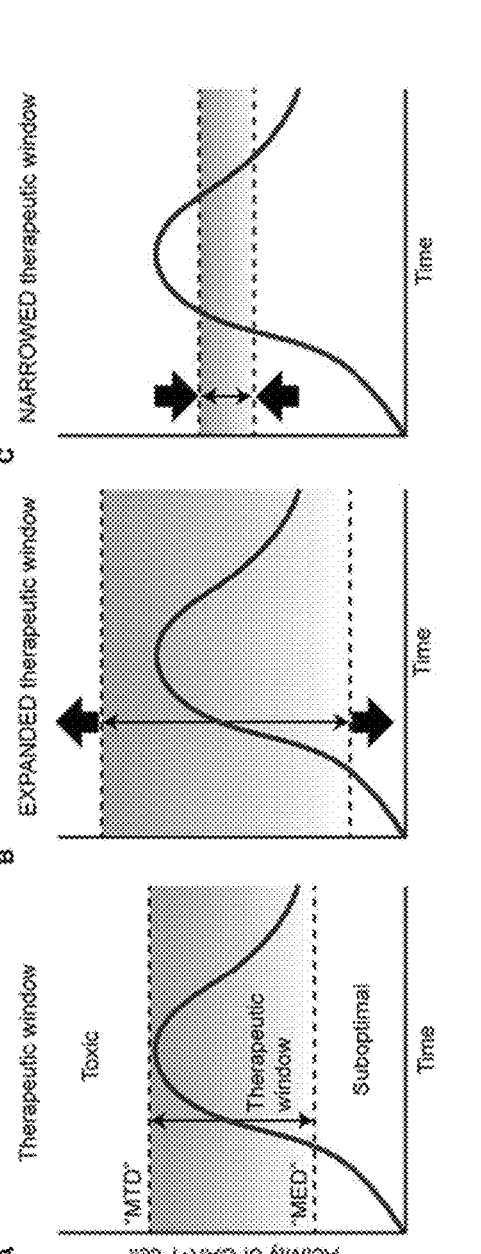
Front Immunol. 2018 Oct 26;9:2486
FIG. 37

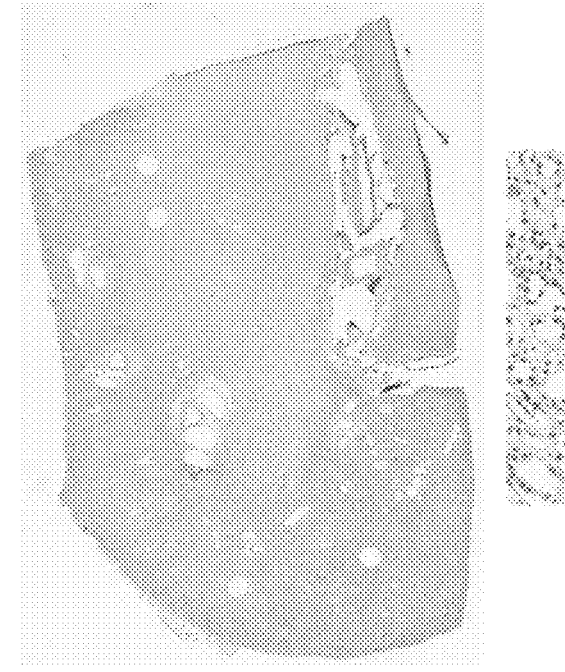
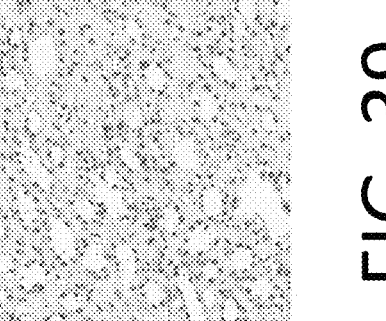
477495 T3a M1
ccRCC
Normal kidney
FIG. 39

477473
Bile duct

| CAIX Abs | Affinity (KD) (nM) | Mapping* (CA-GST) (OD450) | Cross-competition Grouping | % CA inhibition by anti-CAIX scFvFc | Internalization |
|---|---|---|---|---|---|
| G119 | 1.49 |  | 1 | 25 | ++++ |
| G10 | 1.62 | 3 | 1 | 15 | + |
| G37 | 1.89 | 3 | 1 | 40** | +++ |
| G106 | 3.20 | 2.4 | 1 | 20 | ++ |
| G36 | 3.22 | 3 | 1 | 10 | ++++ |
| G45 | 12.50 | - | 1 | - | + |
| G39 | 3.43 | 0.25 | 1 | 50** | - |
| G57 | 4.35 | - | 1 | - | - |
| G60 | 21.78 | - | 1a | 15 | - |
| G6 | 25.90 | 0.9 | 1a | 50** | + |
| G27 | 25.12 | - | 2 | - | + |
| G125 | 40.32 | - | 3 | 40** | - |
| G9 | 99.58 | 0.4 | 3 | - | - |

*All anti-CAIX antibodies recognize the CA domain but only a selected group interacts with bacterially produced CA-GST (Figure 3D &E).

**Percentage of carbonic anhydrase inhibition by CAIX antibodies was estimated from Figure 4B. The rest data are from Figure 4A.

***Internalization measured by both flow cytometry and ImageStream. + and ~ denotes degree of internalization as measured by regular flow cytometry (Figure 5).

doi:10.1371/journal.pone.0009625.t004

PLoS ONE 2010 5(3)e9625

FIG. 41

| scFv-Fc | | KD(nM) | Internalization | MonoCAR killing | MonoCAR-293T binding |
|---|---|---|---|---|---|
| 1 | G6 | 25.90 | - | ++ | 21.3 |
| 2 | G9 | 99.58 | - | ++ | 24.9 |
| 3 | G10 | 1.62 | + | +++ | 39.6 |
| 4 | G17 | | | ++ | 29.6 |
| 5 | G21 | | | +++ | 29.5 |
| 6 | G27 | 25.12 | + | ++ | 15.5 |
| 7 | G28 | | | ++ | 8.4 |
| 8 | G36 | 3.22 | ++ | +++ | 32.1 |
| 9 | G37 | 1.89 | - | ++++ | 33.7 |
| 10 | G39 | 3.43 | - | ++++ | 25.7 |
| 11 | G40 | 21.78 | - | +++ | 29.6 |
| 12 | G45 | 12.50 | + | +++ | 26 |
| 13 | G57 | 4.25 | - | +++ | 19.4 |
| 14 | G62 | | | +++ | 35.1 |
| 15 | G98 | Non-binder | | + | 35 |
| 16 | G104 | | | | 0.9 |
| 17 | G106 | 3.20 | ++ | +++ | 47.7 |
| 18 | G119 | 1.49 | +++ | +++ | 36 |
| 19 | G125 | 40.32 | - | ++++ | 34.5 |
| 20 | G250 | | | | |

FIG. 42

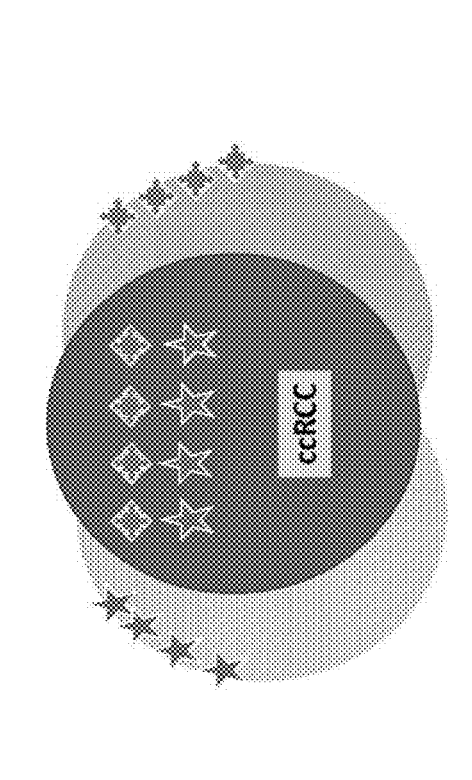
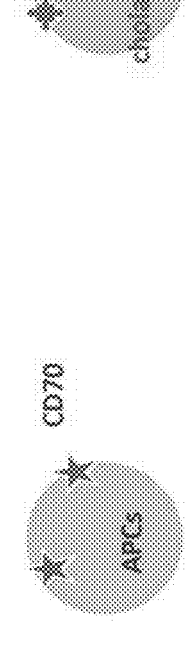
"Or" Gating to Capture Tumor Cell Heterogeneity
But not Kill Low Target Density Healthy Cells
FIG. 43

| Tumor type | CD70+ of total | %CD70+ |
|---|---|---|
| Kidney[a] | 204 of 283 | 72 |
| Pancreas | 35 of 140 | 25 |
| Larynx or pharynx[b] | 18 of 82 | 22 |
| Melanoma | 15 of 96 | 16 |
| Ovary | 37 of 241 | 15 |
| Lung adenocarcinoma | 17 of 173 | 10 |
| Colon | 17 of 194 | 9 |
| Breast | 5 of 204 | 2 |
| Brain | 6 of 59 | 10 | a 189 of 230 (82%) clear cell carcinoma) and 4 of 8 (50%) papillary carcinoma
b Includes nasopharyngeal cancer.

British Journal of Cancer 103 (2010) 676-684

FIG. 44

Stage I
477469 T1b
ccRCC

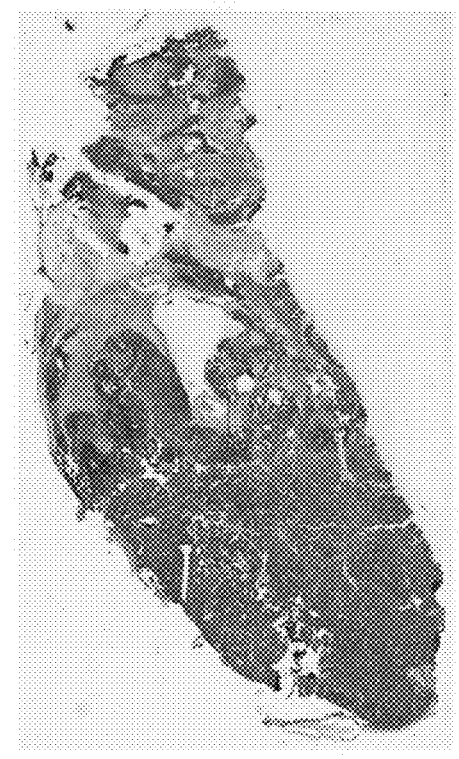
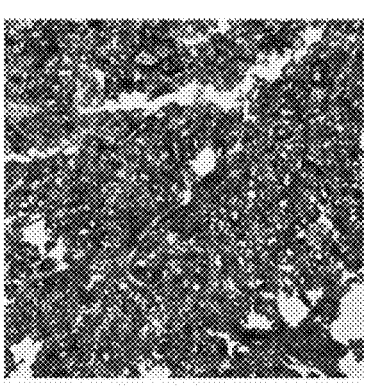
Stage IV
477490 M1
ccRCC
FIG. 46

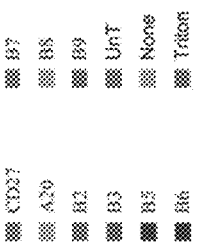
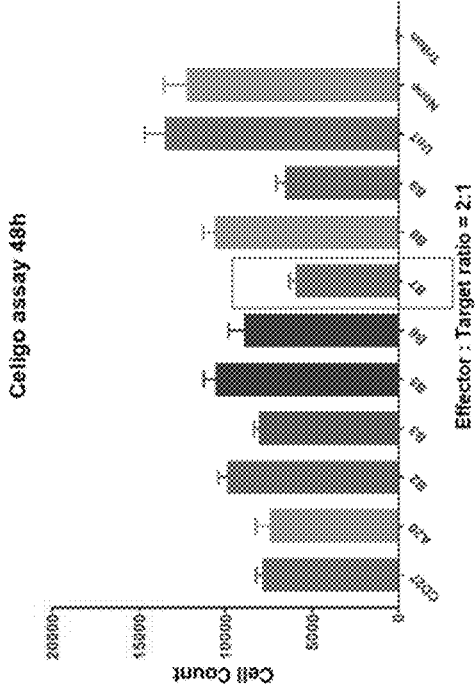
FIG. 49

| | G36-GGGGS1-7 | 7-GGGGS1-G36 | 7-GGGGS3-G36 | G36-GGGGS5-CD27 | 7-GGGGS5-G36 | G36-hinge-7 | 7-hinge-G36 | G36 |
|---|---|---|---|---|---|---|---|---|
| EC50 (ug/ml) | 0.7004 | 0.1093 | 0.1177 | 0.4107 | 0.09124 | 0.5921 | 0.1138 | 0.1315 |

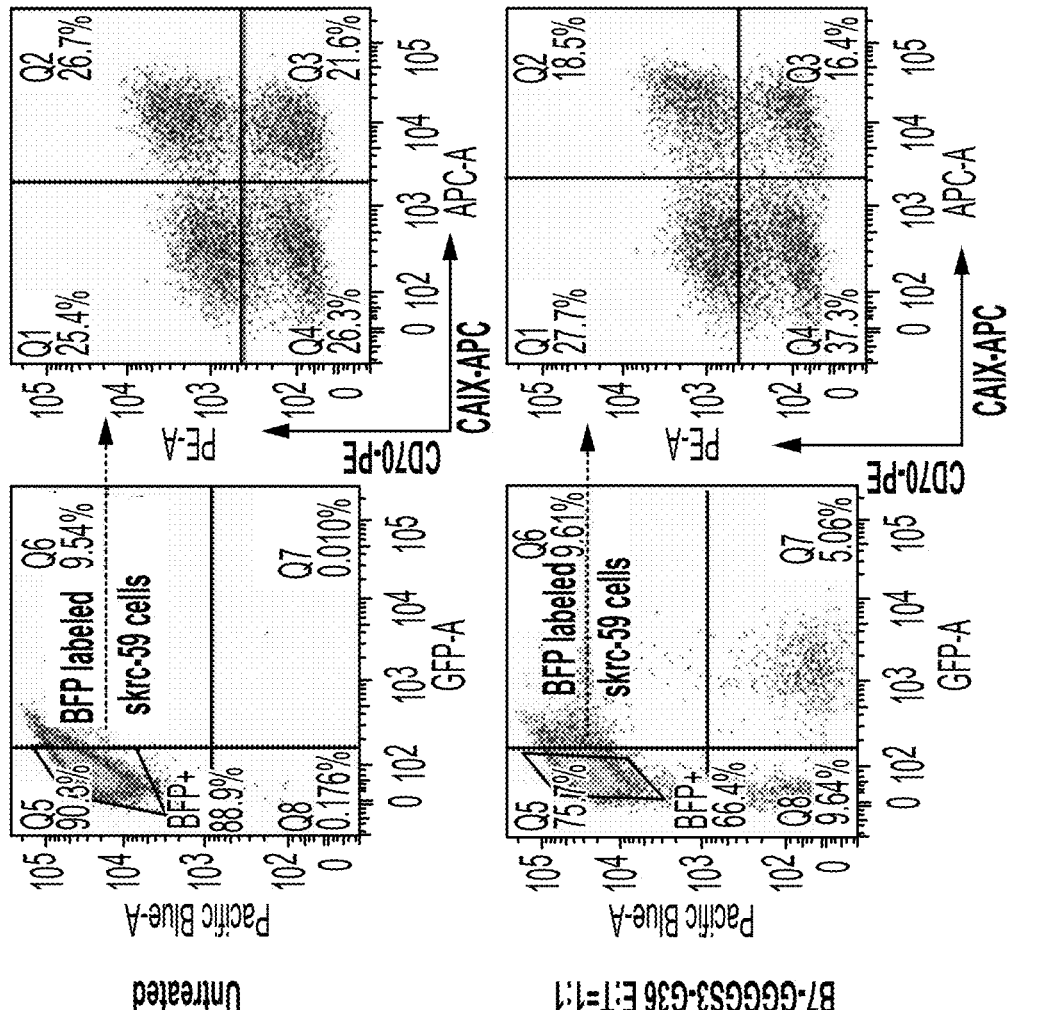
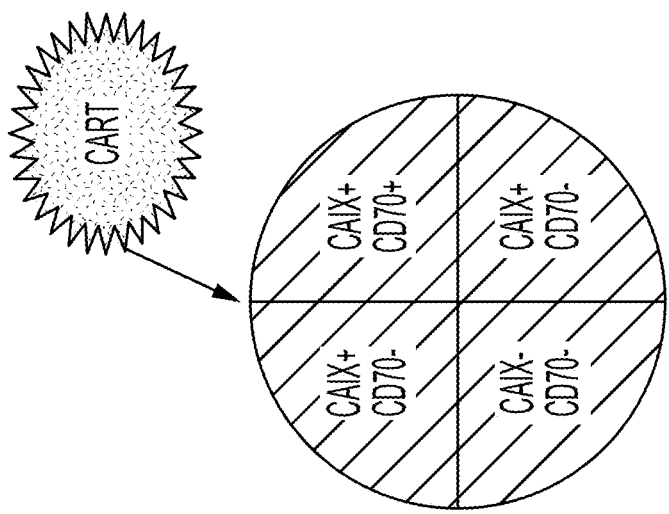
FIG. 55

VH:

| | FW1 | CDR1 | FW2 | CDR2 | FW3 | CDR3 | FW4 | Family: |
|---|---|---|---|---|---|---|---|---|
| | QVQLVQSGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAR | NGNYRGSL*AFDI | WGQGTLCTVSS | VH3 |
| Clone A (36) | EVQLVQSGGGLVQPGGSLRLSCAASGFPFS | SYAMS | WVRQAPGKGLEWVS | AISANGGTYYADSVKG | RFTISRDNSKNTLYLQMNSLRAEDTAVYYCAN | NGNYRG---AFDI | WGQGTMVTVSS | VH3 |
| Clone B (10) | QVQLVQSGGGLVQPGGSLRLSCAASGFPFS | SYAMS | WVRQAPGKGLEWVS | AISANGGTYYADSVKG | RFTISRDNSKNTLYLQMNSLRAEDTAVYYCAN | NGNYRG---AFDI | WGQGTMVTVSS | VH3 |
| Clone C (119) | QVQLVQSGGGLVQPGGSLRLSCAASGFPFS | SYAMS | WVRQAPGKGLEWVS | AISANGGTYYADSVKG | RFTISRDNSKNTLYLQMNSLRAEDTAVYYCAN | NGNYRG---AFDI | WGQGTMVTVSS | VH3 |
| Clone D (6) | QVQLVQSGGGLVQPGGSLRLSCAASEFTFG | TYAMT | WVRQAPGKGLEWVS | AVSGSGGSTYYADSVKG | RFTISRDNSKNTLYLQMNSLRADDTAVYYCAR | GPVLRY---GFDI | WGQGTMVTVSS | VH3 |
| Clone E (37) | QVQLVQSGGGLVQPGGSLRLSCAASGFPFS | SYAMS | WVRQAPGKGLEWVS | AISGSGGSTYYADSVKG | RFTISRDNSKNTLYLQMNSLRAEDTAVYYCAN | NGNYRG---AFDI | WGQGTMVTVSS | VH3 |
| Clone F (104) | QVQLQESGGGLVQPGGSLRLSCAASGFTFS | IYAMS | WVRQAPGKGLEWVS | AISGSGGSTYHADSVKG | RFTISRDNSKNTLYLQMNSLRAEDTAVYYCAK | FSAYSG---YDL | WGQGTMVTVSS | VH3 |
| Clone H (62) | QVQLVQSGGGLVRPGGSLRLSCAASGFPFS | SYAMS | WVRQAPGKGLEWVS | AISANGGTYYADSVKG | RFTISRDNSKNTLYLQMNSLRAEDTAVYYCAK | NGNYRG---AFDI | WGQGTLVTVSS | VH31 |
| Clone I (45) | EVQLVQSGGGLVQPGGSLRLSCAASGFPFS | SYAMS | WVRQAPGKGLEWVS | AISANGGTYYADSVKG | RFTISRDNSKNTLYLQMNSLRAEDTAVYYCAN | NGNYRG---AFDI | WGQGTMVTVSS | VH3 |
| Clone K (106) | QVQLVQSGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAN | NGNYRG---AFDI | WGQGTLVTVSS | VH3 |
| Clone L (18) | QVQLQESGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAR | AAAG------FDY | WGQGTLVTVSS | VH3 |
| Clone M (39) | QVQLQESGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAR | IGRYSSS---LGY | WGQGTLVTVSS | VH3 |
| Clone N (94) | QVQLVQSGGGVVQPGGSLRLSCGRSLRLS | SYGMH | WVRQAPGKGLEWVA | VISYDGSNKYYADSVKG | RFTISRDNSKNTLYLQMNSLRAEDTAVYYCAR | EAPYSSSLDAFDI | WGQGTMVTVSS | VH3 |
| Clone O (9) | QVQLQESGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAR | SHSSGG---FDY | WGQGTLVTVSS | VH3 |
| Clone P (21) | QVQLQESGGGLVQPGGSLRLSCAASGFTFS | SYAMS | WVRQAPGKGLEWVS | AISGSGGSTYYADSVKG | RFTISRDNAKNSLYLQMNSLRAEDDTAVYYCAR | SHSSGG---FDY | WGQGTLVTVSS | VH3 |
| Clone Q (27) | QVTLKESGGGLVQPGGSLRLSCAASGFTFS | NYAMT | WVRQAPGKGLEWVG | LISYDGSTHYDSVKG | RFTISRDNSKNTLYLQMNSLRADDTAVYYCAT | GSGIQEH------ | WGQGTLVTVSS | VH3 |
| Clone R (40) | QVQLVQSGGGLVQPGGSLRLSCAASGFTFS | SYAMS | WVRQAPGKGLEWVS | AISGSGGSTYYADSVKG | RFTISRDNSKNTLYLQMNSLRAEDTAVYYCAR | YGDYGS------LDY | WGQGTLVTVSS | VH3 |
| Clone S (57) | QVQLVQSGGGLVQPGGSLRLSCAASGFTFS | SYAMS | WVRQAPGKGLEWVS | AISGSGGVGTYYADSVKG | RFTISRDNSKNTLYLQMNSLRAEDTAVYYCAR | YCSSTSCYRGMDV | WGKGTLVTVSS | VH3 |
| Clone T (82) | QVQLVQSGGGLVQPGGSLRLSCAASGFTFS | SYGMH | WVRQAPGKGLEWVA | VISYDGSNKYYADSVKG | RFTISRDNSKNTLYLQMNSLRAEDTAVYYCAR | GRAARP---PFDY | WGQGTMVTVSS | VH3 |
| Clone V (98) | QVQLVQSGGGLVQPGGSLRLSCAASGFPFS | SYAMS | WVRQAPGKGLEWVS | AISANGGTYYADSVKG | RFTISRDNSKNTLYLQMNSLRAEDTAVYYCAK | NGNYRG---AFDI | WGQGTLVTVSS | VH3 |
| Clone W (124) | QVQLVQSGGGLVQPGGSLRLSCAAPEFTFS | KYAMS | WVRQAPGKGLEWVS | GISGSGGSTYYADSVKG | RFTISRDNAKNTLYLQMNSLRAEDTAVYYCAK | SSRGYFLP-LDY | WGQGTLVTVSS | VH3 |
| Clone X (125) | EVQLVESGGGLVQPGGSLRLSCAASGFTFS | SYGMH | WVRQAPGKGLEWVS | AISGSGGSTYYADSVKG | RFTISRDNSKNTLYLQMNSLRAEDTAVYYCAR | AAVTGG------FDP | WGQGTLVTVSS | VH3 |

| | FW1 | CDR1 | FW2 | CDR2 | FW3 | CDR3 | FW4 | Family/Subgroup |
|---|---|---|---|---|---|---|---|---|
| | QSVLT1PPSVSGAPGQRVTISC | TGSSSNIGAGYDVH | WYQQLPGTAPKLLIY | GNNNRPS | GVPDRFSGSKSGTSASLAITGLQAEDEADYYC | QSYDSSLSAWV | FGGGTKLTVLG | VL1 |
| Clone A (36) | QSVITQPPSVSGAPGQRVTISC | TGSSSNIGAGFDVH | WYQQLPGTAPKLLIY | GNTNRPS | GVPDRFSGSKSGTSASLAITGLQAEDETDYYC | QSYDRSLSAWV- | FGGGTKLTVLG | VL1 |
| Clone B (10) | QSVITQPPSVSCAPGQRVTISC | TGSSSNIGAGYDVH | WYQQLPGTAPKLLIY | GNSNRPS | GVPDRFSGSKSGSSASLAITGLQAEDEAHYYC | QSYDRSLS-WV- | FGGGTKLTVLG | VL1 |
| Clone C (119) | QSVITQPPSVSGAPGQRVTISC | TGSSSNIGAGYDVH | WYQQLPGTAPKLLIY | GNTNRPS | GVPDRFSGSKSGTSASLAITGLQAEDDEADYYC | QSYESTLRVWW- | FGGGTKLTVLG | VL1 |
| Clone D (6) | QSVITQPPSVSGAPGQRVTISC | TGSRSNIGADYDVH | WYQQLPGTAPKLLIY | ANNNRPS | GVPGRFSASKSGTSASLAISGLQAEDEADYYC | QSYDSSLRAWV- | FGGGTKLAVLG | VL1 |
| Clone E (37) | QSVITQPPSVSGAPGQRVTISC | TGSRSNIGADYDVH | WYQQLPGTAPKLLIY | ANNNRPS | GVPDRFSGSKSGTSASLAITGLQAEDETDYFC | QSYDSSLSAWV- | FGGGTKVTVLG | VL1 |
| Clone F (104) | QSVITQPPSVSGAPGQRVTISC | TGSSSNIGRGYNVH | WYQQLPGTAPKLLIY | DNTNRPS | GVPARFSGSKSATFASLAITGLQAEDDEADYYC | QSYDSGLR-WV- | FGGGTKLRLLG | VL1 |
| Clone H (62) | QSVITQPPSVSGAPGQRVTISC | TGSSSNIGAGYDVH | WYQQLPGTAPKLLIY | GNNNRPS | GVPDRFSGSKSGCASASLAITGLQAEDEAHYYC | QSYDKSLIT-WV- | FGGGTKVTVLG | VL1 |
| Clone I (45) | QSVITQPPSVSGAPGQRVTISC | TGSSSNIGAGYDVH | WYQQLPGKAPRVIIY | GNNNRPS | GVPDRFSGSKSGTSASLAITGLQSEDEADYYC | QSYDKSLS-WV- | FGGGTKLTVLR | VL1 |
| Clone K (106) | QSVITQPPSVSGAPGQRVTISC | TGSSSNIGAGFDVH | WYQQLPGTAPRLLIY | GNNNRPS | GVPDRFSGSKSGTSASLAITGLQAEDETDYFC | QSYDSSLSAWV- | FGGGTKVTVLR | VL1 |
| Clone L (18) | QSVITQPPSVSGAPGQRVTISC | TGSSSNIGRGYNVH | WYQQLPGTAPRLLIY | DDTNRPS | GVPHRFSGSKSGTSASLAITGLQAEDDEADYYC | QSYDSSLRAWV- | FGGGTKLAVLG | VL1 |
| Clone M (39) | QSVITQPPSVSGAPGQRVTISC | TGSSSNIGRGYNVH | WYQQLPGTAPRLLIY | DNTNRPS | GVPARFSGSKSATSASLAITGLQAEDDEADYYC | QSYDSCLR-WV- | FGGGTKLILLR | VL1 |
| Clone N (94) | QSVITQPPSVSGAPGQRVTISC | TGSSSNIGRGYNVH | WYQQLPGTAPKLLIY | GNSNRPS | GVPDRFSGSSGNTASHTTGAQAEDEADYYC | HSRDNWGHHI-- | FGGGTKLTVLS | VL1 |
| Clone O (9) | QSVITQPPSVSGAPGQRVTISC | TGSSSNIGRGYNVH | WYQQLPGTAPKLLIY | GNTNRPS | GVPDRFSGSKSGTSASLAITGLQAEDEGDYYC | QSYDSSLSAWV- | FGGGTKLTVLG | VL1 |
| Clone P (21) | QSVITQPPSVSGAPGQRVTISC | TGSSSNIGRGYNVH | WYQQLPGTAPRLLIY | GNTNRPS | GVPDRFSGSKSGTSASLAITGLQAXDEGDYYC | QSYDSSLSAWV- | FGGGTKLTVLG | VL1 |
| Clone Q (27) | LPVITQPPSVSGAPGQTARITC | -G-GNNIGSKS-VH | WYQQKPGQAPVLVIY | YDSDRPS | GIPERFSGSNSGNTATHTSRVEAGDEADYYC | QWMDSSDHHVV | FGGGTKLAVLG | VL1 |
| Clone R (40) | QSVITQPPSVSGAPGQRVTISC | TGSSSNIGRGYDVH | WYQQLPGTAPKLLIY | ANNNRPS | GVPDRFSGSKSGTSASLAITGLQAEDEADYYC | QSYDSSLRAWV- | FGGGTKLAVLG | VL1 |
| Clone S (57) | QSVITQPPSVSGAPGQRVTISC | TGSSSNIGRGYDVH | WYQQLPGTAPKLLIY | ANNNRPS | GVPDRFSGSKSGTSASLAITGLQAEDEADYYC | QSYDSSLRAWV- | FGGGTKLAVLG | VL1 |
| Clone T (82) | QPVITQPPSASGTPGQRVTISC | SGSSSNIGSNIV- | WYQQLPGTAPKLPIY | RNWQRPS | GVPDRFSGSSSGTSASLAISGLRSEDEADYYC | AAWDDSLNGVV- | FGGGTKLTVLR | VL1 |
| Clone V (98) | QPVITQPPSVSGAPGQRVTISC | TGSSSNIGAGYDVH | WYQHLPGTAPRLLIY | GNSNRPS | GVPDRFSGSKSGTSASLAITGLQAEDETDYFC | QSYDSSLSAWV- | FGGGTKLTVLG | VL1 |
| Clone W (124) | SSEIIQDPAVSVALGQTVRITC | QGNSLRYYYPS--- | WYQQRPGQAPVLVIY | GKNNRPS | GIPDRFSGSSSGNTASLTITCTQAEDEADYYC | SSRDNTDNRVV- | FGGGTKLTVLG | VL3 |
| Clone X (125) | QPGLITQPPSVSVAPGQTARITC | -G-GDNIGRKS-VH | WYQRRGQAPLIVIR | DBRDRPS | GIPERFSGSSSVNTATLIISRVEAGDEADYYC | QVMDSSSKHYV- | FGPGTKVTALG | VL3 |

FIG. 58B

```
          1        10        20        30        40        50      59
HCA IX   MAPLCPSPWLPLLIPAPAPGLTVQLLSILLLMPVHPQRLPRMQ-EDSPLGGGSSGEDDP
MCA IX   MASLGPSPWAPLSTPAP----TAQLLIFLLLQVSAQPGGLSGMQGEPS-LGDSSSGEDE- 61       70        80        90       100       110
HCA IX   LGEED-LPSEEDSPREE-DPPGEEDLPGEEDLPEVKPKSE---EEGSLKLEDLP
MCA IX   LGV-DVLPSEEDAP-EEADPP---D--GE-D-P----PEVN--SEDRMEE-SLGLEDLS 120      130       140       150       160       170
HCA IX   TVEAPGDPQEP-QNNAHRD-KEGDDQSHWRVGDPPWPRVSPACAGRFQSPVDIRPQLA-
MCA IX   TPEAP-----EHSQGS-HGDEKGGGH-SHWSYGGTLLWPQVSPACAGRFQSPVDIR--LER 180      190       200       210       220       230
HCA IX   -AFCPALRPLELLGFQLPPLPELRLRNNGHSVQLTIPPGLEMALGPGREYRALQLHLHWG
MCA IX   TAECRTLQPLELLGYELQPLPELSLSHMGHTVQLTLPPGLKMALGPGQEYRALQLHLHWG 240      250       260       270       280       290
HCA IX   AAGRPGSEHTVEGHRFPAEIHVVHLSTAFARVDEALGRPGGLAVLAAFLEEGPEENSAYE
MCA IX   TSDHPGSEHTVNGHRFPAEIHVVHLSTDHPGGLAVLAAFLQESPEENSAYE 300      310       320       330       340      348
HCA IX   QLLSRLEETAEEGS---ETQVPGLDTSALLPSDFSRYFQYEGSLTTPPCAQGVIWTVFNQT
MCA IX   QLLSHLEETSEEGSKIE---TPGLDVSALLPSDFSRYRVEGSLTTPPCSQGVIWTVFNET 360      370       380       390       400      408
HCA IX   VMLSAKQLHTLSDTLWGPGDSRLQLNFRATQPLNGRVIEASPPAGVDSSPRAAEPYQLNS
MCA IX   VKLSAKQLHTLSVSLWGPRDSRLQLNFRATQPLNGRTIEASPPAAEDSSP---EPVHVNS 420      430       440       450      459
HCA IX   CLAAGDILALVFGLLFAVTSVAFLVQMRRQHRR--GTKGGVSYRPAEVAETGA
HCA IX   CFTAGDILALVFGLLFAVTSIAFLLQLRRQHRHRSGTKDRVSYSPAEMTETGA
```

FIG. 59

- Homology > 60%
- 5 species: cynomolgus monkey, rat, mouse, guinea pig, hamster

| CAIX | chimpanzee | cynomolgus monkey | rhesus monkey | dog | sheep | rat | mouse | guinea pig | golden hamster |
|---|---|---|---|---|---|---|---|---|---|
| human | 97.6% | 91.2% | 91.5% | 83% | 79.8% | 70.6% | 69.2% | 69.1% | 71.2% |

| CD70 | chimpanzee | cynomolgus monkey | rhesus monkey | dog | sheep | rat | mouse | guinea pig | golden hamster |
|---|---|---|---|---|---|---|---|---|---|
| human | 100% | 94.2% | 94.2% | 71% | 73% | 63.5% | 65.1% | 62.5% | 62.7% |

- *Vs* Skrc-59 engineered cell lines (4 species)
- Effector: target ratio = 10:1

- Mouse > monkey > rat, human
- → All potential models for B7
- → Candidate model for B7-GGGGS3-G36 = cynomolgus monkey

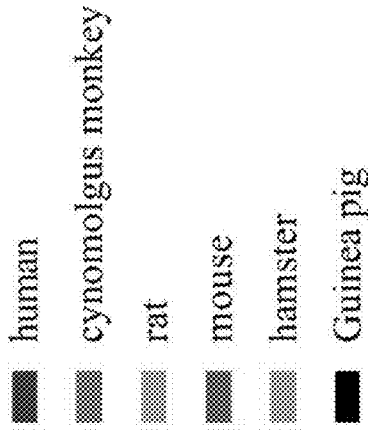
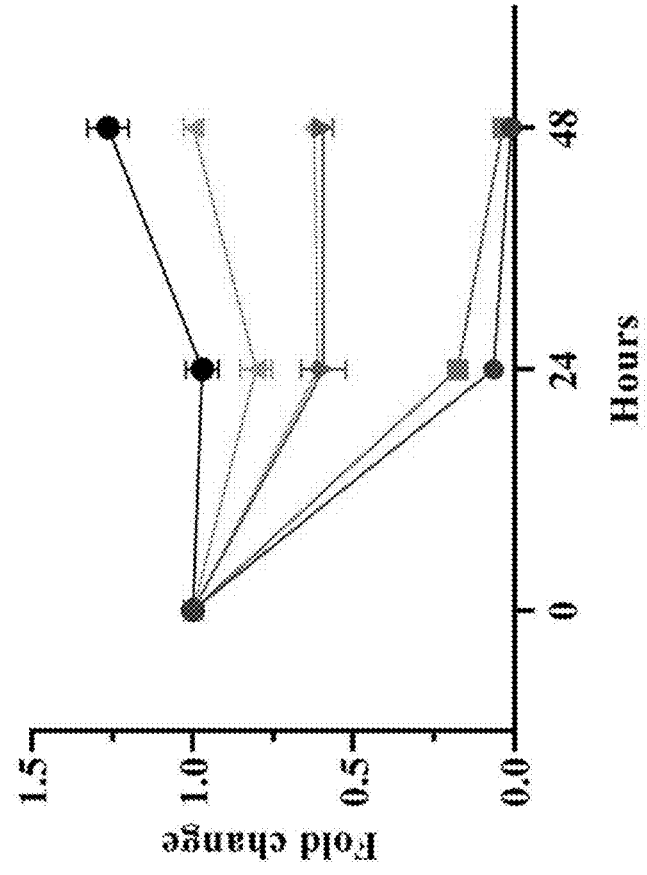
FIG. 68

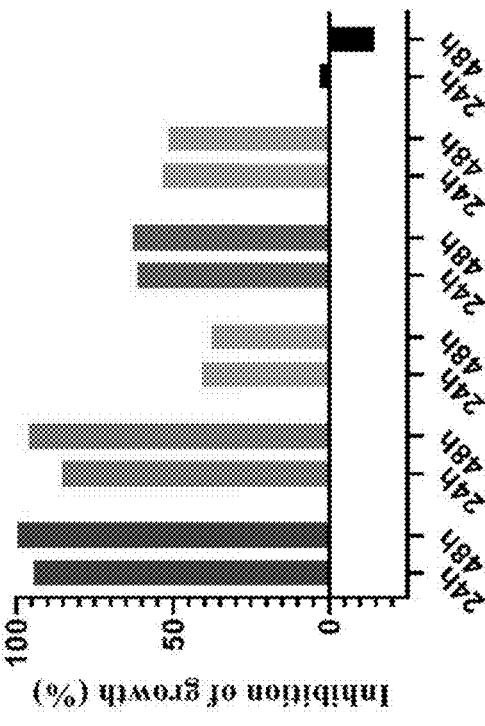
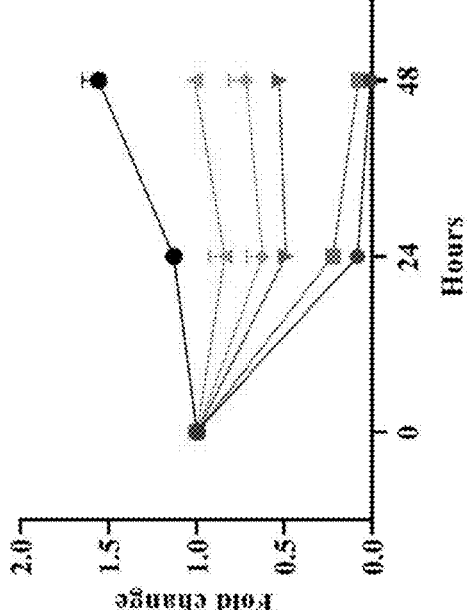
FIG. 69

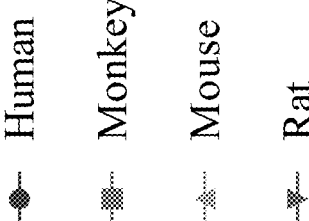
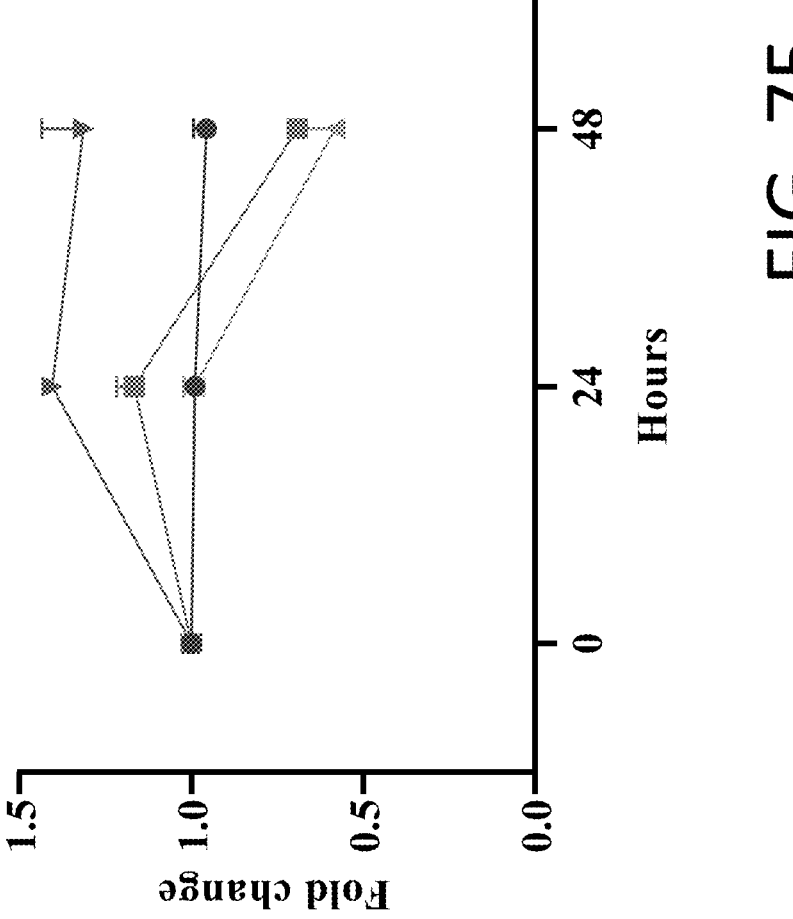
FIG. 75

| HC+LC | FR1-IMGT (1-26) | CDR1-IMGT (27-38) | FR2-IMGT (39-55) | CDR2-IMGT (56-65) | FR3-IMGT (66-104) | CDR3-IMGT |
|---|---|---|---|---|---|---|
| IGHV3-11*05 F | QVQLVESGG.GLVKPGGSLRLSCAAS | GFTF....SDYY | MSWIRQAPGKGLEWVSY | ISSS..SSYT | NYADSVK.GRFTISRDNAKNSLYLQMNSLRAEDTAVYYC | AR |
| B9_H | QVQLVQSGG.GLVKPRGSLRLSCAAS | GFIF....SDYY | MSWIRQAPGKGLQWVAS | IRSR..RGET | NYADSVK.GRFTIARDNAEKSLYLQMNSLRAEDAAVYYC | ARHRKSFTDLDAFDL |
| IGKV1-5*03 F | DIQMTQSPSTLSASVGDRVTITCRAS | QSI......SSW | LAWYQQKPGKAPKLLIY | KA.......S | SLESGVP.SRFSGSG..SGTEFTLTISSLQPDDFATYYC | QQYNSYS |
| B9_L | DIVMTQSPSTLSASVGDRVTITCRAS | QDI......GTD | LSWYQQKPGKAPKLLIY | KA.......S | SLESGVP.SRFSGSG..SGTDFTLTISSLQPDDFATYYC | QHFNWYPAT |
| IGHV3-23*04 F | EVQLVESGG.GLVQPGGSLRLSCAAS | GFTF....SSYA | MSWVRQAPGKGLEWVSA | ISGS..GGST | YYADSVK.GRFTISRDNSKNTLYLQMNSLRAEDTAVYYC | AK |
| B7_H | QVQLVQSGG.GLVQPRGSLRLSCAAS | GFTV....SNYA | MSWVRQAPGKGLEWVAT | KSGS..DGRT | YYADSVK.GRFTIARDNSKNSLYLQMNSLRAEDTAVYYC | AKGIYDVTGSSFDS |
| IGLV6-57*01 F | NFMLTQPHS.VSESPGKTVTISCTRS | SGSI....ASNY | VQWYQQRPGSSPTTVIY | ED.......N | QRPSGVP.DRFSGSIDSSSNSASHTSGLKTEDEADYYC | QSYDSSN |
| B7_L | NFMLTQPHS.VSESPGKTVTISCTRS | SGSI....ASNY | VQWYQQRPGSAPTTVIY | ED.......N | QRPSGVP.DRFSGSIDSSSNSASHTSGLKTEDEADYIC | QSYDSGNRRV |
| IGHV1-69*06 F | QVQLVQSGA.EVKKPGSSVKVSCKAS | GGTF....SSYA | ISWVRQAPGQGLEWMGG | IIPI..FGTA | NYAQKFQ.GRVTITADKSTSTAYMELSSLRSEDTAVYYC | AR |
| B3_H | QVQLVQSGA.EVKKPGSSVKVSCRSS | GGTF....SSQA | FSWVRQAPGQGLEWMGR | IIPF..FGVP | TYAQRFQ.GRVTITADKSPTTAYMELTSLRSDDTAVYYC | AVLKGRGNFDF |
| IGKV4-1*01 F | DIVMTQSPDSLAVSLGERATINCKSS | QSVLYSSNNKNY | LAWYQQKPGQPPKLLIY | WA.......S | TRESGVP.DRFSGSG..SGTDFTLTISSLQAEDVAVYYC | QQYYSTP |
| B3_L | DIVMTQSPDSLAVSLGERATINCKSS | YSVFHSPNNKNY | LAWYQQKPGQPPKLLIY | WA.......S | TRGSGVP.DRFSGSG..SGTDFTLTISSLEPDFAVYYC | QQRSNWPLT |

| | FR1-IMGT (1-26) | CDR1-IMGT (27-38) | FR2-IMGT (39-55) | CDR2-IMGT (56-65) | FR3-IMGT (66-104) | CDR3-IMGT |
|---|---|---|---|---|---|---|
| IGHV3-23*04 F A20_H | EVQLVESGG.GLVQPGGSLRLSCAAS | GFTF....SSYA | MSWVRQAPGKGLEWVSA | ISGS..GGST | YYADSVK.GRFTISRDNSKNTLYLQMNSLRAEDTAVYYC | AK |
| | QVQLVQSGG.GLVQPGGSLRLSCAAS | GFTF....SSYA | MSWVRQAPGKGLEWVSL | ISGS..GGSR | YYADSVK.GRFTISRDNSKNTLYLQMNLRAEDTAVYYC | ARCRGGHGMDV |
| IGLV1-47*01 F A20_L | QSVLTQPPS.ASGTPGQRVTISCSGS | SSNI....GSNY | VTWYQQLPGTAPKLLIY | RN........N | QRPSGVP.DRFSGSK..SGTSASLAISGLRSEDEADYYC | AAWDDSLSG |
| | QPGLTQPPS.ASGTPGQRVTISCSGS | SSNI....GSNY | VTWYQQLPGTAPKLLIY | RN........N | QRPSGVP.DRFSGSK..SGTSASLAISGLQSEDEADYYC | AAWDDSLNGLV |
| IGHV3-23*04 F B5_H | EVQLVESGG.GLVQPGGSLRLSCAAS | GFTF....SSYA | MSWVRQAPGKGLEWVSA | ISGS..GGST | YYADSVK.GRFTISRDNSKNTLYLQMNSLRAEDTAVYYC | AK |
| | QVQLVQSGG.GLVQPGRSLRLSCAAS | GFTV....SNYA | MSWVRQAPGKGLEWVAT | KSGS..DGRT | YYADSVK.GRFTIARDNSKNSLYLQMNSLRAADTAVYYC | AKGIYDVTGSSFDS |
| IGLV3-10*01 F B5_L | SYELTQPPS.VSVSPGQTARITCSGD | ALP......KKY | AYWYQQKSGQAPVLVIY | ED........S | KRPSGIP.ERFSGSS..SGTMATHITSGAQVEDEADYYC | YSTDSSGNH |
| | SYELTQPPS.VSVSPGQTARITCSGD | ALP......KKY | AYWYQQKSGQAPVIVMF | ED........S | KRPSGIP.ERFSGSS..SGTMATHITSGAQVEDEADYYC | YSTDSSGNHKV |
| IGHV3-66*02 F B8_H | EVQLVESGG.GLVQPGGSLRLSCAAS | GFTV....SSNY | MSWVRQAPGKGLEWVSV | IYSG...GST | YYADSVK.GRFTISRDNSKNTLYLQMNSLRAEDTAVYYC | AR |
| | EVQLVESGG.GVVQPGRSLRLSCAAS | GFTV....STSH | MSWVRQAPGKGLEWMLSG | KDSG...GKT | YYADSVR.GRFTIARDDSLNTVFLQMNMRDEDSGVYYC | ARARPSDPYDGSGFDAFDI |
| IGLV10-54*01 F B8_L | QAGLTQPPS.VSKGLRQTATLTCTGN | SNNV....GNQG | AAWLQQHQGHPPRLLSY | RN........N | NRPSGIS.ERLSASR..SGNTASLTITGLQPEDEADYYC | SAWDSSLSA |
| | SYELTQPPS.VSKGLRQTATLTCTGN | SNNV....GNQG | AAWLQQHQGHPPRLLSY | RN........N | NRPSGIS.ERFSASR..SGNTASLTITGLQPEDEADYYC | SAWDSSLSAWV |

FIG. 76B

| HC+LC | | FR1-IMGT (1-26) | CDR1-IMGT (27-38) | FR2-IMGT (39-55) | CDR2-IMGT (56-65) | FR3-IMGT (66-104) | CDR3-IMGT |
|---|---|---|---|---|---|---|---|
| IGHV1-69*06 PDL1_42 | F H | QVQLVQSGA.EVKKPGSSVKVSCKAS QVQLVQSGA.EVKKPGSSVKVSCKAS | GGTF....SSYA GGTF....SSYA | ISWVRQAPGQGLEWMGG ISWVRQAPGQGLEWMGG | II PI..FGTA II PI..FGTA | NYAQKFQ.GRVTITADKSTSTAYMELSSLRSEDTAVYYC NYAQKFQ.GRVTITADKSTSTAYMELSSLRSEDTAVYYC | AR ARGRQMFGAGIDF |
| IGLV6-57*02 PDL1_42 | F L | NFMLTQPHS.VSESPGKTVTISCTGS NFMLTQPHS.VSESPGKTVTISCTRS | SGSI....ASNY SGSI....DSNY | VQWYQQRPGSAPTTVIY VQWYQQRPGSAPTTVIY | ED.......N ED.......N | QRPSGVP.DRFSGSIDSSSNSASHTISGLKTEDEADYYC QRPSGVP.DRFSGSIDSSSNSASHTISGLKTEDEADYYC | QSYDSSN QSYDSNNRHVI |
| IGHV3-9*01 PD1P4B3 | F H | EVQIVESGG.GLVQPGRSLRLSCAAS QVQLVQSGG.GLVQPGRSLRLSCAAS | GFTF....DDYA GFTF....DDFA | MHWVRQAPGKGLEWVSG MHWVRQAPGKGLEWVSG | ISWN..SGSI ISWN..SGSI | GYADSVK.GRFTISRDNAKNSLYLQMNSLRAEDTALYYC GYADSVK.GRFTVSRDNAKNSLYLQMNSLRAEDTAVYYC | AKD ASDYGDKYISYYGMDV |
| IGLV1-44*01 PD1P4B3 | F L | QSVLTQPPS.ASGTPGQRVTISCSGS QPGLTQPPS.ASGTPGQRVTISCSGS | SSNI....GSNT SSNI....GSNT | VNWYQQLPGTAPKLLIY VNWYQQFPGKAPKLLIF | SN.......N DD.......N | QRPSGVP.DRFSGSK.SGTSASLAISGLQSEDEADYYC QRPSGVP.DRFSASK.SGTSASLAISGLQSEDEADYYC | AAWDDSLNG AAWDGGLNGRGV |

| | FR1-IMGT (1-26) | CDR1-IMGT (27-38) | FR2-IMGT (39-55) | CDR2-IMGT (56-65) | FR3-IMGT (66-104) | CDR3-IMGT |
|---|---|---|---|---|---|---|
| IGHV3-23*04 F G17_H | EVQLVESGG.GLVQPGGSLRLSCAAS | GFTF....SSYA | MSWVRQAPGKGLEWVSA | ISGS..GGST | YYADSVK.GRFTISRDNSKNTLYLQMNSLRAEDTAVYYC | AK |
| | QVQLVQSGG.GLVQPGGSLRLSCAAS | GFTF....SSYA | MSWVRQAPGKGLEWVSA | ISGS..GGST | YYADSVK.GRFTISRDNSKNTLYLQMNSLRAEDTAVYYC | ATYGDYGSLDY |
| IGLV1-40*01 F G17_L | QSVLTQPPS.VSGAPGQRVTISCTGS | SSNIG...AGYD | VHWYQQLPGTAPKLLIY | GN......S | NRPSGVP.DRFSGSK..SGTSASLAITGLQAEDEADYYC | QSYDSSLSG |
| | QSVLTQPPS.VSGAPGQRVTISCTGS | SSNIG...AGYD | VHWYQQLPGTAPKLLIY | AN......N | NRPSGVP.DRFSGSK..SGTSASLAITGLQAEDEADYYC | QSYDSSLRAWV |
| IGHV3-30*04 F G28_H | QVQLVESGG.GVVQPGRSLRLSCAAS | GFTF....SSYA | MHWVRQAPGKGLEWVAV | ISYD.GSNK | YYADSVK.GRFTISRDNSKNTLYLQMNSLRAEDTAVYYC | AR |
| | QVTLKESGG.GVVQPGTSLRLSCAAS | GFTF....SNYA | MTWVRQAPGKGLEWVGL | ISYD.GSVT | HYTDSVK.GRFTISRDNAKNSIYLQMNTLRADTAVYYC | ARGSGYQEH |
| IGLV3-21*02 F G28_L | SYVLTQPPS.VSVAPGQTARITCGGN | NIG.....SKS | VHWYQQKPGQAPVLVVY | DD......S | DRPSGIP.ERFSGSN..SGNTATLTISRVEAGDEADYYC | QVWDSSSDH |
| | LPVLTQPPS.VSVAPGQTARITCGGN | NIG.....SKS | VHWYQQKPGQAPVLVIY | YD......S | DRPSGIP.ERFSGSN..SGNTATLTISRVEAGDEADYYC | QVWDSSSDHHVV |

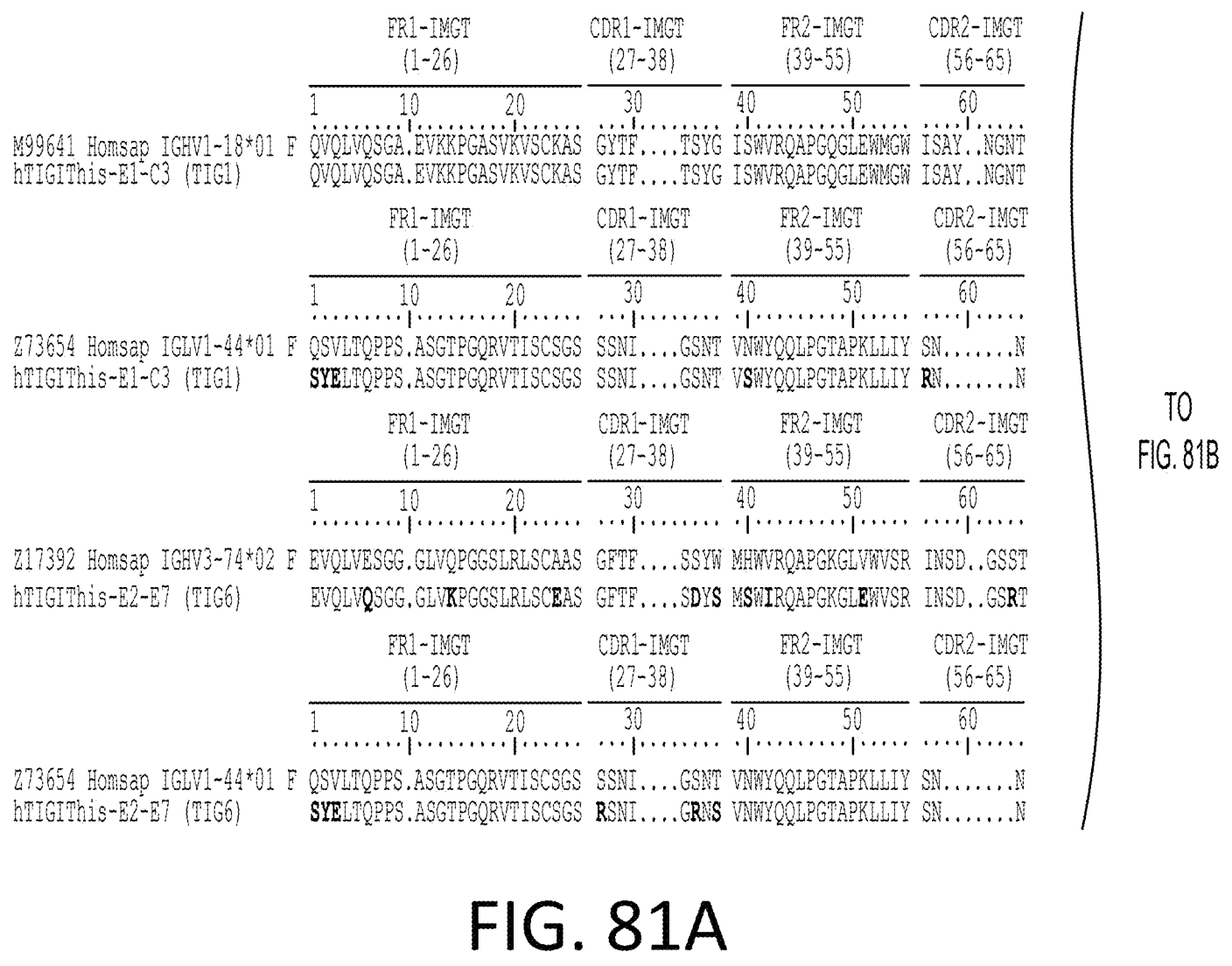

```
                    FR1-IMGT            CDR1-IMGT        FR2-IMGT         CDR2-IMGT
                     (1-26)              (27-38)          (39-55)          (56-65)
                    1       10        20           30          40      50           60
                    ..........|....|  ..........|  ..........|  ..........|  ...|....
M99641 Homsap IGHV1-18*01 F  QVQLVQSGA.EVKKPGASVKVSCKAS  GYTF....TSYG  ISWVRQAPGQGLEWMGW  ISAY..NGNT
hTIGIThis-E1-C3 (TIG1)       QVQLVQSGA.EVKKPGASVKVSCKAS  GYTF....TSYG  ISWVRQAPGQGLEWMGW  ISAY..NGNT 1       10        20           30          40      50           60
                    ..........|....|  ..........|  ..........|  ..........|  ...|....
273654 Homsap IGLV1-44*01 F  QSVLTQPPS.ASGTPGQRVTISCSGS  SSNI....GSNT  VNWYQQLPGTAPKLLIY  SN......N
hTIGIThis-E1-C3 (TIG1)       SYELTQPPS.ASGTPGQRVTISCSGS  SSNI....GSNT  VSWYQQLPGTAPKLLIY  RN......N FR1-IMGT            CDR1-IMGT        FR2-IMGT         CDR2-IMGT
                     (1-26)              (27-38)          (39-55)          (56-65)
                    1       10        20           30          40      50           60
                    ..........|....|  ..........|  ..........|  ..........|  ...|....
217392 Homsap IGHV3-74*02 F  EVQLVESGG.GLVQPGGSLRLSCAAS  GFTF....SSYW  MHWVRQAPGKGLVWVSR  INSD..GSST
hTIGIThis-E2-E7 (TIG6)       EVQLVQSGG.GLVKPGGSLRLSCEAS  GFTF....SDYS  MSWIRQAPGKGLEWVSR  INSD..GSRT FR1-IMGT            CDR1-IMGT        FR2-IMGT         CDR2-IMGT
                     (1-26)              (27-38)          (39-55)          (56-65)
                    1       10        20           30          40      50           60
                    ..........|....|  ..........|  ..........|  ..........|  ...|....
273654 Homsap IGLV1-44*01 F  QSVLTQPPS.ASGTPGQRVTISCSGS  SSNI....GSNT  VNWYQQLPGTAPKLLIY  SN......N
hTIGIThis-E2-E7 (TIG6)       SYELTQPPS.ASGTPGQRVTISCSGS  RSNI....GRNS  VNWYQQLPGTAPKLLIY  SN......N
```

FIG. 81A

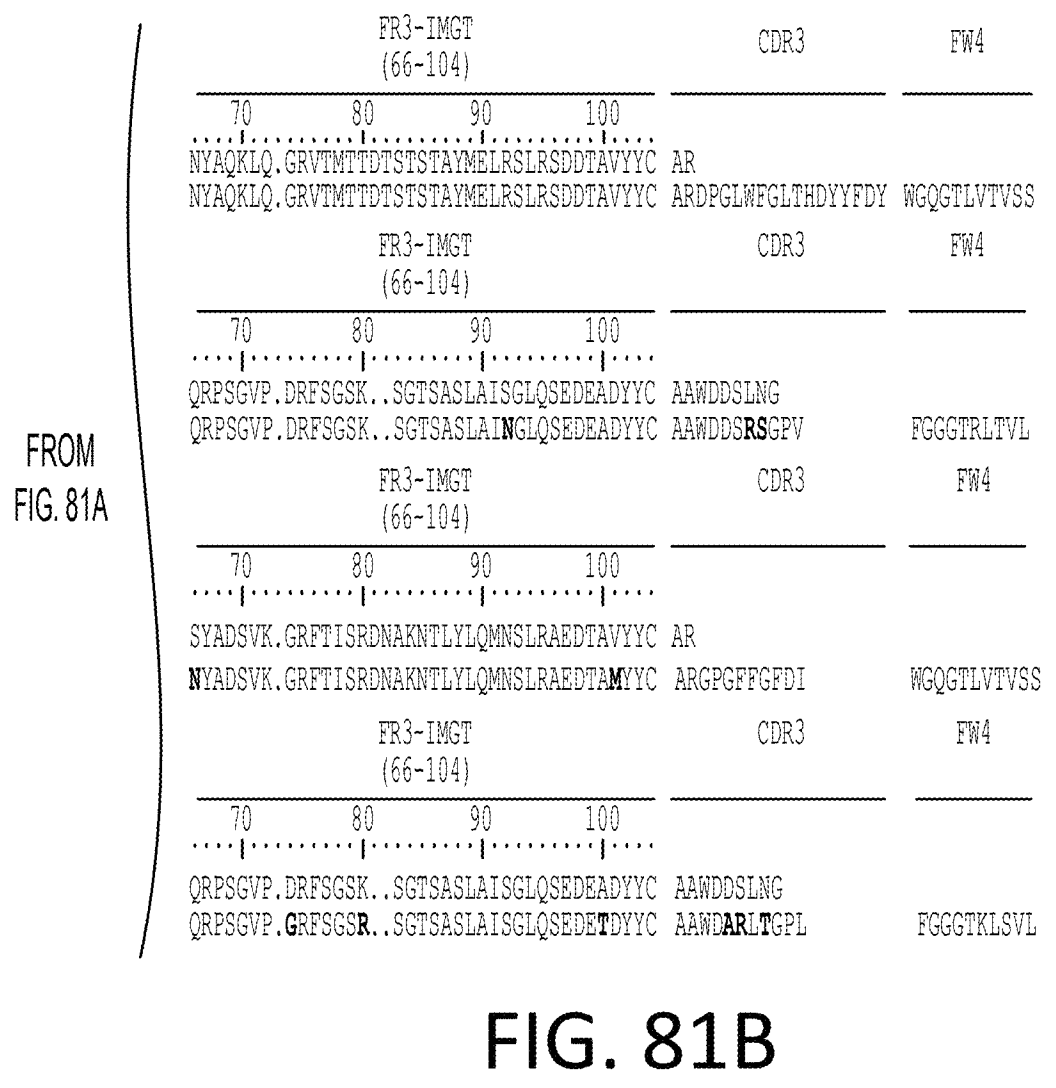

FR3-IMGT
(66-104)                                          CDR3            FW4

70          80          90          100
NYAQKLQ.GRVTMTTDTSTSTAYMELRSLRSDDTAVYYC AR
NYAQKLQ.GRVTMTTDTSTSTAYMELRSLRSDDTAVYYC ARDPGLMFGLHHDYYFDY WGQGTLVTVSS

FR3-IMGT
(66-104)                                          CDR3            FW4

70          80          90          100
QRPSGVP.DRFSGSK..SGTSASLAISGLQSEDEADYYC AAWDDSLNG
QRPSGVP.DRFSGSK..SGTSASLAINGLQSEDEADYYC AAWDDSRSGPV FGGGTRLTVL

FR3-IMGT
(66-104)                                          CDR3            FW4

70          80          90          100
SYADSVK.GRFTISRDNAKNTLYLQMNSLRAEDTAVYYC AR
NYADSVK.GRFTISRDNAKNTLYLQMNSLRAEDTAMYYC ARGPGFGFDI WGQGTLVTVSS

FR3-IMGT
(66-104)                                          CDR3            FW4

70          80          90          100
QRPSGVP.DRFSGSK..SGTSASLAISGLQSEDEADYYC AAWDDSLNG
QRPSGVP.GRFSGSR..SGTSASLAISGLQSEDEDTDYYC AAWDARLTGPL FGGGTKLSVL

FROM
FIG. 81A

FIG. 81B

Figure 81C:
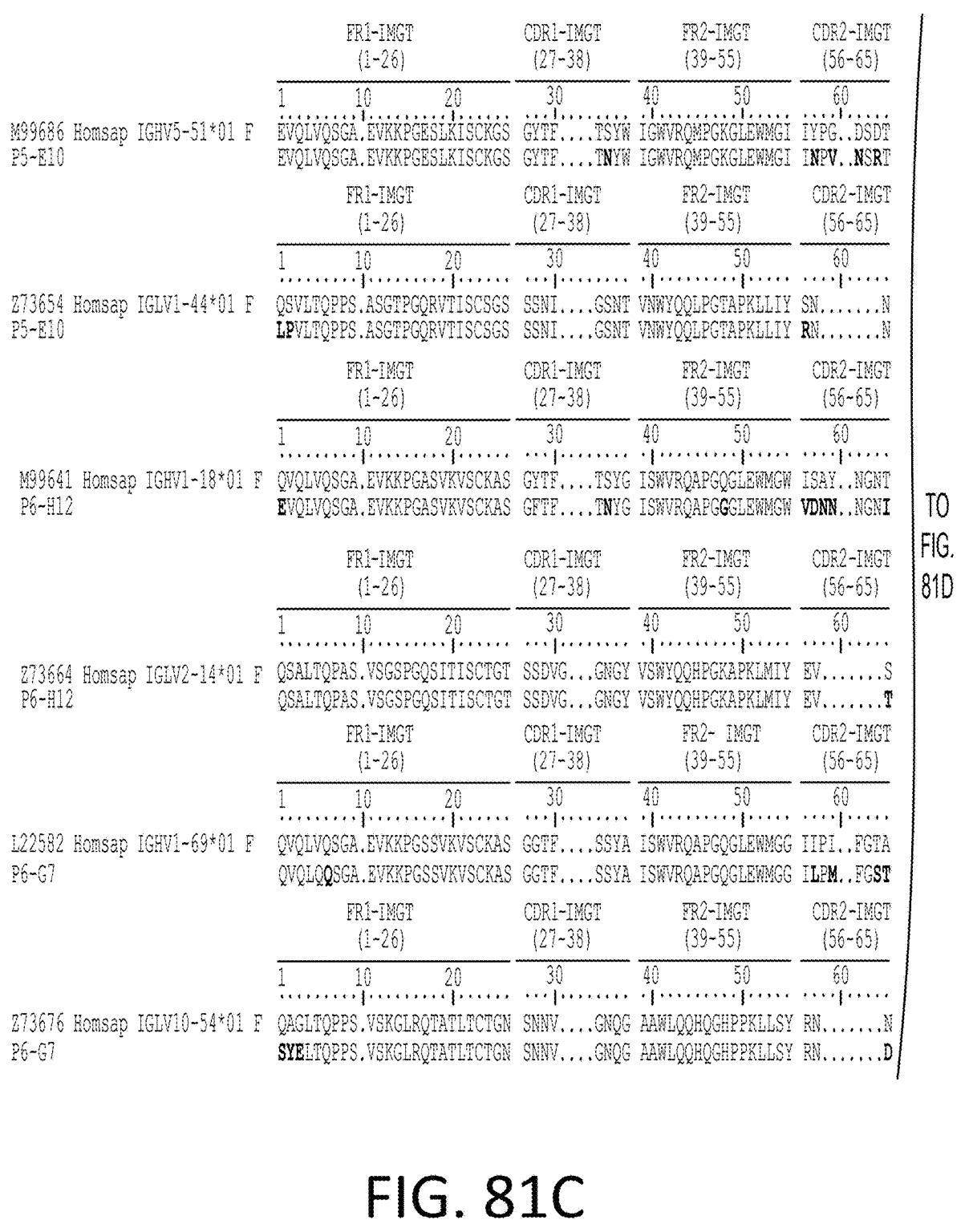

```
                              FR1-IMGT          CDR1-IMGT        FR2-IMGT         CDR2-IMGT
                               (1-26)            (27-38)         (39-55)          (56-65)

1      10    20         30         40       50          60
                          ....|....|....|....    ...|....... .|.......|.... ....|....
M99686 Homsap IGHV5-51*01 F  EVQLVQSGA.EVKKPGESLKISCKGS GYTF....TSYW IGWVRQMPGKGLEWMGI IYPG..DSDT
P5-E10                       EVQLVQSGA.EVKKPGESLKISCKGS GYTF....TNYW IGWVRQMPGKGLEWMGI INPV..NSRT FR1-IMGT          CDR1-IMGT        FR2-IMGT         CDR2-IMGT
                               (1-26)            (27-38)         (39-55)          (56-65)

1      10    20         30         40       50          60
                          ........|....|....|....   ...|....... .|.......|.... ....|....
Z73654 Homsap IGLV1-44*01 F  QSVLTQPPS.ASGTPGQRVTISCSGS SSNI....GSNT VNWYQQLPGTAPKLLIY SN.......N
P5-E10                       LPVLTQPPS.ASGTPGQRVTISCSGS SSNI....GSNT VNWYQQLPGTAPKLLIY RN.......N FR1-IMGT          CDR1-IMGT        FR2-IMGT         CDR2-IMGT
                               (1-26)            (27-38)         (39-55)          (56-65)

1      10    20         30         40       50          60
                          ........|....|....|....   ...|....... .|.......|.... ....|....
M99641 Homsap IGHV1-18*01 F  QVQLVQSGA.EVKKPGASVKVSCKAS GYTF....TSYG ISWVRQAPGQGLEWMGW ISAY..NGNT
P6-H12                       EVQLVQSGA.EVKKPGASVKVSCKAS GFTF....TNYG ISWVRQAPGGGLEWMGW VDNN..NGNI FR1-IMGT          CDR1-IMGT        FR2-IMGT         CDR2-IMGT
                               (1-26)            (27-38)         (39-55)          (56-65)

1      10    20         30         40       50          60
                          ........|....|....|....   ...|....... .|.......|.... ....|....
Z73664 Homsap IGLV2-14*01 F  QSALTQPAS.VSGSPGQSITISCTGT SSDVG...GNGY VSWYQQHPGKAPKLMIY EV.......S
P6-H12                       QSALTQPAS.VSGSPGQSITISCTGT SSDVG...GNGY VSWYQQHPGKAPKLMIY EV.......T FR1-IMGT          CDR1-IMGT        FR2- IMGT        CDR2-IMGT
                               (1-26)            (27-38)         (39-55)          (56-65)

1      10    20         30         40       50          60
                          ........|....|....|....   ...|....... .|.......|.... ....|....
L22582 Homsap IGHV1-69*01 F  QVQLVQSGA.EVKKPGSSVKVSCKAS GGTF....SSYA ISWVRQAPGQGLEWMGG IIPI..FGTA
P6-G7                        QVQLQQSGA.EVKKPGSSVKVSCKAS GGTF....SSYA ISWVRQAPGQGLEWMGG ILPM..FGST FR1-IMGT          CDR1-IMGT        FR2-IMGT         CDR2-IMGT
                               (1-26)            (27-38)         (39-55)          (56-65)

1      10    20         30         40       50          60
                          ........|....|....|....   ...|....... .|.......|.... ...|....
Z73676 Homsap IGLV10-54*01 F QAGLTQPPS.VSKGLRQTATLTCTGN SNNV....GNQG AAWLQQHQGHPPKLLSY RN.......N
P6-G7                        SYELTQPPS.VSKGLRQTATLTCTGN SNNV....GNQG AAWLQQHQGHPPKLLSY RN.......D
```

```
                              FR3-IMGT                          CDR3              FW4
                              (66-104)

70        80        90       100
                  ....|.........|.........|.........|....
                  RYSPSFQ.GQVTISADKSISTAYLQWSSLKASDTAMYYC AR
                  IYSPSFQ.GQVTISVDKSVTTAYLQWSSLKASDTAMYYC ARYYYYAMEV        WGRGTLVTVSS

FR3-IMGT                          CDR3              FW4
                              (66-104)

70        80        90       100
                  ....|.........|.........|.........|....
                  QRPSGVP.DRFSGSK..SGTSASLAISGLQSEDEADYYC AAWDDSLNG
                  QRPSGVP.DRFSGST..SGTSASLAISGLQSEDEADYYC EAWDDSLNGPV       FGGGTKLTVL

FR3-IMGT                          CDR3              FW4
                              (66-104)

70        80        90       100
                  ....|.........|.........|.........|....
                  NYAQKLQ.GRVTMTTDTSTSTAYMELRSLRSDDTAVYYC AR
                  NYAQKFL.GRVTMTTDTSTSTAYMELRSLRSDDTAVYYC ARGLFSSRWYLWFDP    WGQGTLVTVSS

FR3-IMGT                          CDR3              FW4
                              (66-104)

70        80        90       100
                  ....|.........|.........|.........|....
                  NRPSGVS.NRFSGSK..SGNTASLTISGLQAEDEADYYC SSYTSSSTL
                  ERPSGVS.NRFSGSK..SGNTASLTISGLQAEDEGDYYC SSYTRSSTSYVV      FGGGTKVTVL

FR3-IMGT                          CDR3              FW4
                              (66-104)

70        80        90       100
                  ....|.........|.........|.........|....
                  NYAQKFQ.GRVTITADESTSTAYMELSSLRSEDTAVYYC AR
                  NYAQKFQ.GRLTLIADESTRTVYLELNSLTSEDTAVYYC ARGRDIVAPSNSGFDV   WGQGTTVTVSS

FR3-IMGT                          CDR3              FW4
                              (66-104)

70        80        90       100
                  ....|.........|.........|.........|....
                  NRPSGIS.ERLSASR..SGNTASLTITGLQPEDEADYYC SAWDSSLSA
                  NRPSGIS.ERFSASR..SGNTASLTISGLQPEDEADYYC SAYDRSLNAWV       FGGGTKLTVL
```

FROM
FIG. 81C

FIG. 81D

| Sequence ID | V-GENE and allele | J-GENE and allele | D-GENE and allele | FR1-IMGT | CDR1-IMGT |
|---|---|---|---|---|---|
| hTIGIThis-E1-C3 (TIG1) | HV1-18*01 F | HJ4*02 F | HD3-10*01 F | QVQLVQSGA.EVKKPGASVKVSCKAS | GYTF....TSYG |
| hTIGIThis-E2-E7 (TIG6) | HV3-74*02 F | HJ3*02 F | HD3-9*01 F | EVQLVQSGG.GLVKPGGSLRLSCEAS | GFTF....SDYS |
| P5-E10 | HV5-51*01 F | HJ6*02 F | | EVQLVQSGA.EVKKPGESLKISCKGS | GYSF....TNYW |
| P6-H12 | HV1-18*01 F | HJ5*02 F | HD6-13*01 F | EVQLVQSGA.EVKKPGASVKVSCKAS | GYTF....TNYG |
| P6-G7 | HV1-69*01 F | HJ6*02 F | HD5-12*01 F | QVQLQQSGA.EVKKPGSSVKVSCKAS | GGTF....SSYA |

| Sequence ID | V-GENE and allele | J-GENE and allele | D-GENE and allele | FR1-IMGT | CDR1-IMGT |
|---|---|---|---|---|---|
| hTIGIThis-E1-C3 (TIG1) | LV1-44*01 F | LJ3*02 F | | SYELTQPPS.ASGTPGQRVTISCSGS | SSNI....GSNT |
| hTIGIThis-E2-E7 (TIG6) | LV1-44*01 F | LJ2*01 F | | SYELTQPPS.ASGTPGQRVTISCSGS | RSNI....GRNS |
| P5-E10 | LV1-44*01 F | LJ3*02 F | | LPVLTQPPS.ASGTPGQRVTISCSGS | SSNI....GSNT |
| P6-H12 | LV1-14*01 F | LJ2*01 F | | QSALTQPAS.VSGSPGQSITISCTGT | SSDVG...GYNY |
| P6-G7 | LV1-54*01 F | LJ3*02 F | | SYELTQPPS.VSKGLRQTATLTCTGN | SNNV....GNQG |

| FR2-IMGT | CDR2-IMGT | FR3-IMGT | CDR3-IMGT | FR4-IMGT |
|---|---|---|---|---|
| ISWVRQAPGQGLEWMGW | ISAY..NGNT | NYAQKLQ.GRVTMTTDTSTSTAYMELRSLRSDDTAVYYC | ARDPGLWFGLTHDYYFDY | WGQGTLVTVSS |
| MSWIRQAPGKGLEWVSR | INSD..GSRT | NYADSVK.GRFTISRDNAKNTLYLQMNSLRAEDTAMYYC | ARGPGFFGFDI | WGQGTLVTVSS |
| IGWVRQMPGKGLEWMGI | INPV..NSRT | IYSPSFQ.GQVTISVDKSVTTAYLQWSSLKASDTAMYYC | ARYYYYAMEV | WGRGTLVTVSS |
| ISWVRQAPGGGLEWMGW | VDNN..NGNI | NYAQKFL.GRVTMTTDTSTSTAYMELRSLRSDDTAVYYC | ARGLFSSRWYLWFDP | WGQGTLVTVSS |
| ISWVRQAPGQGLEWMGG | ILPM..FGST | NYAQKFQ.GRLTLIADESTRTVYLELNSLTSEDTAVYYC | ARGRDIVAPSNSGFDV | WGQGTLVTVSS |

| FR2-IMGT | CDR2-IMGT | FR3-IMGT | CDR3-IMGT | FR4-IMGT |
|---|---|---|---|---|
| VSWYQQLPGTAPKLLIY | RN.......N | QRPSGVP.DRFSGSK..SGTSASLAINGLQSEDEADYYC | AAWDDSRSGPV | FGGGTRLTVL |
| VNWYQQLPGTAPKLLIY | SN.......N | QRPSGVP.GRFSGSR..SGTSASLAISGLQSEDETDYYC | AAWDARLTGPL | FGGGTKLSVL |
| VNWYQQLPGTAPKLLIY | RN.......N | QRPSGVP.DRFSGST..SGTSASLAISGLQSEDEADYYC | EAWDDSLNGPV | FGGGTKLTVL |
| VSWYQQHPGKAPKLMIY | EV.......T | ERPSGVS.NRFSGSK..SGNTASLTISGLQAEDEGDYYC | SSYTRSSTSYVV | FGGGTKVTVL |
| AAWLQQHQGHPPKLLSY | RN.......D | NRPSGIS.ERFSASR..SGNTASLTISGLQPEDEADYYC | SAYDRSLNAWV | FGGGTKLTVL |

FROM FIG. 81E

FIG. 81F

The anti-PD-L1 amino acid sequences

VH

| Sequence ID | FR1 | CDR1 | FR2 | CDR2 | FR3 | CDR3 | FR4 |
|---|---|---|---|---|---|---|---|
| 40 mut | QVQLVQSGAEVKKPGSSVKVSCKAS | GGTFSSYA | ISWVRQAPGQGLEWMGG | IIPIFGTA | NYAQKFQGRVTITADKSTSTAYMELSSLRSEDTAVYYC | ARGRQMFGAGIDF | WGPGTLVTVSS |
| 50-6B6.1 mut | QVQLVQSGGGEVKKPGASVKVSCKAS | GYTLSSHG | ITWVRQAPGQGLEWMGW | ISAHNGHA | SNAQKVEDRVTMTTDTSTNTAYMELRSLTADDTAVYYC | ARVHAALYYGMDV | WGQGTLVTVSS |
| 50-6B6.2 | QVQLVQSGGGEVKKPGASVKVSCKAS | GYTLSSHG | ITWVRQAPGQGLEWMGW | ISAHNGHA | SNAQKVEDRVTMTTDTSTNTAYMELRSLTADDTAVYYC | ARVHAALYYGMDV | WGQGTLVTVSS |
| 50-7B3 | QVQLVQSGGGEVKKPGASVKVSCKAS | GYTLSSHG | ITWVRQAPGQGLEWMGW | ISAHNGHA | SNAQKVEDRVTMTTDTSTNTAYMELRSLTADDTAVYYC | ARVHAALYYGMDV | WGQGTLVTVSS |
| 50-5B9 | QVQLVQSGGGEVKKPGASVKVSCKAS | GYTLSSHG | ITWVRQAPGQGLEWMGW | ISAHNGHA | SNAQKVEDRVTMTTDTSTNTAYMELRSLTADDTAVYYC | ARVHAALYYGMDV | WGQGTLVTVSS |

VL

| Sequence ID | FR1 | CDR1 | FR2 | CDR2 | FR3 | CDR3 | FR4 |
|---|---|---|---|---|---|---|---|
| 40 mut | NFMLTQPHSVSESPGKTVTISCTRS | SGSIDSNY | VQWYQQRPGSAPTTVIY | EDN | QRPSGVPDRFSGSIDSSSNSASLTISGLKTEDEADYYC | QSYDSNNRHVI | FGGGTKLTVL |
| 50-6B6.1 mut | SYELTQPPSVSLAPGQSARISCGGD | NIGSKG | VHWYQQKPGQAPVVVVY | DDR | DRPSGIPERFSGSNSGNTATLTISRVEAGDEADYYC | QVWDSGSDHWV | FGGGTKLTVL |
| 50-6B6.2 | LPVLTQPPSVSAAPGQTARISCGGS | NIGDKG | VHWYQQKPGQAPVLVIY | DDS | DRPSGIPERFSGSNSGNTATLTISRVEAGDEADYYC | QVWDSSSDHWV | FGGGTKLTVL |
| 50-7B3 | SYELTQPPSVSVAPGQTARITCGGN | NIGNKG | VHWYQQKPGQAPVLVVY | DDS | DRPSGIPERFSGSNSGNTATLTISRVEAGDEADYYC | QVWDSSSDHWV | FGGGTKLTVL |
| 50-5B9 | LPVLTQPPSVSVALGQTARITCRGN | NIGGKG | VHWYQQKPGQAPVLVVY | DDY | SRRSGIPERFSGSHSGSAATLTISRVEAGDEADYYC | QVWDSSSDHWV | FGGGTKLTVL |

FIG. 82

Ab P4-B3 Variable Region nucleic acid sequences

V<sub>H</sub> chain of Ab P4-B3 VH (IGHV3-9*01)

```
CAGGTGCAGCTGGTGCAGTCTGGGGGAGGCTTGGTACAGCCTGGCAGGTCCCTGAGAC
TCTCCTGTGCAGCCTCTGGATTCACCTTTGATGATTATGCCATGCACTGGGTCCGGCAAG
CTCCAGGGAAGGGCCTGGAGTGGGTCTCAGGTATTAGTTGGAATAGTGGTAGCATAGG
CTATGCGGACTCTGTGAAGGGCCGATTCACCGTCTCCAGAGACAACGCCAAGAACTCA
CTGTATCTGCAAATGAACAGCCTGAGAGCCGAGGACACGGCTGTGTATTACTGTGCGA
GTGACTACGGTGACAAATACTACTACGGTATGGACGTCTGGGGCAAAGGGACCAC
GGTCACCGTCTCCTCA
```

V<sub>L</sub> chain of Ab P4-B3 VL (IGLV1-44*01)

```
CAGCCTGGGCTGACTCAGCCACCCTCAGCGTCTGGGACCCCCGGGCAGAGGGTCACCA
TCTCTTGTTCTGGAAGCAGCTCCAACATCGGAAGTAATACTGTCAACTGGTATCAGCAA
TTCCCCGGAAAGGCCCCCAAACTCCTCATCTTTAATGATAATCAGCGGCCCTCAGGGGT
CCCTGACCGCTTCTCTGCTTCCAAGTCTGGCACCTCAGCCTCCCTGGCCATTAGTGGCCT
CCAGTCTGAGGATGAGGCTGACTATTACTGTGCGGCATGGGATGGCGGTCTGAATGGTC
GAGGGGTGTTCGGCGGAGGGACCAAACTGACCGTCCTA
```

Ab P4-B3 Variable Region amino acid sequences

V<sub>H</sub> chain of Ab P4-B3 VH (IGHV3-9*01)

```
QVQLVQSGGGLVQPGRSLRLSCAASGFTFDDYAMHWVRQAPGKGLEWVSGISWNSGSIGY
ADSVKGRFTVSRDNAKNSLYLQMNSLRAEDTAVYYCASDYGDKYYYYGMDVWGKGTTV
TVSS
```

V<sub>L</sub> chain of Ab P4-B3 VL (IGLV1-44*01)

```
QPGLTQPPSASGTPGQRVTISCSGSSSNIGSNTVNWYQQFPGKAPKLLIFNDNQRPSGVPDRF
SASKSGTSASLAISGLQSEDEADYYCAAWDGGLNGRGVFGGGTKLTVL
```

FIG. 83A

Ab P4-B3 Constant Region nucleic acid sequences – wild type IgG1 monomer

CH1

ACCAAGGGCCCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAA

Hinge

GCAGAGCCCAAATCTTGTGACAAAACTCACACATGCCCACCGTGCCCA

CH2

GCACCTGAACTCCTGGGGGGACCGTCAGTCTTCCTCTTCCCCCCAAAACCCAAGGACAC
CCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACCGTC
CTGCACCAGGACTGGCTGAATGGCAAGGAGTACAAGTGCAAGGTCTCCAACAAAGCCC
TCCCAGCCCCCATCGAGAAAACCATCTCCAAAGCCAAA

CH3

GGGCAGCCCCGAGAACCACAGGTGTACACCCTGCCCCCATCCCGGGATGAGCTGACCA
AGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAG

FIG. 83B

CAGGGGAACGTCTTCTCATGCTCCGTGATGCATGAGGCTCTGCACAACCACTACACGCA
GAAGAGCCTCTCCCTGTCTCCGGGTAAATGA

CL
GGTCAGCCCAAGGCTGCCCCCTCGGTCACTCTGTTCCCGCCCTCCTCTGAGGAGCTTCA
AGCCAACAAGGCCACACTGGTGTGTCTCATAAGTGACTTCTACCCGGGAGCCGTGACA
GTGGCCTGGAAGGCAGATGGCAGCCCCGTCAAGGCGGGAGTGGAGACCACCACACCCT
CCAAACAAAGCAACAACAAGTACGCGGCCAGCAGCTATCTGAGCCTGACGCCTGAGCA
GTGGAAGTCCCACAGAAGCTACAGCTGCCAGGTCACGCATGAAGGGAGCACCGTGGAG
AAGACAGTGGCCCCTACAGAATGTTCATGA

| Ab P4-B3 Constant Region amino acid sequences – wild type IgG1 monomer |
|---|

CH1
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKK

Hinge
AEPKSCDKTHTCPPCP

CH2
APELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK

CH3
GQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

CL
GQPKAAPSVTLFPPSSEELQANKATLVCLISDFYPGAVTVAWKADGSPVKAGVETTTPSKQ
SNNKYAASSYLSLTPEQWKSHRSYSCQVTHEGSTVEKTVAPTECS

FIG. 83C

| Ab P4-B7 Variable Region nucleic acid sequences |
| --- |
| V$_H$ chain of Ab P4-B7 VH (IGHV5-51*01) |
| CAGGTGCAGCTGGTGCAGTCTGGAGCAGAGGTGAAGAAGCCCGGGGAGTCTCTGAAGA<br>TCTCCTGTAAGGATTCTGGATACACCTTTACCACCTACTGGATCGGCTGGGTGCGCCAG<br>CTGCCCGGGAAAGGCCTGGAGTTGATGGGGATCATCTATCCTGATGACTCTGATACCAC<br>ATACAGCCCGTCCTTCCAAGGCCATGTCACCATCTCAGCCGACAAGTCCATCAACACCG<br>CCTACCTGCAGTGGAGCAGCCTGAAGGCCTCGGACACCGCCATGTATTACTGTGCGTTT<br>TGGGGTGCGAGTGGAGCGCCAGTGAATGGTTTTGATATCTGGGGCCAAGGCACCCTGG<br>TCACCGTCTCCTCA |
| V$_L$ chain of Ab P4-B7 VL (IGLV1-44*01) |
| CTGCCTGTGCTGACTCAGCCACCCTCAGCGTCTGGGACCCCCGGGCAGAGGGTCACCAT<br>CTCCTGCACTGGGAGCAGCTCCAACATCGGGGCAGGTTATGTTGTACACTGGTACCAGC<br>AGCTCCCAGGAACGGCCCCCAAACTCCTCATCTATAGTAATAATCAGCGGCCCTCAGGG<br>GTCCCTGACCGATTCTCTGGCTCCAAGTCTGGCACCTCAGCCTCCCTGGCCATCAGTGG<br>GCTCCAGTCTGAGGATGAGGCTGATTATTACTGTGCAGCATGGGATGACAGCCTGAATG<br>CTCCGGTGTTCGGCGGAGGGACCAAGCTGACCGTCCTA |

| Ab P4-B7 Variable Region amino acid sequences |
| --- |
| V$_H$ chain of Ab P4-B7 VH (IGHV5-51*01) |

FIG. 83D

QVQLVQSGAEVKKPGESLKISCKDSGYTFTTYWIGWVRQLPGKGLELMGIIYPDDSDTTYS
PSFQGHVTISADKSINTAYLQWSSLKASDTAMYYCAFWGASGAPVNGFDIWGQGTLVTVS
S

---

V_L chain of Ab P4-B7 VL (IGLV1-44*01)

LPVLTQPPSASGTPGQRVTISCTGSSSNIGAGYVVHWYQQLPGTAPKLLIYSNNQRPSGVPD
RFSGSKSGTSASLAISGLQSEDEADYYCAAWDDSLNAPVFGGGTKLTVLL

---

PD1#2 Variable Region nucleic acid sequences

V_H chain of Ab PD1#2 VH (IGHV4-61*01)

CAGGTACAGCTGCAGCAGTCAGGCCCAGGACTGGTGAGGCCTTCGGCGACCCTGTCCCT
CACCTGCACTGTCTCTGGTGACTCCGTCAGCAGTGATAATTACTTCTGGAGTTGGATTCG
GCAGCCCCCAGGGAAGCCACTGGAGTGGATTGGCTATGTCTATTACAATGGGAACACC
AACTACAACCCCTCCTTCAACAGTCGAGTCACCATGTCACTTGACACGTCCAAGAACCA
GTTCTCCTTGAAGCTGAGGTCTGTGACCGCCGCGGACACGGCCTTTTATTACTGTGCGA
CAGAGACGCCCCCAACCAGCTATTTTAATAGTGGACCCTTTGACTCCTGGGGCCAGGGC
ACCCTGGTCACCGTCTCCTCG

---

V_L chain of Ab PD1#2 VL (IGLV10-54*01)

CAGCCTGGGCTGACTCAGCCACCCTCGGTGTCCAAGGGCTTGAGACAGACCGCCACACT
CACCTGCACTGGGAGCAGCAACAATGTAGGCGCCCACGGAGCAGCTTGGCTGCAGCAG
CACCAGGGCCACCCTCCCAAACTCCTTGCCTACAGGAATAACAACCGGCCCTCAGGGAT
CTCAGAGAGATTCTCTGCATCCAGGTCAGGAAACACAGCCTCCCTGACCATTATTGGAC
TCCAGCCTGAGGACGAGGGTGACTATTACTGCTCATCATGGGACAGCAGCCTCAGTGGT
TATGTCTTCGGAACCTGGGACCAAAGTCACCGTCCTA

---

Ab PD1#2 Variable Region amino acid sequences

V_H chain of Ab PD1#2 VH (IGHV4-61*01)

QVQLQQSGPGLVRPSATLSLTCTVSGDSVSSDNYFWSWIRQPPGKPLEWIGYVYYNGNTNY
NPSFNSRVTMSLDTSKNQFSLKLRSVTAADTAFYYCATETPPTSYFNSGPFDSWGQGTLVT
VSS

---

V_L chain of Ab PD1#2 VL (IGLV10-54*01)

QPGLTQPPSVSKGLRQTATLTCTGSSNNVGAHGAAWLQQHQGHPPKLLAYRNNNRPSGISE
RFSASRSGNTASLTIIGLQPEDEGDYYCSSWDSSLSGYVFGPGTKVTVL

FIG. 83E

| PD1#3 Variable Region nucleic acid sequences |
|---|
| V_H chain of Ab PD1#3 VH (IGHV1-18*01) |
| CAGGTGCAGCTGGTGCAGTCTGGGGCTGAGGTGAAGAAGCCTGGGTCCTCAGTGAAGG<br>TCTCCTGCAAGACTTCTGGCTACACCTTTAACAGGTTTGGTCTCACCTGGGTGCGACAG<br>GCCCCTGGACAAGGGCTTGAGTGGATGGGATGGACCAACCCTTACAATGGTAACACAA<br>GGTATGCACAGAAGTTCCAGGGCAGAGTCACCATGACCACAGACACATCCACGAGCAC<br>AGCCTACATGGAGCTGAGGAGCCTGAGATCTGACGACACGGCCATGTATTTCTGTGCGA<br>GAGTCGTAGCCGTAAACGGTATGGACGTCTGGGGCCAAGGGACCACGGTCACCGTCTC<br>CTCA |
|  |
| V_L chain of Ab PD1#3 VL (IGLV6-57*01) |
| AATTTTATGCTGACTCAGCCCCACTCTGTGTCGGAGTCTCCGGGGAAGACGGTTACCAT |

FIG. 83F

CTCCTGCACCCGCAACAGTGGCAGCATTGCCGCCTACTATGTGCAGTGGTACCAGCAGC
GCCCGGGCAGTTCCCCCACCACTGTGATCTATGAAGATAACCAAAGACCCTCTGGGGTC
CCTGATCGGTTCTCTGGCTCCATCGACAGCTCCTCCAACTCTGCCTCCCTCACCATCTCT
GGACTGAAGACTGAGGACGAGGCTGACTACTACTGTCAGTCTTATGATAGCAGCAATCT
TTGGGTGTTCGGCGGAGGGACCAAGCTGACCGTCCTA

Ab PD1#3 Variable Region amino acid sequences

V$_H$ chain of Ab PD1#3 VH (IGHV1-18*01)

QVQLVQSGAEVKKPGSSVKVSCKTSGYTFNRFGLTWVRQAPGQGLEWMGWTNPYNGNT
RYAQKFQGRVTMTTDTSTSTAYMELRSLRSDDTAMYFCARVVAVNGMDVWGQGTTVTV
SS

V$_L$ chain of Ab PD1#3 VL (IGLV6-57*01)

NFMLTQPHSVSESPGKTVTISCTRNSGSIAAYYVQWYQQRPGSSPTTVIYEDNQRPSGVPDR
FSGSIDSSSNSASLTISGLKTEDEADYYCQSYDSSNLWVFGGGTKLTVL

Ab PD1#13 Variable Region nucleic acid sequences

V$_H$ chain of Ab PD1#13 VH (IGHV3-30*01)

GAGGTGCAGCTGGTGCAGTCTGGGGGAGGCGTGGTCCAGCCTGGGAGGTCCCTGAGAC
TCTCCTGTGCAGCCTCTGGATTCACCTTCAGTAGCTATGCTATGCACTGGGTCCGCCAGG
CTCCAGGCAAGGGGCTGGAGTGGGTGGCAGTTATATCATATGATGGAAGCAATAAATA
CTACGCAGACTCCGTGAAGGGCCGATTCACCATCTCCAGAGACAATTCCAAGAACACG
CTGTATCTGCAAATGAACAGCCTGAGAGCTGAGGACACGGCTGTGTATTACTGTGCGAG
CCAAACAGTGGCTGGAAGTGACTACTGGGGCCAGGGCACCCTGGTCACCGTCTCCTCA

V$_L$ chain of Ab PD1#13 VL (IGLV1-44*01)

CAGCCTGGGCTGACTCAGCCACCCTCGGTGCCAGTGGCCCCAGGACAGACGGCCAGGA
TTACCTGTGGGGGAAACAACATTGGAAGTAAAAGTGTGCACTGGTACCAGCAGAAGCC
AGGCCAGGCCCCTGTGCTGGTCGTCTATGATGATAGCGACCGGCCCTCAGGGATCCCTG
AGCGATTCTCTGGCTCCAACTCTGGGAACACGGCCACCCTGACCATCAGCAGGGTCGAA
GCCGGGGATGAGGCCGACTATTACTGTCAGGTGTGGCATAGTGTTAGTGATCAAGGGG
TCTTCGGAACTGGGACCAAAGTCACCGTCCTA

FIG. 83G

| Ab PD1#13 Variable Region amino acid sequences |
| --- |
| V$_H$ chain of Ab PD1#13 VH (IGHV3-30*01) |
| EVQLVQSGGGVVQPGRSLRLSCAASGFTFSSYAMHWVRQAPGKGLEWVAVISYDGSNKY<br>YADSVKGRFTISRDNSKNTLYLQMNSLRAEDTAVYYCASQTVAGSDYWGQGTLVTVSS |
| |
| V$_L$ chain of Ab PD1#13 VL (IGLV1-44*01) |
| QPGLTQPPSVPVAPGQTARITCGGNNIGSKSVHWYQQKPGQAPVLVVYDDSDRPSGIPERFS<br>GSNSGNTATLTISRVEAGDEADYYCQVWHSVSDQGVFGTGTKVTVL |

| Sequence ID | FR1 | CDR1 | FR2 | CDR2 | FR3 |
|---|---|---|---|---|---|
| P4-B3 | QVQLVQSGAEVKKPGSSVKVSCKAS | GGTFSSYA | ISWVRQAPGQGLEWMGG | IIPIFGTA | NYAQKFQGRVTITADKSTSTAYMELSSLRSEDTAVYYC |
| P4-B7 | QVQLVQSGAEVKKPGESLRISCKDS | GYTFTTYW | IGWVRQLPGKGLEWMGI | IYPDDSDT | TYSPSFQGHVTISADKSINTAYLQWSSLKASDTAMYYC |
| PD1#2 | QVQLQQSGPGLVRPSATLSLTCTVS | GDSVSSDNYF | WSWIRQPPGKPLEWIGY | VYYNGNT | NYNPSFNSRVTMSLDTSKNQFSLKLRSVTAADTAFYYC |
| PD1#3 | QVQLVQSGAEVKKPGSSVKVSCKTS | GYTFNRFG | LTWVRQAPGQGLEWMGW | TNPYNGNT | RYAQKFQGRVTMTDTSTSTAYMELRSLRSDDTAMYFC |
| PD1#13 | EVQLVQSGGGVVQPGRSLRLSCAAS | GFTFSSYA | MHWVRQAPGKGLEWVAV | ISYDGSNK | YYADSVKGRFTISRDNSKNTLYLQMNSLRAEDTAVYYC |

| Sequence ID | FR1 | CDR1 | FR2 | CDR2 | FR3 |
|---|---|---|---|---|---|
| P4-B3 | QPGLTQPPSASGTPGQRVTISCSGS | SSNIGSNT | VNWYQQFPGKAPKLLIF | NDN | QRPSGVPDRFSASKSGTSASLAISGLQSEDEADYYC |
| P4-B7 | LPVLTQPPSASGTPGQRVTISCTGS | SSNIGAGYV | VHWYQQLPGTAPKLLIY | SNN | QRPSGVPDRFSGSKSGTSASLAISGLQSEDEADYYC |
| PD1#2 | QPGLTQPPSVSKGLRQTATITCTGS | SNNVGAHG | AAWLQQHQHPPKLLAY | RNN | NRPSGISERFSASRSGNTASLTITGLQPEDEGDYYC |
| PD1#3 | NFMLTQPHSVSESPGKTVTISCTRN | SGSIAAYY | VQWYQQRPGSSPTTVIY | EDN | QRPSGVPDRFSGSIDSSSNSASLTISGLKTEDEADYYC |
| PD1#13 | QPGLTQPPSVPVAPGQTARITCGGN | NIGSKS | VHWYQQKPGQAPVLVVY | DDS | DRPSGIPERFSGSNSGNTATLTISRVEAGDEADYYC |

FIG. 83I

| CDR3 | FR4 | Sequence ID | V-GENE and allele | J-GENE and allele | D-GENE and allele |
|---|---|---|---|---|---|
| ARGRQMFGAGIDF | WGPGTLVTVSS | P4-B3 | HV3-9*01 F | HJ6*04 F | HD4-17*01 F |
| AFWGASGAPVNGFDI | WGQGTLVTVSS | P4-B7 | HV5-51*01 F | HJ3*02 F | HD1-1*01 F |
| ATHTPPTSYFNSGPFDS | WGQGTLVTVSS | PD1#2 | HV4-61*01 F | HJ4*02 F | HD3-22*01 F |
| ARVVAVNGMDV | WGQGTTVTVSS | PD1#3 | HV1-18*01 F | HJ6*02 F | HD1-14*01 ORF |
| ASQTVAGSDY | WGQGTLVTVSS | PD1#13 | HV3-30-3*01 F | HJ4*02 F | HD6-19*01 F |
|  |  |  |  |  |  |
| CDR3 | FR4 | Sequence ID | V-GENE and allele | J-GENE and allele |  |
| AAWDGGLNGRGV | FGGGTKLTVL | P4-B3 | LV1-44*01 F | LJ3*02 F |  |
| AAWDDSLNAPV | FGGGTKLTVL | P4-B7 | LV1-44*01 F | LJ3*02 F |  |
| SSWDSSLSGYV | FGPGTKVTVL | PD1#2 | LV10-54*01 F | LJ1*01 F |  |
| QSYDSSNLWV | FGGGTKLTVL | PD1#3 | LV6-57*01 F | LJ3*02 F |  |
| QVWHSVSDQGV | FGTGTKVTVL | PD1#13 | LV3-21*02 F | LJ1*01 F |  |

FROM
FIG. 83I

FIG. 83J

CHIMERIC ANTIGEN RECEPTOR FACTORIES AND METHODS OF USE THEREOF

This application application is a national stage application of International Application No. PCT/US2019/064032, filed on Jan. 12, 2019, which claims priority from U.S. Provisional Application No. 62/773,885, filed on Nov. 30, 2018, and U.S. Provisional Application No. 62/826,462, filed on Mar. 29, 2019, the entire contents of each of which are incorporated herein by reference in their entireties.

GOVERNMENT INTEREST

This invention was made with government support under Grant No. W81XWH-18-1-0568 awarded by The Department of Defense. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INCORPORATION-BY-REFERENCE OF SEQUENCE LISTING

The contents of the text file named "5031461-051-WO1_SL.txt", which was created on Mar. 10, 2020 and is 205,398 bytes in size, are hereby incorporated by reference in their entirety.

FIELD OF THE INVENTION

This invention is directed to chimeric antigen receptors and cells comprising the same, wherein the cells further secrete monoclonal antibodies locally at a tumor site.

BACKGROUND OF THE INVENTION

Clear cell renal cell carcinoma (ccRCC) is the major type of RCC which is among the 10 most common cancers in both men and women. Other types of renal carcinoma include papillary renal cell carcinoma, chromophobe renal cell carcinoma, and other or unclassified types of renal cell carcinoma. See, for example, Lancet 373 (2009) 1119-32.

SUMMARY OF THE INVENTION

Other objects and advantages of this invention will become readily apparent from the ensuing description.

Aspects of the invention are drawn towards an engineered cell comprising a chimeric antigen receptor. In embodiments, the chimeric antigen receptor comprises an extracellular ligand binding domain that is specific for a first antigen and a second antigen on the surface of a cancer cell, wherein the first antigen comprises CAIX and the second antigen comprises CD70.

In embodiments, the CAR further comprises a transmembrane polypeptide, an intracellular signaling domain, and/or a co-stimulatory domain.

In embodiments, the extracellular ligand binding domain comprises an antibody or fragment thereof. For example, the antibody comprises a VH and/or VL according to Table 2, or any combination thereof. For example, the antibody comprises a VH and/or VL according to Table 4, or any combination thereof. For example, the extracellular binding domain comprises a a VH and/or a VL of Table 2 and Table 4, or any combination thereof. For example, the antibody comprises a CDR1, CDR2, and/or CDR3 of Table 1, or any combination thereof. For example, the antibody comprises a CDR1, CDR2, and/or CDR3 of Table 3, or any combination thereof. For example, the extracellular binding domain comprises a CDR1, CDR2, and/or CDR3 of Table 1 and Table 3, or any combination thereof.

In embodiments, the engineered cell expresses and secretes a recombinant polypeptide.

In embodiments, the recombinant polypeptide comprises an antibody or fragment thereof, or a cytokine. For example, the recombinant polypeptide comprises an antibody or fragment thereof specific for TIGIT, GITR, PD-L1, PD-L2, PD-1, CTLA-4, VISTA, CD70, TIM-3, LAG-3, CD40L, or CCR4. For example, the recombinant polypeptide comprises a cytokine comprising IL-12, IL-15, or IL-18.

In embodiments, the recombinant polypeptide modulates the immune system of a subject. For example, the recombinant polypeptide is an immune checkpoint blockade antibody.

In embodiments, the recombinant polypeptide modulates tumor vasculogenesis. For example, the recombinant polypeptide can be specific for VEGF, VEGFR1, VEGFR2, PDGF, Ang-1, or AT1.

In embodiments, the engineered cell is a T cell, an NK cell, or an NKT cell. For example, the T cell is CD4+, CD8+, CD3+ panT cells, or any combination thereof. For example, the T cell is a mixed population of CD4+ and CD8+ T cells.

Aspects of the disclosure are further drawn towards a nucleic acid construct encoding a chimeric antigen receptor. In embodiments the chimeric antigen receptor comprises an extracellular ligand binding domain that is specific for a first antigen and a second antigen on the surface of a cancer cell, wherein the first antigen comprises CAIX and the second antigen comprises CD70.

In embodiments, the nucleic acid construct further encodes for a transmembrane polypeptide, an intracellular signaling domain, and/or a co-stimulatory domain.

In embodiments, the nucleic acid construct further encodes for a recombinant polypeptide.

Aspects of the disclosure are further drawn towards a vector comprising the nucleic acid construct described herein.

Still further, aspects of the disclosure are drawn towards a cell comprising the vector described herein.

Aspects of the disclosure are also drawn towards a method for treating a subject afflicted with cancer. In embodiments, the method comprises administering to a subject a therapeutically effective amount of the engineered cell described herein.

Also, aspects of the disclosure are drawn towards a method of reducing progression or promoting regression of a cancer in a subject. In embodiments, the method comprises administering the subject a therapeutically effective amount of the engineered cell described herein.

Still further, aspects of the disclosure are drawn towards a method of reducing cellular proliferation of a cancer cell in a subject. In embodiments, the method comprises administering the subject a therapeutically effective amount of the engineered cell described herein.

In embodiments, the cancer comprises renal cell carcinoma.

Aspects of the disclosure are drawn to a chimeric antigen receptor (CAR) comprising an extracellular ligand binding domain, wherein the extracellular ligand binding domain is specific for a first antigen and a second antigen on the surface of a cancer cell, wherein the first antigen comprises CAIX and the second antigen comprises CD70.

In embodiments, the CAR further comprises a transmembrane polypeptide, an intracellular signaling domain, and/or a co-stimulatory domain.

In embodiments, the extracellular ligand binding domain comprises an antibody or fragment thereof.

Further, aspects of the invention are drawn towards a cell comprising the chimeric antigen receptor (CAR) as described herein.

Still further, aspects of the invention are drawn towards an engineered cell comprising a first chimeric antigen receptor and a second chimeric antigen receptor, wherein the first chimeric antigen receptor comprises an extracellular ligand binding domain specific for CAIX, and wherein the second chimeric antigen receptor comprises an extracellular ligand binding domain that is specific for CD70.

In embodiments, the engineered cell expresses and secretes a recombinant polypeptide.

In embodiments, the first chimeric antigen receptor and the second chimeric antigen receptor are expressed from a single nucleic acid construct.

BRIEF DESCRIPTION OF THE FIGURES

FIG. 3 shows CAIX and CD70 upregulated and co-expressed on ccRCC. IHC staining of ccRCC primary cell lines generated from patient samples indicates that CAIX and CD70 are both highly expressed and co-expressed on ccRCC. Without wishing to be bound by theory, CAIX and CD70 are two potential targets for ccRCC therapy. To validate targets, we conducted IHC for staining of CAIX and CD70 in primary cell line which is generated from ccRCC patients. From these images, we can see that CAIX and CD70 staining are 100% positive, demonstrating that CAIX and CD70 are highly and simultaneously expressed in ccRCC. This is presently being validated in a study which determines CAIX and CD70 expression on ccRCC patients with at least 150 samples.

Figure 4:
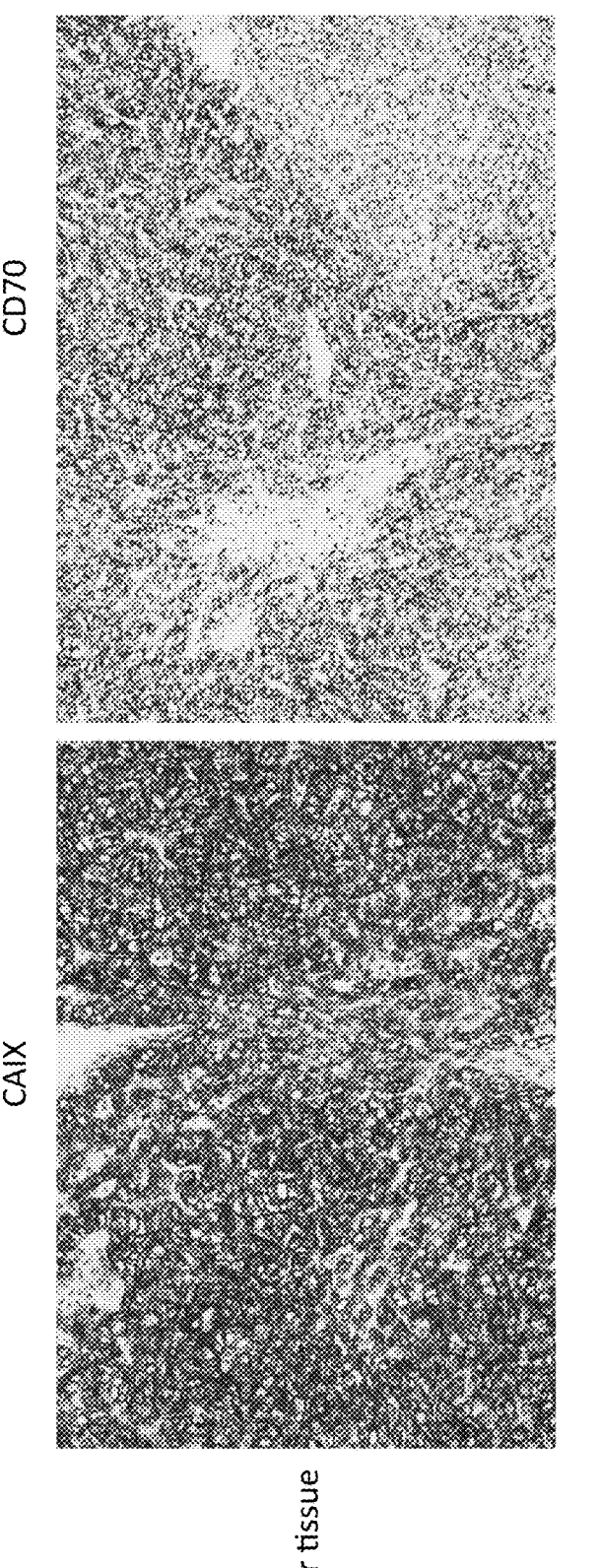

FIG. 4 shows CAIX and CD70 upregulated and co-expressed on ccRCC. IHC staining of ccRCC patient samples indicates that CAIX and CD70 are both highly expressed and co-expressed on ccRCC.

Figure 5A:
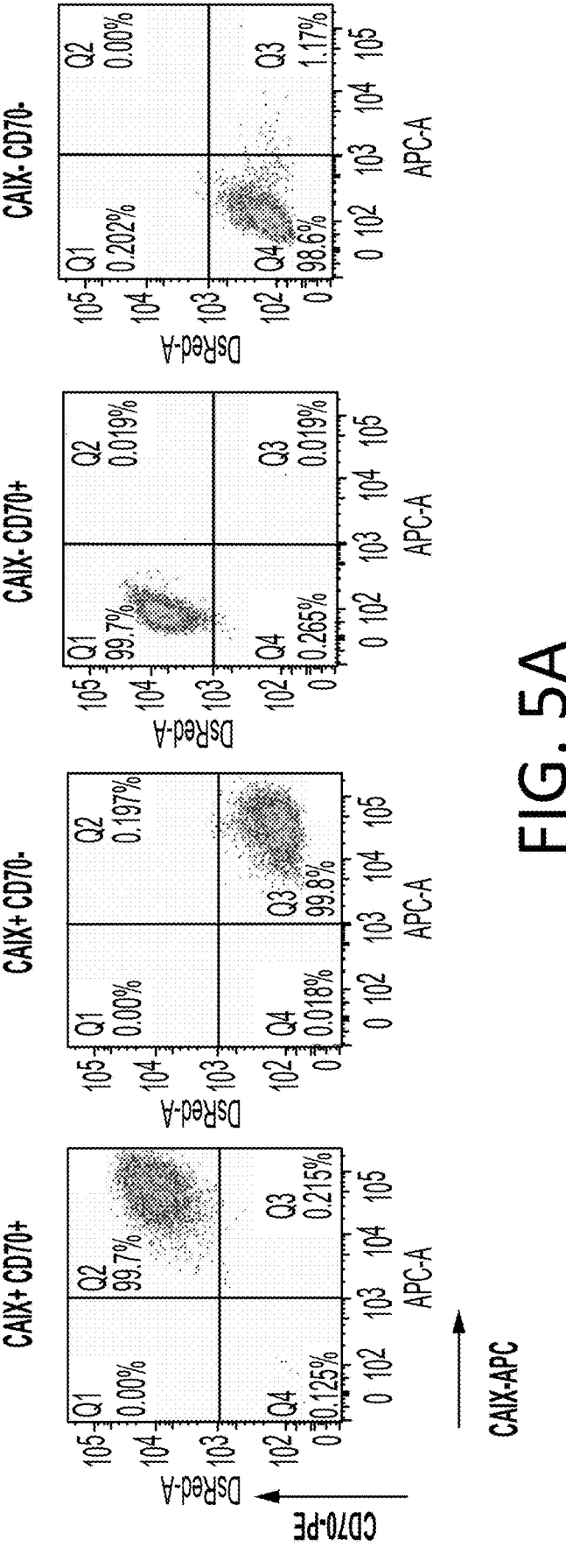

FIG. 5 shows establishment of CRISPR skrc-59 cell lines. For further evaluation in vitro, four CRISPR engineered skrc-59 cell lines were established with four different phenotypes, (i) CAIX+CD70+, (ii) CAIX+CD70-, (iii) CAIX-CD70+, and (iv) CAIX-CD70-. Four CRISPR skrc-59 cell lines have been established. Four different phenotypes, (i) CAIX+CD70+, (ii) CAIX+CD70-, (iii) CAIX-CD70+, and (iv) CAIX-CD70- are used for the in vitro assay described herein. The corresponding table shows CAIX and CD70 expression level on 4 different cell lines that were quantified.

Figure 6:
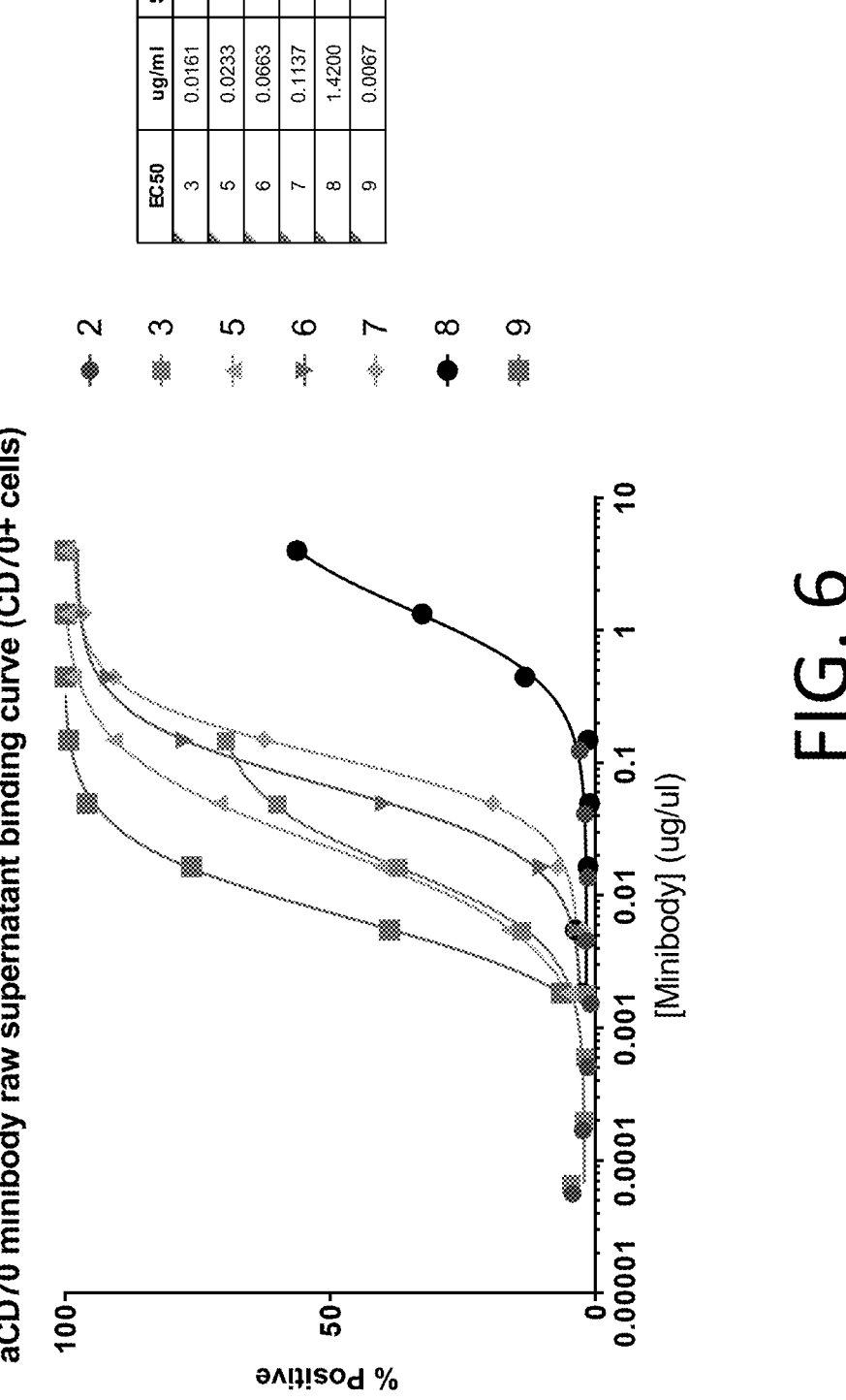

FIG. 6 shows graphs of anti-CD70 minibodies that showed selective binding to CD70+ SKRC59 cells. Phage display (panned against CD70+ skrc-59 cells and subtracted against CD70-skrc-59 cells) indicates that a series of anti-CD70 minibodies showed binding with CD70 positive ccRCC skrc-59 cells. Anti-CD70 minibodies were expressed via Expi293 cells in a 6 well plate. 3 days after transfection, the supernatant was harvested and IgG quantification ELISA (Bethyl) was conducted to approximate the concentration of minibody in the supernatant. This approximate concentration was used to normalize the supernatants for FACS binding curves. Staining was carried out via standard FACS staining protocol using an anti-hFc-APC secondary. As can be seen, one of the hits with killing activity (#9) is very nonspecific. The other two monoCARs which exhibit killing activity (#3, 7) show good specificity to CD70.

Figure 7:
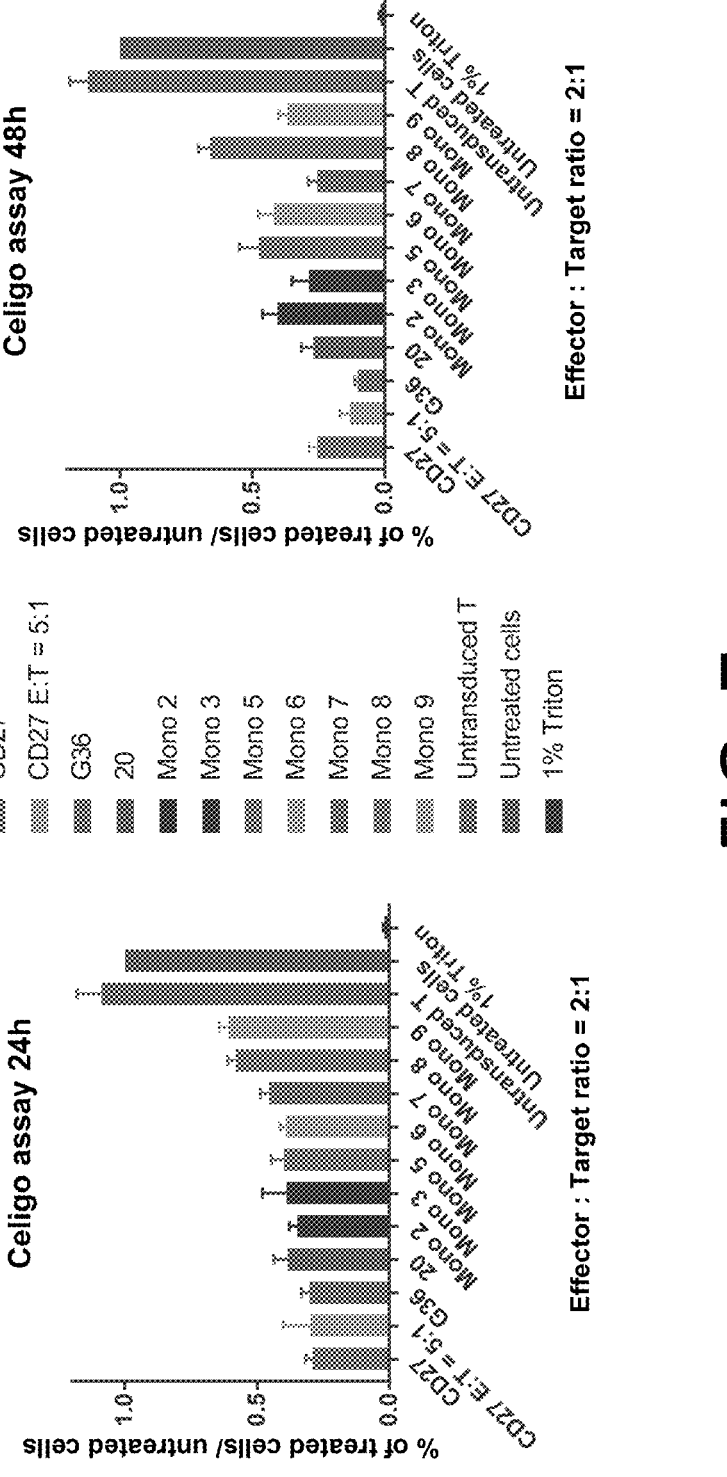

FIG. 7 demonstrates anti-CD70 CAR T cells show killing activity in Celigo killing assay. These anti-CD70 scFv candidates were cloned into vectors and were packaged into lentiviruses to transduce primary T cells. CAR T cells were assessed for antiproliferation activity in Celigo assay. Results showed that #3, #7, #9 have efficacy compared to CD70 ligand CD27 CAR T cells. Also, these hits were cloned into pHAGE vector and conducted Celigo killing assay. These graphs showed that anti-CD70 CAR T cells exhibited killing activity in Celigo killing assay with Effector: Target ratio of 2:1. We compared the cell number in different time points and normalized with untreated cells in corresponding time point. So that Y axis is the percentage of treated cells/untreated cells and X axis is different treatment. After 24 h coculture with T cells, the SKRC59 cell number of treatment group is significantly decreased compared to untreated group and untransduced T cell group, demonstrating the anti-proliferation activity of these CAR T cells. After 48 h coculture, we found 3 candidates which are comparable to CD27, a ligand of CD70. So that 3,7,9 were used for the further Chromium 51 killing assay.

Figure 8:
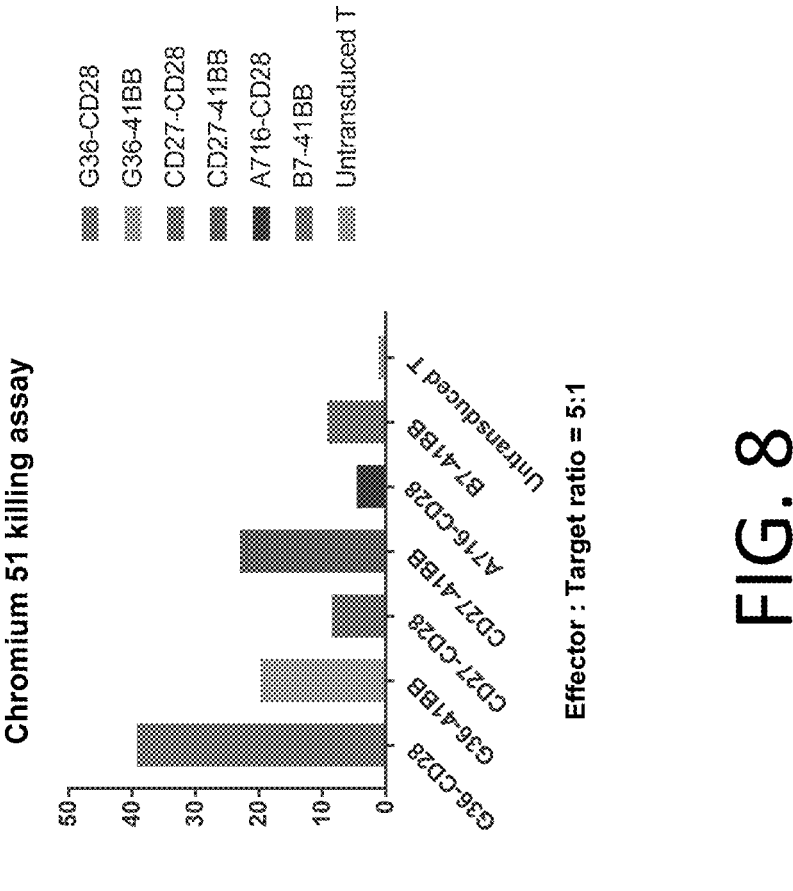

FIG. 8 demonstrates anti-CD70 CAR T cells show killing activity in Chromium 51 killing assay on CAIX+CD70+ cells. CAR T cells were also assessed for killing activity in Chromium 51 release assay. Results showed that #7 CAR T cells have the enhanced efficacy compared to CD27 (CD70 ligand) CAR T cells. A chromium 51 4 h release assay was conducted. After 4 h incubation with chromium 51 labeled target cells, it validated that B7 has killing activity against SKRC59 CD70+ cells.

Figure 9:
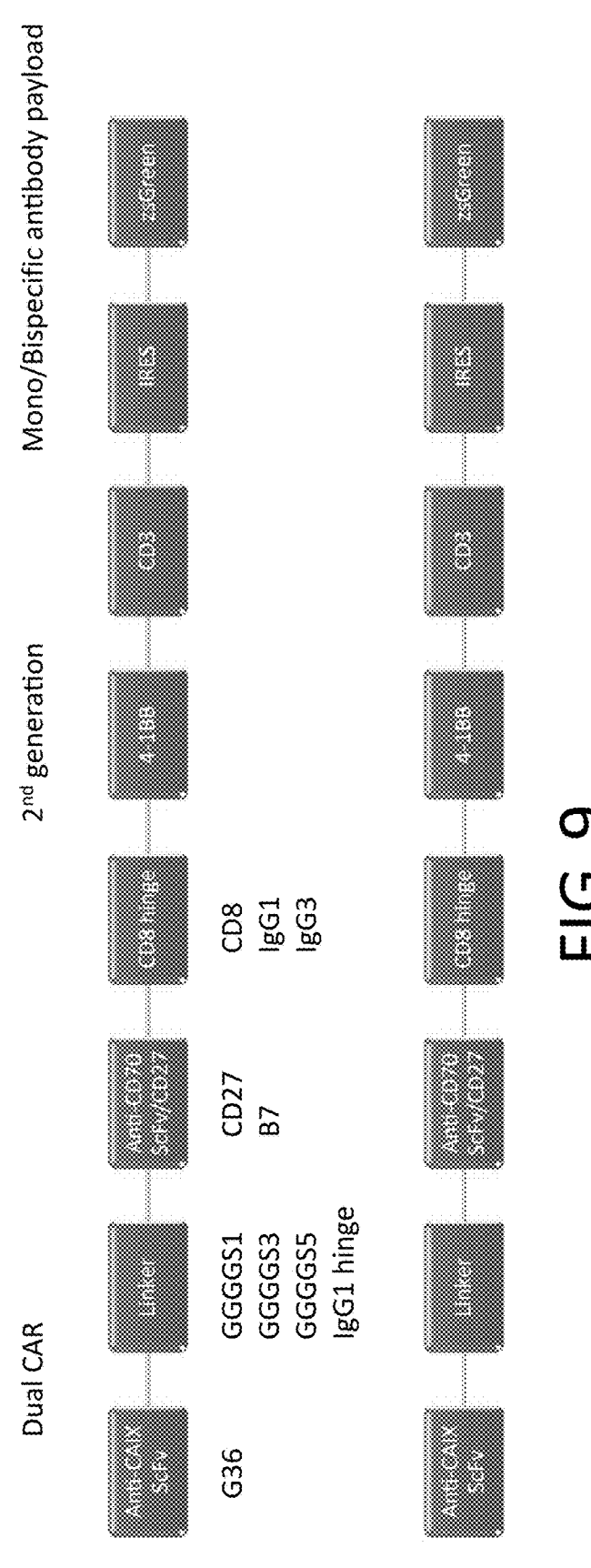

FIG. 9 shows 2nd generation CAR-T cells. CAR T cells can be generated by using zsGreen instead of immune checkpoint blockade. Based on these data, 8 constructs were established by using G36 as the anti-CAIX scFv and B7 as the anti-CD70 scFv. The dual CAR engineering is the most important part and the payload was replaced with zsgreen to indicate the transduction efficiency. Figure discloses SEQ ID NOS 267 and 41-42, respectively, in order of appearance.

Figure 10:
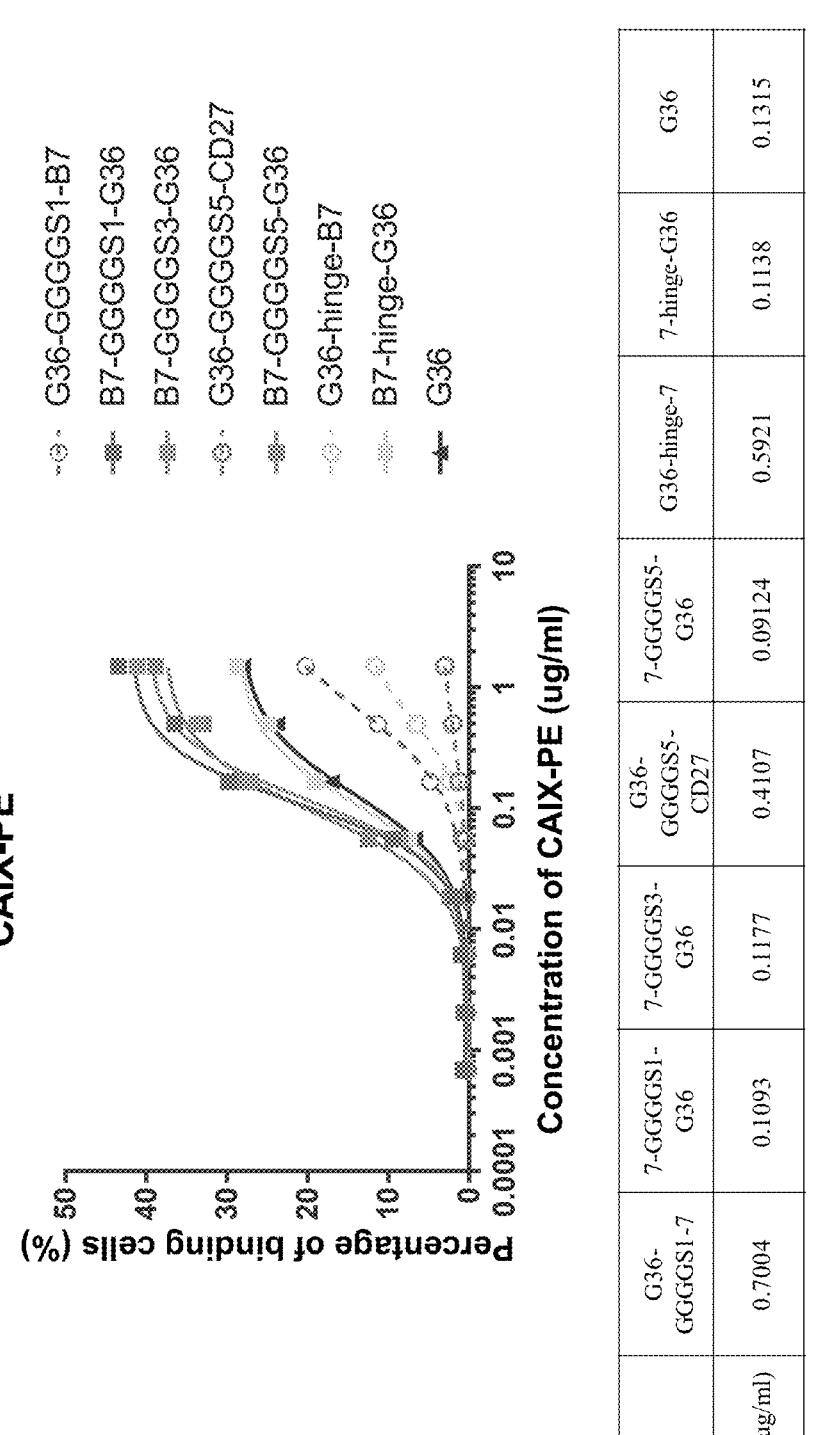

FIG. 10 shows transfected 293T cells binding with CAIX-PE. 293T cells were transfected with different constructs of dual CAR and the binding assay with PE labeled CAIX protein was performed. All dual CARs bind to CAIX, and different orientation of two scFvs influence the EC50 of anti-CAIX scFv binding. Anti-CAIX scFv G36 prefer the 2nd cassette after linker. For example, 293T cells were transfected with these 8 bispecific constructs and also corresponding monoCARs and stained with CAIX-PE. After normalization by transfect efficiency, different orientation of two scFvs influence the EC50 of anti-CAIX scFv binding. Anti-CAIX scFv G36 prefer to in the 2nd cassette after linker.

Figure 11:
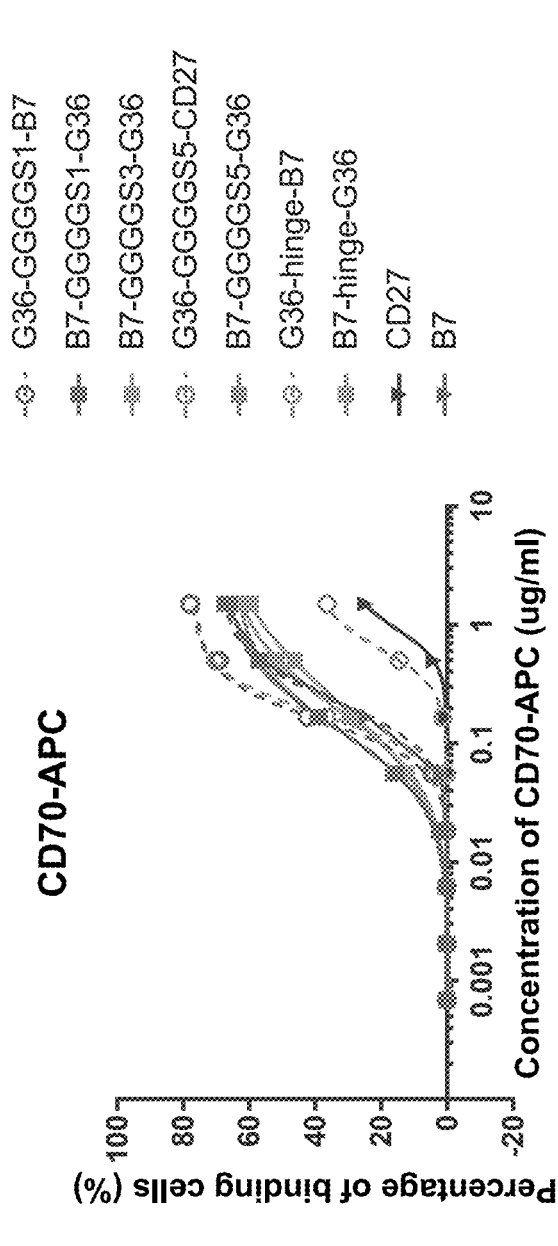

FIG. 11 shows transfected 293T cells binding with CD70-APC. 293T cells were transfected with different constructs of dual CAR and the binding assay was performed with PE labeled CAIX protein. All dual CARs bind to CD70, and different orientation of two scFvs does not influence the EC50 of anti-CD70 scFv binding. Anti-CD70 scFv B7 does not have a significant preference. For example, 293T cells were transfected with these 8 bispecific constructs and corresponding monoCARs and stained with CD70-PE. After normalization by transfect efficiency, different orientation of the two scFvs does not influence the EC50 of anti-CD70 scFv binding. Anti-CD70 scFv B7 does not have a significant preference.

FIG. 12 shows B7-GGGGS3-G36 killing assay with Celigo. B7-GGGGS3-G36 CAR for example was taken and selective killing assay was performed on mixed CAIX+CD70+ dual positive cells with CAIX+ or CD70+ single positive or CAIX-CD70-cells. B7-GGGGS3-G36 CAR T cells had more killing activity on the targeted cells (CAIX+CD70+) than non-targeted cells (CAIX+CD70−, CAIX-CD70+, CAIX-CD70−).

Figure 13:
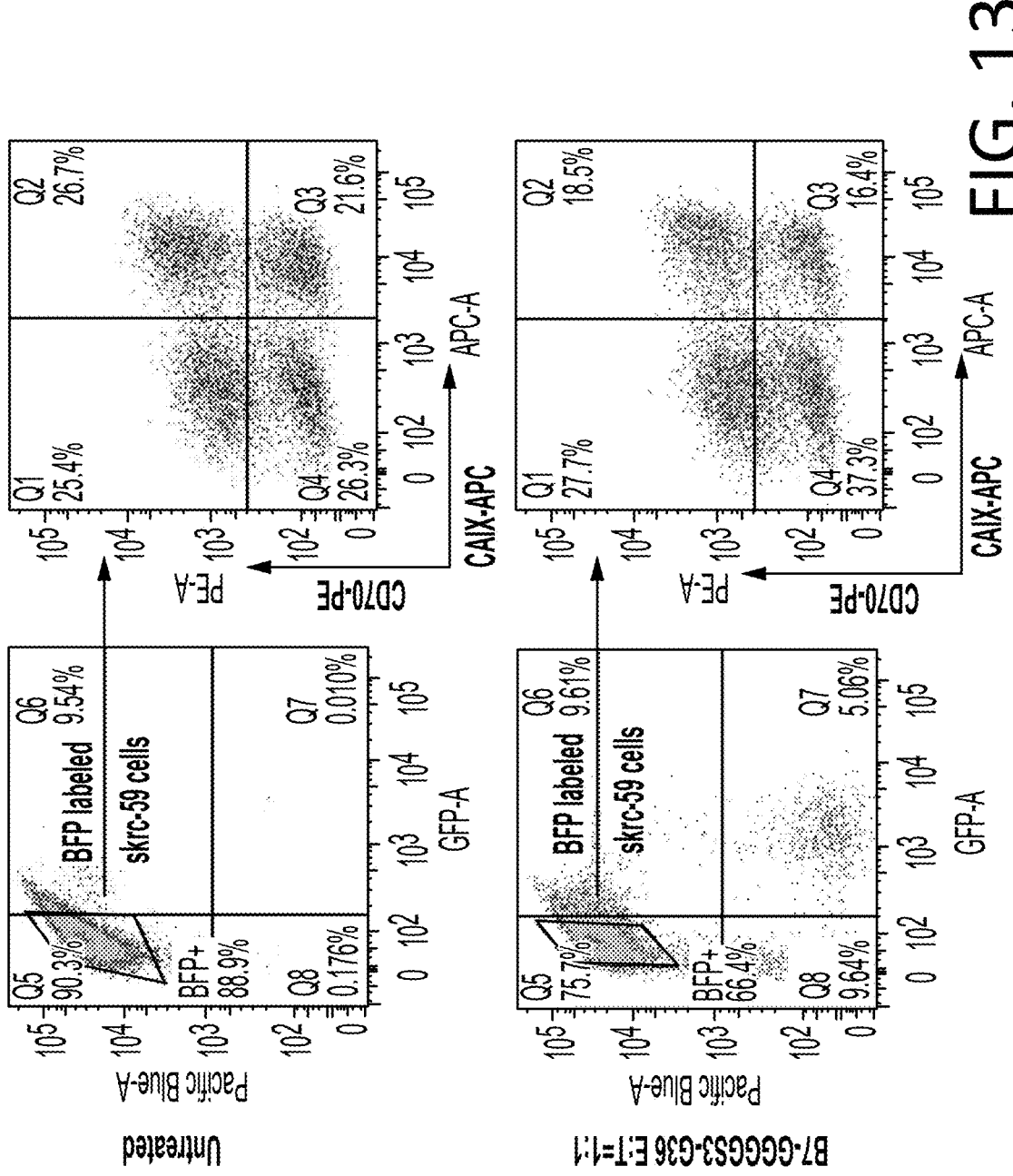

FIG. 13 shows B7-GGGGS3-G36 killing assay with FACS. Four different CRISPR engineered skrc-59 cells were transduced with BFP fluorescence group. Cells were mixed with 1:1:1:1 ratio and were treated with B7-GGGGS3-G36 CAR T cells or culture medium. After treatment, stain cells with PE labeled anti-CD70 antibody and APC labeled anti-CAIX antibody and, perform flow cytometry. It showed that B7-GGGGS3-G36 has selective killing to CAIX+CD70+ cells whose population is reduced from 26.7% to 18.5%.

Figure 14:
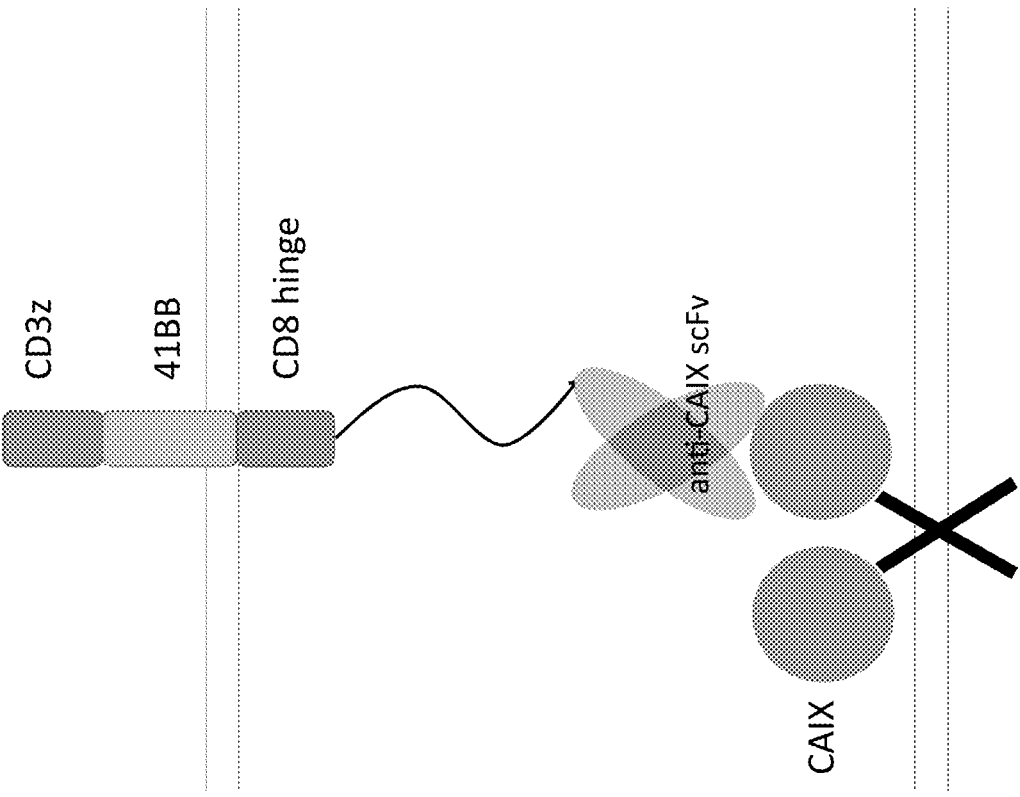

FIG. 14 is a schematic of fine-tuned anti-CAIX CAR T. anti-CAIX scFvs with various KDs were generated as CARs and corresponding killing activity was assessed. In order to limit on-target off-tumor effect, the 2nd generation CAR T cell factories have been designed with the introduction of the second cassette anti-CD70 scFv.

Figure 15:
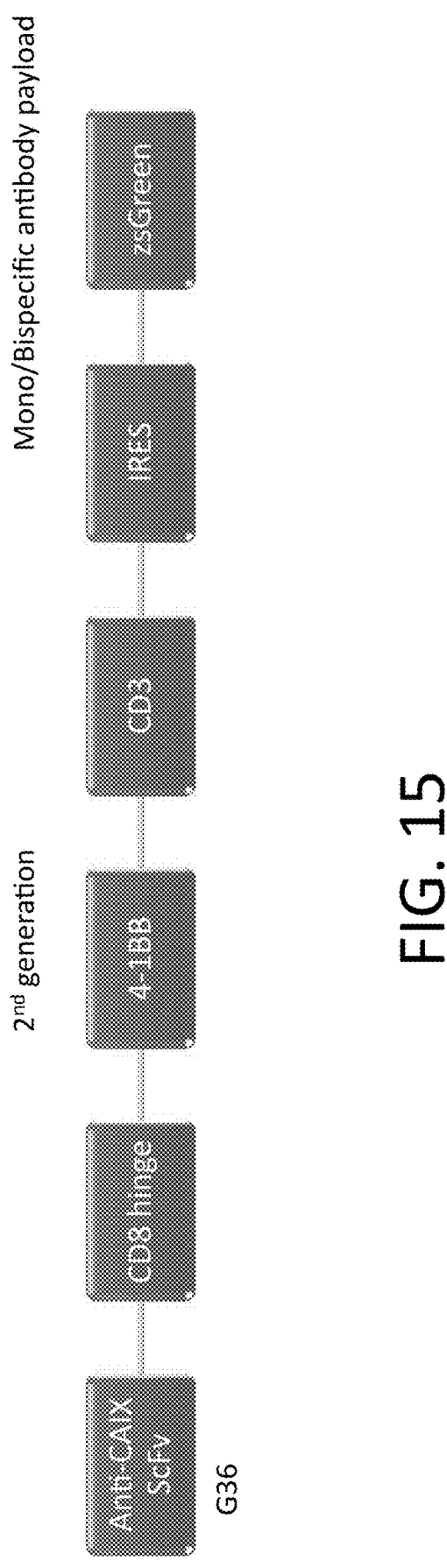

FIG. 15 is a diagram rendering of fine-tuned anti-CAIX CAR-T cells. For validation experiments, CAR T cells were generated by using zsGreen instead of immune checkpoint blockade. 8 constructs were established by using G36 as the anti-CAIX scFv and B7 as the anti-CD70 scFv. The dual CAR engineering is an important part and the payload was replaced with zsgreen to indicate the transduction efficiency. A series of antibodies against CAIX were identified with different KD values from 1.49 nM to 99.58 nM (See also FIG. 16). 13 antibodies were classified into 4 groups by binding experiment.

FIG. 16 depicts table showing 19 anti-CAIX ScFvs identified and the corresponding binding.

FIG. 17 shows graphs of anti-CAIX monoCAR T killing on CAIX+CD70+. These anti-CAIX CAR T cells were assessed for antiproliferation activity in Celigo assay. Results showed based on killing activity, 19 CARs can be separated into 4 groups. G37, G39, G125 (++++)>G10, G21, G36, G40, G45, G57, G62, G98, G106, G119 (+++)>G6, G9, G17, G27, G28 (++)>G104 (++).

Figure 18:
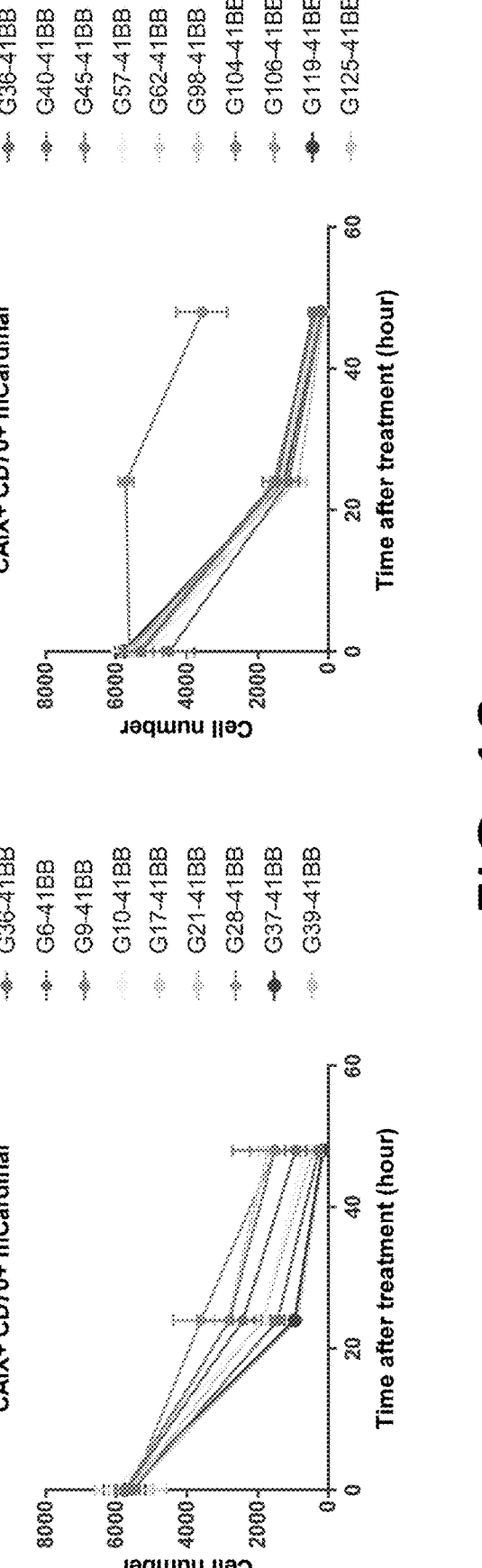

FIG. 18 shows graphs of Anti-CAIX monoCAR T killing on CAIX+CD70+. These anti-CAIX CAR T cells were assessed for antiproliferation activity in Celigo assay. Results showed based on killing activity, that19 CARs can be separated into 4 groups. G37, G39, G125 (++++)>G10, G21, G36, G40, G45, G57, G62, G98, G106, G119 (+++)>G6, G9, G17, G27, G28 (++)>G104 (++).

Figure 19:
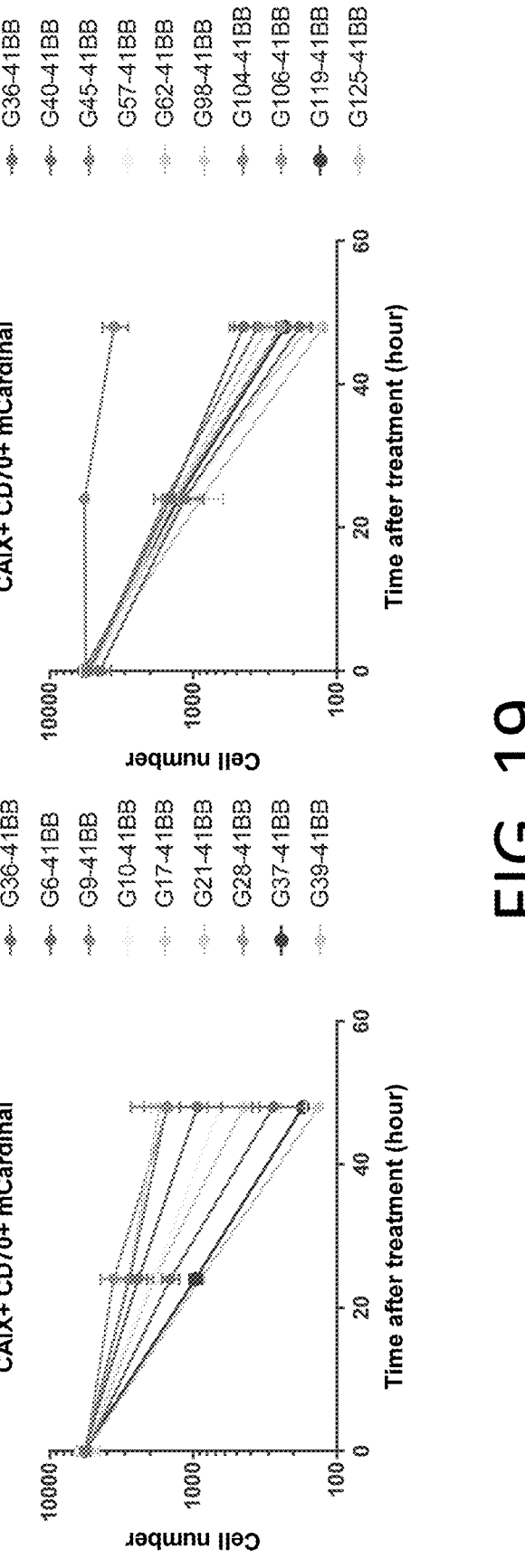

FIG. 19 shows Anti-CAIX monoCAR T killing on CAIX+CD70+. These anti-CAIX CAR T cells were assessed for antiproliferation activity in Celigo assay. Results showed based on killing activity, 19 CARs can be separated into 4 groups. G37, G39, G125 (++++)>G10, G21, G36, G40, G45, G57, G62, G98, G106, G119 (+++)>G6, G9, G17, G27, G28 (++)>G104 (++).

Figure 20:
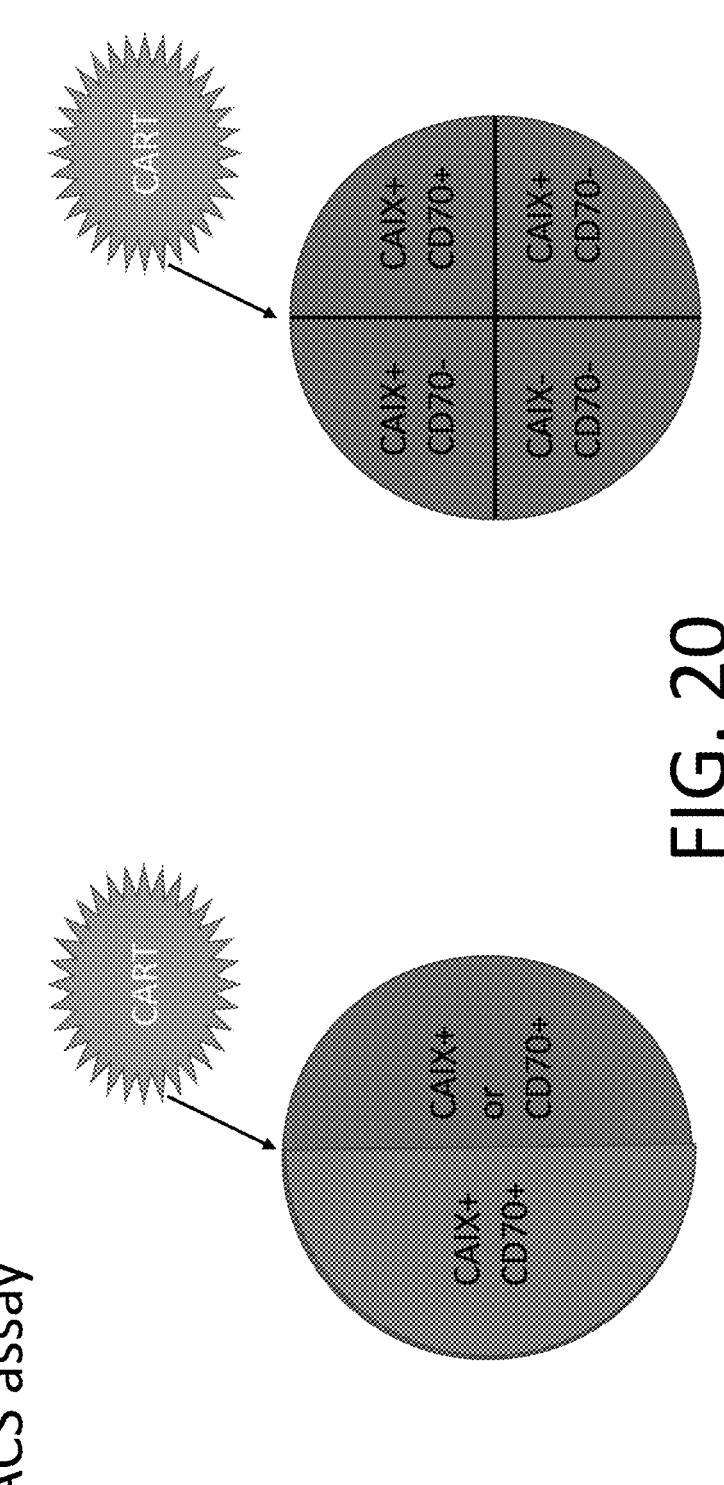

FIG. 20 is a schematic of a selective killing assay (e.g., using either a Celigo assay or FACS assay). In order to explore the selectivity of bispecific CARs on 4 different cell lines, 2 different selectivity assay were performed. For example, CAIX+CD70+ cells were mixed with mono positive cells and then CART cells were added. After certain time incubation, the number of double positive cells and single positive cells were measured through Celigo. Also, 4 different cell lines were mixed with the ratio of 1:1:1:1, and CART cells were added. After 24 h coculture, all the cells are collected and stained with CAIX-APC and CD70-PE by FACS.

Figure 21:
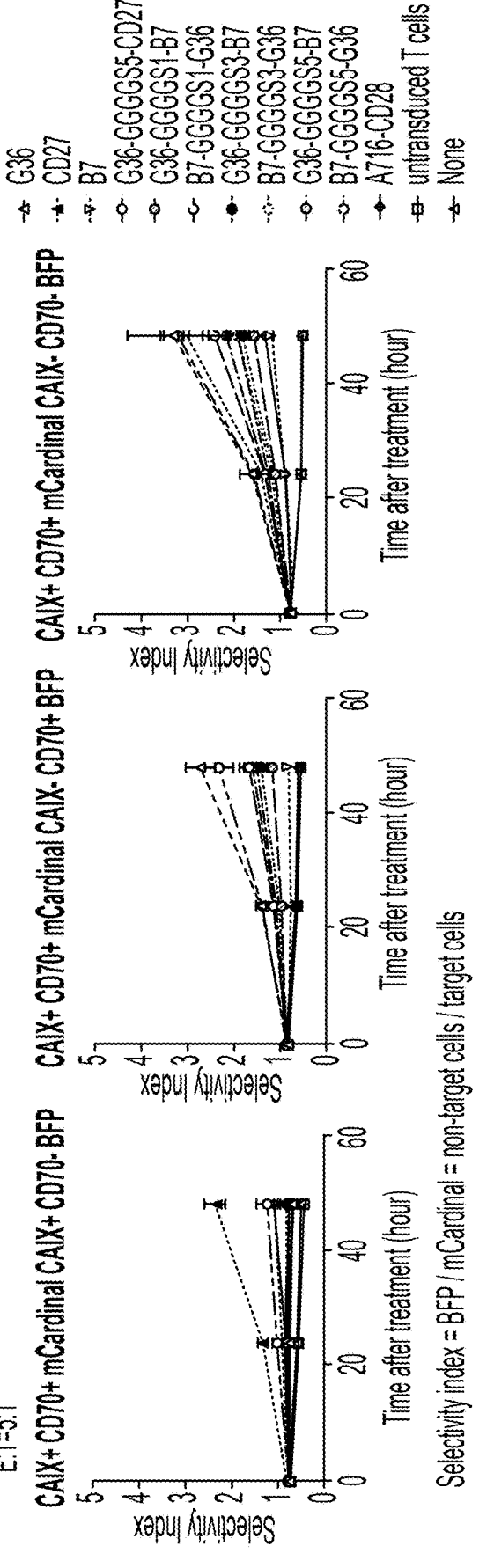

FIG. 21 are graphs showing tandem CAR killing on skrc-59 mixed cells. Selective killing assay was performed on mixed CAIX+CD70+ dual positive cells with CAIX+, or CD70+ single positive, or CAIX-CD70-cells. Bispecific CAR T cells had more killing activity on the targeted cells (CAIX+CD70+) than non-targeted cells (CAIX+CD70−, CAIX-CD70+, CAIX-CD70−) with E: T=5:1.

Figure 22:
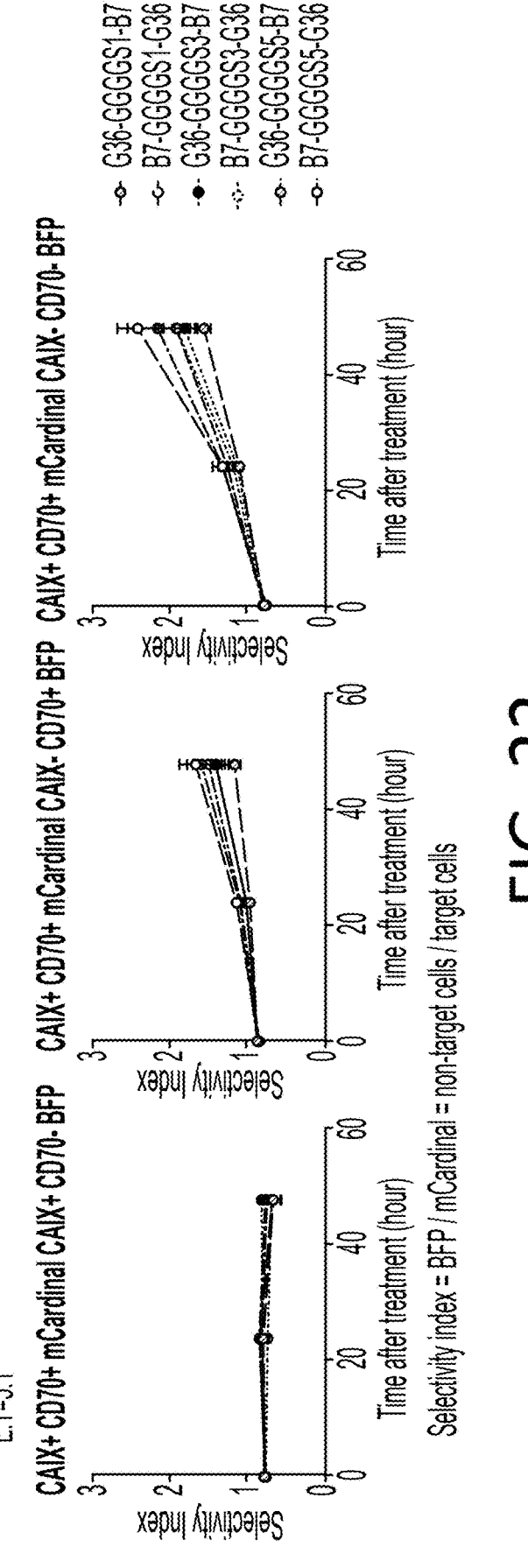

FIG. 22 are graphs showing tandem CAR killing on skrc-59 mixed cells. Selective killing assay was performed on mixed CAIX+CD70+ dual positive cells with CAIX+, or CD70+ single positive, or CAIX-CD70-cells. Bispecific CAR T cells had more killing activity on the targeted cells (CAIX+CD70+) than non-targeted cells (CAIX+CD70−, CAIX-CD70+, CAIX-CD70−) with E: T=5:1.

Figure 23:
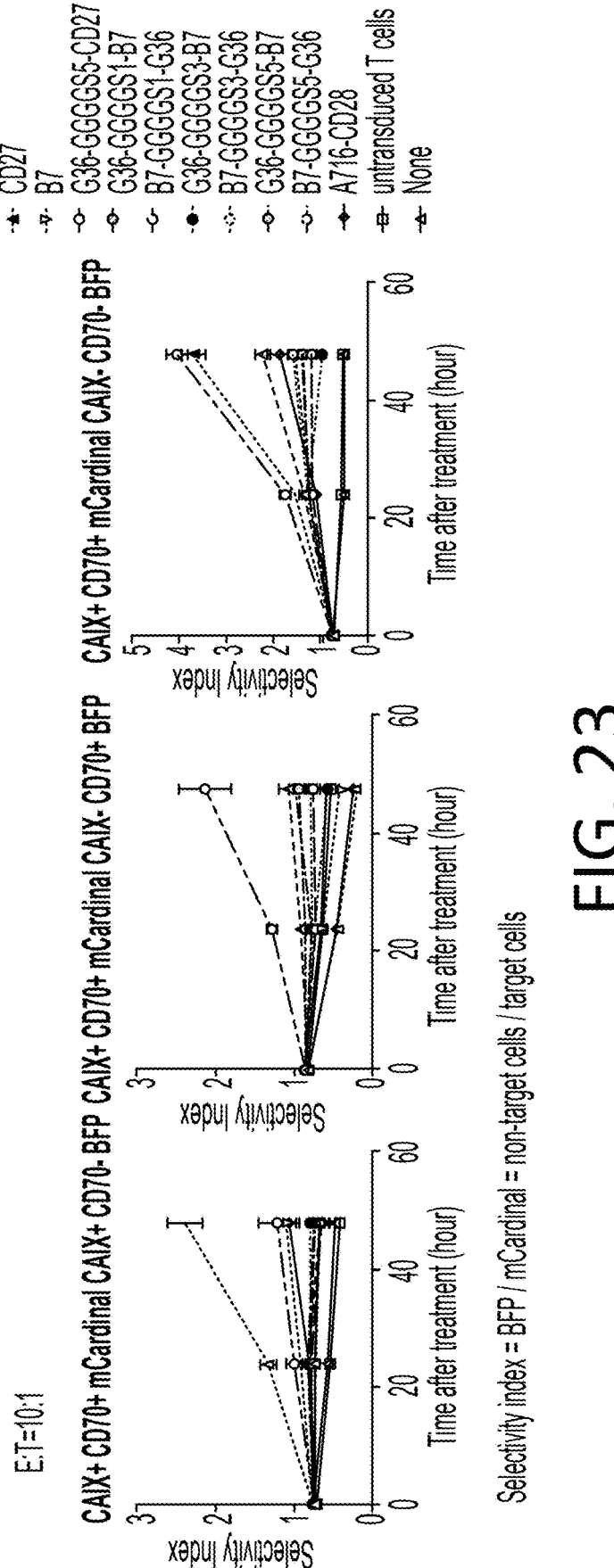

FIG. 23 are graphs showing tandem CAR killing on skre-59 mixed cells. Selective killing assay was performed on mixed CAIX+CD70+ dual positive cells with CAIX+, or CD70+ single positive, or CAIX-CD70-cells. Bispecific CAR T cells had more killing activity on the targeted cells (CAIX+CD70+) than non-targeted cells (CAIX+CD70−, CAIX-CD70+, CAIX-CD70−) with E: T=10:1.

Figure 24:
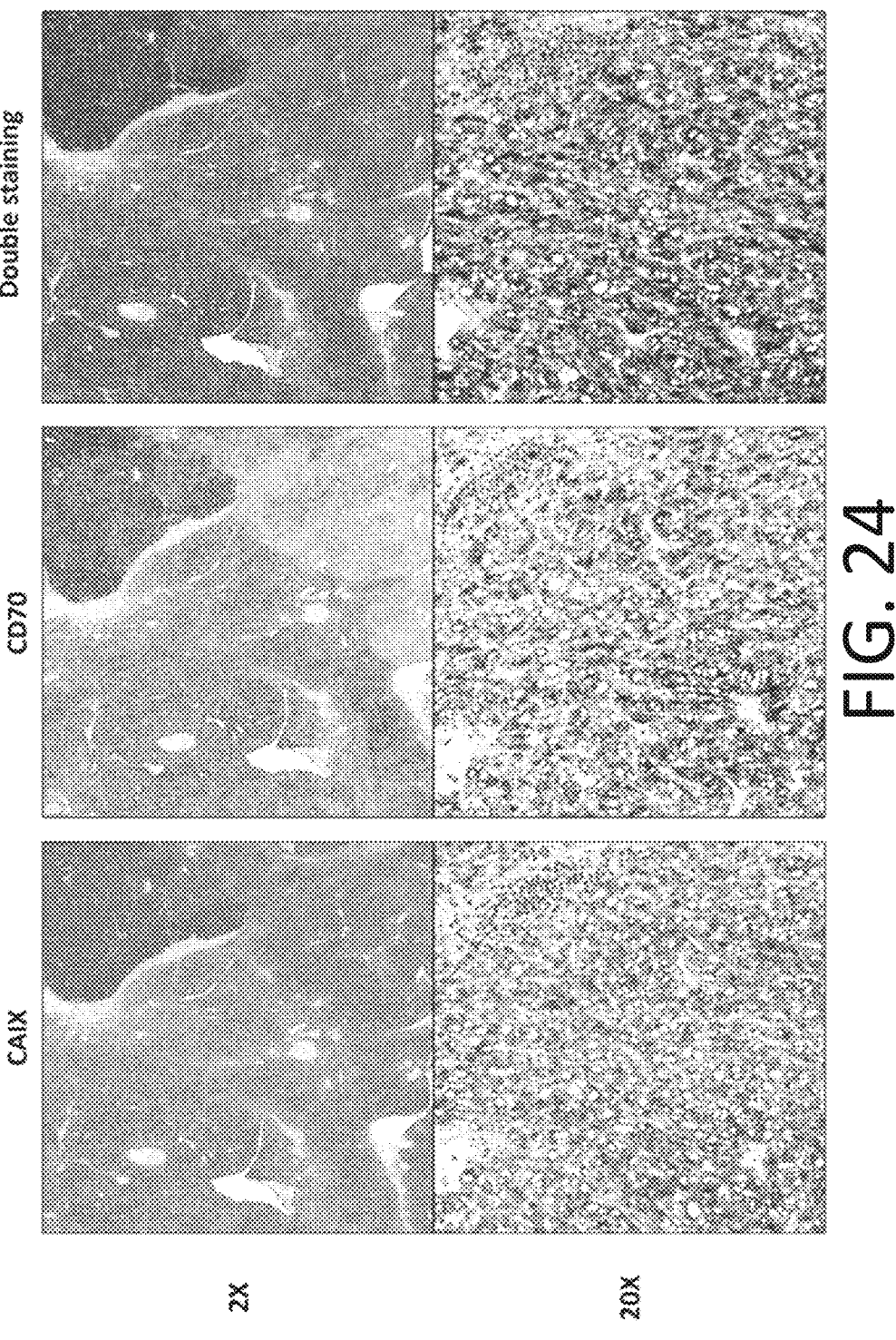

FIG. 24 shows CAIX and CD70 upregulated and co-expressed on ccRCC.

Figure 25:
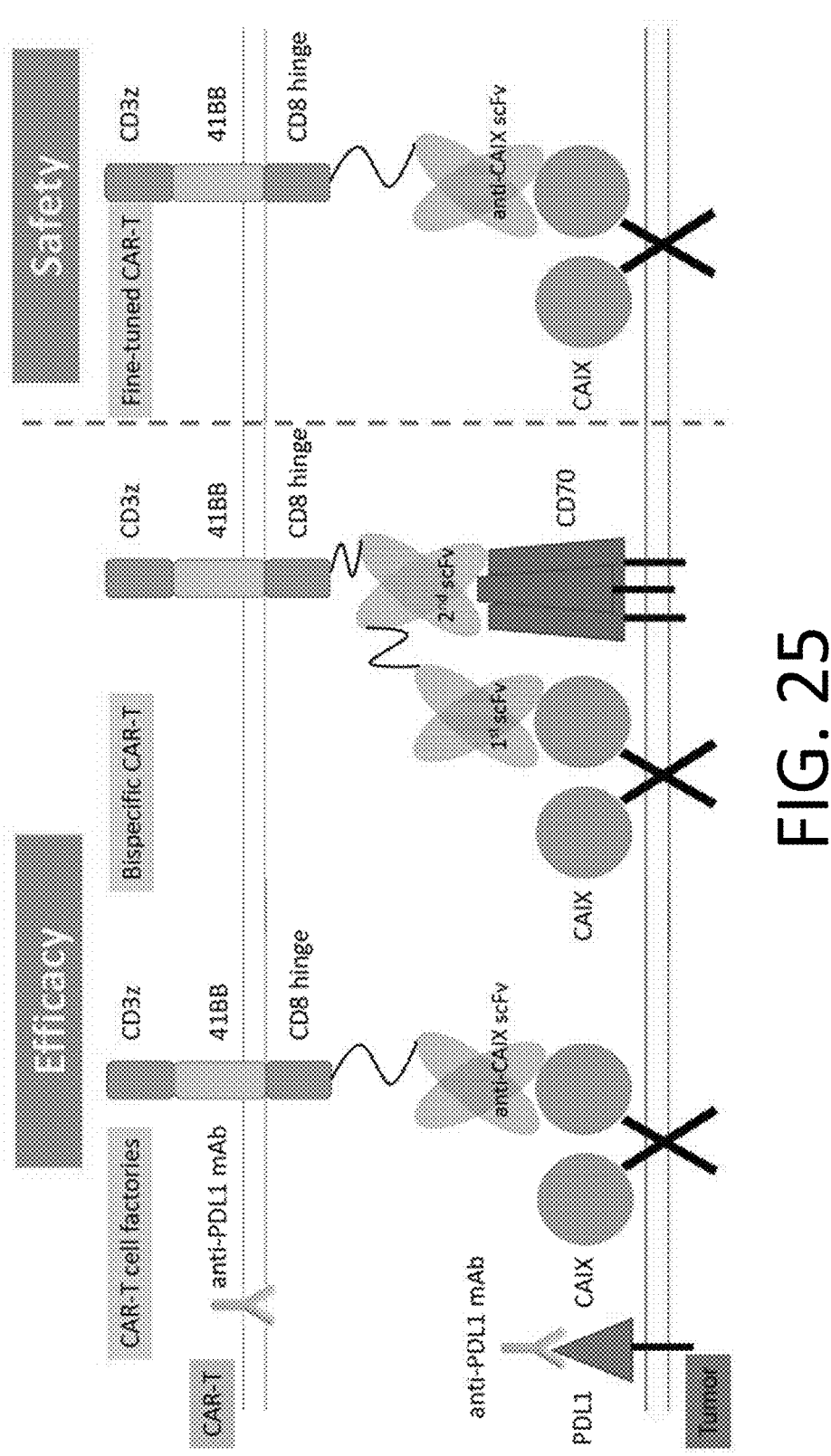

FIG. 25 shows design of CARs to address unwanted side-effects previously associated with CART cell therapy. To apply CART cell therapy in solid tumors, we elevate the efficacy and safety profiling. First, to restore the effective anti-cancer immunity, CAR-T cell factories were developed, which is able to modulate the tumor microenvironment through secreting human anti-immune checkpoint inhibitor monoclonal antibodies (mAbs) locally at the tumor site to reverse T cell exhaustion. In order to limit on-target off-tumor side effects, fine-tuned CARs were designed with reduced affinity scFv to expand the therapeutic window by limiting the recognition of the tumor associated antigen on normal tissues. Also, bispecific CARs were designed by introducing the second cassette, such as anti-CD70 scFv, to increase the preferential killing on the double positive population, resulting in the elevation of safety profiling.

Figure 26:
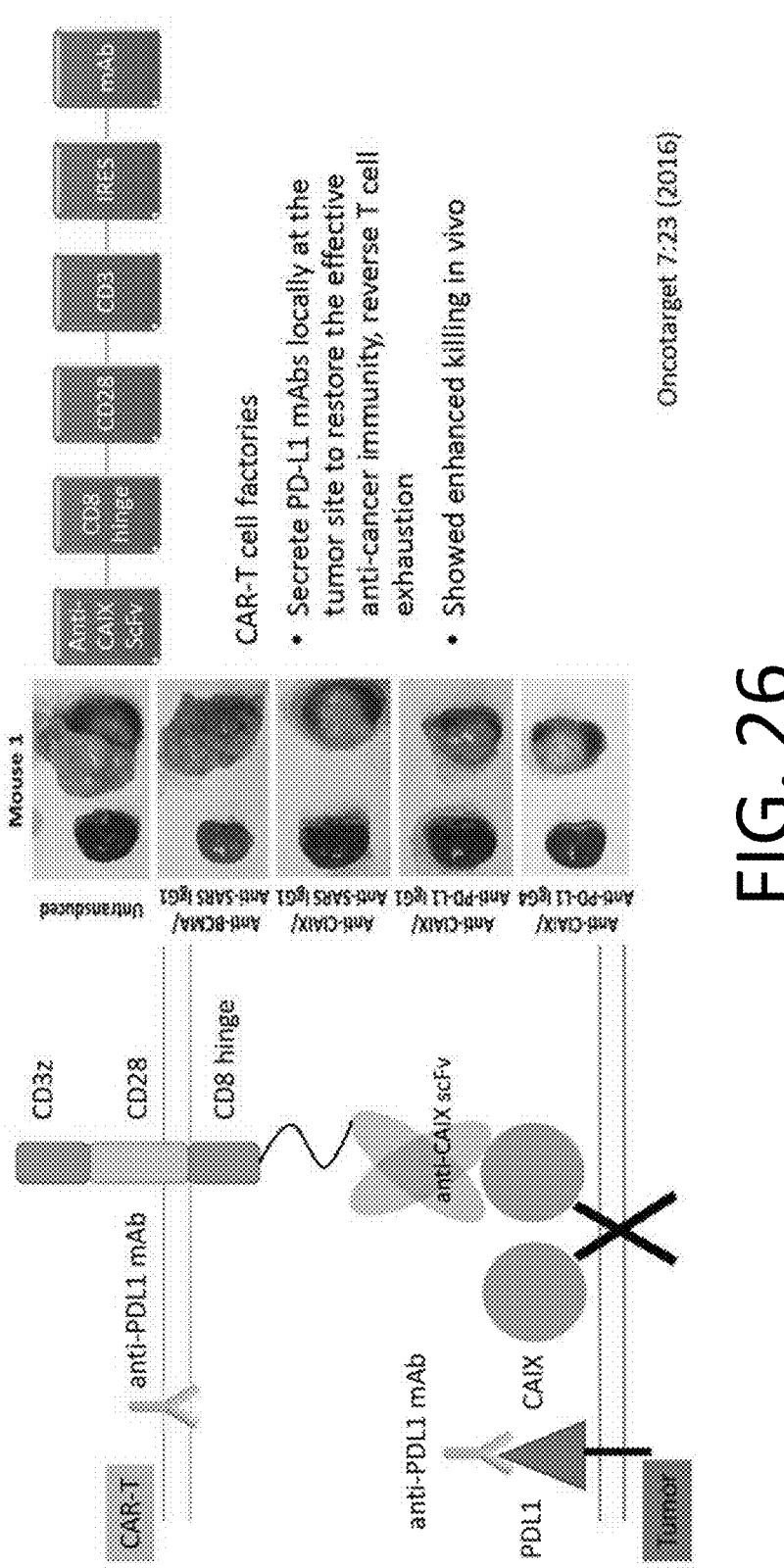

FIG. 26 shows CAR-T cell factories show enhanced killing. We engineered a bicistronic lentiviral vector to express the anti-CAIX scFv linked to CD28 and CD3z signaling domains in the first cassette and anti-PDL1 mAb in the second expression cassette. So that the CAR-T cell factories are able to target CAIX and secrete checkpoint blockade inhibitor at the tumor site to convert suppressive tumor microenvironment. In RCC orthotopic mouse model, 1E7 CAR-T cells were injected by i.v. on Day 0 and 2.5E6 CAR-T cells were injected on Day 17. CAR-T cell factories showed enhanced killing efficacy compared to the CAR-T cells secreting irrelevant antibodies in our orthotopic RCC mouse model.

Figure 27:
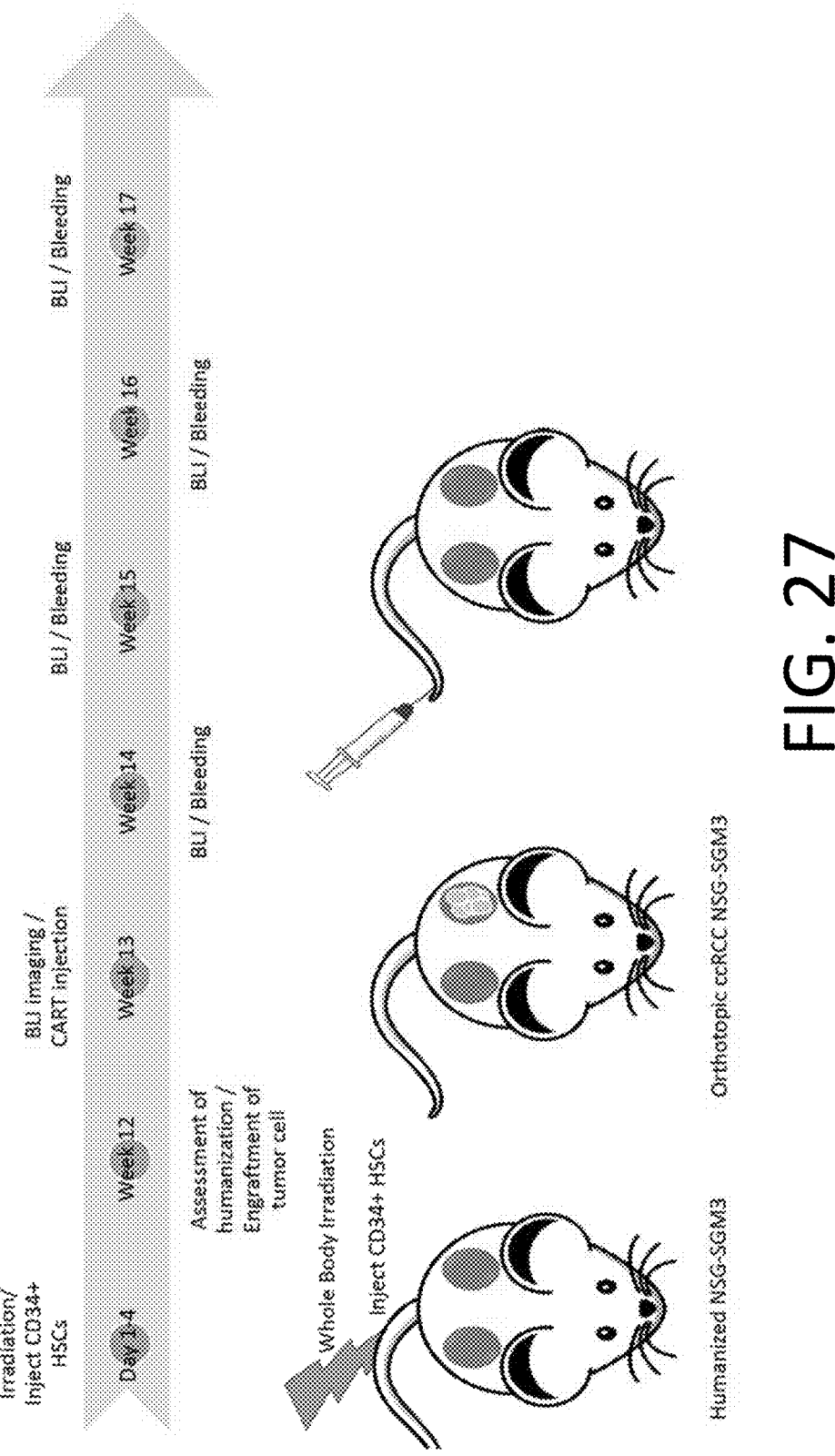

FIG. 27 shows schematic of assessment of CAR-T on humanized orthotopic ccRCC mouse model.

Figure 28:
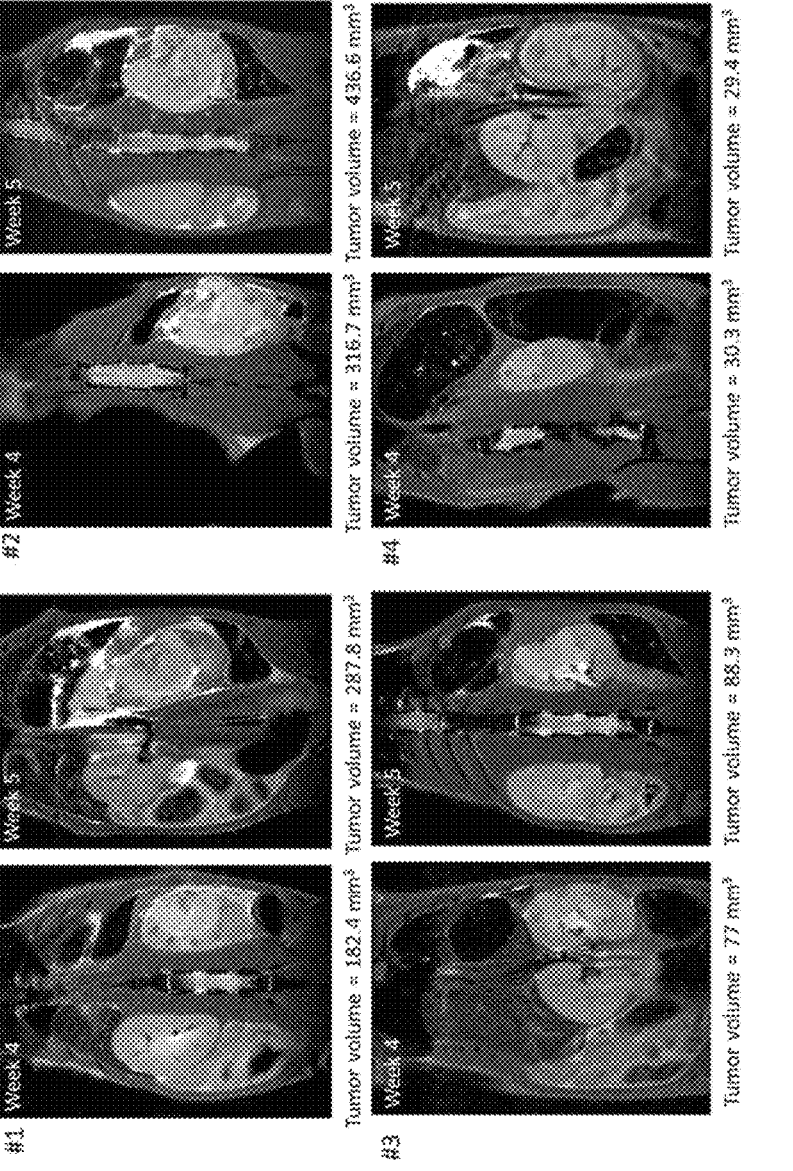

FIG. 28 shows MRI imaging of RCC mouse model.

Figure 30:
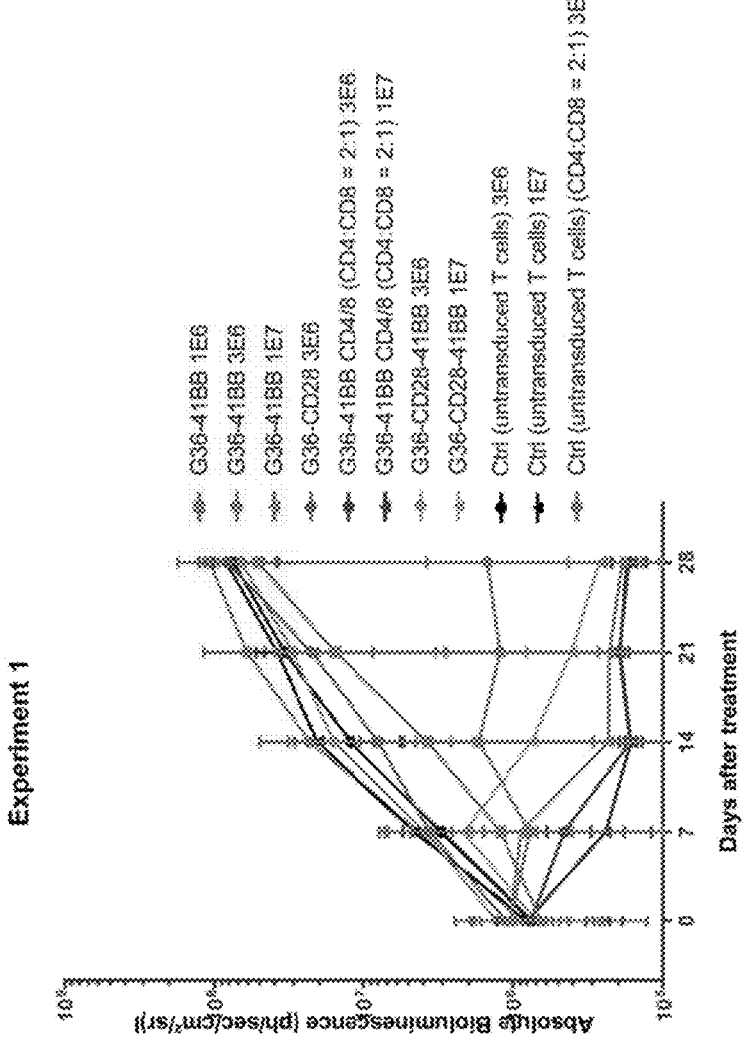
Figure 31:
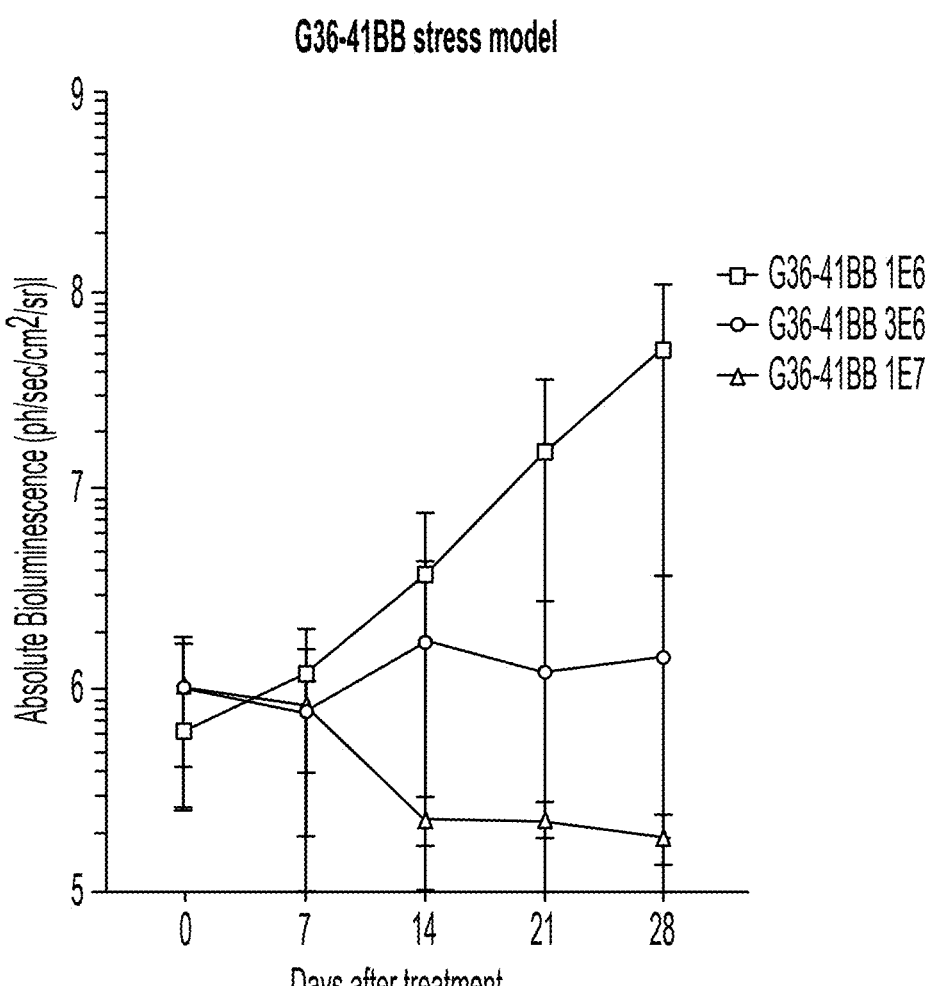

FIG. 29 shows a schematic of an experiment designed to establish stress model and compare 2nd generation and 3rd generation CAR and CD8 vs. CD4/8 on orthotopic ccRCC mouse model FIG. 30 shows 41BB performed superior killing in vivo. Efficient tumor regression was observed in G36-41BB and G36-CD28-41BB treated group at the dose of 1E7. Mixed CD4/CD8 G36-41BB CAR-T performed superior killing even at the dose of 3E6. Comparing two $2^{nd}$ generation CAR constructs and one 3rd generation CAR construct, G36-41BB outperformed than G36-CD28 and G36-CD28-41BB FIG. 31 shows G36-41BB stress model. Dose of 3E6 can be used for G36-41BB stress model.

Figure 32:
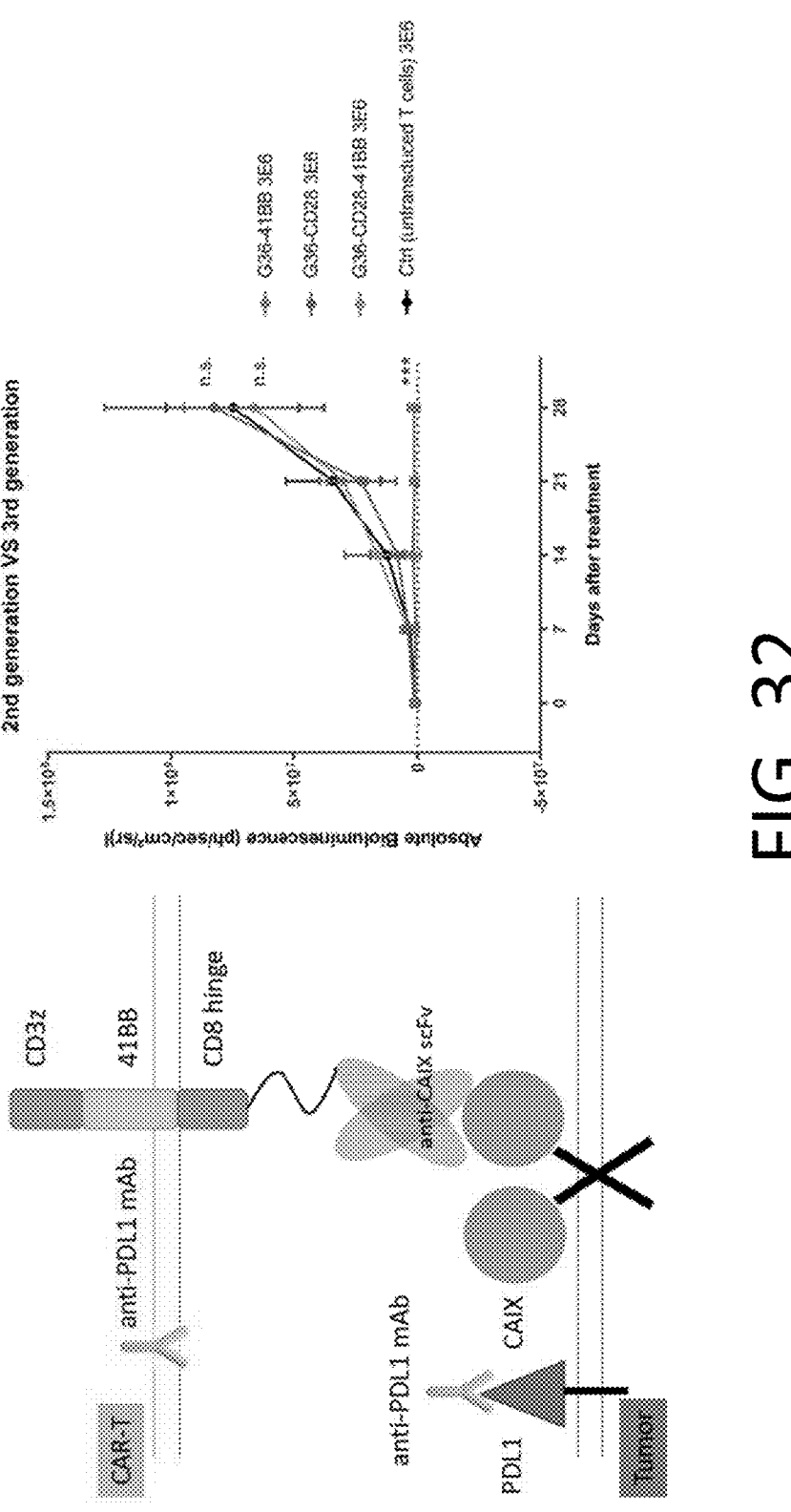

FIG. 32 shows 41BB performed superior killing in vivo.

Figure 33:
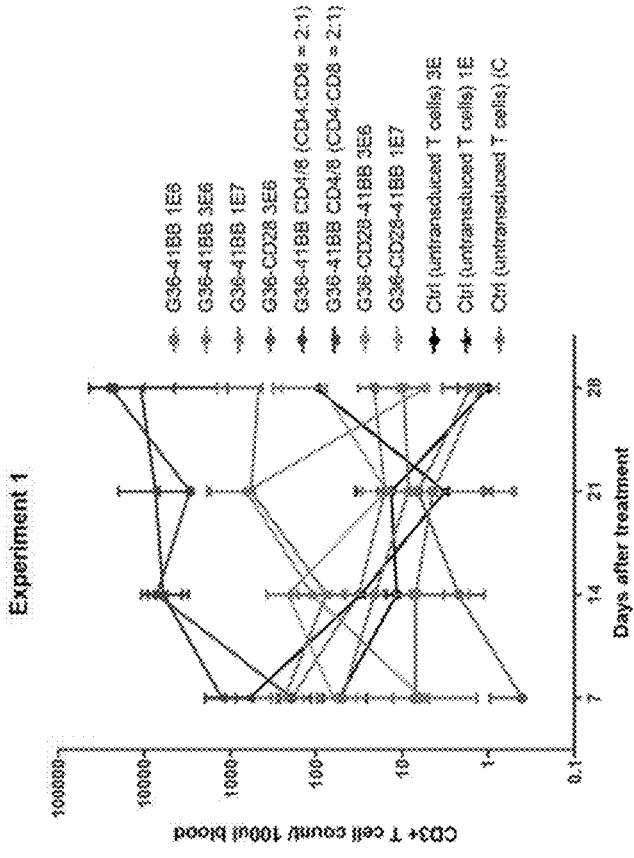

FIG. 33 shows 41BB CAR-T cell performed the best expansion in vivo.

Figure 34:
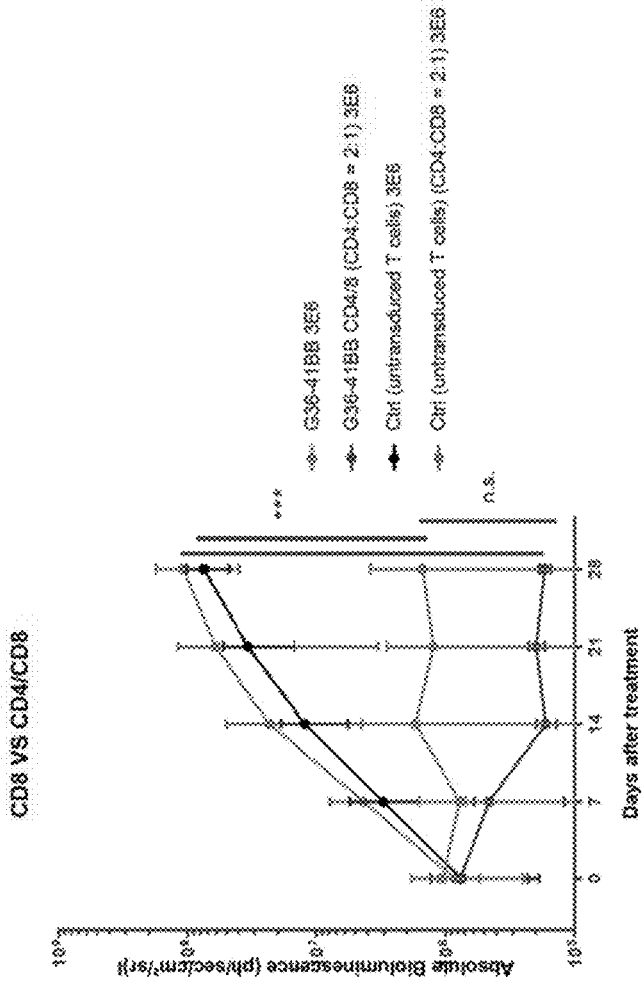

FIG. 34 shows CD8 vs. CD4/CD8.

Figure 35:
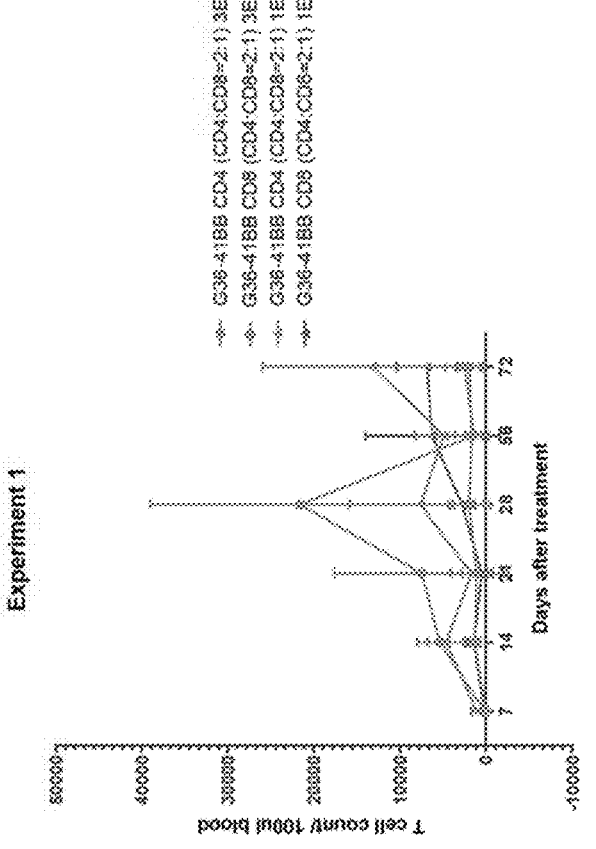

FIG. 35 shows CD4 and CD8 T cells expansion in vivo.

Figure 36:
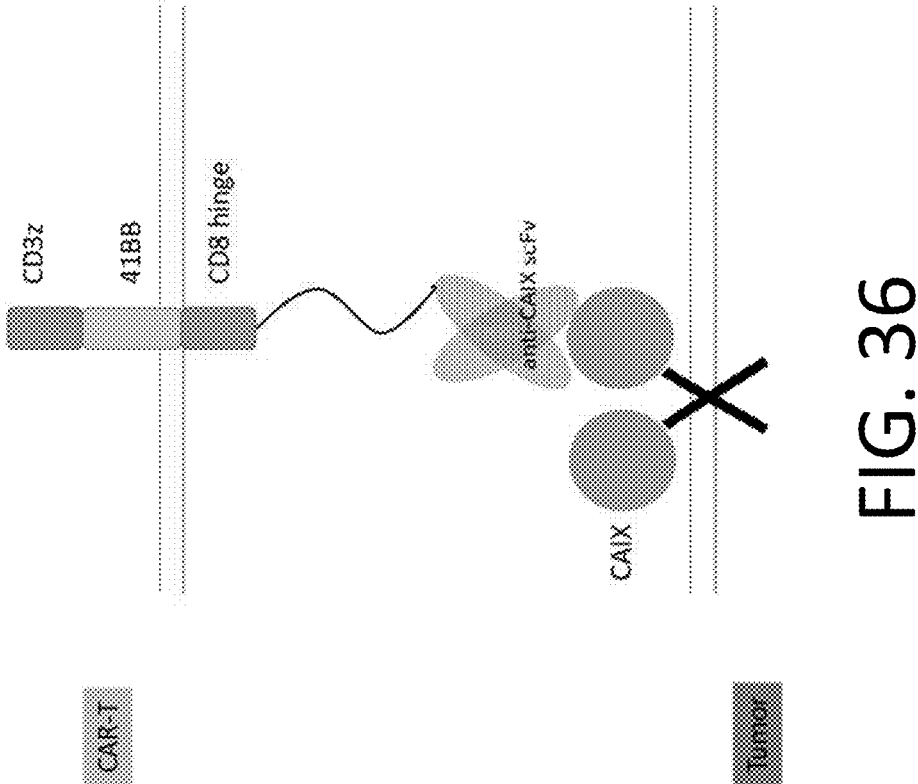

FIG. 36 shows a schematic of a fine-tuned anti-CAIX CAR-T which has been designed to limit on-target off-tumor effect. Without wishing to be bound by theory, lowering the affinity of anti-CAIX scFv, the CAR only recognizes the high density of CAIX on ccRCC. A series of anti-CAIX scFvs with various KDs were cloned into lentiviral vectors and corresponding CAR-T cells were generated and assessed the killing activity.

Figure 38:
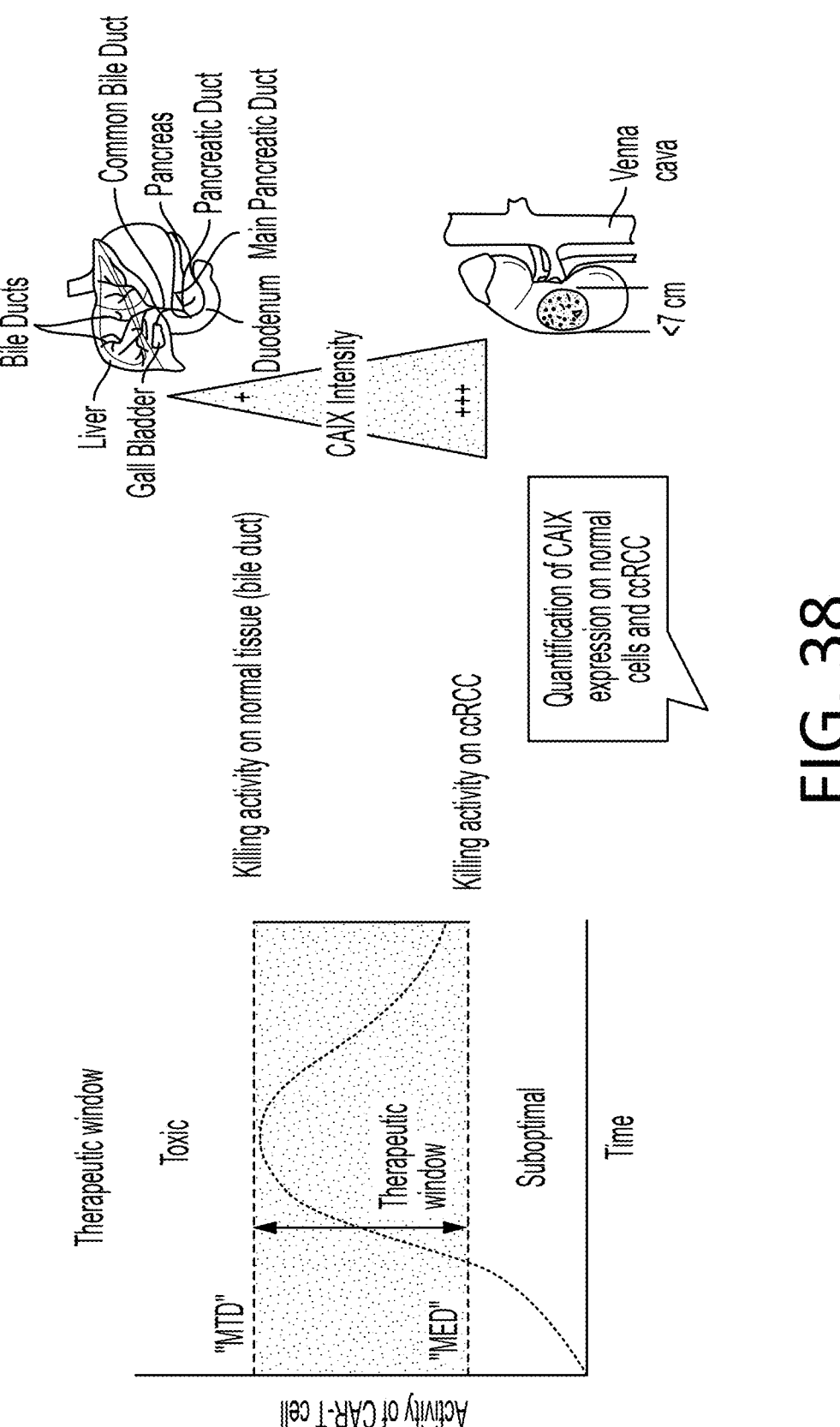

FIG. 37 is a schematic detailing the "therapeutic window". "Therapeutic window" is a term originally from pharmaceutical toxicology and can refer to a range of doses between efficacy and toxicity, achieving the highest therapeutic benefit without resulting in unacceptable toxicity; it is the range between the minimum effective dose (MED) and the maximum tolerated dose (MTD. This concept was applied to optimize CAR-T therapy. To expand the therapeutic window, we can fine tune the CAR affinity with the antigens by assembling the scFvs with different KDs in the CAR construct, such as from 1 nm to 100 nm. Ideally, after optimization, the CAR only recognize the high density antigens on tumor cells not the low density antigens on normal cells. Targeting antigens expressed exclusively on tumor cells or antigens that are expressed only on non-critical tissues widens the therapeutic window as direct toxicity on vital tissues would not occur. On the other hand, targeting antigens that are expressed in critical normal tissues/cells narrows the window by decreasing MTD FIG. 38 is a schematic describing expanding the therapeutic window to address on-target off-tumor side effects.

FIG. 39 shows IHC double staining of CAIX and CD70 on patient samples. We found that CD70 and CAIX are highly expressed and co-expressed on ccRCC. Thus, we choose CD70 as our second target.

Figure 40:
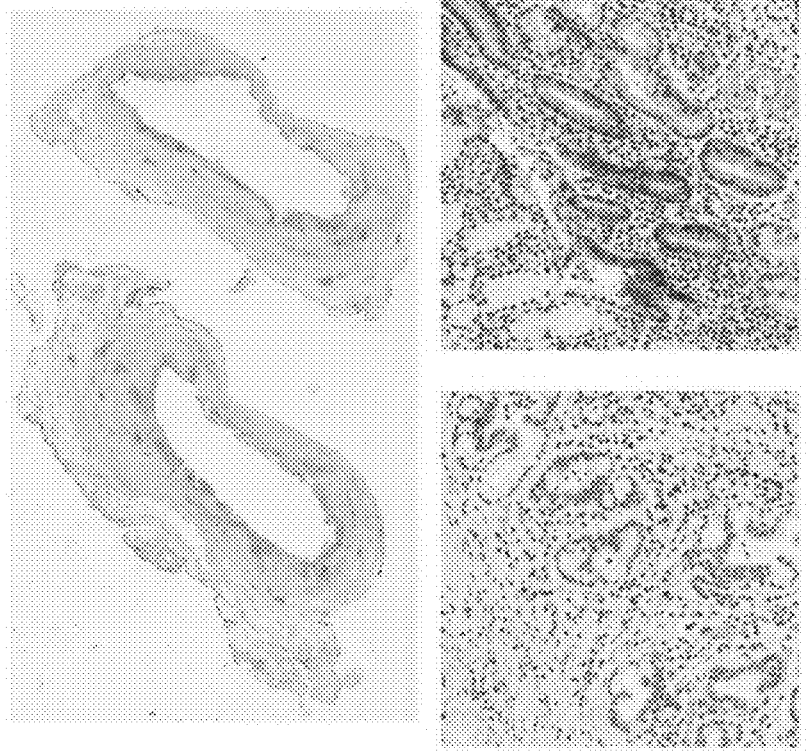

FIG. 40 shows IHC double staining of CAIX and CD70 on patient samples.

FIG. 41 shows a panel of scFvs against CAIX with different KD values from 1.49 nM to 99.58 nM as the table shows. Corresponding CAR-T cells were generated and screened by Celigo killing assay FIG. 42 shows that there is correlation between affinity of scFv and killing of CART cells, 19 CARs were divided into 4 groups according to the cytotoxicity and to be tested against skrc-59 cells with different expression levels of CAIX. G37, G39, G125>G10, G21, G36, G40, G45, G57, G62, G98, G106, G119>G6, G9, G17, G27, G28>G104.

FIG. 43 shows "Or" gating to capture tumor cell heterogeneity but not kill low target density healthy cells.

FIG. 44 shows CD70 can be an ideal target as the second target for our bispecific CAR since it's highly expressed on kidney cancer, especially clear cell renal cell carcinoma.

Figure 45:
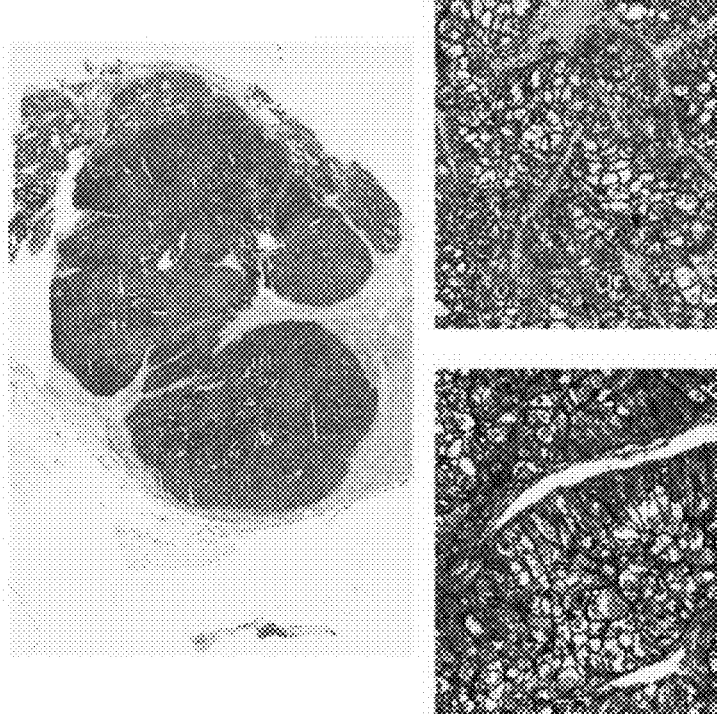

FIG. 45 shows IHC double staining of CAIX and CD70 on ccRCC patient samples. CD70 and CAIX are highly expressed and co-expressed on ccRCC. Thus, we choose CD70 as our second target.

FIG. 46 shows IHC double staining of CAIX and CD70 on ccRCC patient samples. CD70 and CAIX are highly expressed and co-expressed on ccRCC. Thus, we choose CD70 as our second target.

Figure 47:
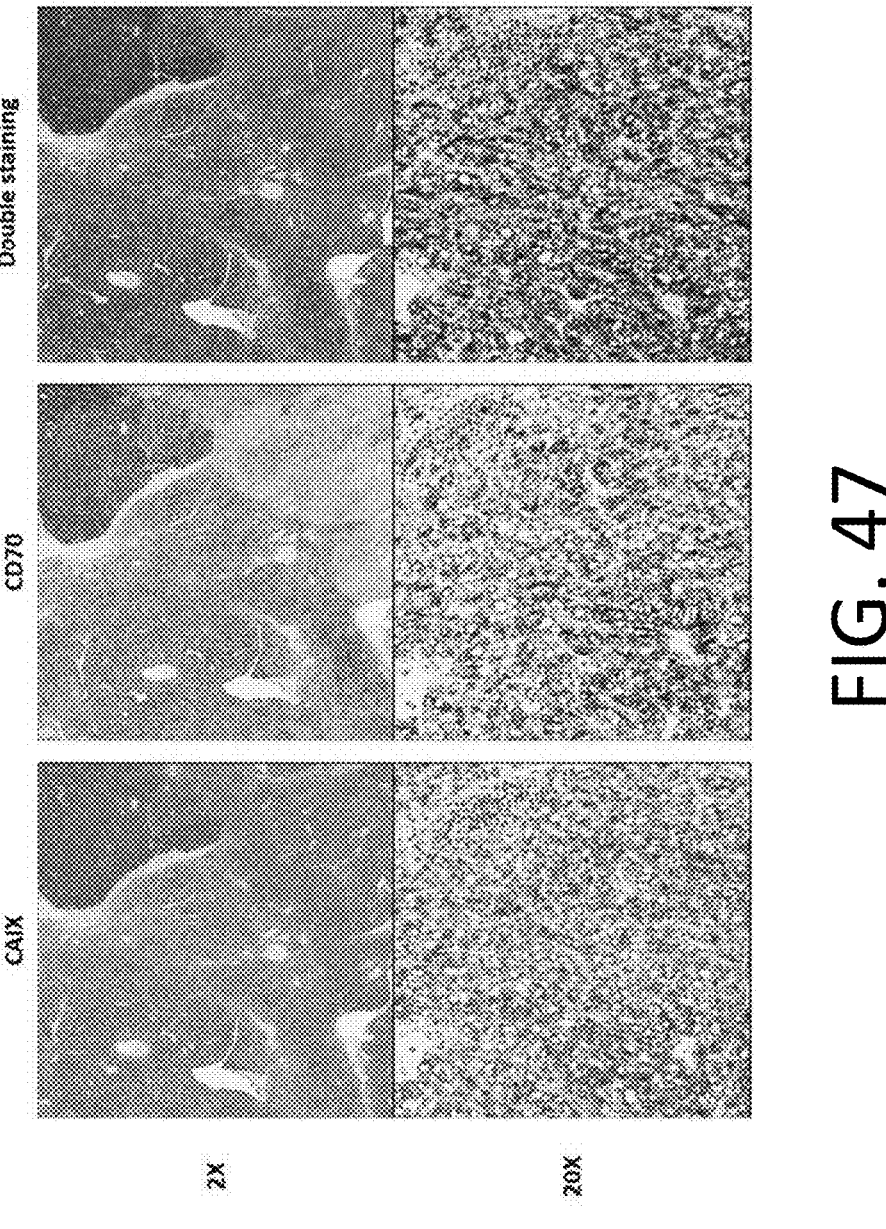

FIG. 47 shows CAIX and CD70 upregulated and co-expressed on ccRCC.

Figure 48:
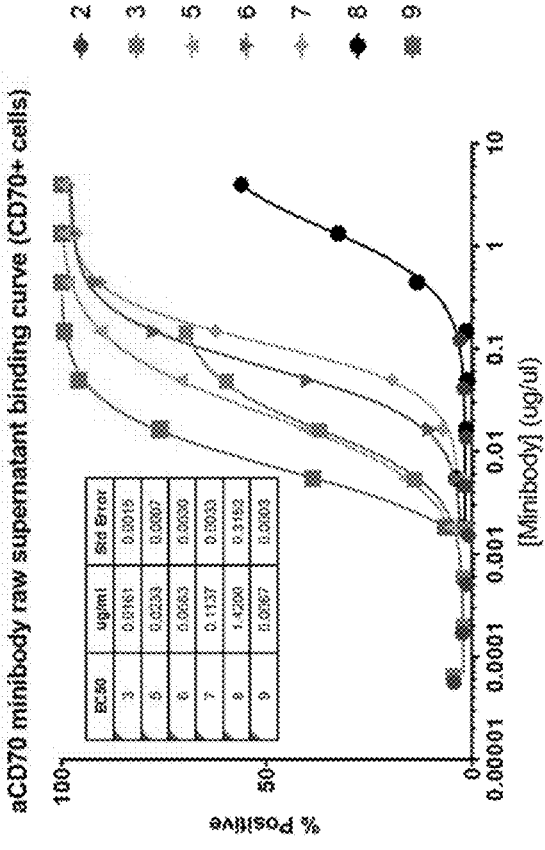

FIG. 48 shows anti-CD70 minibodies showed selective binding to CD70+ SKRC59 cells. By phage display (panned against CD70+ skrc-59 cells and subtracted against CD70-skrc-59 cells), we discovered a series of anti-CD70 minibodies which showed promising binding with CD70 positive ccRCC skrc-59 cells. Anti-CD70 minibodies were expressed via Expi293 cells in a 6 well plate. 3 days after transfection, the supernatant was harvested and IgG quantification ELISA (Bethyl) was conducted to approximate the concentration of minibody in the supernatant. This approximate concentration was used to normalize the supernatants for FACS binding curves. Staining was carried out via standard FACS staining protocol using an anti-hFc-APC secondary. One of the hits with killing activity (#9) is very nonspecific. The other two monoCARs which exhibit killing activity (#3, 7) show good specificity to CD70.

FIG. 49 shows anti-CD70 B7 CAR-T cells showed promising killing against CD70+ skrc-59 cells. By phage display (panned against CD70+ skrc-59 cells and subtracted against CD70-skrc-59 cells), we discovered a series of anti-CD70 minibodies which showed promising binding with CD70 positive ccRCC skrc-59 cells. Also, these hits were cloned into lentiviral vector and corresponding CART cells were conducted Celigo killing assay. From the screening, we found B7 as the candidate.

Figure 50:
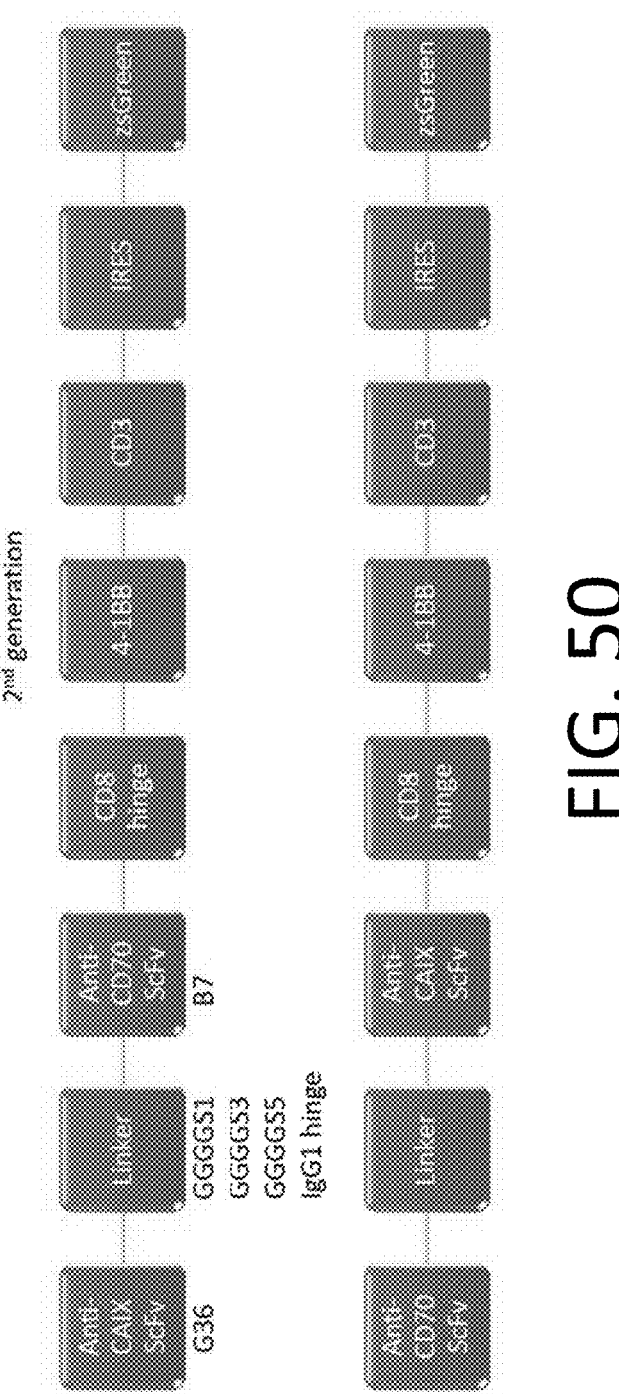

FIG. 50 shows bispecific CAR constructs. A series of constructs were established by using G36 as the anti-CAIX scFv and B7 as the anti-CD70 scFv in different rotations (or orientations) with different linkers. Figure discloses SEQ ID NOS 267 and 41-42, respectively, in order of appearance.

Figure 51:
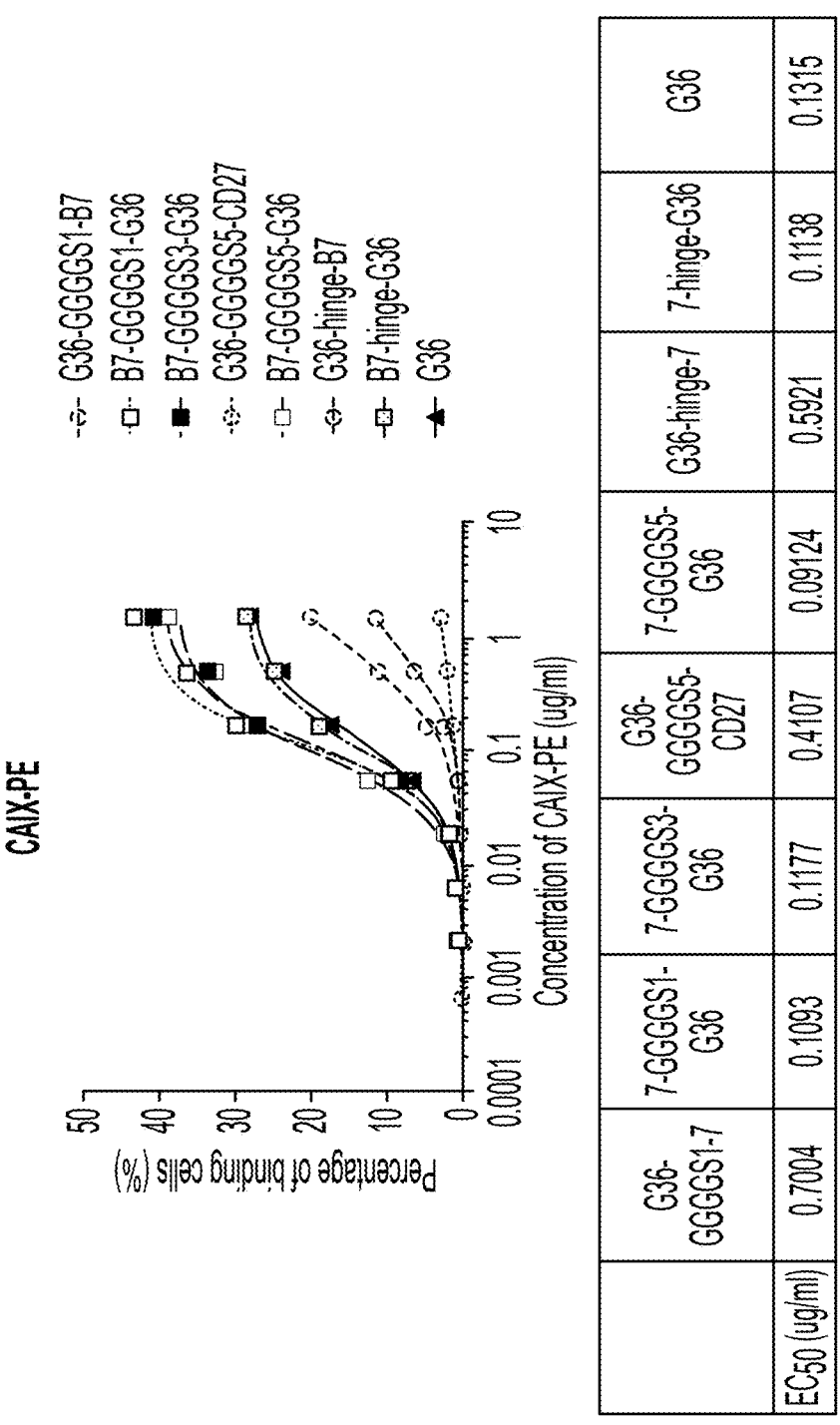

FIG. 51 shows that anti-scFv G36 prefer to be in the 2nd cassette after the linker. Transfect 293T cells with these 8 bispecific constructs and also corresponding monoCARs and stain with CAIX-PE. After normalization by transfect efficiency, it shows that different orientation of two scFvs influence the EC50 of anti-CAIX scFv binding. Anti-CAIX scFv G36 prefer to in the 2nd cassette after linker.

Figure 52:
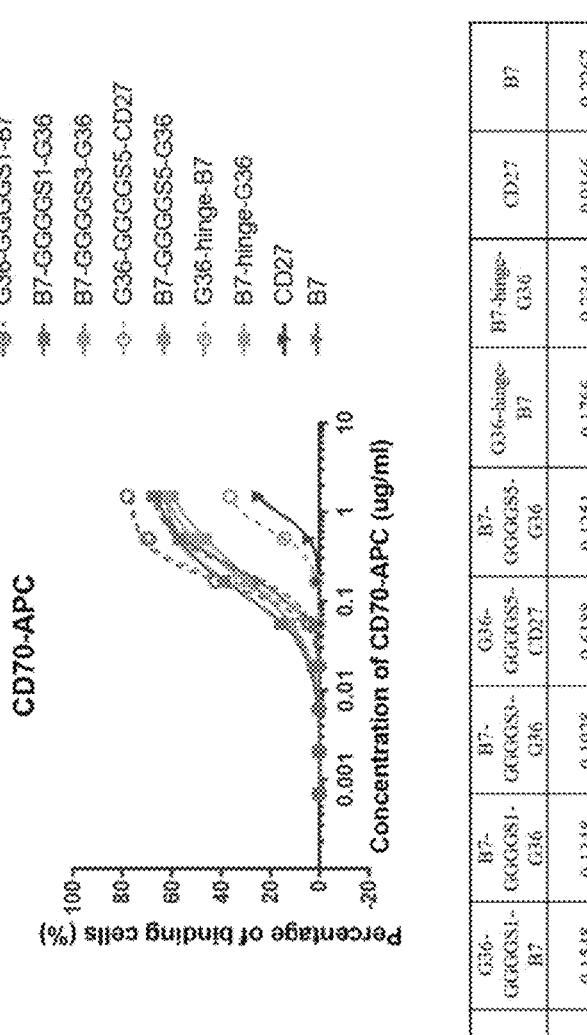

FIG. 52 shows that anti-CD70 scFv B7 has no preference. Transfect 293T cells with different constructs of dual CAR and perform the binding assay with APC labeled CD70 protein. After normalization by transfection efficiency, it shows that different orientation of two scFvs doesn't influence the EC50 of anti-CD70 scFv binding. Anti-CD70 scFv B7 doesn't have a significant preference.

Figure 53:
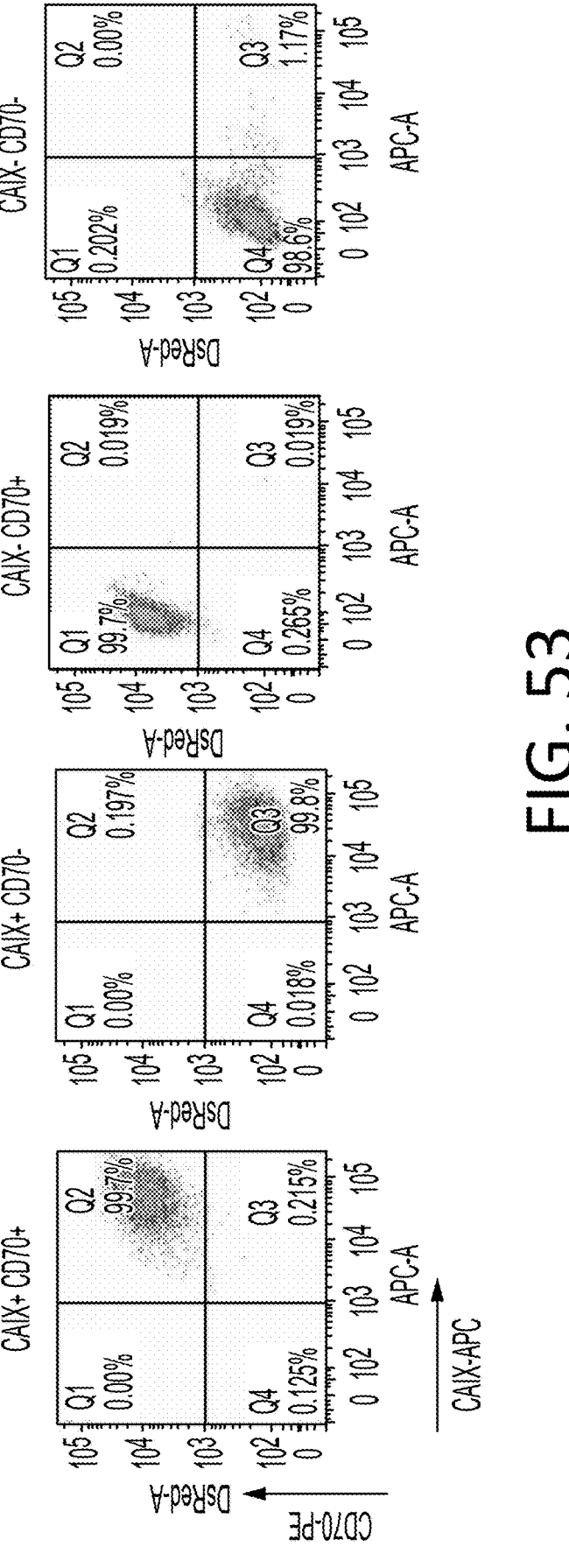

FIG. 53 shows that establishment of 4 CRISPR skrc-59 cell lines. For further evaluation in vitro, 4 CRISPR engineered skrc-59 cell lines were established with 4 different phenotypes, CAIX+CD70+, CAIX+CD70–, CAIX-CD70+, and CAIX-CD70–.

Figure 54:
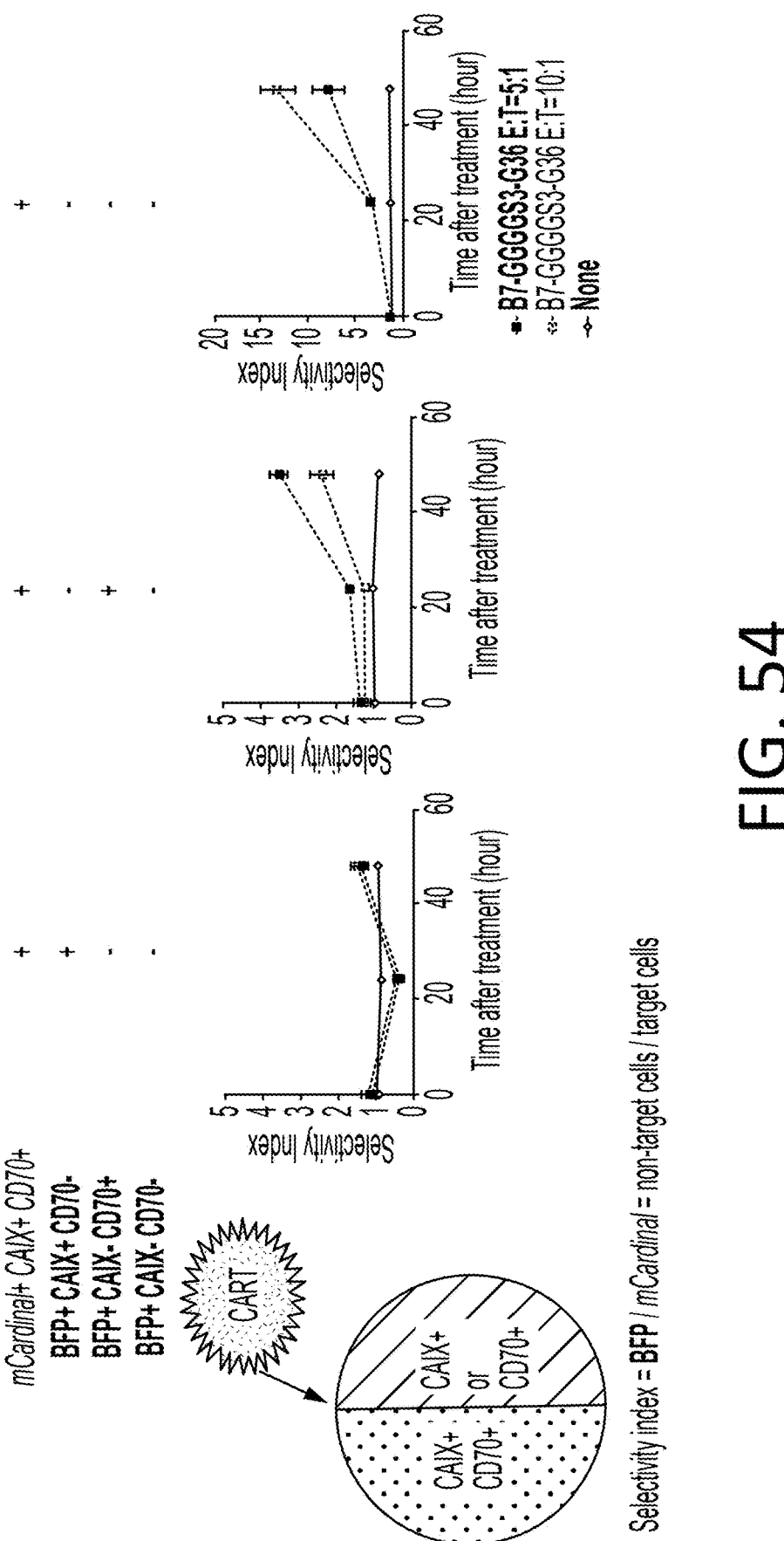

FIG. 54 shows B7-GGGGS3-G36 shows preferential killing. Take B7-GGGGS3-G36 CAR as example we performed selective killing assay on mixed CAIX+CD70+ dual positive cells, with CAIX+ or CD70+ single positive cells, or CAIX-CD70-cells. It showed that B7-GGGGS3-G36 CAR-T cells have preferential killing activity against the targeted cells (CAIX+CD70+) than non-targeted cells (CAIX+CD70–, CAIX-CD70+, CAIX-CD70–). After certain time incubation, the number of double positive cells and single positive cells were measured through Celigo. And we can see that B7-GGGGS3 has limited selective index on CAIX+CD70+ while mixed with CAIX+ cells.

FIG. 55 shows that B7-GGGGS3-G36 shows preferential killing. 4 different CRISPR engineered skrc-59 cells were transduced with BFP fluorescence group. Cells were mixed with 1:1:1:1 ratio and were treated with B7-GGGGS3-G36 CAR-T cells or culture medium. After treatment, stain cells with PE labeled anti-CD70 antibody and APC labeled anti-CAIX antibody and, perform flow cytometry. It showed that B7-GGGGS3-G36 has selective killing to CAIX+CD70+ cells whose population is reduced from 26.7% to 18.5%. In this selective killing data from FACS, it showed that B7-GGGGS3-G36 has selective killing to CAIX+CD70+ cells whose population is reduced from 26.7% to 18.5%.

Figure 56:
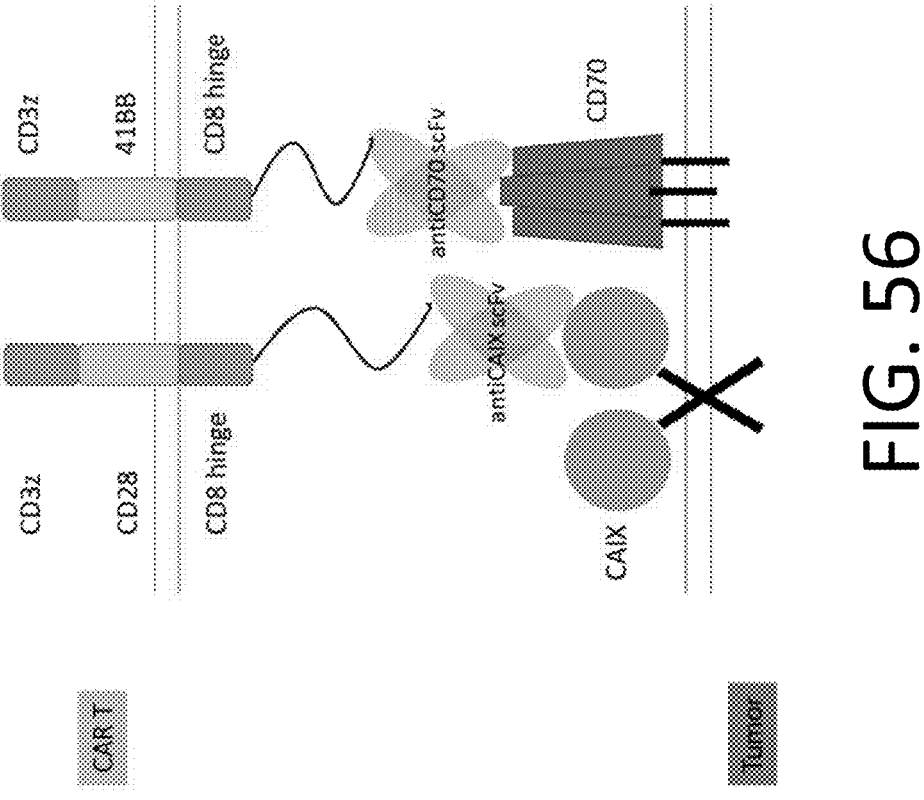

FIG. 56 shows a schematic of a bispecific split CAR T. Anti-CD70 and anti-CAIX scFvs were expressed on cell surface with different costimulation domains. See, for example, dual (split) CAR T, Nat Rev Cancer 16 (9): 566-81.

Figure 57:
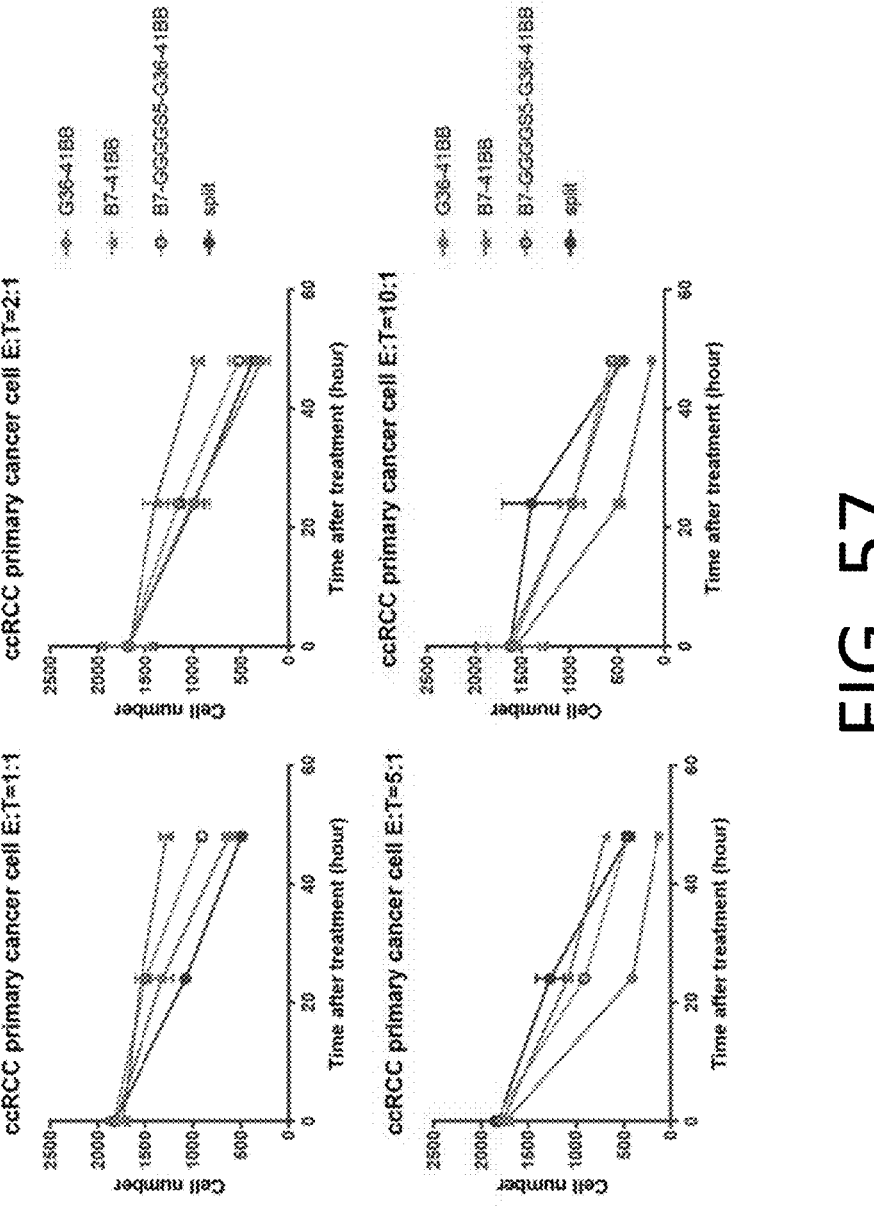

FIG. 57 shows split CAR killing on ccRCC primary cancer cell. Split CAR T cells were assessed killing activity on primary ccRCC cancer cells with monoCAR T and Tandem CAR T cells. It showed that split CAR achieved a superior killing at low E: T ratio, like 1:1 ratio.

FIG. 58 provides multiple sequence alignment of amino acid sequences of anti-carbonic anhydrase IX (G250) scFv clones. Figure discloses SEQ ID NOS 268, 127, 116, 116, 269, 129, 145, 137, 116, 147, 120, 131, 141, 114, 114, 123, 133, 136, 139, 129, 151, 153, 270, 128, 117, 150, 113, 130, 146, 138, 135, 148, 271, 132, 142, 115, 122, 272, 134, 134, 140, 144, 152, and 154, respectively, in order of appearance.

FIG. 59 provides alignment of human and mouse CAIX amino acid sequences. Figure discloses SEQ ID NOS 273-274, respectively, in order of appearance.

Figure 60:
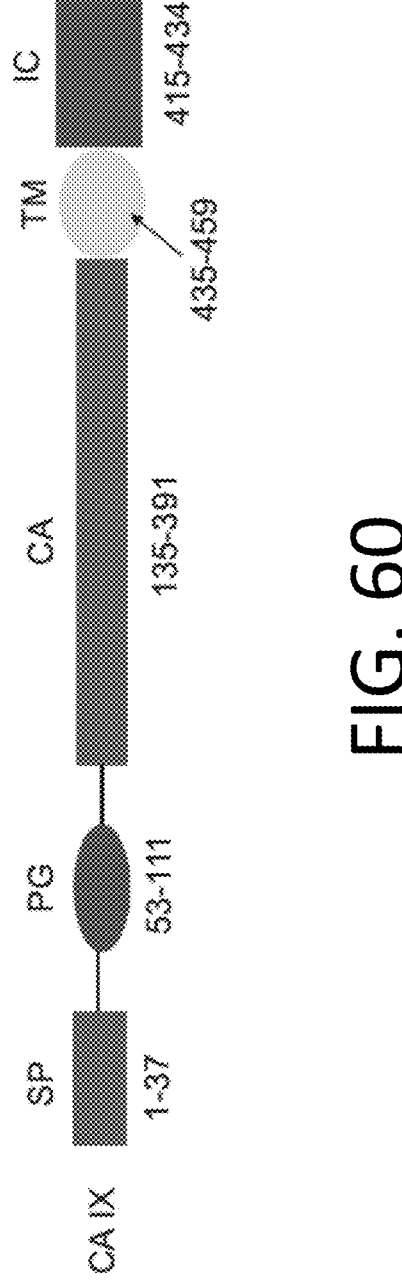

FIG. 60 provides structure of carbonic anhydrase IX (G250).

Figure 61:
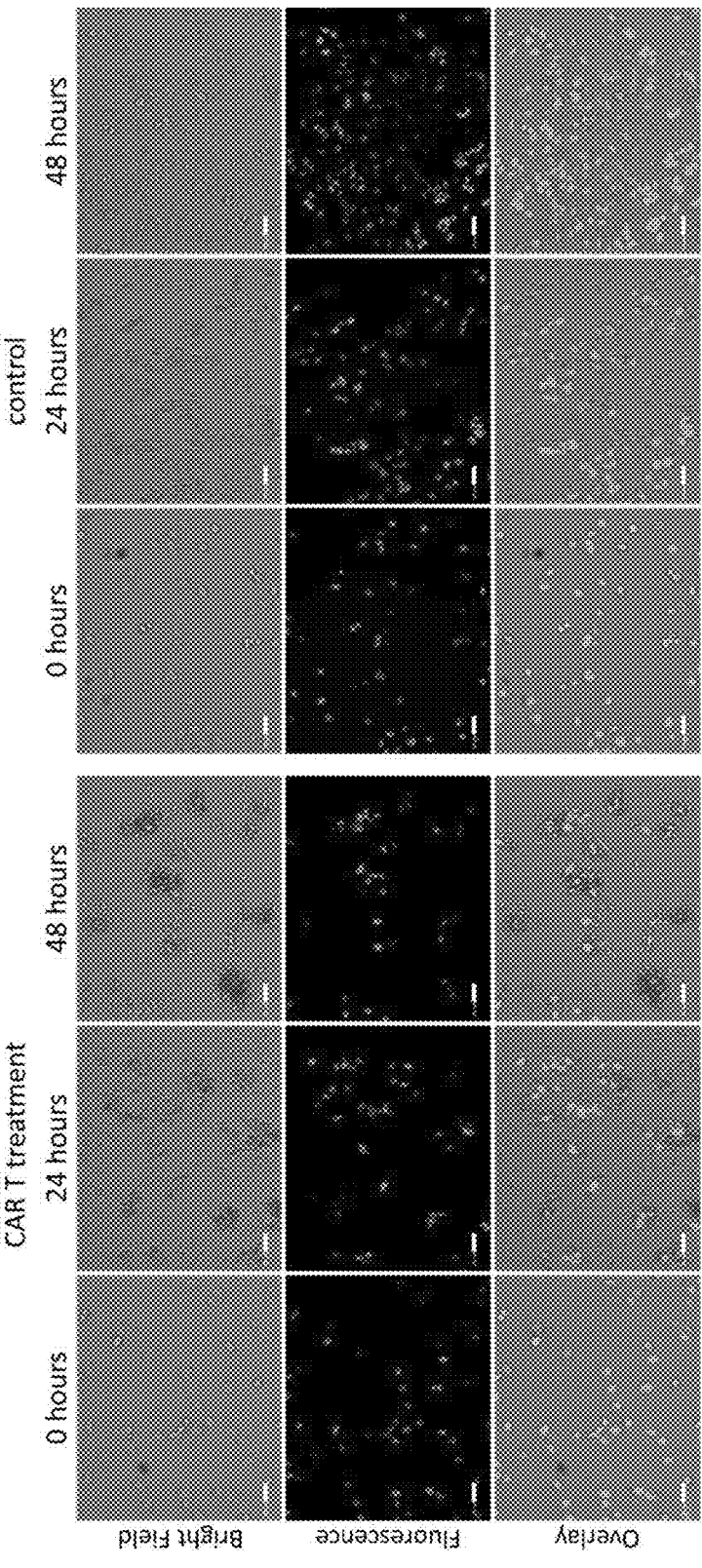

FIG. 61 shows CAR T cell killing assay of Skrc-59 transduced cells. Celigo image cytometry is shown.

Figure 62:
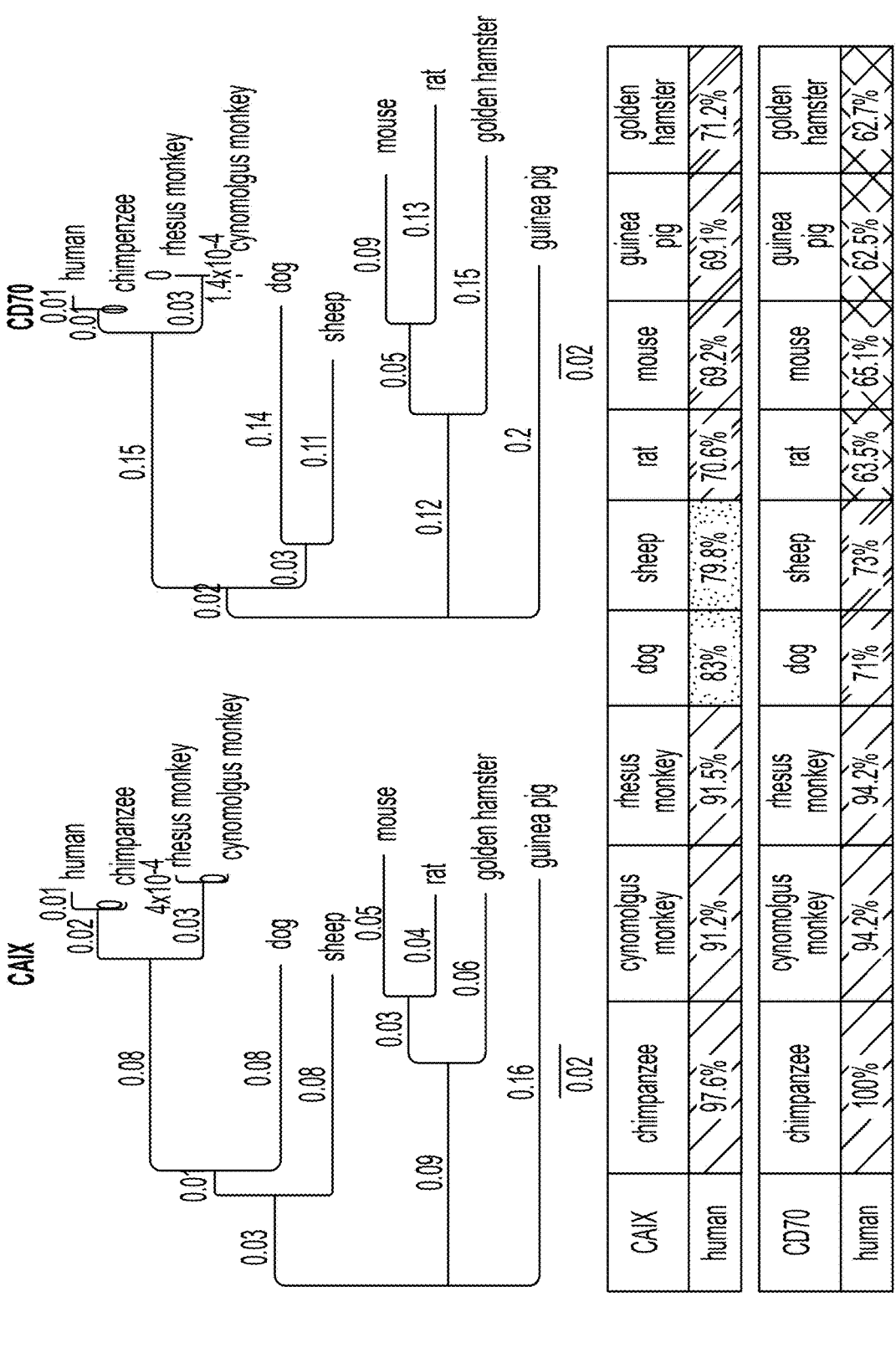

FIG. 62 shows homology study of 10 different species. Tree: distance on each branch equals number of differences between sequences (e.g. 0.1 means 10% differences between two sequences); distance between 2 species equals sum length of all branches connecting them. homology >60%→potential cross reactivity.

Figure 63:
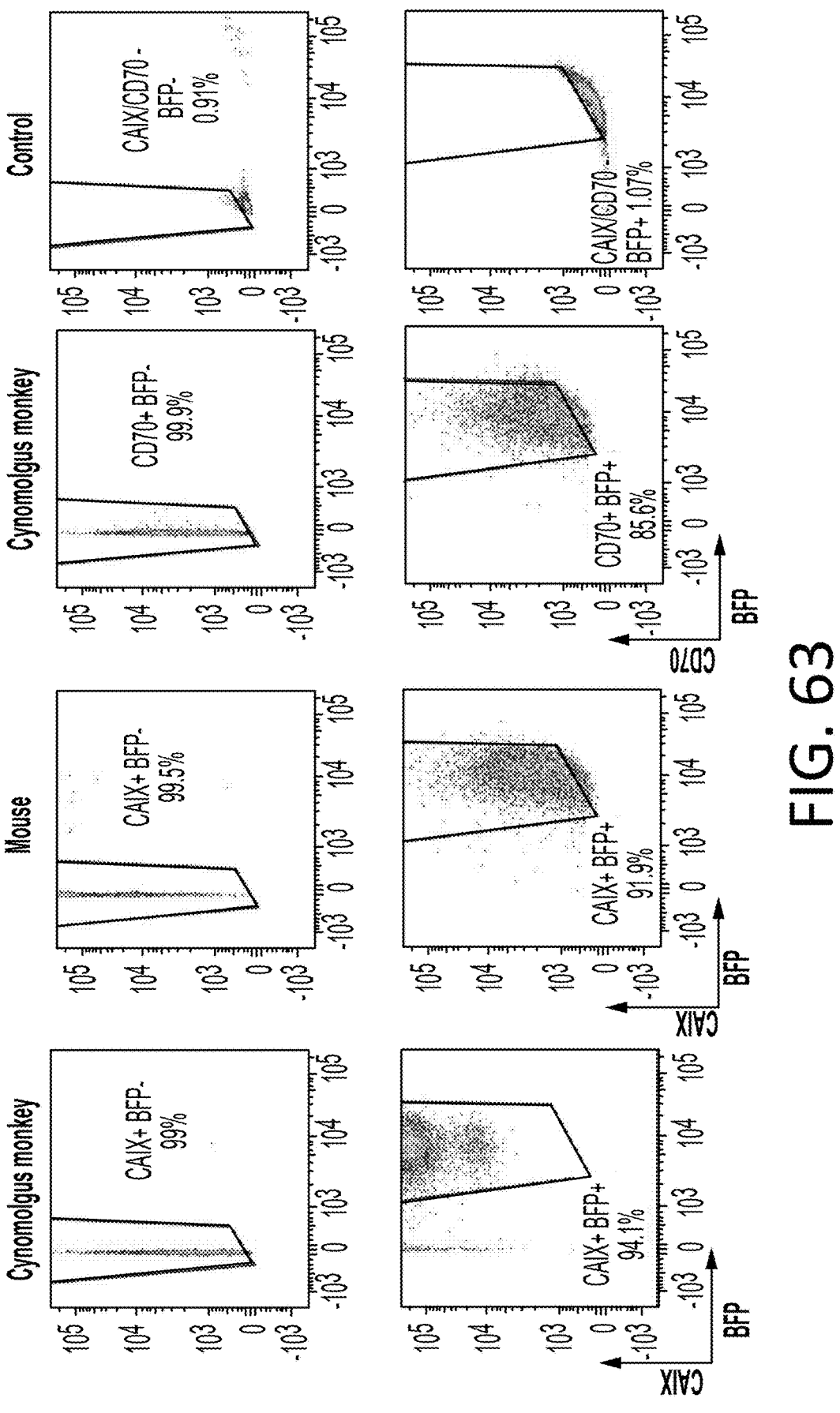

FIG. 63 shows establishment of skrc-59 stable cell lines expressing CAIX or CD70 from different species. CRISPR knock out CAIX-/CD70-skrc-59 cells→transduced with the 10 different constructs (CD70 or CAIX from the 5 different species)→sorted by FACS. Half transduced with BFP (for Celigo). Stained with commercial antibodies.

Figure 64:
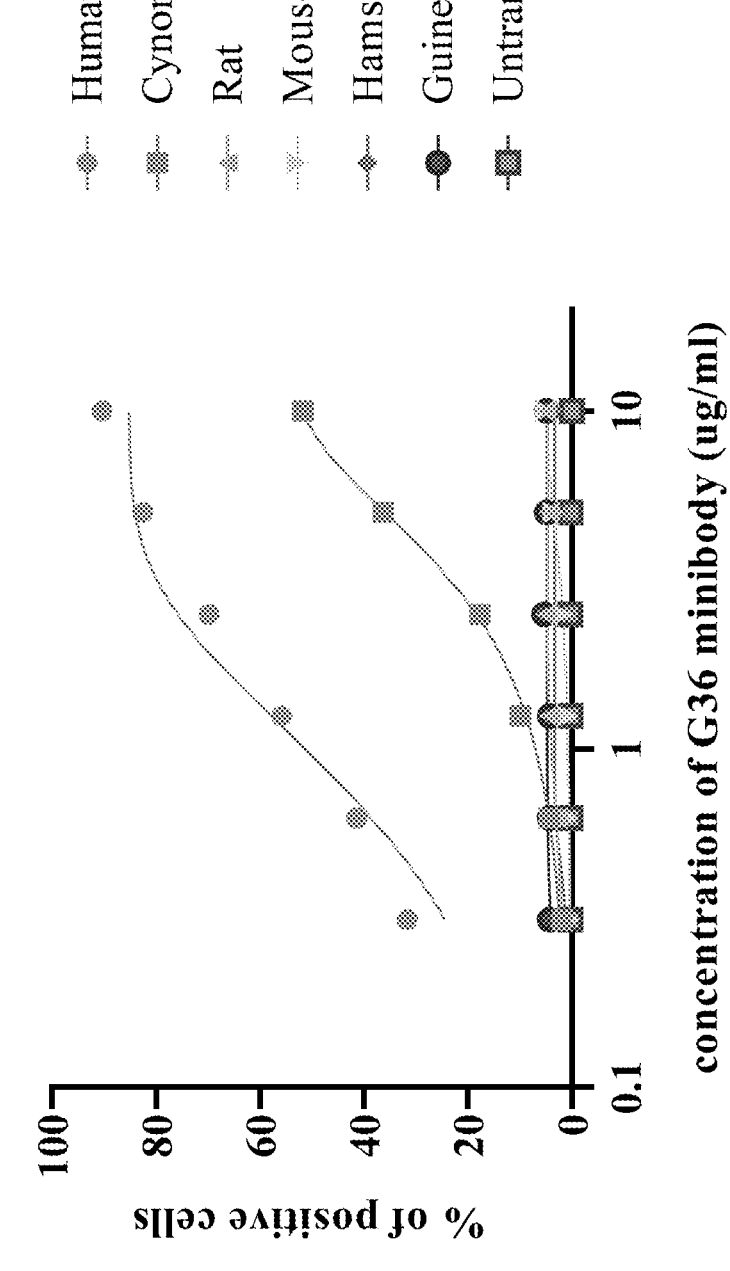

FIG. 64 shows binding assay of anti-CAIX (G36) scFv. Normalized with the binding data of commercial antibodies. Analyzed using a non-linear regression and a log (agonist) vs. response model.

Figure 65:
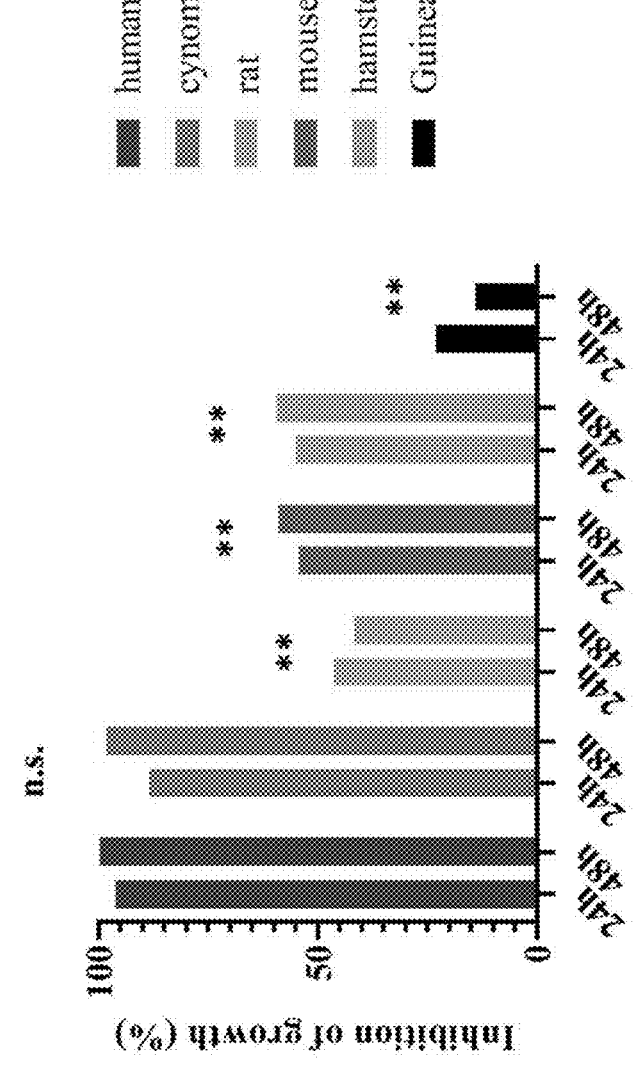

FIG. 65 shows killing assay of anti-CAIX (G36) CAR T cells. Monkey 100% (same killing as human, cross reactive); mouse, hamster 50% (significant killing).

Figure 66:
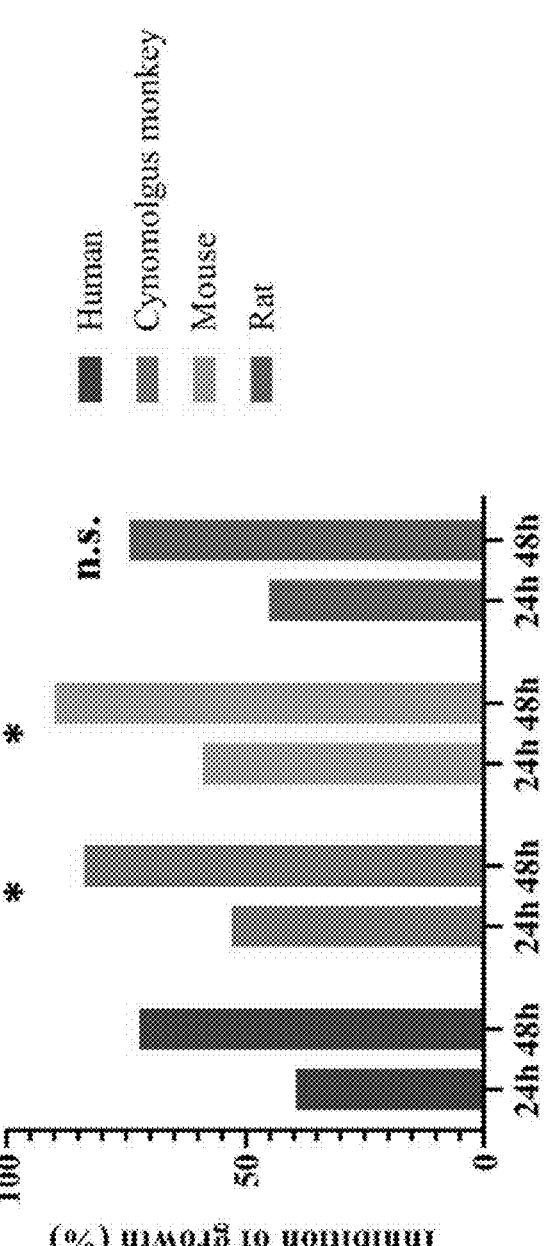

FIG. 66 shows killing assay of anti-CD70 (B7) CAR T cells.

Figure 67:
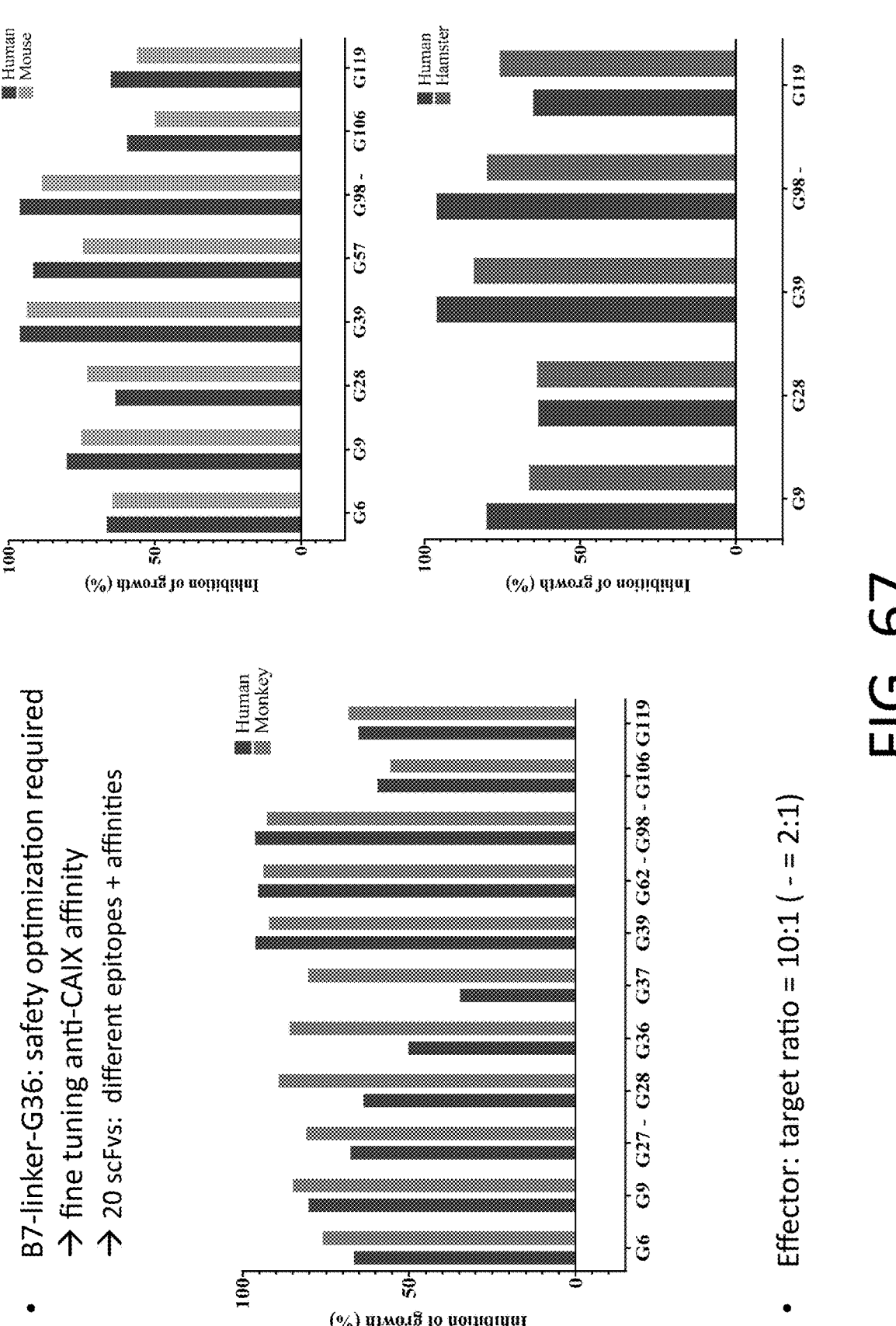

FIG. 67 shows killing assay of 20 different anti-CAIX CAR T cells.

FIG. 68 shows fold change killing assay G36 E: T 10:1.

FIG. 69 shows killing assay G36 E: T 5:1.

Figure 70:
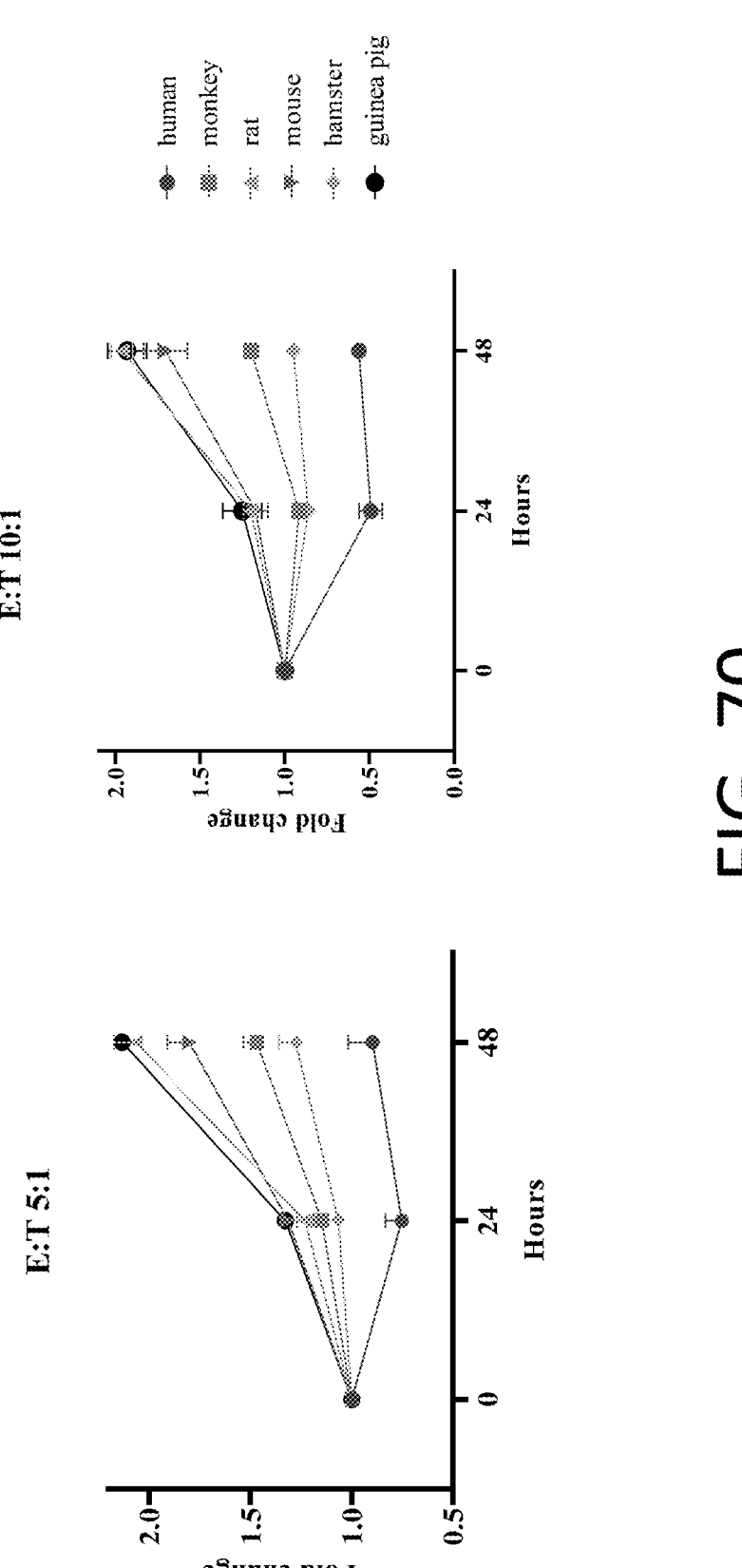

FIG. 70 shows killing assay G36 n=2.

Figure 71:
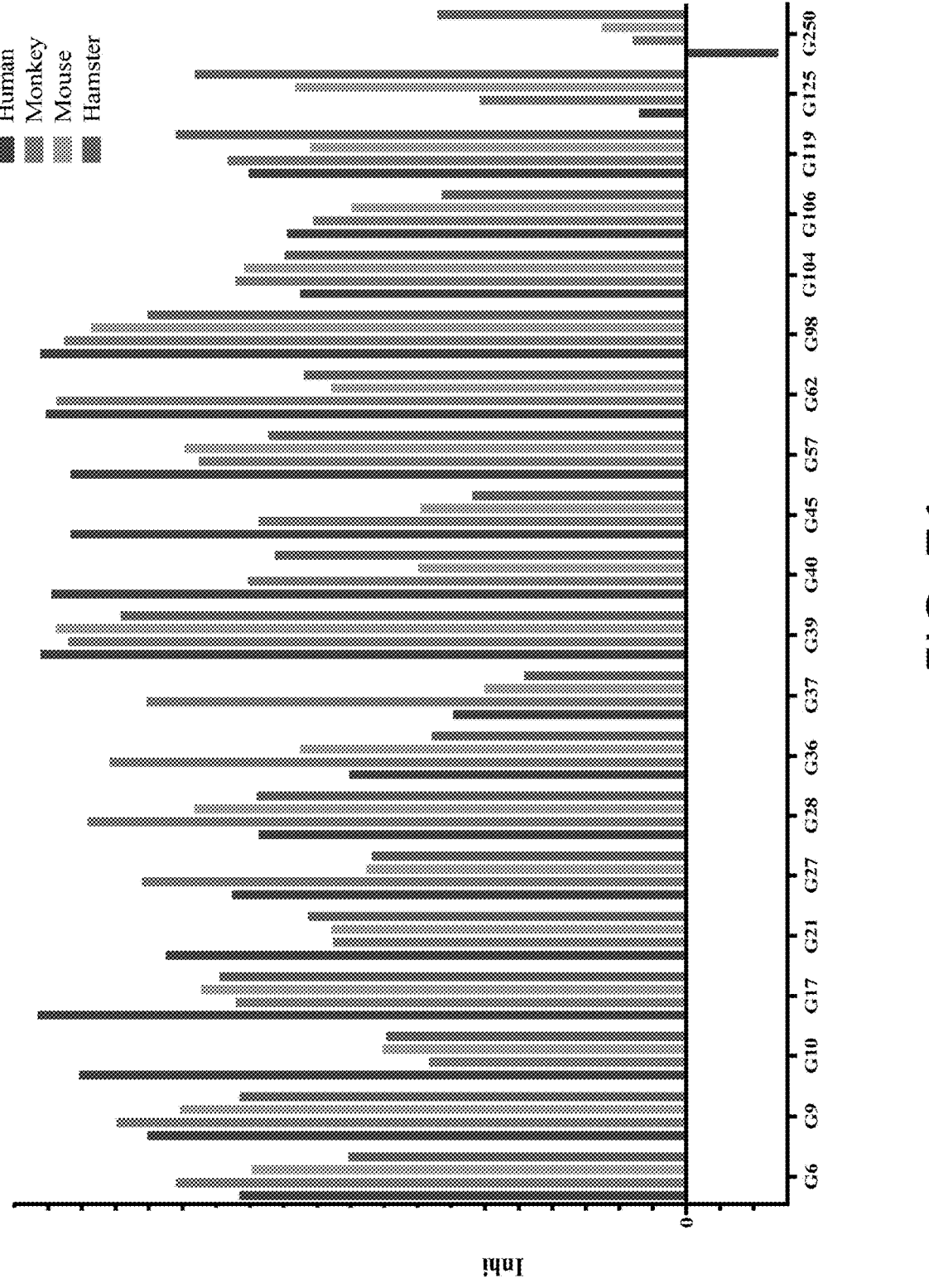

FIG. 71 shows killing assay 20 anti-CAIX scFvs.

Figure 72:
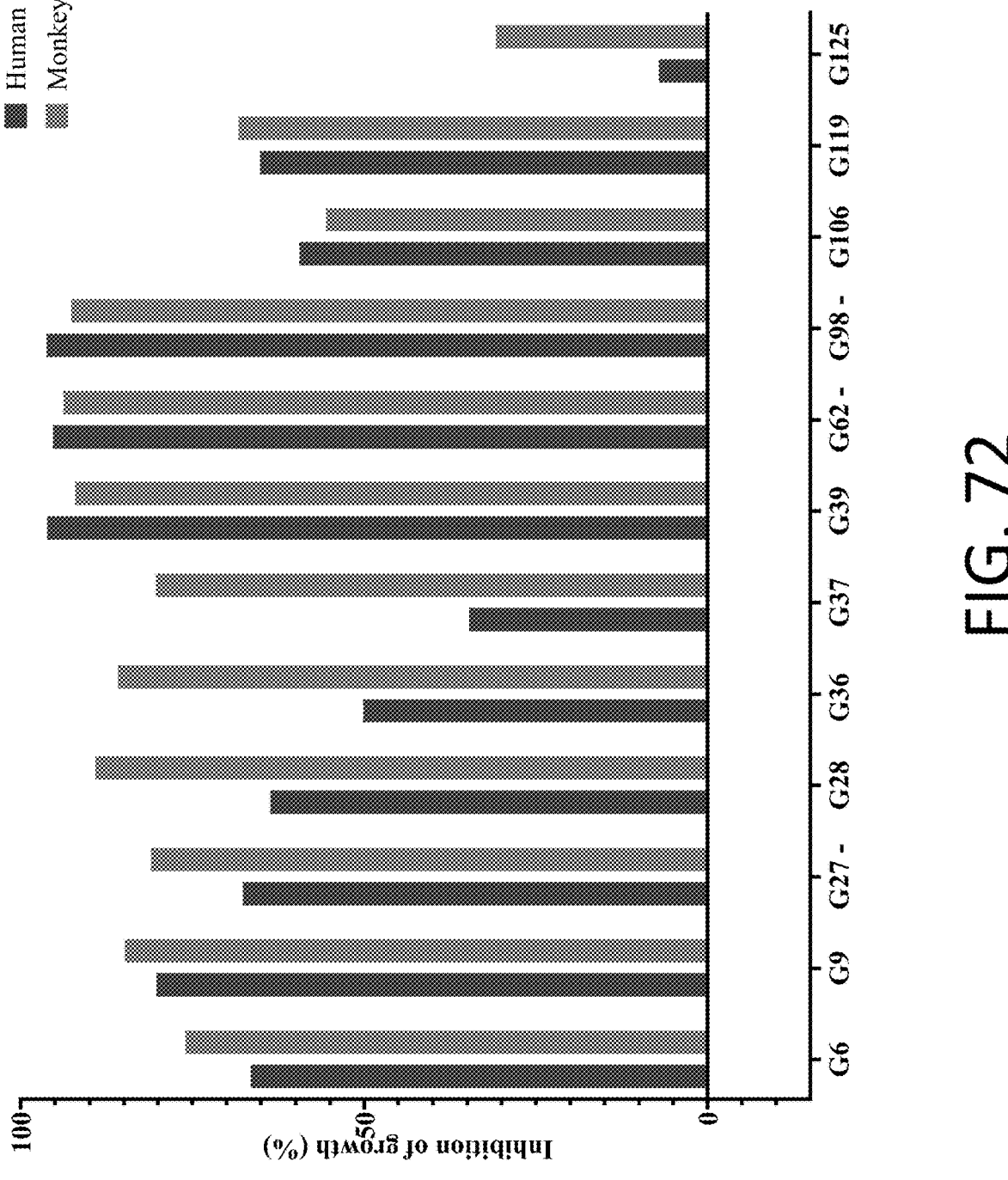

FIG. 72 shows all candidates monkey.

Figure 73:
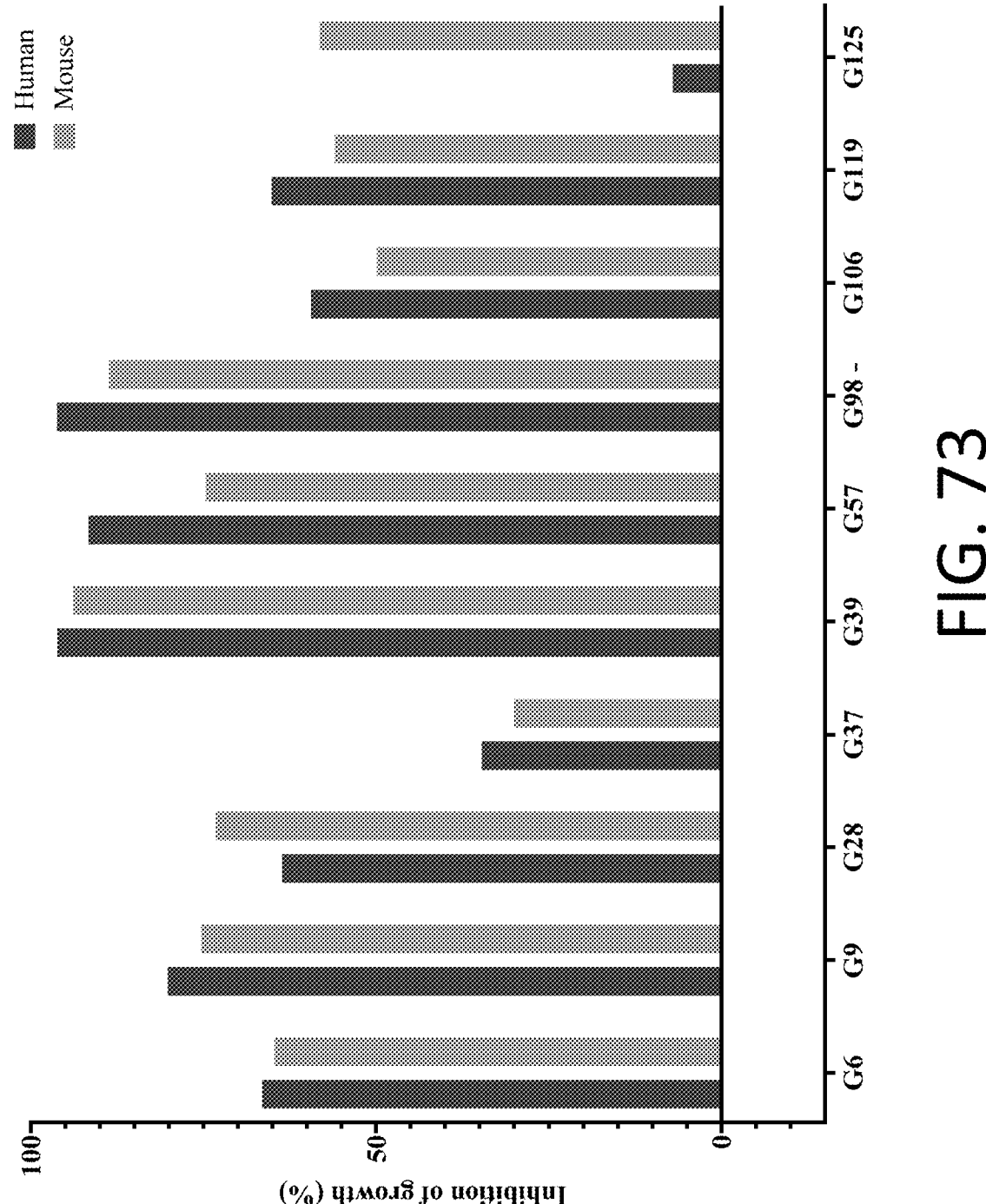

FIG. 73 shows all candidates mouse.

Figure 74:
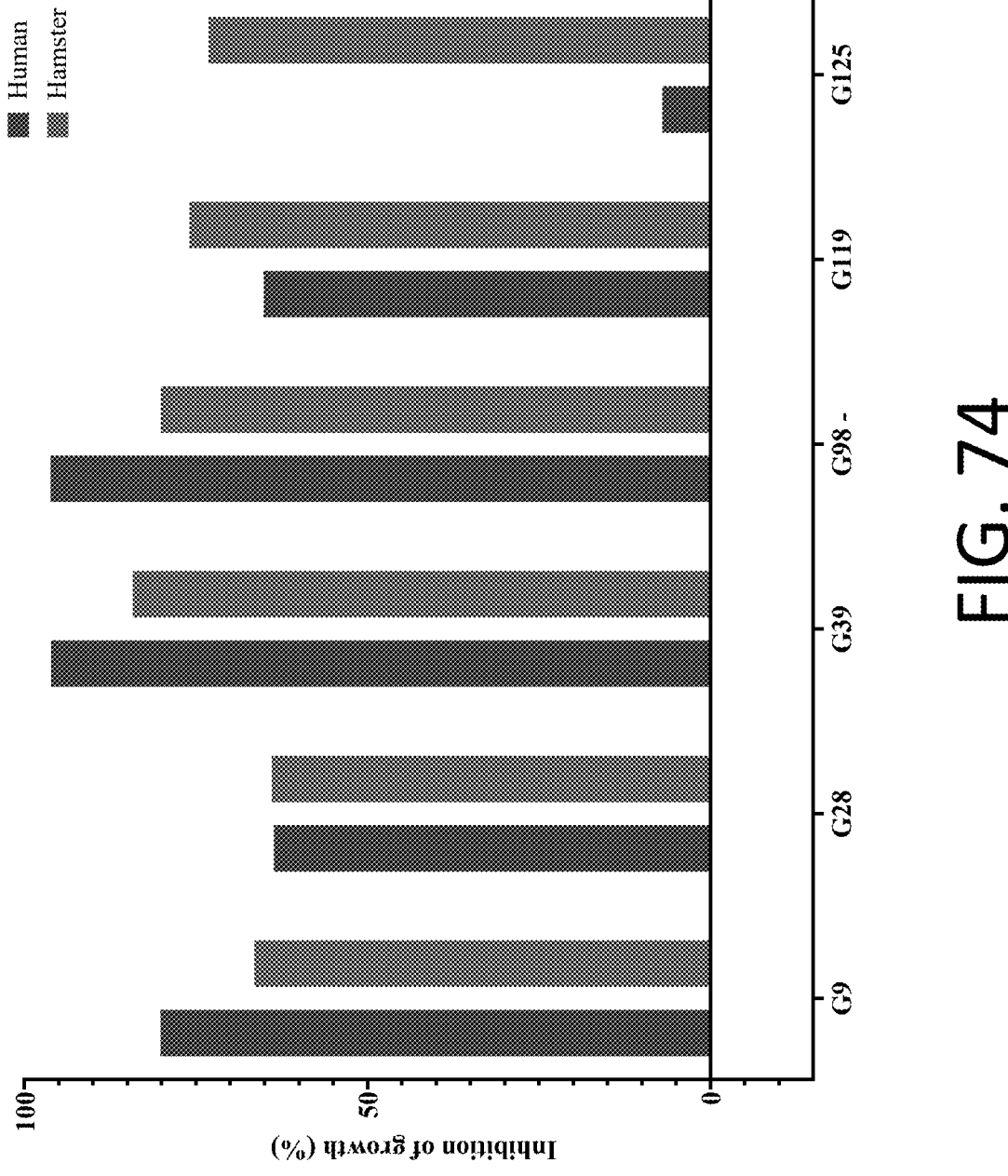

FIG. 74 shows all candidates hamster.

FIG. 75 shows fold change B7 killing assay.

FIG. 76 shows the amino acid sequence and germline alignment of anti-cd70 antibodies. Figure discloses SEQ ID NOS 275, 190, 276, 191, 277, 185, 278, 187, 279, 183, 280, 184, 277, 181, 281, 182, 277, 185, 282, 186, 283, 188, 284, and 189, respectively, in order of appearance.

Figure 77:
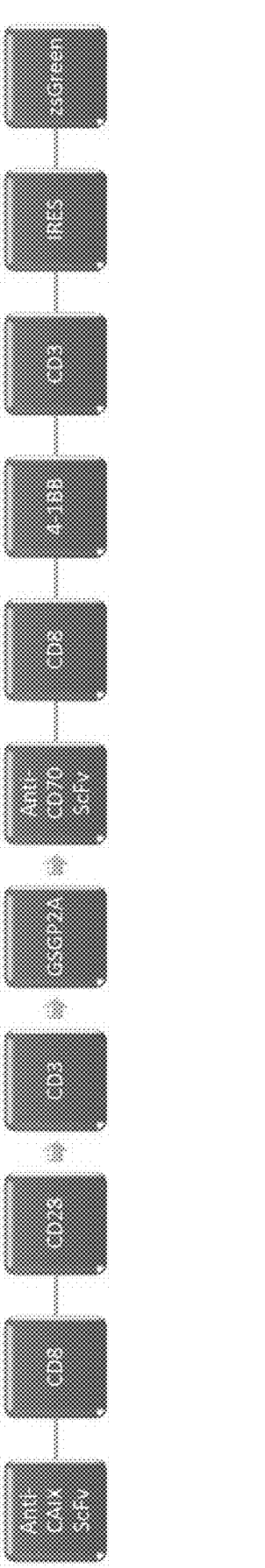

FIG. 77 shows a nucleic acid construct of a split car.

FIG. 78 shows the amino acid sequence and germline alignment of anti-PDL1 and anti-PD1 sequences. Figure discloses SEQ ID NOS 279 and 285-291, respectively, in order of appearance.

FIG. 79 shows the amino acid sequence and germline alignment of anti-CAIX antibodies. Figure discloses SEQ ID NOS 277, 118, 292, 119, 293, 125, 294, and 126, respectively, in order of appearance.

Figure 80:
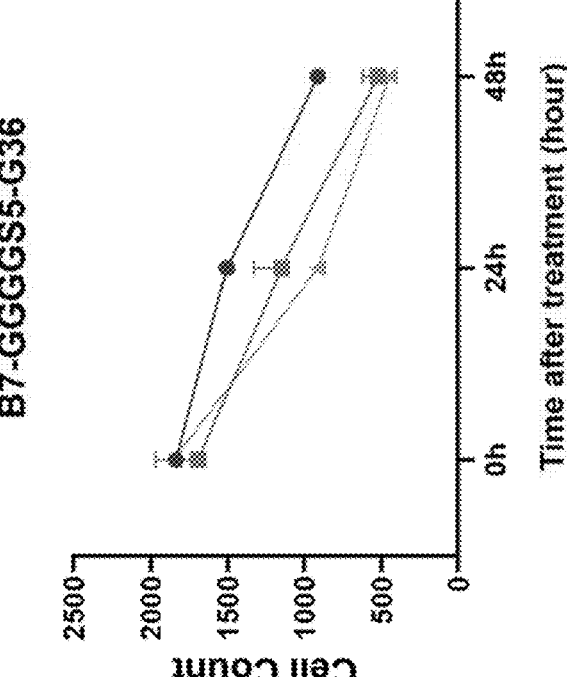

FIG. 80 shows tandem CAR B7-GGGGS5-G36 cytotoxicity.

FIG. 81 shows the amino acid sequence and germline alignment of anti-TIGIT antibodies. Figure discloses SEQ ID NOS 295-296, 351, 297-299, 351, 300-302, 351, 303, 295, 304-308, 352, 309, 296, 299, 302, 304, 308, 297, 300, 303, 306, and 309, respectively, in order of appearance.

FIG. 82 shows the anti-PD-L1 amino acid sequences. Figure discloses SEQ ID NOS 310-311, 311, 311, and 311-316, respectively, in order of appearance.

FIG. 83 shows the anti-PD1 nucleic acid and amino acid sequences. Figure discloses SEQ ID NOS 317-346, 310, 333, 347, 341, 345, 320, 348-349, 342, and 350, respectively, in order of appearance.

DETAILED DESCRIPTION OF THE INVENTION

Chimeric Antigen Receptor (CAR) T-cell therapies represent an exciting area of discovery that has already revolutionized treatment in several blood-borne cancers. In Acute Lymphoblastic Leukemia (ALL), for example, remission rates were demonstrated to be 80 to 90 percent, leading to FDA approval. The technology can utilize a patient's own immune cells to fight their cancer by engineering them to better recognize particular proteins located on the cancer cells. For example, after that change has been effected in the lab, the immune cells are grown extensively in the lab, multiplying their cancer-killing potential, and finally infused back to the patient where they can attack cancer wherever it is in the body with increased efficacy and numbers.

CAR T-cell therapies have been largely elusive in solid tumors such as renal cell carcinoma (RCC) because the cancer cells create a tumor microenvironment that turns off immune penetration. We have successfully created and advanced mouse models that can provide crucial information for this technology. Our approach relies upon the creation of humanized RCC in mice that can be studied to better understand their immunologic fingerprint. Examining how human RCC behaves in mice has allowed the lab to identify antigens, such as Carbonic Anhydrase IX [CAIX] and CD70, that could be targeted using CAR T-cell therapy in humans and other mammals. To large degree, these two antigens, namely CAIX and CD70, are only found together on kidney cancer tumor cells, allowing the immune system to attack locally with minimal impact on healthy tissue. There have also been advances in counteracting the immunosuppressive effects within the microtumor environment by engineering T-cells that produce and/or secrete checkpoint inhibitor antibodies. Pairing these approaches could allow for dramatically improved efficacy within the tumor microenvironment.

Described herein are CAR T-cells that target CAIX and CD70, for example, that can be administered to animals with close monitoring for changes in the tumor microenvironment and subsequent anti-tumor effects. The skilled artisan will recognize that these approaches can also be combined with currently available technology, such as the use of immune checkpoint inhibitors, that have already positive impacted the RCC clinical landscape.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Chimeric Antigen Receptor (CAR) T-cell Therapies

Figure 1:
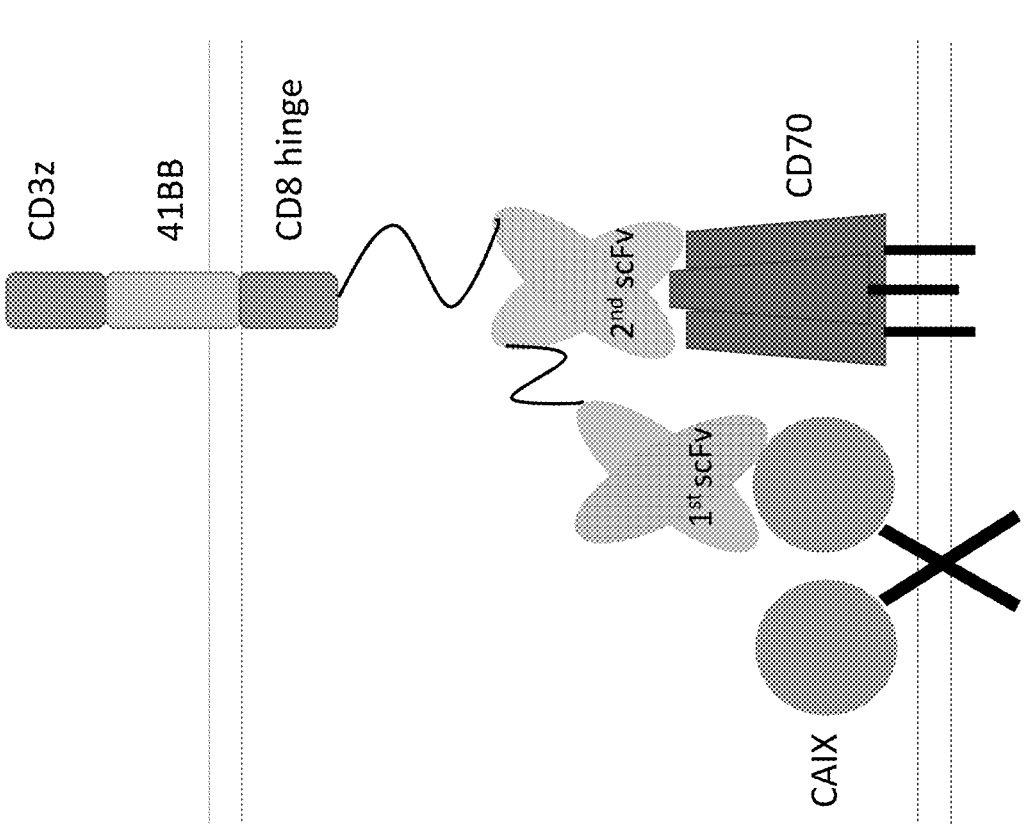
FIG. 1 shows a schematic of bispecific tandem CAR T anti-CD70 and anti-CAIX scFvs were combined in different permutations by changing the order of the two targeting scFvs with various linkers and hinges connected to a costimulatory domain (non-limiting examples comprising CD28, 41BB, CD28-41BB, or 41BB-CD28) and an activating domain (such as, CD3). In order to elevate the efficacy (such as, address heterogeity) and safety (such as, limit on-target off-tumor effect), the 2nd generation CAR T cell factories can be designed with the introduction of the second cassette anti-CD70 scFv.

Chimeric-antigen receptor (CAR) T-cell therapies redirect a patient's T-cells to kill tumor cells by the exogenous expression of a CAR. Referring to FIG. 1, for example, a CAR is a membrane spanning fusion protein that links the antigen recognition domain of an antibody or fragment to the intracellular signaling domains of the T-cell receptor and co-receptor. For example, chimeric antigen receptors fuse antigen-specific antibody fragments to T-cell co-stimulatory domains and the CD3 zeta intracellular signaling domain, allowing for the re-direction of T-cells towards an antigen presented on a cell of interest, for example, onto tumor cells.

The term "antibody" herein is used in the broadest sense and can refer to immunoglobulin molecules and immunologically active portions of immunoglobulin (Ig) molecules, i.e., molecules that contain an antigen binding site that specifically binds (immunoreacts with) an antigen. "Specifically binds" or "immunoreacts with" can refer to the antibody reacting with one or more antigenic determinants of the desired antigen and does not react with other polypeptides. Antibodies of the disclosure can include, but are not limited to, polyclonal, monoclonal, humanized, fully human, bispecific, multispecific, chimeric, dAb (domain antibody), single chain antibodies, Fab, Fab' and F(ab') 2 fragments, scFvs, diabodies, minibodies, scFv-Fc fusions, and Fab expression libraries. Unless specified to the contrary, any reference to "antibody" or "antibodies" made herein encompasses, for example, any (or all) of these molecules so long as they exhibit the desired antigen-binding activity.

A single chain Fv ("scFv") polypeptide molecule is a covalently linked VH::VL heterodimer, which can be expressed from a gene fusion including VH- and VL-encoding genes linked by a peptide-encoding linker. (See Huston et al. (1988) Proc Nat Acad Sci USA 85 (16): 5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Solid tumors offer unique challenges for CAR-T therapies. Unlike blood cancers, tumor-associated target proteins are overexpressed between the tumor and healthy tissue resulting in on-target/off-tumor T-cell killing of healthy tissues. Furthermore, immune repression in the tumor microenvironment (TME) limits the activation of CAR-T cells towards killing the tumor. Aspects of the disclosure address these problems. For example, embodiments comprise T cells comprising a bispecific CAR that (a) targets two antigens on a cancer cell to mitigate on-target/off-tumor T-cell killing. Referring to FIG. 12, for example, B7-GGGGS-G36 CAR T cells had more killing activity on the targeted renal carcinoma cells (CAIX+CD70+) than non-targeted cells (CAIX+CD70−, CAIX-CD70+, CAIX- CD70−). In embodiments, the bispecific CAR can also (b) secrete a checkpoint blockade antibody that removes repression in the tumor microenvironment. Other embodiments comprise a fine-tuned CAR that only recognizes the high density antigens on tumor cells, not the low density antigens on normal cells. Without wishing to be bound by theory, this can be accomplished by, for example, lowering the affinity of the antibody or antibodies associated with the CAR.

FIG. 1, for example, provides a schematic of a bispecific CAR that targets two antigens, such as CAIX and CD70. Bispecific CARs can refer to CARs that has binding specificities for at least two different antigens. For example, bispecific CARs can comprise monoclonal antibodies, such as human or humanized antibodies, or fragments thereof. In the present case, one of the binding specificities is CAIX and/or CD70. The second binding target is any other antigen, and advantageously is a cell-surface protein or receptor or receptor subunit. For example, one of the binding specificities is for CAIX and the second binding specificity is for CD70.

As reported (see, for example, J Clin Oncol 24 (2006) 20-22; Molecular Therapy 21 (2013) 4), the first clinical trial of the first generation anti-CAIX G250 CAR-T cells on renal cell carcinoma RCC (RCC) patients failed due to on-target, off-tumor side effects. 2 of the first 3 patients developed hepatitis due to CAIX expression on bile ducts. The introduction of a second antibody, such as a second scFv, can result in elevated safety to the subject, because the dual targeted CAR T can reduce or eliminate on-target/off-tumor effects. Referring to FIG. 24, for example, CAIX and CD70 expression is upregulated and co-expressed on ccRCC. On the other hand, CAIX is expressed on bile duct (mostly in cytoplasm), and CD70 is not expressed on bile duct. See, for example, British Journal of Cancer 103 (2010) 676-684.

Bispecific antibodies can be prepared as full length antibodies or antibody fragments (e.g. F(ab') 2 bispecific antibodies). Methods for making bispecific antibodies are known in the art. See for example U.S. Pat. No. 8,329,178, which is incorporated herein by reference in its entirety.

Antibody molecules obtained from humans relate to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain.

The term "antigen-binding site," or "binding portion" can refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." See, for example, Tables 1 and 3, which provide the CDRs for anti-CAIX and anti-CD70 antibodies.

An emerging mechanism associated with the progression of tumors is the immune checkpoint pathway, which include cellular interactions that prevent excessive activation of T cells under normal conditions, allowing T cell function in a self-limited manner. As an evasion mechanism, many tumors are able to stimulate the expression of immune checkpoint molecules, resulting in an anergic phenotype of T cells that cannot restrain tumor progression. For example, emerging clinical data highlight the importance of one inhibitory ligand and receptor pair as an immune checkpoint: the programmed death-ligand 1 (PD-L1; B7-H1 and CD274) and programmed death receptor-1 (PD-1; CD279), in preventing killing of cancer cells by cytotoxic T-lymphocytes. PD1 receptor is expressed by many cell types like T cells, B cells, Natural Killer cells (NK) and host tissues. Tumors and Antigen-presenting cells (APC) expressing PD-L1 can block T cell receptor (TCR) signaling of cytotoxic T-lymphocytes through binding to receptor PD-1, decreasing the production of cytokines and T cell proliferation. PD-L1 overexpression can be found in many tumor types and may also mediate an immunosuppressive function through its interaction with other proteins, including CD80 (B7.1), blocking its ability to activate T cells through binding to CD28.

Genetic engineering of human lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the disclosure, there are lymphocytes (CARTS) that are modified to comprise at least a CAR, and in particular embodiments of the invention, a single CAR targeting two or more antigens (e.g., a bispecific CAR). In some embodiments, the cells comprise a split CAR, such as anti-CD70 and anti-CAIX scFvs expressed on cell surface with different costimulation domains. Further, some embodiments comprise a fine-tuned CAR. In some embodiments, the CARTS are further modified to express and secrete one or more polypeptides, such as for example an antibody or a cytokine, such as IL-12, IL-15, or IL-18. Such CARTS are referred to herein as armed CARTS or CAR factories. Armed CARTS allow for simultaneous secretion of the polypeptide locally at the targeted site (i.e., tumor site).

Referring to FIG. 56, for example, a split CAR comprises two or more CARs on the surface of a cell, such as a T cell or NK cell. The CARs can be specific for two or more antigens, such as CD70 and CAIX. FIG. 77 provides an example of a nucleic acid construct encoding split CARs. In this example, the first CAR is specific for CAIX, and the second CAR is specific for CD70. As described herein, the CARs can be in any orientation desired. For example, the first CAR can be specific for CD70 and the second CAR can be specific for CAIX. As shown in the example, first and the second CARs can be expressed from a single nucleic acid construct. In such an example, a nucleic acid encoding a cleavable linker can be located between the nucleic acids encoding the first and the second CAR. In other embodiments, the two CARs can be expressed in the same cell but from two separate nucleic acid constructs.

A modified TCR called chimeric antigen receptor (CAR), such as a CAR containing single chain variable antibody fragment (scFv) previously selected by high affinity against a specific tumor associated antigen, is a powerful new approach against cancer. The scFv presented in the CAR is linked to an intracellular signaling block that includes CD3ζ to induce T cell activation followed by antigen binding. This structure is characteristic for first-generation CARs, which were improved to second—and generation CARs that link the signaling co-stimulatory endodomains of CD28, 4-1BB, or OX40 to CD3 or 3rd-generation CARs that links two elements to CD3ζ in tandem. These endodomains are required for complete T cell activation during TCR recognition by antigen-presenting cells (APCs), improving cytokine production and proliferation of CAR-T cells. The effect of CART cells has heretofore been modest for the treatment of solid tumors, due to difficulty in finding unique tumor associated antigens, inefficient homing of T cells to tumor locations, low persistence of T cells in the body and the immunosuppressive microenvironment of solid tumors.

In particular cases, the lymphocytes can include a receptor that is chimeric, non-natural and engineered at least in part by the hand of man. In particular cases, the engineered chimeric antigen receptor (CAR) has one, two, three, four, or more components, and in some embodiments the one or more components facilitate targeting or binding of the lymphocyte to one or more tumor antigen-comprising cancer cells.

The CAR according to the disclosure comprises at least one transmembrane polypeptide comprising at least one extracellular ligand-biding domain and; one transmembrane polypeptide comprising at least one intracellular signaling domain; such that the polypeptides assemble together to form a Chimeric Antigen Receptor. Exemplary CARS useful in aspects of the disclosure include those disclosed in for example PCT/US2006/046350, PCT/US2015/067178, PCT/US2015/067225, and PCT/US2019/022272, each of which are incorporated by reference herein in their entireties . . .

The term "extracellular ligand-binding domain" as used herein can refer to an oligo- or polypeptide that can bind a ligand. The domain can interact with a cell surface molecule. For example, the extracellular ligand-binding domain can be chosen to recognize a ligand that acts as a cell surface marker on target cells associated with a particular disease state.

In particular, the extracellular ligand-binding domain can comprise an antigen binding domain or antigen recognition domain derived from an antibody against an antigen of the target. The antigen binding domain or antigen recognition domain can be an antibody fragment. An "antibody fragment" can be a molecule other than an intact antibody that comprises a portion of an intact antibody that binds the antigen to which the intact antibody binds. Examples of antibody fragments include but are not limited to Fv, Fab, Fab', Fab'-SH, F(ab') 2; diabodies; linear antibodies; single-chain antibody molecules (e.g. scFv); and multispecific antibodies formed from antibody fragments. Referring to FIG. 1, for example, one embodiment comprises a CAR with two scFvs as the antigen recognition domains. Referring to FIG. 14, for example, one embodiment comprises a CAR with one scFv as the antigen recognition domain.

The antigen recognition domain can be directed towards any antigen target of interest. In embodiments, the antigen target of interest is on the surface of a cell, such as the surface of a cancer cell. Non-limiting examples of antigen targets comprise CAIX and/or CD70.

In some embodiments, the CAR is specific for CAIX and/or CD70.

Figure 2:
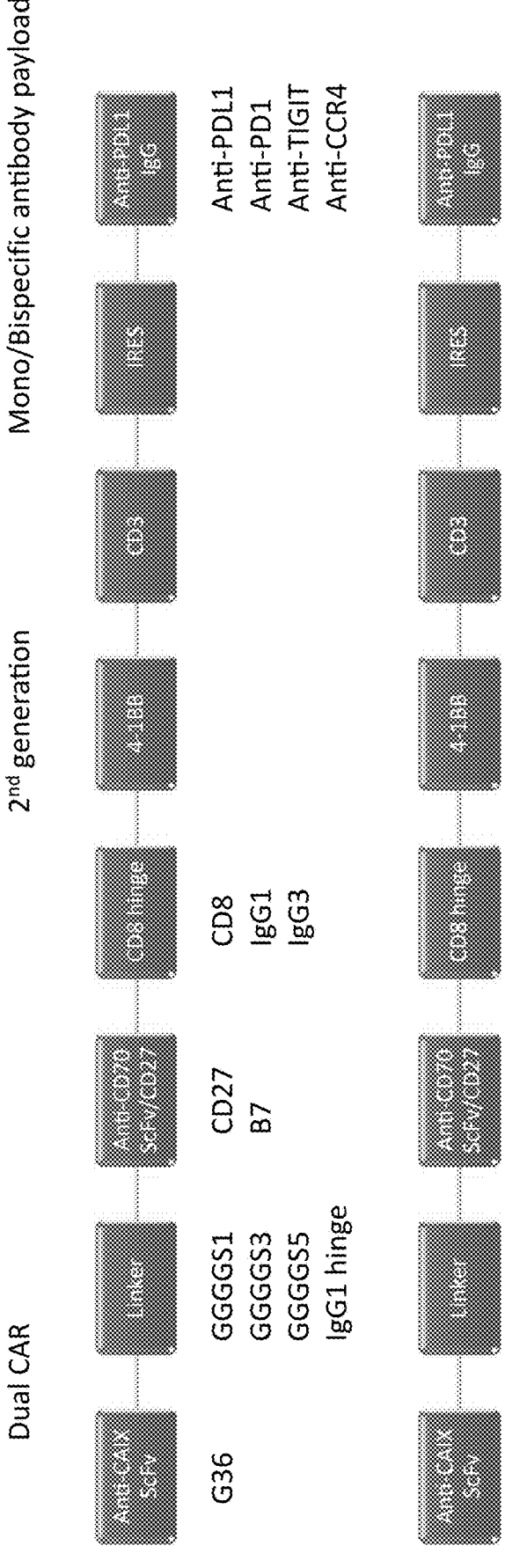
FIG. 2 shows that 2nd generation CAR T cell factories can be established by combining a series of CARs (such as different scFvs, linkers, and hinges) with immune checkpoint blockade as payload. Based on these data, 8 constructs were established by using G36 as the anti-CAIX scFv and B7 as the anti-CD70 scFv. The skilled artisan will recognize that any scFvs can be utilized according to the invention. The dual CAR engineering is the most important part and the payload was replaced with zsgreen to indicate the transduction efficiency. Figure discloses SEQ ID NOS 267 and 41-42, respectively, in order of appearance.

In embodiments, said extracellular ligand-binding domain is a single chain antibody fragment (scFv) comprising the light (VL) and the heavy (VH) variable fragment of a target antigen specific monoclonal antibody joined by a flexible linker. The skilled artisan will recognize that embodiments can comprise different linkers which are typically known in the art. See, for example, Chen, et al. "Fusion protein linkers: property, design and functionality." Advanced drug delivery reviews 65.10 (2013): 1357-1369, which is incorporated by reference herein in its entirety. For example, using different linkers will allow one to fine tune the dual-targeting CAR construct. The linker length can vary depending on the antibodies of the dual-targeting CAR construct, their angle of approach to the target epitope, topography of the target on the tumor cell membrane. Referring to FIG. 2, for example, the flexible linkers can include GGGS1 (SEQ ID NO: 40), GGGGS3 (SEQ ID NO: 41), GGGGS5 (SEQ ID NO: 42), or IgG1 hinge. In some embodiments, the number of Gs in the linker can be 2, 3, 4, 5, 6, or 7 in combination with either S1, S2, S3, S4, S5, or S6. For example, the scFv antibody is specific for CAIX and/or CD70. As shown in FIG. 10 and FIG. 50, for example, the orientations of the scFvs to the linker can vary. In one nucleic acid construct displayed in FIG. 50, the anti-CAIX scFv can be in the first cassette (i.e., before the linker), and the anti-CD70 cassette can be in the second cassette (i.e., after the linker). Alternatively, the anti-CAIX scFv can be in the second cassette, and the anti-CD70 scFv can be in the first cassette. Referring to FIG. 51, for example, anti-CAIX scFv G36 can be in the first cassette, and anti-CD70 B7 can be in the second cassette. Alternatively, anti-CAIX scFv G36 can be in the second cassette, and anti-CD70 B7 can be in the first cassette. Linkers of various lengths and flexibilities can be utilized as described herein. As shown, different orientations of the two scFvs can influence binding. For example, G36 has higher binding what engineered as the second cassette. On the other hand, as shown in FIG. 11, anti-CD70 scFv B7 does not have significant preference.

Examples of antibodies useful in constructing the CARs according to the disclosure include those detailed in Table 1, 2, 3 or 4 herein. See also, for example, WO/2007/065027 and WO/2016/100985, the contents of which are hereby incorporated by reference in their entireties.

The antigen recognition domain useful in constructing the CAR-Ts, for example scFVs directed toward CAIX and/or CD70, can be synthesized, engineered, and/or produced using nucleic acids (e.g., DNA). The DNA encoding the antigen recognition domain can be cloned in frame to DNA encoding necessary CAR-T elements such as, but not limited to, CD8 hinge regions, transmembrane domains, co-stimulatory domains of molecules of immunological interest such as, but not limited to, CD28 and 41BB and CD3-zeta intracellular signaling domains. See FIG. 2, for example.

Binding domains other than scFv can also be used for predefined targeting of lymphocytes, such as camelid single-domain antibody fragments or receptor ligands, antibody binding domains, antibody hypervariable loops or CDRs as non-limiting examples.

In an embodiment, the transmembrane domain further comprises a stalk region between said extracellular ligand-binding domain and said transmembrane domain. The term "stalk region" used herein can mean any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, for example, 10 to 100 amino acids or, for example, 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In an embodiment said stalk region is a part of human CD8 alpha chain.

The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" can refer to the portion of a protein which transduces the effector signal function signal and directs the cell to perform a specialized function.

Signal transduction domain can comprise two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCR zeta, FcR gamma, FcR beta, FcR epsilon, CD3 gamma, CD3 delta, CD3 epsilon, CD5, CD22, CD79a, CD79b and CD66d. In another embodiment, the signaling transducing domain of the CAR can comprise the CD3 zeta signaling domain, or the intra-cytoplasmic domain of the Fc epsilon RI beta or gamma chains. In another embodiment, the signaling is provided by CD3 zeta together with costimulation provided by CD28 and a tumor necrosis factor receptor (TNFr), such as 4-1BB or OX40), for example.

In an embodiment the intracellular signaling domain of the CAR of the disclosure comprises a co-stimulatory signal molecule. In some embodiments the intracellular signaling domain contains 2, 3, 4 or more co-stimulatory molecules in tandem. A co-stimulatory molecule is a cell surface molecule other than an antigen receptor or their ligands that is required for an efficient immune response.

"Co-stimulatory ligand" can refer to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, MICB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, a ligand that specifically binds with CD83.

A "co-stimulatory molecule" can refer to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class 1 molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A) X(Q/E) E) or the minor motif (PXQXXD), wherein X is any amino acid. TRAF proteins are recruited to the intracellular tails of many TNFRs in response to receptor trimerization.

Chimeric antigen receptors fuse antigen-recognition domains to signaling domains (also referred to as stimulatory domains) that modulate (i.e., stimulate) cell signaling. Non-limiting examples of such stimulatory domains comprise those of CD28, 41BB, and/or CD3-zeta intracellular signaling domains. See FIG. 2, for example.

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein.

The term "a part of" used herein can refer to any subset of the molecule, that is a shorter peptide. Alternatively, amino acid sequence functional variants of the polypeptide can be prepared by mutations in the DNA which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity. The functionality of the CAR of the invention within a host cell is detectable in an assay suitable for demonstrating the signaling potential of said CAR upon binding of a particular target. Such assays are available to the skilled person in the art. For example, this assay allows the detection of a signaling pathway, triggered upon binding of the target, such as an assay involving measurement of the increase of calcium ion release, intracellular tyrosine phosphorylation, inositol phosphate turnover, or interleukin (IL) 2, interferon. gamma., GM-CSF, IL-3, IL-4 production thus effected.

Carbonic Anhydrase IX (CAIX)

A number of mAbs have been identified that react with surface antigens on RCC. These include mAbs that recognize differentiation and overexpressed antigens as well as mAbs that identify RCC-associated antigens not expressed in normal kidney (Michael, 2003; Yang, 2003). The gene for CAIX, also known as G250 and MN is located on chromosomes 9p12 to 13 and encodes a transmembrane protein that binds zinc and has CA activity (Zavada, 1997; Grabmaier, 2000). In HeLa cells derived from human carcinoma of cervix uteri and in RCC cell lines, CAIX/G250/MN/is found both at the plasma membrane and as a nuclear protein with apparent molecular weights of 58 and 54 kDa. It is N-glycosylated, and in the non-reduced state it forms oligomers (Pastorekova, 1992). Sequence analysis of the predicted CAIX protein shows that it contains a signal peptide (aa 1-37), an extracellular (EC) part (aa 38-414), a hydrophobic transmembrane region of 20 amino acids (aa 415-434) and a small C-terminus cytoplasmic portion of 25 amino acids (aa 435-459). The human and murine CAIX amino acid sequences are shown in FIG. 59. The extracellular portion is composed of two distinct domains. The region between the signal peptide and the CA domain (aa 53-111) shows significant homology (38% identity) with a keratin sulfate attachment domain of a human large aggregating proteoglycan, aggrecan (Doege, 1991). In the PG-like domain of CAIX, a hexapeptide motif with consensus E-E-D-L-P-E (SEQ ID NO: 43) is repeated 7 times. The carbonic anhydrase domain is located close to the plasma membrane (aa 135-391). The CAIX antigen appears at malignant transformation and stains positive in about 95% of clear cell RCC specimens as well as in most renal cell metastases.

Epitopes expressed on the cell surface of tumor cells are superior targets for humoral anti-cancer therapy since, unlike intracellular antigens, they are accessible to circulating antibodies in vivo. Human monoclonal antibodies (mAbs) have become a well-tolerated treatment option in an increasing number of cancers. The concept of selective tumor targeting with antibodies is based on the avid interaction between the antibody and an antigen that is expressed on malignant cells, but not on normal tissues. Many mechanisms have been proposed for the ability of antibodies against tumors to mediate their effects in vivo. For example, engagement of the antibody Fc domain with effector cell FcγRs leads to antibody-dependent cell-mediated cytotoxicity (ADCC). Some (antagonist or inhibitory) antibodies can block the signaling on tumor cells and in this way may act synergistically with immune effector responses by rendering the tumor cells more susceptible to immune effector cell triggered apoptosis or lytic cell death (Baselga, 1998). Another way that antibodies can be utilized is through the construction and functional expression of chimeric-immune receptors or "T-bodies" on T-lymphocytes otherwise known as "designer T-cells". The antigen binding domain of the chimeric receptor can consist of an antigen-binding domain, for example, a single-chain antibody (scFv), while the intracellular signaling domain is derived from the cytoplasmic part of a membrane-bound receptor that can induce cellular activation (Maher, 2002; Pinthus, 2003). T-lymphocytes grafted with a chimeric receptor have the combined advantages of MHC-independence and antibody-based antigen binding with efficient T-cell activation upon specific binding to the receptor ligand. This activation results in the production and secretion of cytokines such as IL-2, interferon, GM-CSF and TNF-α. Antigen-specific lysis of tumor cells both in vitro and in vivo have been reported. T-lymphocytes can be permanently grafted with antigen-specific chimeric receptors by retroviral transduction of vector constructs encoding the receptor molecule of choice (reviewed by Rivière, 2004).

Embodiments of the present invention can comprise an isolated human monoclonal antibody or fragment thereof that immunospecifically binds to a carbonic anhydrase IX (G250) protein. Such antibodies can reduce carbonic anhydrase activity of said protein. For example, such anti-CAIX antibodies can include those described in WO 2007/065027 and U.S. Pat. No. 8,466,263, each of which are incorporated herein by reference in their entireties. See, for example, FIG. 58, which provides multiple sequence alignment of amino acid sequences of anti-carbonic anhydrase IX (G250) scFv clones. For example, embodiments of the invention comprise single chain antibodies, such as scFvs G6, G9, G10, G17, G21, G27, G28, G36, G37, G39, G40, G45, G57, G62, G98, G104, G119, or G125 as well as any other scFvs identified according to the methods disclosed herein.

For example, the amino acids of the CDRs of the anti-CAIX antibodies are provided in Table 1:

| CLONE | | CDR1 (SEQ ID NO) | CDR2 (SEQ ID NO) | CDR3 (SEQ ID NO) |
|---|---|---|---|---|
| G6 | (VH) | TYAMT ([ ]) | AVSGSGGSTYYADSVKG ([ ]) | GPVLRYGFDI ([ ]) |
| G6 | (VL) | TGSRSNIGADYDVH ([ ]) | ANNNRPS ([ ]) | QSYDSSLRAWV ([ ]) |
| G9 | (VH) | SYAMS ([ ]) | AISGSGGSTYYADSVKG ([ ]) | SHSSGG FDY ([ ]) |
| G9 | (VL) | TGSSSNIGRGYNVH ([ ]) | GNTNRPS ([ ]) | QSYDSSLSAWV ([ ]) |
| G10 | (VH) | SYAMS ([ ]) | AISANGGTTYYADSVKG ([ ]) | NGNYRGAFDI ([ ]) |
| G10 | (VL) | TGSSSNIGAGYDVH ([ ]) | GNSNRPS ([ ]) | QSYDRSLSWV ([ ]) |
| G17 | (VH) | GFTFSSYA ([ ]) | ISGSGGST ([ ]) | ATYGDYGSLDY ([ ]) |
| G17 | (VL) | SSNIGAGYD ([ ]) | ANN ([ ]) | QSYDSSLRAWV ([ ]) |
| G18 | (VH) | SYAMS ([ ]) | AISGSGGSTYYADSVKG ([ ]) | AAAGFDY ([ ]) |
| G18 | (VL) | TGSSSNIGRGYNVH ([ ]) | DD'INRPS ([ ]) | QSYDSSLRAWV ([ ]) |
| G21 | (VH) | SYAMS ([ ]) | AISGSGGSTYYADSVKG ([ ]) | SHSSGGFDY ([ ]) |
| G21 | (VL) | TGSSSNIGRGThTVH ([ ]) | GNTNRPS ([ ]) | QSYDSSLSAWV ([ ]) |
| G27 | (VH) | NYAMT ([ ]) | LISYDGSVTHYTDSVKG ([ ]) | GSGYQE ([ ]) |
| G27 | (VL) | GGNNIGSKSVE ([ ]) | YDSDRPS ([ ]) | QVWDSSSDHHVV ([ ]) |
| G28 | (VH) | GFTFSNYA ([ ]) | ISYDGSVT ([ ]) | ARGSGYQEH ([ ]) |
| G28 | (VL) | NIGSKS ([ ] | YDS ([ ]) | QVWDSSSDHHVV ([ ]) |
| G36 | (VH) | SYAMS ([ ]) | AISANGGTTYYADSVKG ([ ]) | NGNYRGAFDI ([ ]) |
| G36 | (VL) | TGSSSNIGAGFDVH ([ ]) | GNTNRPS ([ ]) | QSYDSRLSAWV ([ ]) |

-continued

| CLONE | CDR1 (SEQ ID NO) | CDR2 (SEQ ID NO) | CDR3 (SEQ ID NO) |
|---|---|---|---|
| G37 (VH) | SYAMS ([ ]) | AISANGGTTYYADSVKG ([ ]) | NGNYRGAFDI ([ ]) |
| G37 (VL) | TGSRSNIGADYDVH ([ ]) | ANNNRPS ([ ]) | QSYDSSLSAWV ([ ]) |
| G39 (VH) | SYAMS ([ ]) | AISGSGGSTYYADSVKG ([ ]) | IGRYSSSLGY ([ ]) |
| G39 (VL) | TGSSSNIGRGYNVH ([ ]) | DNTNRPS ([ ]) | QSYDSGLRWV ([ ]) |
| G40 (VH) | SYAMS ([ ]) | AISGSGGSTYYADSVKG ([ ]) | YGDYGSLDY ([ ]) |
| G40 (VL) | TGSSSNIGAGYDVH ([ ]) | ANNNRPS ([ ]) | QSYDSSLRAWV ([ ]) |
| G45 (VH) | SYAMS ([ ]) | AISANGGTTYYADSVKG ([ ]) | NGNYRGAFDI ([ ]) |
| G45 (VL) | TGTSSNIGAGYDVH ([ ]) | GNNNRPS ([ ]) | QSYDKSLSWV ([ ]) |
| G57 (VH) | SYAMS ([ ]) | AISGSGVSTYYADSVKG ([ ]) | YCSSTSCYRGMDV ([ ]) |
| G57 (VL) | TGSSSNIGAGYDVH ([ ]) | ANNNRPS ([ ]) | QSYDSSLRAWV ([ ]) |
| G62 (VH) | SYAMS ([ ]) | AISANGGTTYYADSVKG ([ ]) | NGNYRGAFDI ([ ]) |
| G62 (VL) | TGSSSNIGAGYDVH ([ ]) | GNNNRPS ([ ]) | QSYDKSLTWV ([ ]) |
| G82 (VH) | SYGMH ([ ]) | VISYDGSNKYYADSVKG ([ ]) | GRAARPPFDY ([ ]) |
| G82 (VL) | SGSSSNIGSNYVY ([ ]) | RNNQRPS ([ ]) | AAWDDSLNGVV ([ ]) |
| G94 (VH) | SYGMH ([ ]) | VISYDGSNKYYADSVKG ([ ]) | EAPYSSSLDAFDI ([ ]) |
| G94 (VL) | TGSSSNIGRGYNVH ([ ]) | GNSRPS ([ ]) | HSRDNNGHHI ([ ]) |
| G98 (VH) | SYAMS ([ ]) | AISANGGTTYYADSVKG ([ ]) | NGNYRGAFDI ([ ]) |
| G98 (VL) | TGSSSNIGAGYDVH ([ ]) | GNSRPS ([ ]) | QSYDSSLSAWV ([ ]) |
| G104 (VH) | IYAMS ([ ]) | AISGSGGGTYHADSVKG ([ ]) | FSAYSGYDL ([ ]) |
| G104 (VL) | TGSSSNIGRGYNVH ([ ]) | DNTNRPS ([ ]) | QSYDSGLRWV ([ ]) |
| G106 (VH) | SYAMS ([ ]) | AISANGGTTYYADSVKG ([ ]) | NGNYRGAFDI ([ ]) |
| G106 (VL) | TGSSSNIGAGFDVH ([ ]) | GNNNRPS ([ ]) | QSYDSSLSAWV ([ ]) |
| G119 (VH) | SYAMS ([ ]) | AISANGGTTYYADSVKG ([ ]) | NGNYRGAFDI ([ ]) |
| G119 (VL) | TGSSSNIGAGYDVH ([ ]) | GNTNRPS ([ ]) | QSYDSTLRVWM ([ ]) |
| G124 (VH) | KYAMS ([ ]) | GISGSGGSTYYADSVKG ([ ]) | SSRSGYFLP-LDY ([ ]) |
| G124 (VL) | QGNSLRYYYPS ([ ]) | GKNNRPS ([ ]) | SSRDNTDNRVV ([ ]) |
| G125 (VH) | SYGMH ([ ]) | AISGSGGSTYYADSVKG ([ ]) | AAVTGGFDP ([ ]) |
| G125 (VL) | GGDNIGRKSVH ([ ]) | DDRDRPS ([ ]) | QVWDSSSKHYV ([ ]) |

For example, the amino acid sequences of the VH and VL 40 regions of the anti-CAIX antibodies are provided in Table 2:

| CLONE | VH/VL | SEQ ID NO: |
|---|---|---|
| G6 (VH) | QVQLVQSGGGLVQPGGSLRLSCAASEFTFGTYAMTWVRQAPGKGLEW VSAVSGSGGSTYYADSVKGRFTISRDNSRNTLYLQMNSLRADDTAVYY CAR GPVLRYGFDI WGQGTMVIVSS | ([ ]) |
| G6 (VL) | QSVLTQPPSVSGAPGQRITISCTGSRSNIGADYDVHWYQQLPGTAPKLLI YANNNRPSGVPGRFSASKSGTSASLAISGLQAEDEADYYCQSYDSSLRA WVFGGGTKLAVLG | ([ ]) |
| G9 (VH) | QVQLQESGGGLVQPGGSLRLSCAASGFTFSSYAMSWVRQAPGKGLEW VSAISGSGGSTYYADSVKGRFTISRDNSKNTLYLQMNSLRAEDTAVYYC ARSHSSGGFDYWGQGTLVTVSS | ([ ]) |
| G9 (VL) | QSVLTQPPSVSGAPGQRVTISCTGSSSNIGRGYNVHWYQQLPGTAPKLLI YGNTNRPSGVPDRFSGSKSGTSASLAITGLQAEDEGDYYCQSYDSSLSA WVFGGGTKLTVLG | ([ ]) |
| G10 (VH) | QVQLVQSGGGLVQPGGSLRLSCAASGFPFSSYAMSWVRQAPGKGLEW VSAISANGGTTYYADSVKGRFTISRDNSKNTLYLQMNSLRAEDTAVYY CANNGNYRGAFDI WGQGTMVTVSS | ([ ]) |
| G10 (VL) | QSVLTQPPSVSGAPGQRVTISCTGSSSNIGAGYDVHWYQQLPGTAPKLLI YGNSNRPSGVPDRFSGSKSGSSASLAITGLQAEDEAHYYCQSYDRSLSW VFGGGTKLTVLG | ([ ]) |
| G17 (VH) | QVQLVQSGGGLVQPGGSLRLSCAASGFTFSSYAMSWVRQAPGKGLEW VSAISGSGGSTYYADSVKGRFTISRDNSKNTLYLQMNSLRAEDTAVYYC ATYGDYGSLDY | ([ ]) |

-continued

| CLONE | VH/VL | SEQ ID NO: |
|---|---|---|
| G17 (VL) | QSVLTQPPSVSGAPGQRVTISCTGSSSNIGAGYDVHWYQQLPGTAPKLLI YANNNRPSGVP.DRFSGSK.SGTSASLAITGLQAEDEADYYCQSYDSSLR AWV | ([ ]) |
| G18 (VH) | QVQLVQSGGGLVQPGGSLRLSCAASGFTFSSYAMSWVRQAPGKGLEW VSAISGSGGSTYYADSVKGRFTISRDNSKNTLYLQMNSLRAEDTAVYYC ARAAAGFDYWGQGTLVTVSS | ([ ]) |
| G18 (VL) | QSVLTQPPSVSGAPGQRVTISCTGSSSNIGRGYNVHWYQQLPGTAPKLLI YDDINRPSGVPHRFSGSKSGTSASLAITGLQAEDEADYYCQSYDSSLRA WVFGGGTKLAVLG | ([ ]) |
| G21 (VH) | QVQLQESGGGLVQPGGSLRLSCAASGFTFSSYAMSWVRQAPGKGLEW VSAISGSGGSTYYADSVKGRFTISRDNSKNTLYLQMNSLRAEDTAVYYC ARSHSSGGFDYWGQGTLVTVSS | ([ ]) |
| G21 (VL) | QSVLTQPPSVSGAPGQRVTISCTGSSSNIGRGYNVHWYQQLPGTAPKLLI YGNTNRPSGVPDRFSGSKSGTSASLAITGLQAXDEGDYYCQSYDSSLSA WVFGGGTKLTVLG | ([ ]) |
| G27 (VH) | QVTLKESGGGVVQPGTSLRLSCAASGFTFSNYAMTWVRQAPGKGLEW VGLISYDGSVTHYTDSVKGRFTISRDNAKNSLYLQMNTLRADDTAVYY CAR GSGYQEHWGQGTL VTVSS | ([ ]) |
| G27 (VL) | LPVLTQPPSVSVAPGQTARITCGGNNIGSKSVEWYQQKPGQAPVLVIYY DSDRPSGIPERFSGSNSGNTATLTISRVEAGDEADYYCQVWDSSSDHHV VFGGGTKLTVLG | ([ ]) |
| G28 (VH) | QVTLKESGG.GVVQPGTSLRLSCAASGFTFSNYAMTWVRQAPGKGLEW VGLISYDGSVTHYTDSVK.GRFTISRDNAKNSLYLQMNTLRADDTAVYY CARGSGYQEH | ([ ]) |
| G28 (VL) | LPVLTQPPS.VSVAPGQTARITCGGNNIGSKSVHWYQQKPGQAPVLVIY YDSDRPSGIP.ERFSGSNSGNTATLTISRVEAGDEADYYCQVWDSSSDHH VV | ([ ]) |
| G36 (VH) | EVQLVQSGGGVVQPGGSLRLSCAASGFPFSSYAMSWVRQAPGKGLEW VSAISANGGTTYYADSVKGRFTISRDNSKNTLYLQMNSLRAEDTAVYY CANNGNYRGAFDIWGQGTMVTVSS | ([ ]) |
| G36 (VL) | QSVLTQPPSVSGAPGQRVTISCTGSSSNIGAGFDVHWYQQLPGTAPKLLI YGNTNRPSGVPDRFSGSKSGTSASLAITGLQAEDETDYYCQSYDSRLSA WVFGGGTKLTVLG | ([ ]) |
| G37 (VH) | QVQLVQSGGGVVQPGGSLRLSCAASGFPFSSYAMSWVRQAPGKGLEW VSAISANGGTTYYADSVKGRFTISRDNSKNTLYLQMNSLRAEDTAVYY CANNGNYRGAFDI WGQGTMVTVSS | ([ ]) |
| G37 (VL) | QSVLTQPPSVSGAPGQRITISCTGSRSNIGADYDVHWYQQLPGTAPKLLI YANNNRPSGVPDRFSGSKSGTSASLAITGLQAEDETDYFCQSYDSSLSA WVFGGGTKVTVLG | ([ ]) |
| G39 (VH) | QVQLQESGGGLVQPGGSLRLSCAASGFTFSSYAMSWVRQAPGKGLEW VSAISGSGGSTYYADSVKGRFTISRDNSKNTLYLQMNSLRAEDTAVYYC AKIGRYSSSLGYWGQGTLVTVSS | ([ ]) |
| G39 (VL) | QSVLTQPPSVSGAPGQRVTISCTGSSSNIGRGYNVHWYQQLPGTAPKLLI YDNTNRPSGVPARFSGSKSATSASLAITGLQADDEADYYCQSYDSGLR WVFGGGTKLTLLR | ([ ]) |
| G40 (VH) | QVQLVQSGGGLVQPGGSLRLSCAASGFTFSSYAMSWVRQAPGKGLEW VSAISGSGGSTYYADSVKGRFTISRDNSKNTLYLQMNSLRAEDTAVYYC ATYGDYGSLDYWGQGTLVTVSS | ([ ]) |
| G40 (VL) | QSVLTQPPSVSGAPGQRVTISCTGSSSNIGAGYDVHWYQQLPGTAPKLLI YANNNRPSGVPDRFSGSKSGTSASLAITGLQAEDEADYYCQSYDSSLRA WVFGGGTKLAVLG | ([ ]) |
| G45 (VH) | QVQLVQSGGGLVQPGGSLRLSCAASGFPFSSYAMSWVRQAPGKGLEW VSAISANGGTTYYADSVKGRFTISRDNSKNTLYLQMNSLRAEDTAVYY CANNGNYRGAFDI WGQGTMVTVSS | ([ ]) |
| G45 (VL) | QSVLTQPPSVSGAPGQRITISCTGTSSNIGAGYDVHWYQQLPGAAPRVLI YGNNNRPSGVPDRFSGSKSGTSASLAITGLQSEDEADYYCQSYDKSLS- WVFGGGTKLTVLR | ([ ]) |
| G57 (VH) | QVQLVQSGGGLVQPGGSLRLSCAASGFTFS SYAMS WVRQAPGKGLEWVSAISGSGVSTYYADSVKG RFTISRDNSKNTLYLQMNSLRAEDTAVYYCAK YCSSTSCYRGMDV WGKGTLVTVSS | ([ ]) |
| G57 (VL) | QSVLTQPPSVSGAPGQRVTISCTGSSSNIGAGYDVHWYQQLPGTAPKLLI YANNNRPSGVPDRFSGSKSGTSASLAITGLQAEDEADYYCQSYDSSLRA WVFGGGTKLAVLG | ([ ]) |

-continued

| CLONE | VH/VL | SEQ ID NO: |
|---|---|---|
| G62 (VH) | QVQLVQSGGGLVRPGGSLRLSCAASGFPFSSYAMSWVRQAPGKGLEW VSAISANGGTTYYADSVKGRFTISRDNSKNTLYLQMNSLRAEDTAVYY CANNGNYRGAFDI WGQGTTVTVSS | ([ ]) |
| G62 (VL) | QSVLTQPPSVSGAPGQRITISCTGSSSNIGAGYDVHWYQQVPGKAPKVV IYGNNNRPSGVPDRFSGSKSGASASLAITGLQTEDEADYYCQSYDKSLT WVFGGGTKVTVLG | ([ ]) |
| G82 (VH) | QVQLVQSGGGVVQPGRSLRLSCAASGFTFSSYGMHWVRQAPGKGLEW VAVISYDGSNKYYADSVKGRFTISRDNSKNTLYLQMNSLRAEDTAVYY CARGRAARPPFDYWGQGTLVTVSS | ([ ]) |
| G82 (VL) | QPVLTQPPSASGTPGQRVTISCSGSSSNIGSNYVYWYQQLPGTAPKLPIY RNNQRPSGVPDRFSGSKSGTSASLAISGLRSEDEADYYCAAWDDSLNG VVFGGGTKLTVLR | ([ ]) |
| G94 (VH) | QVQLVQSGGGVVQPGRSLRLSCAASGFTFSSYGMHWVRQAPGKGLEW VAVISYDGSNKYYADSVKGRFTISRDNSKNTLYLQMNSLRAEDTAVYY CAREAPYSSSLDAFDIWGQGTMVTVSS | ([ ]) |
| G94 (VL) | QSVLTQPPSVSGAPGQRVTISCTGSSSNIGRGYNVHWYQQLPGTAPKLLI YGNSNRPSGVPDRFSGSSSGNTASLTITGAQAEDEADYYCHSRDNNGH HIFGGGTKLTVLS | ([ ]) |
| G98 (VH) | QVQLVQSGGGVVQPGGSLRLSCAASGFPFSSYAMSWVRQAPGKGLEW VSAISANGGTTYYADSVKGRFTISRDNSKNTLYLQMN'SLRAEDTAVYY CANNGNYRGAFDI WGQGTMVTVSS | ([ ]) |
| G98 (VL) | QSVLTQPPSVSGAPGQRVTISCTGSSSNIGAGYDVHWYQHLPGTAPKLLI YGNSNRPSGVPDRFSGSKSGTSASLAITGLQAEDETDYFCQSYDSSLSA WVFGGGTKVTVLG | ([ ]) |
| G104 (VH) | QVQLQESGGGLVQPGGSLRLSCAASGFTFSIYAMSWVRQAPGKGLEWV SAISGSGGGTYHADSVKGRFTISRDNSKNTLYLQMNSLRAEDTAVYYC AK FSAYSGYDLWGQGTLVTVSS | ([ ]) |
| G104 (VL) | QSVLTQPPSVSGAPGQRVTISCTGSSSNIGRGYNVHWYQQLPGTAPKLLI YDNTNRPSGVPARFSGSKSATSASLTITGLQADDEADYYCQSYDSGLR WVFGGGTKLTLLG | ([ ]) |
| G106 (VH) | EVQLVQSGGGLVQPGGSLRLSCAASGFTFSSYAMSWVRQAPGKGLEW VSAISANGGTTYYADSVKGRFTISRDNSKNTLYLQMNSLRAEDTAVYY CANNGNYRGAFDIWGQGTTVTVSS | ([ ]) |
| G106 (VL) | QSVLTQPPSVSGAPGQRVTISCTGSSSNIGAGFDVHWYQQLPGTAPRLLI YGNNNRPSGVPDRFSGSKSGTSASLAITGLQAEDETDYFCQSYDSSLSA WVFGGGTKVTVLR | ([ ]) |
| G119 (VH) | QVQLVQSGGGLVQPGGSLRLSCAASGFPFSSYAMSWVRQAPGKGLEW VSAISANGGTTYYADSVKGRFTISRDNSKNTLYLQMNSLRAEDTAVYY CANNGNYRGAFDIWGQGTMVIVSS | ([ ]) |
| G119 (VL) | QSVLTQPPSVSGAPGQRVTISCTGSSSNIGAGYDVHWYQQLPGTAPKLLI YGNTNRPSGVPDRFSGSKSGTSASLAIIGLQADDEADYYCQSYDSTLRV WMFGGGTKLTVLG | ([ ]) |
| G124 (VH) | QVQLVQSGGGLVQPGGSLRLSCAAPEFTFSKYAMSWVRQAPGKGLEW VSGISGSGGSTYYADSVKGRFTISRDNSKNTLYLQMNSLRAEDTAVYYC AKSSRSGYFLPLDYWGQGTLVTVSS | ([ ]) |
| G124 (VL) | SSELTQDPAVSVALGQTVRITCQGNSLRYYYPSWYQQKPGQAPVLVIY GKNNRPSGIPDRFSGSSSGNTASLTITGTQAEDEADYYCSSRDNTDNRV VFGGGTKLTVLG | ([ ]) |
| G125 (VH) | EVQLVESGGGVVQPGRSLRLSCAASGFTFSSYGMHWVRQAPGKGLEW VSAISGSGGSTYYADSVKGRFTISRDNAKNTLYLQMNSLRAEDTAVYY CARAAVTGGFDPWGQGTLVTVSS | ([ ]) |
| G125 (VL) | QPGLTQPPSVSVAPGQTARITCGGDNIGRKSVHWYQQRPGQAPILVIR DDRDRPSGIPERFSGSSSVNTATLIISRVEAGDEADYYCQVWDSSSKHY VFGPGTKVTALG | ([ ]) |

Embodiments can also comprise a consensus sequence of any of the amino acid sequences described herein. For example, when four or more clones have the same amino acid at a given position, that position in the consensus is designated by that amino acid.

CD70

CD70 is found on the surface of tumors cells of the kidney (clear cell carcinoma and papillary carcinoma, for example), pancreas, larynx or pharynx, melanoma, ovary, lung adenocarcinoma, colon, breast, and brain. See, for example, British Journal of Cancer 103 (2010) 676-684.

Embodiments of the present invention can comprise an isolated human monoclonal antibody or fragment thereof that immunospecifically binds to CD70. For example, embodiments of the invention comprise single chain antibodies, such as scFvs A20, B2, B3, B5, B7, B8, or B9 as well as any other scFvs identified according to the methods disclosed herein.

For example, the amino acids of the CDRs of the anti-CD70 antibodies are provided in Table 3:

| CLONE | CDR1 (SEQ ID NO) | CDR2 (SEQ ID NO) | CDR3 (SEQ ID NO) |
|---|---|---|---|
| A20 (VH) | GFTFSSYA([ ]) | ISGSGGSR([ ]) | ARGRGGHGMDV([ ]) |
| A20 (VL) | SSNIGSNY([ ]) | RNN([ ]) | AAWDDSLNGLV([ ]) |
| B2 (VH) | | | |
| B2 (VL) | | | |
| B3 (VH) | GGTFSSQA ([ ]) | IIPFFGVP ([ ]) | AVLKGRGNFDF ([ ]) |
| B3 (VL) | YSVFHSPNNKNY([ ]) | WAS ([ ]) | QQRSNWPLT ([ ]) |
| B5 (VH) | GFTVSNYA([ ]) | KSGSDGRT([ ]) | AKGIYDVTGSSFDS([ ]) |
| B5 (VL) | ALPKKY([ ]) | EDS([ ]) | YSTDSSGNHK([ ]) |
| B7 (VH) | GFTVSNYA ([ ]) | KSGSDGRT ([ ]) | AKGIYDVTGSSFDS ([ ]) |
| B7 (VL) | SGSIASNY ([ ]) | EDN ([ ]) | QSYDSGNRRV ([ ]) |
| B8 (VH) | GFTVSTSH([ ]) | KDSGGKT([ ]) | ARARPSDPYDGSGFDAFDI([ ]) |
| B8 (VL) | SNNVGNQG([ ]) | RNN([ ]) | SAWDSSLSAWV([ ]) |
| B9 (VH) | GFIFSDYY ([ ]) | IRSRRGET ([ ]) | ARHRKSFTDLDAFDL ([ ]) |
| B9 (VL) | QDIGTD ([ ]) | KAS ([ ]) | QHFNNYPAT ([ ]) |

For example, the amino acid sequences of the VH and VL regions of the anti-cd70 antibodies are provided in Table 4:

acid at a given position, that position in the consensus is designated by that amino acid.

| CLONE | VH/VL | SEQ ID NO: |
|---|---|---|
| A20 (VH) | QVQLVQSGG.GLVQPGGSLRLSCAASGFTFSSYAMSWVRQAPGKGLE WVSLISGSGGSRYYADSVK.GRFTISRDNSKNTLYLQMNNLRAEDTAV YYCARGRGGHGMDV | ([ ]) |
| A20 (VL) | QPGLTQPPSASGTPGQRVTISCSGSSSNIGSNYVYWYQQLPGTAPKLLI YRNNQRPSGVPDRFSGSKSGTSASLAISGLQSEDEADYYCAAWDDSLN GLV | ([ ]) |
| B2 (VH) | | |
| B2 (VL) | | |
| B3 (VH) | QVQLVQSGAEVKKPGSSVKVSCRSSGGTFSSQAFSWVRQAPGQGLEW MGRIIPFFGVPTYAQRFQGRVTITADKSPTTAYMELTSLRSDDTAVYYC AVLKGRGNFDF | ([ ]) |
| B3 (VL) | DIVMTQSPDSLAVSLGERATINCKSSYSVFHSPNNKNYLAWYQQRPGQ PPKLLIYWASTRGSGVP.DRFSGSGSGTDFTLTISSLEPEDFAVYYCQQR SNWPLT | ([ ]) |
| B5 (VH) | QVQLVQSGGGLVQPRGSLRLSCAASGFTVSNYAMSWVRQAPGKGLE WVATKSGSDGRTYYADSVKGRFTIARDNSKNSLYLQMNSLRAADTA VYYCAKGIYDVTGSSFDS | ([ ]) |
| B5 (VL) | SYELTQPPS.VSVSPGQTARITCSGDALPKKYAYWYQQKSGQAPVLVM FEDSKRPSGIPERFSGSSSGTMATLTISGAQVEDEADYYCYSTDSSGNH KV | ([ ]) |
| B7 (VH) | QVQLVQSGG.GLVQPRGSLRLSCAASGFTVSNYAMSWVRQAPGKGLE WVATKSGSDGRTYYADSVKGRFTIARDNSKNSLYLQMNSLRAADTA VYYCAKGIYDVTGSSFDS | ([ ]) |
| B7 (VL) | NFMLTQPHS.VSESPGKTVTISCTRSSGSIASNYVQWYQQRPGSAPTTVI YEDNQRPSGVPDRFSGSIDSSSNSASLTISGLKTEDEADYYCQSYDSGN RRV | ([ ]) |
| B8 (VH) | EVQLVESGG.GVVQPGRSLRLSCAASGFTVSTSHMSWVRQAPGKGLE WLSGKDSGGKTYYADSVR.GRFTIARDDSLNTVFLQMNNMRDEDSGV YYCARARPSDPYDGSGFDAFDI | ([ ]) |
| B8 (VL) | SYELTQPPS.VSKGLRQTATLTCTGNSNNVGNQGAAWLQQHQGHPPKL LSYRNNNRPSGIS.ERFSASRSGNTASLTITGLQPEDEADYYCSAWDSSL SAWV | ([ ]) |
| B9 (VH) | QVQLVQSGG.GLVKPRGSLRLSCAASGFIFSDYYMSWIRQAPGKGLQW VASIRSRRGETNYADSVK.GRFTIARDNAEKSLYLQMNSLRAEDAAVY YCARHRKSFTDLDAFDL | ([ ]) |
| B9 (VL) | DIVMTQSPSTLSASVGDRVTITCRASQDIGTDLSWYQQKPGKAPKLLIY KASSLESGVPSRFSGSGSGTDFTLTISSLQPDDFATYYCQHFNNYPAT | ([ ]) |

Embodiments can also comprise a consensus sequence of any of the amino acid sequences described herein. For example, when four or more clones have the same amino Cells Embodiments of the disclosure include cells that express a CAR (i.e, CARTS). The cell can be of any kind, including an immune cell that can express the CAR for cancer therapy or a cell, such as a bacterial cell, that harbors an expression vector that encodes the CAR. As used herein, the terms "cell," "cell line," and "cell culture" can be used interchangeably. All of these terms also include their progeny, which is any and all subsequent generations. For example, all progeny may not be identical due to deliberate or inadvertent mutations. In the context of expressing a heterologous nucleic acid sequence, "host cell" can refer to a eukaryotic cell that is can replicate a vector and/or expressing a heterologous gene encoded by a vector. A host cell can, and has been, used as a recipient for vectors. A host cell can be "transfected" or "transformed," which can refer to a process by which exogenous nucleic acid is transferred or introduced into the host cell. A transformed cell includes the primary subject cell and its progeny. As used herein, the terms "engineered" and "recombinant" cells or host cells can refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T-cells or killer T cell); NK cells and NKT cells are also encompassed in the disclosure.

Some vectors can employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

Armed CARTS

The invention further includes CARTs that are modified to secrete one or more polypeptides. Such CARTs can be referred to as CART factories, CAR T cell factories, or armed CARTs. The polypeptide can be, for example, an antibody or fragment thereof as described herein. For example, the polypeptide can be an antibody or cytokine. In embodiments, the antibody is specific for TIGIT, CAIX, GITR, PD-L1, PD-L2, PD-1, CCR4, CTLA-4, VISTA, or CD70. For example, CAR T cell factories can secrete PD-L1 mAbs locally at the tumor site to restore the effective anti-cancer immunity and/or reverse T cell exhaustion. In embodiments, the armed CART secretes IL-12, IL-15, or IL-18.

For example, a second expression construct, which can be in the same DNA vector as that which encodes the CAR (e.g. the antigen-recognition domain) or in a second separate vector, can be used to encode a mini body (scFv-Fc) or antibody, or a fragment thereof, that is directed against a single or multiple antigens of interest, and can be cloned after an internal ribosomal entry site (IRES). Referring to the figures, the second expression cassette comprises either a fluorescent molecule or an immune-modulating minibody.

Armed CARTS have the advantage of simultaneously secreting a polypeptide at the targeted site, e.g. tumor site. For example, armed CARTS can secrete anti-TIGIT antibodies or fragments thereof. TIGIT is a T-cell coinhibitory receptor that limits antitumor and other T-cell dependent chronic immune responses, such as CD8+ T cell-dependent immune responses. TIGIT is expressed on subsets of activated T cells and natural killer (NK) cells. For example, TIGIT is highly expressed on tumor-infiltrating T-cells. In cancer models, antibody blockade of TIGIT contributed to enhanced CD8+ T cell effector function and tumor clearance.

In embodiments, the anti-TIGIT antibody of the armed CART comprises one or more of the anti-TIGIT antibody clones (or fragments thereof, such as FR1, FR2, FR3, FR4, CDR1, CDR2, CDR3, or any combinations of the framework and/or CDR regions therein) described in FIG. 81.

For example, the anti-TIGIT antibody can comprise a CDR1 of the VH region of having the sequence: GYTF . . . TSYG (SEQ ID NO: 192); CDR2 of the VH region having the sequence: ISAY . . . NGNT (SEQ ID NO: 193); CDR3 of the VH region having the sequence: ARDPGLWFGLTHDYYFDY (SEQ ID NO: 194); CDR1 of the VL region having the sequence SSNI . . . GSNT (SEQ ID NO: 195); CDR2 of the VL region having the sequence: RN . . . N; and CDR3 of the VL region having the sequence: AAWDDSRSGPV (SEQ ID NO: 196).

For example, the anti-TIGIT antibody can comprise a CDR1 of the VH region of having the sequence: GFTF . . . SDYS (SEQ ID NO: 197); CDR2 of the VH region having the sequence: INSD . . . GSRT (SEQ ID NO: 198); CDR3 of the VH region having the sequence: ARGPGFFGFDI (SEQ ID NO: 199); CDR1 of the VL region having the sequence RSNI . . . GRNS (SEQ ID NO: 200); CDR2 of the VL region having the sequence: SN. . . . N; and CDR3 of the VL region having the sequence: AAWDARLTGPL (SEQ ID NO: 201).

For example, the anti-TIGIT antibody can comprise a CDR1 of the VH region of having the sequence: GYSF . . . TNYW (SEQ ID NO: 202); CDR2 of the VH region having the sequence: INPV . . . NSRT (SEQ ID NO: 203); CDR3 of the VH region having the sequence: ARYYYYAMEV (SEQ ID NO: 204); CDR1 of the VL region having the sequence SSNI . . . GSNT (SEQ ID NO: 195); CDR2 of the VL region having the sequence: RN . . . N; and CDR3 of the VL region having the sequence: EAWDDSLNGPV (SEQ ID NO: 205).

For example, the anti-TIGIT antibody can comprise a CDR1 of the VH region of having the sequence: GYTF . . . TNYG (SEQ ID NO: 206); CDR2 of the VH region having the sequence: VDNN . . . NGNI (SEQ ID NO: 207); CDR3 of the VH region having the sequence: ARGLFSSRWYLWFDP (SEQ ID NO: 208); CDR1 of the VL region having the sequence SSDVG . . . GYNY (SEQ ID NO: 209); CDR2 of the VL region having the sequence: EV . . . T; and CDR3 of the VL region having the sequence: SSYTRSSTSYVV (SEQ ID NO: 210).

For example, the anti-TIGIT antibody can comprise a CDR1 of the VH region of having the sequence: GGTF . . . SSYA (SEQ ID NO: 211); CDR2 of the VH region having the sequence: ILPM . . . FGST (SEQ ID NO: 212); CDR3 of the VH region having the sequence: ARGRDIVAPSNSGFDV (SEQ ID NO: 213); CDR1 of the VL region having the sequence SNNV . . . GNQG (SEQ ID NO: 162); CDR2 of the VL region having the sequence: RN . . .

D; and CDR3 of the VL region having the sequence: SAYDRSLNAWV (SEQ ID NO: 214).

In other embodiments, armed CARTS can secrete anti-PDL1 antibodies or fragments thereof. For example, the armed CARTS can secrete anti-PDL1 antibodies or fragments thereof disclosed in provisional patent application No. 62/624,455, which is incorporated by reference herein in its entirety. Exemplary anti-PDL1 antibodies include antibodies having a VH amino acid sequence having SEQ ID NO: [ ] and/or a VL amino acid sequence having SEQ ID NO: [ ]. See FIG. 78 and FIG. 81, for example.

In embodiments, the anti-PDL1 antibodies of the armed CART comprises on or more of the anti-PDL1 antibody clones (or fragments thereof, such as FR1, FR2, FR3, FR4, CDR1, CDR2, CDR3, or any combinations of the framework and/or CDR regions therein) described in FIG. 78 and/or FIG. 81.

For example, the amino acid sequences of the heavy and light chain complementary determining regions of the PDL-1 antibodies are below:

For example, the anti-PDL1 antibodies have a heavy chain with three CDRs including the amino acid sequences SEQ ID NO: [ ], [ ], and/or [ ], respectively and a light chain with three CDRs including the amino acid sequence.

In other embodiments, armed CARTS can secrete anti-PD1 antibodies or fragments thereof. Exemplary anti-PD1 antibodies include antibodies having a VH amino acid sequence having SEQ ID NO: [ ] and a VL amino acid sequence having SEQ ID NO: [ ]. See FIG. 78 and FIG. 83, for example.

In embodiments, the anti-PD1 antibodies of the armed CART comprises on or more of the anti-PD1 antibody clones (or fragments thereof, such as FR1, FR2, FR3, FR4, CDR1, CDR2, CDR3, or any combinations of the framework and/or CDR regions therein) described in FIG. 78 and FIG. 83. For example, the anti-PD1 antibodies have a heavy chain with three CDRs including the amino acid sequences SEQ ID NO: [ ], [ ], and/or [ ], respectively and a light chain with three CDRs including the amino acid sequences SEQ ID NO: [ ], [ ], and/or [ ], respectively. See FIG. 78 and FIG. 83, for example.

In embodiments, the amino acid sequences of the heavy and light chain complementary determining regions of the PD-1 antibodies are shown below:

| Sequence ID | $V_H$ CDR1 | $V_H$ CDR2 | $V_H$ CDR3 |
|---|---|---|---|
| 42 mut | GGTFSSYA (SEQ ID NO: [ ]) | IIPIFGTA (SEQ ID NO: [ ]) | ARGRQMFGAGIDF (SEQ ID NO: [ ]) |
| 50-6B6.1 mut | GYTLSSHG (SEQ ID NO: [ ]) | ISAHNGHA (SEQ ID NO: [ ]) | ARVHAALYYGMDV (SEQ ID NO: [ ]) |
| 50-6B6.2 | GYTLSSHG (SEQ ID NO: [ ]) | ISAHNGHA (SEQ ID NO: [ ]) | ARVHAALYYGMDV (SEQ ID NO: [ ]) |
| 50-7B3 | GYTLSSHG (SEQ ID NO: [ ]) | ISAHNGHA (SEQ ID NO: [ ]) | ARVHAALYYGMDV (SEQ ID NO: [ ]) |
| 50-5B9 | GYTLSSHG (SEQ ID NO: [ ]) | ISAHNGHA (SEQ ID NO: [ ]) | ARVHAALYYGMDV (SEQ ID NO: [ ]) |

| Sequence ID | $V_L$ CDR1 | $V_L$ CDR2 | $V_L$ CDR3 |
|---|---|---|---|
| 42 mut | SGSIDSNY (SEQ ID NO: [ ]) | EDN (SEQ ID NO: [ ]) | QSYDSNNRHVI (SEQ ID NO: [ ]) |
| 50-6B6.1 mut | NIGSKG (SEQ ID NO: [ ]) | DDR (SEQ ID NO: [ ]) | QVWDSGSDHWV (SEQ ID NO: [ ]) |
| 50-6B6.2 | NIGDKG (SEQ ID NO: [ ]) | DDS (SEQ ID NO: [ ]) | QVWDSSSDHWV (SEQ ID NO: [ ]) |
| 50-7B3 | NIGNKG (SEQ ID NO: [ ]) | DDS (SEQ ID NO: [ ]) | QVWDSSSDHWV (SEQ ID NO: [ ]) |
| 50-5B9 | NIGGKG (SEQ ID NO: [ ]) | DDY (SEQ ID NO: [ ]) | QVWDSSSDHWV (SEQ ID NO: [ ]) |

| Heavy chain (V$_H$) complementary determining regions (CDRs) of the PD-1 antibodies | | | |
|---|---|---|---|
| Sequence ID | V$_H$ CDR1 | V$_H$ CDR2 | V$_H$ CDR3 |
| P4-B3 | GFTFDDYA (SEQ ID NO: [ ]) | ISWNSGSI (SEQ ID NO: [ ]) | ASDYGDKYYYGMDV (SEQ ID NO: [ ]) |
| P4-B7 | GYTFTTYW (SEQ ID NO: [ ]) | IYPDDSDT (SEQ ID NO: [ ]) | AFWGASGAPVNGFDI (SEQ ID NO: [ ]) |
| PD1#2 | GDSVSSDNYF (SEQ ID NO: [ ]) | VYYNGNT (SEQ ID NO: [ ]) | ATETPPTSYFNSGPFDS (SEQ ID NO: [ ]) |
| PD1#3 | GYTFNRFG (SEQ ID NO: [ ]) | TNPYNGNT (SEQ ID NO: [ ]) | ARVVAVNGMDV (SEQ ID NO: [ ]) |
| PD1#13 | GFTFSSYA (SEQ ID NO: [ ]) | ISYDGSNK (SEQ ID NO: [ ]) | ASQTVAGSDY (SEQ ID NO: [ ]) |
| HL-7 | GFTFDDYA (SEQ ID NO: [ ]) | ISWNSGSI (SEQ ID NO: [ ]) | ASDYGDKYYYGMDV (SEQ ID NO: [ ]) |
| HL-14 | GFTFDDYA (SEQ ID NO: [ ]) | ISWNSGSI (SEQ ID NO: [ ]) | ASDYGDKYSYYGMDV (SEQ ID NO: [ ]) |
| HLkin-1 | GFTFDDFA (SEQ ID NO: [ ]) | ISWNSGSI (SEQ ID NO: [ ]) | ASDYGDKYYYGMDV (SEQ ID NO: [ ]) |
| HLkin-1 HL-7 mut2 | GFTFDDFA (SEQ ID NO: [ ]) | ISWNSGSI (SEQ ID NO: [ ]) | ASDYGDKYYYGMDV (SEQ ID NO: [ ]) |
| HLkin-1 HL-7 HL-14 mut3 | GFTFDDFA (SEQ ID NO: [ ]) | ISWNSGSI (SEQ ID NO: [ ]) | ASDYGDKYSYYGMDV (SEQ ID NO: [ ]) |

| Light chain (V$_L$) complementary determining regions (CDRs) of the PD-1 antibodies | | | |
|---|---|---|---|
| Sequence ID | V$_L$ CDR1 | V$_L$ CDR2 | V$_L$ CDR3 |
| P4-B3 | SSNIGSNT (SEQ ID NO: [ ]) | NDN (SEQ ID NO: [ ]) | AAWDGGLNGRGV (SEQ ID NO: [ ]) |
| P4-B7 | SSNIGAGYV (SEQ ID NO: [ ]) | SNN (SEQ ID NO: [ ]) | AAWDDSLNAPV (SEQ ID NO: [ ]) |
| PD1#2 | SNNVGAHG (SEQ ID NO: [ ]) | RNN (SEQ ID NO: [ ]) | SSWDSSLSGYV (SEQ ID NO: [ ]) |
| PD1#3 | SGSIAAYY (SEQ ID NO: [ ]) | EDN (SEQ ID NO: [ ]) | QSYDSSNLWV (SEQ ID NO: [ ]) |
| PD1#13 | NIGSKS (SEQ ID NO: [ ]) | DDS (SEQ ID NO: [ ]) | QVWHSVSDQGV (SEQ ID NO: [ ]) |
| HL-7 | SSNIGSNT (SEQ ID NO: [ ]) | DDN (SEQ ID NO: [ ]) | AAWDGGLNGRGV (SEQ ID NO: [ ]) |
| HL-14 | SSNIGSNT (SEQ ID NO: [ ]) | NDN (SEQ ID NO: [ ]) | AAWDGGLNGRGV (SEQ ID NO: [ ]) |
| HLkin-1 | SSNIGSNT (SEQ ID NO: [ ]) | NDN (SEQ ID NO: [ ]) | AAWDGGLNGRGV (SEQ ID NO: [ ]) |
| HLkin-1 HL-7 mut2 | SSNIGSNT (SEQ ID NO: [ ]) | DDN (SEQ ID NO: [ ]) | AAWDGGLNGRGV (SEQ ID NO: [ ]) |
| HLkin-1 HL-7 HL-14 mut3 | SSNIGSNT (SEQ ID NO: [ ]) | DDN (SEQ ID NO: [ ]) | AAWDGGLNGRGV (SEQ ID NO: [ ]) |

In other embodiments, armed CARTS can secrete anti-CCR4 antibodies or fragments thereof. For example, armed CARTS can secrete anti-CCR4 antibodies or fragments as described in WO2009/086514, WO 2013/166500, PCT/US2015/054202, or PCT/US2016/026232.

For example, the anti-CCR4 protein antibody or fragment thereof of the armed CART can comprise an antibody having a VH CDR1 region having the amino acid sequence GYTFASYY (SEQ ID NO: 21); a VH CDR2 region having the amino acid sequence WINPGNVNTKYNEKFKG (SEQ ID NO: 252); a VH CDR3 region having the amino acid sequence STYYRPLDY (SEQ ID NO: 29); and/or VL CDR1 region having amino acid sequence KSSQSI-LYSSNQKNYLA (SEQ ID NO: 253); a VL CDR2 region having the amino acid sequence WASTRES (SEQ ID NO: 254) and/or a VL CDR3 region having the amino acid sequence HQYLSSYT (SEQ ID NO: 34).

For example, the anti-CCR4 protein or fragment thereof of the armed CAR can comprise an antibody having

```
a VH amino acid sequence
                                       (SEQ ID NO: [ ])
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSS
and/or a VL amino acid sequence
                                       (SEQ ID NO: [ ])
DIVMTQSPDSLAVSLGERATINCKSSQSILYSSNQKNYLAWYQQKPGQSP

KLLIYWASTRESGVPDRFSGSGSGTDFTLTISSLQAEDVAVYYCHQYLSS

YTFGQGTKLEIK.
```

For example, the anti-CCR4 protein antibody or fragment thereof of the armed CART can comprise an antibody having a:

```
VH chain of antibody 1-44:
                                       (SEQ ID NO: [ ])
QVQLVQSGAEVKKPGASVKVSCKASGYTFASQWMHWMRQAPGQGLEWIGW

INPGNVNTKYNEKFKGRATLTVDTSTNTAYMELSSLRSEDTAVYYCARST

WYRPLDYWGQGTLVTVSS
VL chain of antibody 1-44
                                       (SEQ ID NO: [ ])
DIVMTQSPDSLAVSLGERATINCKSSQSILYSSNQKNYLAWYQQKPGQSP

KLLIYWASTR ESGVPDRFSGSGSGTDFTLTISSLQAEDVAVYYCHQYIS

SYTFGQGTKLEIK
VH chain of antibody 1-49
                                       (SEQ ID NO: [ ])
QVQLVQSGAEVKKPGASVKVSCKASGYTFASSWMHWMRQAPGQGLEWIGW

INPGNVNTKYNEKFKGRATLTVDTSTNTAYMELSSLRSEDTAVYYCARST

WYRPNDYWGQGTLVTV SS
```

```
VL chain of antibody 1-49
                                       (SEQ ID NO: [ ])
DIVMTQSPDSLAVSLGERATINCKSSQSILYSSNQKNYLAWYQQKPGQSP

KLLIYWASTRESGVPDRFSGSGSGTDFTLTISSLQAEDVAVYYCHQYKSS

YTFGQGTKLEIK

VH chain of antibody 2-1
                                       (SEQ ID NO: [ ])
QVQLVQSGAEVKKPGASVKVSCKASGYTFASSWMHWMRQAPGQGLEWIGW

INPGNVNTKYNEKFKGRATLTVDTSTNTAYMELSSLRSEDTAVYYCARTT

RYRPLDYWGQGTLVTVSS

VL chain of antibody 2-1
                                       (SEQ ID NO: [ ])
DIVMTQSPDSLAVSLGERATINCKSSQSILYSSNQKNYLAWYQQKPGQSP

KLLIYWAST RESGVPDRFSGSGSGTDFTLTISSLQAEDVAVYYCHQYRS

SYTFGQGTKLEIK

VH chain of antibody 2-2
                                       (SEQ ID NO: [ ])
QVQLVQSGAEVKKPGASVKVSCKASGYTFASQYMHWMRQAPGQGLEWIGW

INPGNVNTKYNEKFKGRATLTVDTSTNTAYMELSSLRSEDTAVYYCARLT

YYRPPDYWGQGTLVTVSS

VL chain of antibody 2-2
                                       (SEQ ID NO: [ ])
DIVMTQSPDSLAVSLGERATINCKSSQSILYSSNQKNYLAWYQQKPGQSP

KLLIYWAST RESGVPDRFSGSGSGTDFTLTISSLQAEDVAVYYCHQYYS

SYTFGQGTKLEIK

VH chain of antibody 2-3
                                       (SEQ ID NO: [ ])
QVQLVQSGAEVKKPGASVKVSCKASGYTFASAWMHWMRQAPGQGLEWIGW

INPGNVNTKYNEKFKGRATLTVDTSTNTAYMELSSLRSEDTAVYYCARST

YYRPLDYWGQGTLV TVSS

VL chain of antibody 2-3
                                       (SEQ ID NO: [ ])
DIVMTQSPDSLAVSLGERATINCKSSQSILYSSNQKNYLAWYQQKPGQSP

KLLIYWASTRESGVPDRFSGSGSGTDFTLTISSLQAEDVAVYYCHQYMSS

YTFGQGTKLEIK
```

The amino acid sequences of the heavy and light chain complementary determining regions of the anti-CCR4 antibodies are shown in the Table below.

| Antibody | Variable region | CDR1 | CDR2 | CDR3 |
|---|---|---|---|---|
| Mouse 1567 | VH | GYTFASYY (SEQ ID NO: 21) | INPGNVNT (SEQ ID NO: 27) | STYYRPLDY (SEQ ID NO: 29) |
| Humanized 1567 | VH | GYTFASYY (SEQ ID NO: 21) | INPGNVNT (SEQ ID NO: 27) | STYYRPLDY (SEQ ID NO: 29) |
| Ab1-44 | VH | GYTFASQW (SEQ ID NO: 22) | INPGNVNT (SEQ ID NO: 27) | STWYRPLDY (SEQ ID NO: 30) |
| Ab1-49 | VH | GYTFASSW (SEQ ID NO: 23) | INPGNVNT (SEQ ID NO: 27) | STWYRPNDY (SEQ ID NO: 31) |
| Ab2-1 | VH | GYTFASSW (SEQ ID NO: 23) | INPGNVNT (SEQ ID NO: 27) | TTRYRPLDY (SEQ ID NO: 32) |
| Ab2-2 | VH | GYTFASQY (SEQ ID NO: 24) | INPGNVNT (SEQ ID NO: 27) | LTYYRPPDY (SEQ ID NO: 33) |
| Ab2-3 | VH | GYTFASAW (SEQ ID NO: 25) | INPGNVNT (SEQ ID NO: 27) | STYYRPLDY (SEQ ID NO: 29) |
| Mouse 1567 | VL | QSILYSSNQKNY (SEQ ID NO: 26) | WASTRE (SEQ ID NO: 28) | HQYLSSYT (SEQ ID NO: 34) |
| Humanized 1567 | VL | QSILYSSNQKNY (SEQ ID NO: 26) | WASTRE (SEQ ID NO: 28) | HQYLSSYT (SEQ ID NO: 34) |
| Ab1-44 | VL | QSILYSSNQKNY (SEQ ID NO: 26) | WASTRE (SEQ ID NO: 28) | HQYISSYT (SEQ ID NO: 35) |
| Ab1-49 | VL | QSILYSSNQKNY (SEQ ID NO: 26) | WASTRE (SEQ ID NO: 28) | HQYKSSYT (SEQ ID NO: 36) |
| Ab2-1 | VL | QSILYSSNQKNY (SEQ ID NO: 26) | WASTRE (SEQ ID NO: 28) | HQYRSSYT (SEQ ID NO: 37) |
| Ab2-2 | VL | QSILYSSNQKNY (SEQ ID NO: 26) | WASTRE (SEQ ID NO: 28) | HQYYSSYT (SEQ ID NO: 38) |
| Ab2-3 | VL | QSILYSSNQKNY (SEQ ID NO: 26) | WASTRE (SEQ ID NO: 28) | HQYMSSYT (SEQ ID NO: 39) |

Armed CART can be constructed by including a nucleic acid encoding the polypeptide of interest after the intracellular signaling domain. In embodiments, there is an internal ribosome entry site, (IRES), positioned between the intracellular signaling domain and the polypeptide of interest. One skilled in the art can appreciate that more than one polypeptide can be expressed by employing multiple IRES sequences in tandem.

In one embodiment, the methods and compositions presented herein provide a target-specific T cell, such as a T cell with specificity for CAIX and/or CD70, armed with the power to secrete polypeptides in the tumor microenvironment, for example to combat T cell exhaustion. For example, myeloid-derived suppressor cells (MDSCs) are a heterogeneous population of early myeloid progenitors, immature granulocytes, macrophages, and dendritic cells at different stages of differentiation that comprise the tumor microenvironment. MDSCs are induced by pro-inflammatory cytokines and are found in increased numbers in infectious and inflammatory disease conditions. Without wishing to be bound by theory, their presence in the tumor microenvironment indicates a causative role in promoting tumor-associated immune suppression. Human MDSCs express Siglec-3/CD33 (GENBANK Accession No. NM_001772.4 (for nucleotide sequence) and NP_001763.3 (for amino acid sequence) and have heterogeneous expression of CD14 (GENBANK Accession No. NM_000591.4 (for nucleotide sequence) and NP_000582.1 (for amino acid sequence)) and CD15 (GENBANK Accession No. NM_002033.3 (for nucleotide sequence) and NP_002024.1 (for amino acid sequence)) which show that multiple subsets exist. Other MDSC markers useful for identifying MDSCs include, but are not limited to B7-1/CD8 (NM_001145873.1 (for nucleotide sequence), NP_001139345.1 (for amino acid sequence)), CCR2 (NM_001123041.2 (for nucleotide sequence), NP_001116513.2 (for amino acid sequence)), CD1d (NM_001766.3 (for nucleotide sequence), NP_001757.1 (for amino acid sequence)), CD2 (NM_001328609.2 (for nucleotide sequence), NP_001315538.1 (for amino acid sequence)), CD31/PE-CAM-1 (NM_000442.5 (for nucleotide sequence), NP_000433.4 (for amino acid sequence)), CD43 (NM_001030288.3 (for nucleotide sequence), NP_001025459.1 (for amino acid sequence)), CD44 (NM_000610.4 (for nucleotide sequence), NP_000601.3 (for amino acid sequence)), gp130 (NM_002184.4 (for nucleotide sequence), NP_002175.2 ((for amino acid sequence)), PD-L1 (NM_014143.4 (for nucleotide sequence), NP_054862.1 (for amino acid sequence)), and CD162 (NM_001206609.2 (for nucleotide sequence), NP_001193538.1 (for amino acid sequence)).

In one embodiment, the methods and compositions presented herein provide a target-specific T cell, such as a T cell with specificity for CAIX and/or CD70, armed with the power to secrete polypeptides that target MDSCs in the tumor microenvironment. For example the secreted polypeptides can target one or more MDSC markers (e.g., CD33, CD14, and/or CD15, or other MDSC markers listed herein).

Introduction of Constructs into CTLs

Expression vectors that encode the CARs can be introduced as one or more DNA molecules or constructs, where there may be at least one marker that will allow for selection of host cells that contain the construct(s).

The constructs can be prepared in conventional ways, where the genes and regulatory regions can be isolated, as appropriate, ligated, cloned in an appropriate cloning host, analyzed by restriction or sequencing, or other convenient means. Particularly, using PCR, individual fragments including all or portions of a functional unit can be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection. Alternatively, the construct may be introduced by fusion, electroporation, biolistics, transfection, lipofection, or the like. The host cells can be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one can have a target site for homologous recombination, where a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either OMEGA. or O-vectors. See, for example, Thomas and Capecchi, Cell (1987) 51, 503-512; Mansour, et al., Nature (1988) 336, 348-352; and Joyner, et al., Nature (1989) 338, 153-156.

The constructs can be introduced as a single DNA molecule encoding at least the CAR and optionally another gene, or different DNA molecules having one or more genes. Other genes include genes that encode therapeutic molecules or suicide genes, for example. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

Methods of Use

Aspects of the disclosure are directed towards methods of treating a subject afflicted with a cancer.

For example, aspects of the disclosure are directed towards methods of killing a cancer cell, such as a renal cancer cell. Referring to FIG. 12, for example, B7-GGGGS-G36 CAR T cells had more killing activity on the targeted renal carcinoma cells (CAIX+CD70+) than non-targeted cells (CAIX+CD70−, CAIX-CD70+, CAIX-CD70−). Further, referring to FIG. 57, for example, bispecific split CAR achieved superior killing when compared to mono CAR or bispecific CARs.

Aspects of the disclosure are further directed towards methods of stopping or reducing progression or promoting regression of a cancer in a subject.

Still further, aspects of the disclosure are directed towards a method of reducing cellular proliferation of a cancer cell in a subject. See, for example, FIG. 80. "Cancer" and "cancerous" can refer to or describe, for example, the physiological condition in mammals that is characterized by unregulated cell growth. Examples of cancer include but are not limited to, carcinoma, lymphoma, blastoma, sarcoma, and leukemia. More particular examples of such cancers include squamous cell cancer, smallcell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. For example, the cancer is renal cell carcinoma, such as ccRCC.

In cancer, the normal intercellular interactions in tissues are disrupted, and the tumor microenvironment evolves to accommodate the growing tumor. The tumor microenvironment (TME) can refer to the cellular environment in which a tumor exists, including components such as surrounding blood vessels, immune cells, fibroblasts, bone marrow-derived inflammatory cells, lymphocytes, signaling molecules and the extracellular matrix (ECM). Tumor microenvironment is complex and is heavily influenced by immune system.

This invention provides CAR-T cell therapy for renal cell carcinoma, among others (such as those described herein). The secretion of a mono, bi-, or tri-specific minibody, antibody or minibody/antibody fusion protein by the CAR-T cell at the tumor site could provide additional benefit by altering (i.e., modulating) the immune-repressive tumor microenvironment.

In embodiments, the method comprises administering to a subject afflicted with a cancer a therapeutically effective amount of an engineered cell as described herein. Therapeutically effective amounts can depend on the severity and course of the cancer, previous therapy, the subject's health status, weight, and response to the drugs, and the judgment of the treating physician.

The subject can be afflicted with cancer such as liquid cancers (i.e., blood cancers) and/or solid cancers (i.e., tumors). The cancer can be benign or malignant, and can be one that is influenced by the immune system.

Embodiments as described herein can modulate the immune system so as to treat the subject afflicted with cancer. "Modulating" can refer to up-regulation, induction, stimulation, potentiation, and/or relief of inhibition, as well as inhibition, attenuation and/or down-regulation or suppression. In embodiments, the activity of the subject's immune system is modulated, the microenvironment surround the cancer cell and/or tumor is modulated, or both. For example, embodiments as described herein can alter the immune-repressive tumor microenvironment, reducing the microenvironment-dependent immune suppression, so as to modulate (or allow) the immune system to kill tumor cells.

One embodiment is directed towards methods of treating a subject afflicted with renal cell carcinoma. Immune therapies, such as those described herein, offer an exciting therapeutic option for RCC. For example, embodiments comprise engineering a chimeric-antigen receptor (CAR) T-cell for RCC.

An "individual" or "subject" can be a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The cells according to the disclosure can be used for treating cancer in a patient in need thereof. In another embodiment, said isolated cell according to the invention can be used in the manufacture of a medicament for treatment of a cancer, viral infections of autoimmune disorders, in a patient in need thereof.

The present disclosure can rely on methods for treating patients in need thereof, said method comprising at least one of the following steps: (a) providing a chimeric antigen receptor cells according to the invention and (b) adminis-trating the cells to said patient.

Said treatment can be ameliorating, curative or prophy-lactic. It can be either part of an autologous immunotherapy or part of an allogenic immunotherapy treatment. By autolo-gous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immu-notherapy, insofar as it allows the transformation of T-cells, obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer. Cancers that may be treated include tumors that are not vascularized, or not yet substantially vascularized, as well as vascularized tumors. The cancers may comprise nonsolid tumors (such as hema-tological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melano-mas. Adult tumors/cancers and pediatric tumors/cancers are also included.

It can be a treatment in combination with one or more therapies against cancer selected from the group of antibod-ies therapy, chemotherapy, cytokines therapy, dendritic cell therapy, gene therapy, hormone therapy, laser light therapy and radiation therapy.

According to an embodiment of the invention, said treat-ment can be administrated into patients undergoing an immunosuppressive treatment. The present invention uses cells or population of cells, which have been made resistant to at least one immunosuppressive agent due to the inacti-vation of a gene encoding a receptor for such immunosup-pressive agent. In this aspect, the immunosuppressive treat-ment should help the selection and expansion of the T-cells according to the invention within the patient.

In a further embodiment, the cell compositions of the present invention are administered to a patient in conjunc-tion with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell trans-plantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells compris-ing inactivated TCR alpha and/or TCR beta genes.

Administration of Cells

The disclosure is particularly suited for allogenic immu-notherapy, insofar as it allows the transformation of T-cells, obtained from donors, into non-alloreactive cells. This can be done under standard protocols and reproduced as many times as needed. The resulted modified T cells may be pooled and administrated to one or several patients, being made available as an "off the shelf" therapeutic product.

Depending upon the nature of the cells, the cells can be introduced into a host organism, e.g. a mammal, in a wide variety of ways. The cells can be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombi-nant construct, and the like. The cells may be applied as a dispersion, for example, being injected at or near the site of interest. The cells may be in a physiologically-acceptable medium.

In some embodiments, the cells are encapsulated to inhibit immune recognition and placed at the site of the tumor.

The cells can be administered as desired. Depending upon the response desired, the manner of administration, the life of the cells, the number of cells present, various protocols may be employed. The number of administrations will depend upon the factors described above at least in part.

The administration of the cells or population of cells according to the present invention can be carried out in any convenient manner, including by aerosol inhalation, injec-tion, ingestion, transfusion, implantation or transplantation. The compositions described herein may be administered to a patient subcutaneously, intradermally, intratumorally, intranodally, intramedullary, intramuscularly, by intrave-nous or intralymphatic injection, or intraperitoneally. In one embodiment, the cell compositions of the present invention are administered by intravenous injection.

The administration of the cells or population of cells can consist of the administration of 104-109 cells per kg body weight, for example, 105 to 106 cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, for each individual patient, even if there were universal cells which could be administered to the population at large, each patient would be monitored for the proper dosage for the individual, and such practices of monitoring a patient are routine in the art.

Nucleic Acid-Based Expression Systems

The CARs of the disclosure can be expressed from an expression vector. Recombinant techniques to generate such expression vectors are well known in the art.

DNA constructs, which can also be referred to as "DNA vectors", as described herein, can be cloned into a vector which will be used to transduce and produce chimeric-antigen receptor T-cells that secrete polypeptides and/or fragments thereof. For example, DNA constructs can be cloned into a lentiviral vector for production of lentivirus, which will be used to transduce and produce chimeric-antigen receptor T-cells that secrete a mono, bi- or tri-specific immune-modulating antibody/minibody and/or antibody-fusion protein at the tumor site.

Vectors

The term "vector" can refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA that can be transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and translation of an operably linked coding sequence in a particular host cell. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It can contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. These are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter can be one naturally associated with a nucleic acid sequence, as may be obtained by isolating the 5 prime' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR.TM., in connection with the compositions disclosed herein (see U.S. Pat. Nos. 4,683,202 and 5,928,906, each incorporated herein by reference). Furthermore, the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily determine this and providing the necessary signals In certain embodiments of the disclosure, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to allow exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

Plasmid Vectors

In certain embodiments, a plasmid vector can be used to transform a host cell. Plasmid vectors containing replicon and control sequences which are derived from species compatible with the host cell are used in connection with these hosts. The vector ordinarily carries a replication site, as well as marking sequences which can provide phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM.TM. 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, for example, between 2 and 24 h, the cells are collected by centrifugation and washed to remove residual media.

Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; Mclaughlin et al., 1988). Details concerning the generation and use of rAAV vectors are described in U.S. Pat. Nos. 5,139,941 and 4,797,368, each incorporated herein by reference.

Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the sequence of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors can infect non-dividing cells and can be used for both in vivo and ex vivo gene transfer and expression of nucleic acid sequences. For example, recombinant lentivirus can infect a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A new approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

Ex Vivo Transformation

Methods for transfecting eukaryotic cells and tissues removed from an organism in an ex vivo setting are known to those of skill in the art. Thus, cells or tissues may be removed and transfected ex vivo using nucleic acids of the present invention. In some embodiments, the transplanted cells or tissues may be placed into an organism. In other embodiments, a nucleic acid is expressed in the transplanted cells.

Kits of the Invention

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits can include at least one vial, test tube, flask, bottle, syringe or other container means, into which a component may be placed, and suitably aliquoted. Where there are more than one component in the kit, the kit also can contain a second, third or other additional container into which the additional components may be separately placed. However, various combinations of components may be comprised in a vial. The kits of the present invention also can include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. For example, the solvent may also be provided in another container means. The kits may also comprise a second container means for containing a sterile, pharmaceutically acceptable buffer and/or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

Combination Therapy

In certain embodiments of the invention, methods of the present invention for clinical aspects are combined with other agents effective in the treatment of hyperproliferative disease, such as anti-cancer agents. An "anti-cancer" agent can negatively affect cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. For example, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapies. In one embodiment, cell therapy could be used similarly in conjunction with chemotherapeutic, radiotherapeutic, or immunotherapeutic intervention, as well as pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, one may contact the cell with both modalities within about 12-24 h of each other (for example, within about 6-12 h of each other). In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

The treatment cycles would be repeated as necessary. For example, various standard therapies, as well as surgical intervention, may be applied in combination with the inventive cell therapy.

Chemotherapy

Cancer therapies also include a variety of combination therapies with both chemical and radiation based treatments. Combination chemotherapies include, but are not limited to, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention Radiotherapy Other factors that cause DNA damage and have been used extensively include what are commonly known as .gamma.-rays, X-rays, and/or the directed delivery of radioisotopes to tumor cells. Other forms of DNA damaging factors are also useful such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The approach for combined therapy is discussed herein. For example, the tumor cell must bear some marker that is amenable to targeting, i.e., is not present on the majority of other cells. Many tumor markers exist and any of these may be suitable for targeting in the context of the present invention. Common tumor markers include PD-1, PD-L1, CTLA4, carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). For example, the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents

In some embodiments, other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. In some embodiments, upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion can also be used to improve the efficacy of the present invention. Examples of cell adhesion inhibitors are focal adhesion kinase (FAKs) inhibitors and Lovastatin. In some embodiments, other agents that increase the sensitivity of a hyperproliferative cell to apoptosis, such as the antibody c225, could be used in combination with the present invention to improve the treatment efficacy.

Methods of Assessing Activity of Engineered CAR T cells

Aspects of the disclosure are further directed towards methods of and kits for assessing the killing capabilities of engineered CAR T cells. Specifically, embodiments are directed towards an immune complex analysis method and kits to determine the CAR T cell activity during co-culture with cancer cells. First, different target cancer cells (for example, HEK293T, MDA-MB-231, MDA-MB-468, HCC38, and skrc59) are stained with a dye, (for example, ViaStain™ Tracer Blue dye), seeded in a plate (for example a 96-well plate), and incubated for a period of time (for example 12 hours, or overnight). Next, different T cell types (for example, two different T cell types) are added to the wells (for example at a ratio of 20:1 effector-to-target (E: T) ratios) and allowed to co-culture for a period of time (for example, 24 hours). Finally, the plate is scanned and analyzed (for example, using the bright field and blue fluorescent channels). The immune complexes were analyzed by confluence measurement and compared to the negative control of untransduced T cells. As a result, data plots displayed the CAR T cell activities for all of tested target and effector cells combinations. Utilization of an image cytometry platform can visually confirm interactions between effector and target cells, thus making results highly accurate and robust.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Clear cell renal cell carcinoma (ccRCC) is the major type of RCC which is among the 10 most common cancers in both men and women. Chimeric Antigen Receptor (CAR) T cells have proven to be a powerful, clinically translatable immunotherapy for hematologic malignancies. However, these results have not been translatable to solid tumors due to inefficient homing of CAR T cells, the suppressive tumor microenvironment, and on-target off-tumor toxicities resulted from the sharing of CAR T targeting epitopes on healthy tissues. To combat the suppressive microenviron-
ment, immune checkpoint blockade has shown an enhanced
effect on antitumor response by restoring the local antitumor
immunity. CAR T cell factories were designed to empower
CAR T cells through the secretion of human anti-immune
checkpoint inhibitor monoclonal antibodies (mAbs) locally
at the tumor site. Our results show a dramatic improvement
in CAR T killing of ccRCC in vitro and in vivo by reversing
CAR T cell and tumor infiltrating lymphocyte (TIL) exhaus-
tion.

CAIX is an ideal target for ccRCC therapy and used as a
CAR target for the first clinical trial (see, for example,
Lamers, Sleijfer et al. 2006; Lamers, Willemsen et al. 2011).
However, it led to serious side effects due to CAIX expres-
sion on the bile duct. Therefore, it is crucial to develop a
CAR with elevated efficacy and safety (such as limited
on-target off-tumor effect). To achieve that, second genera-
tion CARs were developed by introducing a 2nd targeting
scFv (for example, anti-CD70 scFv) in the CAR T cell
factory together with the first targeting scFv (for example,
anti-CAIX scFv) to allow the CAR to target two unique
antigens simultaneously. See, for example, FIG. 1. By IHC
staining of ccRCC patient samples, we found that target
CD70 is an ideal target to be utilized as the 2nd target since
it is highly expressed on ccRCC and co-expressed with
CAIX.

Our 27 billion-member human scFv-phage display library
was panned against the antigen expressing skrc-59 ccRCC
cells and subtracted with the antigen absent skrc-59 ccRCC
cells to identify new scFvs. Their binding kinetics (Kon/
Koff) and affinity (Kd) were then measured via an OctetRed
96 instrument and scFvs with desirable kinetics were evalu-
ated for their ability to bind with antigen expressing cells.
Candidates were cloned into vectors where anti-CD70 and
anti-CAIX scFvs were combined in different permutations
by changing the order of the two targeting scFvs with
various linkers connected to a costimulatory domain (CD28,
41BB) and an activating domain (CD3). The 4th generation
lentivirus packaging system was used to obtain CAR lenti-
viruses and primary T cells isolated from PBMCs were
transduced to express dual CAR and were tested against
different cell lines in vitro. For further evaluation in vivo, a
humanized orthotopic ccRCC mouse model was established
by injecting luciferized ccRCC cells under the kidney cap-
sule of NSG-SGM3 mice with a reconstituted human
immune system.

In summary, utilizing a dual CAR T discovery platform,
we generated a series of CARs with different scFvs, linkers,
and hinges. The skilled artisan will recognize that embodi-
ments can comprise different combinations of scFvs, linkers,
and hinges. For example, difference combinations of scFvs,
linkers, and hinges can be used to treat different cancers.

By combining the best dual CAR with a payload, such as
an immune checkpoint blockade payload, the 2nd generation
CAR T was discovered. Without wishing to be bound by
theory, the 2nd generation CAR T cell factories can be used
for the treatment of cancers, such as ccRCC, and are able to
eliminate side effects on normal tissues.

REFERENCES CITED IN THIS EXAMPLE

Lamers, C. H., S. Sleijfer, A. G. Vulto, W. H. Kruit, M.
Kliffen, R. Debets, J. W. Gratama, G. Stoter and E.
Oosterwijk (2006). "Treatment of metastatic renal cell
carcinoma with autologous T-lymphocytes genetically
retargeted against carbonic anhydrase IX: first clinical
experience." J Clin Oncol 24 (13): e20-22.
Lamers, C. H., R. Willemsen, P. van Elzakker, S. van
Steenbergen-Langeveld, M. Broertjes, J. Oosterwijk-
Wakka, E. Oosterwijk, S. Sleijfer, R. Debets and J. W.
Gratama (2011). "Immune responses to transgene and
retroviral vector in patients treated with ex vivo-engi-
neered T cells." Blood 117 (1): 72-82.

Example 2

Chimeric Antigen Receptor (CAR) T cells have proven to
be a powerful immunotherapy for hematologic malignan-
cies, however, these have not been translated to solid tumors.
Our CAR T cell factories empower CAR T cells through
secreting antibodies, such as human anti-immune check-
point inhibitor monoclonal antibodies (mAbs), locally at the
tumor site to restore tumor microenvironment to achieve
solid tumor cure. With the introduction of one or more
additional scFvs, the 2nd generation CAR has elevated
efficacy and safety and holds great promise in clinic.

Figure 3:
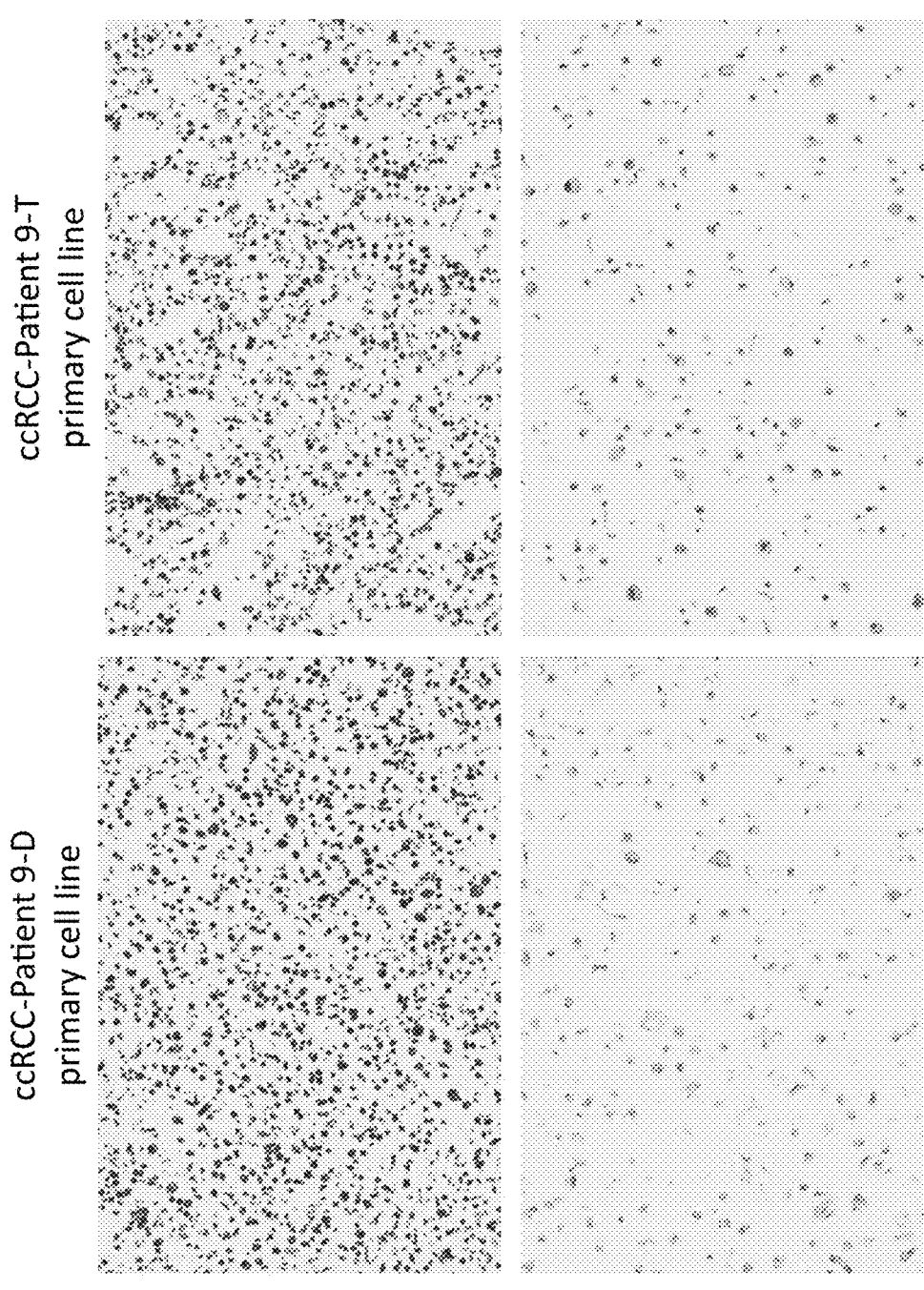

The bispecific tandem CAR was designed to target anti-
gens associated with tumors, such as CAIX and CD70 (see
FIG. 1 and FIG. 2, for example) which are both highly
expressed and co-expressed on ccRCC primary cell by IHC
(FIG. 3). Successful panning of a 27 billion member phage
display library has led to the identification of several anti-
CD70 scFvs (see FIG. 6, for example). The anti-CAIX scFvs
we discovered before and anti-CD70 scFvs were cloned into
pHAGE vector with different linkers (See FIG. 9, for
example). Then lentiviruses were packaged and transduced
with primary T cells. CAR T cells were obtained and
evaluated on 4 different CRISPR engineered cell lines (see
FIG. 5, for example). The killing activity was assessed in
Celigo and Cr51 release assay (See FIGS. 12 and 13, for
example). Selectivity was shown as described herein.

This CAR T cell factories can be used in therapy of CAIX
and/or CD70 overexpressed cancers or in combination with
other therapies.

Example 3

CAIX and CD70 dual IHC staining quantification

| | Scan # | Tissue | RCCT numbers | T | N | M | Stage | % CD70 Positive Cells | % CAIX Positive Cells | % CD70 & CAIX Positive Cells | % CD70 or CAIX Positive Cells |
|---|---|---|---|---|---|---|---|---|---|---|---|
| 1 | 477491 | Normal Kidney | RCCT0461 | 3a | 2 | | III | | | | 0.0 |
| 2 | 477495 | Normal Kidney | RCCT0487 | 3a | 0 | 1 | IV | | | | 0.0 |
| 3 | 477471 & 477472 | Fat cells and liver with bile duct | | | | | | | | | |
| 5 | 477473 & 477474 | Bile duct | | | | | | | | | |

-continued

| | Scan # | Tissue | RCCT numbers | T | N | M | Stage | % CD70 Positive Cells | % CAIX Positive Cells | % CD70 & CAIX Positive Cells | % CD70 or CAIX Positive Cells |
|---|---|---|---|---|---|---|---|---|---|---|---|
| 7 | 477465 | PRCC | RCCT0165 | 2 | | | II | | | | 0.0 |
| 8 | 477466 | PRCC | RCCT0115 | 3b | 0 | 0 | III | 59.8 | 96.5 | 59.4 | 96.9 |
| 9 | 477470 | PRCC | RCCT0564 | 3 | | 0 | III | | | | 0.0 |
| 10 | 477477 | ccRCC | RCCT0015 | T1a | x | x | I | 38.5 | 93.3 | 37.2 | 94.6 |
| 11 | 477501 | ccRCC | RCCT0257 | 1a | 0 | 0 | I | 25.5 | 98.4 | 25.5 | 98.4 |
| 12 | 477469 | ccRCC | RCCT0434 | 1b | | | I | 88.1 | 93.3 | 85.7 | 95.7 |
| 13 | 477496 | ccRCC | RCCT0574 | 1b | | 0 | I | 93.4 | 93.7 | 93.2 | 93.9 |
| 14 | 477498 | ccRCC | RCCT0581 | 2 | 0 | 0 | II | 15.7 | 92.4 | 15.2 | 92.9 |
| 15 | 477504 | ccRCC | RCCT0402 | 2 | 0 | 0 | II | 89.5 | 89.6 | 82.6 | 96.4 |
| 16 | 477475 | ccRCC | RCCT0520 | 2a | | 0 | II | 84.8 | 94.8 | 84.0 | 95.6 |
| 17 | 477481 | ccRCC | RCCT0565 | 2a | 0 | 0 | II | 0.8 | 95.1 | 0.8 | 95.1 |
| 18 | 477482 | ccRCC | RCCT0566 | 2a | 0 | | II | 25.6 | 86.9 | 18.5 | 94.0 |
| 19 | 477483 | ccRCC | RCCT0573 | 2a | 0 | 0 | II | 81.0 | 97.0 | 81.0 | 97.1 |
| 20 | 477479 | ccRCC | RCCT0049 | 2a | 0 | 0 | II | 0.2 | 91.3 | 0.2 | 91.3 |
| 21 | 477476 | ccRCC | RCCT0533 | 3 | 0 | 0 | III | 0.5 | 95.7 | 0.5 | 95.7 |
| 22 | 477487 | ccRCC | RCCT0129 | 3 | 1 | | III | 68.0 | 95.7 | 68.0 | 95.7 |
| 23 | 477488 | ccRCC | RCCT0010 | 3a | 0 | | III | 94.2 | 95.0 | 93.9 | 95.3 |
| 24 | 477497 | ccRCC | RCCT0411 | 3a | 1 | | III | 31.1 | 98.6 | 30.8 | 98.9 |
| 25 | 477499 | ccRCC | RCCT0330 | T3b | 0 | X | III | 80.2 | 81.3 | 65.6 | 96.0 |
| 26 | 477500 | ccRCC | RCCT0334 | 3b | | 0 | III | 83.6 | 90.8 | 81.0 | 93.3 |
| 27 | 477490 | ccRCC | RCCT0317 | | | 1 | IV | | | | 0.0 |
| 28 | 477478 | ccRCC | RCCT0444 | 1b | 0 | 1 | IV | | | | 0.0 |
| 29 | 477484 | ccRCC | RCCT0156 | 2 | 0 | 1 | IV | | | | 0.0 |
| 30 | 477502 | ccRCC | RCCT0394 | 2 | 0 | 1 | IV | 70.1 | 91.3 | 64.4 | 97.0 |
| 31 | 477485 | ccRCC | RCCT0056 | 3 | 0 | 1 | IV | 42.7 | 93.0 | 41.9 | 93.8 |
| 32 | 477486 | ccRCC | RCCT0170 | 3a | 0 | 1 | IV | 46.0 | 17.7 | 12.6 | 51.0 |
| 33 | 477468 | ccRCC | RCCT0400 | 3b | | 1 | IV | 10.8 | 62.2 | 9.7 | 63.3 |
| 34 | 477489 | ccRCC | RCCT0447 | 3b | 1 | 1 | IV | 21.8 | 95.3 | 21.8 | 95.3 |
| 35 | 477494 | ccRCC | RCCT0119 | 3b | 1 | 1 | IV | 0.6 | 96.7 | 0.6 | 96.7 |
| 36 | 477503 | ccRCC | RCCT0383 | 3b | 0 | 1 | IV | 89.1 | 93.9 | 88.5 | 94.5 |
| 37 | 477493 | ccRCC | RCCT0016 | 4 | 0 | 1 | IV | 3.4 | 94.7 | 3.1 | 95.0 |
| 38 | 477467 | ccRCC | RCCT0384 | | | | | 45.3 | 97.3 | 45.2 | 97.3 |
| 39 | 477480 | ccRCC | | | | | | 56.7 | 97.1 | 56.5 | 97.4 |
| 40 | 477492 | ccRCC | RCCT0563 | | | 0 | | 30.5 | 95.8 | 29.9 | 96.5 |

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed:

1. An engineered immune cell comprising a chimeric antigen receptor (CAR), wherein the chimeric antigen receptor comprises an extracellular ligand binding domain comprising an antibody, or antigen-binding fragment thereof wherein the antibody, or antigen-binding fragment thereof comprises an antigen binding domain specific for carbonic anhydrase XI (CAIX) and an antigen binding domain specific for cluster of differentiation 70 (CD70), wherein the antigen binding domain specific for CAIX comprises a sequence consisting of a variable heavy chain (VH), comprising a CDR1, CDR2, and CDR3, and a variable light chain (VL) comprising a CDR1, CDR2, and CDR3; wherein the antigen binding domain specific for CAIX is selected from the group consisting of:

a) A VH CDR1, CDR2, and CDR3 according to SYAMS (SEQ ID NO: 46), AISGSGGSTYYADSVKG (SEQ ID NO: 66), SHSSGGFDY (SEQ ID NO: 86), And a VL CDR1, CDR2, and CDR3 according to TGSSSNI-GRGYNVH (SEQ ID NO: 47), GNTNRPS (SEQ ID NO: 67), and QSYDSSLSAWV (SEQ ID NO: 87), b) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR3 according to TGSSSNI-GAGFDVH (SEQ ID NO: 56), GNTNRPS (SEQ ID NO: 67), and QSYDSRLSAWV (SEQ ID NO: 95), c) A VH CDR1, CDR2, and CDR3 according to TYAMT (SEQ ID NO: 44), AVSGSGGSTYYADSVKG (SEQ ID NO: 64), GPVLRYGFDI (SEQ ID NO: 84), And a VL CDR1, CDR2, and CDR2 according to TGSRSNI-GADYDVH (SEQ ID NO: 45), ANNNRPS (SEQ ID NO: 65), and QSYDSSLRAWV (SEQ ID NO: 85), d) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR3 according to TGSSSNI-GAGYDVH (SEQ ID NO: 48), GNSNRPS (SEQ ID NO: 69), and QSYDRSLSWV (SEQ ID NO: 89), e) A VH CDR1, CDR2, and CDR3 according to GFTFSSYA (SEQ ID NO: 49), ISGSGGST (SEQ ID NO: 70), ATYGDYGSLDY (SEQ ID NO: 90), And a VL CDR1, CDR2, and CDR3 according to SSNI-GAGYD (SEQ ID NO: 50), ANN, and QSYDSSL-RAWV (SEQ ID NO: 85), f) A VH CDR1, CDR2, and CDR3 according to SYAMS (SEQ ID NO: 46), AISGSGGSTYYADSVKG (SEQ ID NO: 66), AAAGFDY (SEQ ID NO: 91), And a VL CDR1, CDR2 and CDR3 according to TGSSSNI-GRGYNVH (SEQ ID NO: 47), DDINRPS (SEQ ID NO: 71), and QSYDSSLRAWV (SEQ ID NO: 85), g) A VH CDR1, CDR2, and CDR3 according to SYAMS (SEQ ID NO: 46), AISGSGGSTYYADSVKG (SEQ ID NO: 66), SHSSGGFDY (SEQ ID NO: 86), And a VL CDR1, CDR2, and CDR3 according to TGSSSNI-GRGYNVH (SEQ ID NO: 47), GNTNRPS (SEQ ID NO: 67), and QSYDSSLSAWV (SEQ ID NO: 87), h) A VH CDR1, CDR2, and CDR3 according to NYAMT (SEQ ID NO: 52), LISYDGSVTHYTDSVKG (SEQ ID NO: 72), GSGYQE (SEQ ID NO: 92), And a VL CDR1, CDR2, and CDR3 according to GGNNIG-SKSVE (SEQ ID NO: 53), YDSDRPS (SEQ ID NO: 73), and QVWDSSSDHHVV (SEQ ID NO: 93), i) A VH CDR1, CDR2, and CDR3 according to GFTFSNYA (SEQ ID NO: 54), ISYDGSVT (SEQ ID NO: 74), and ARGSGYQEH (SEQ ID NO:94), And a VL CDR1, CDR2, and CDR3 according to NIGSKS (SEQ ID NO: 55), YDS, and QVWDSSSDHHVV (SEQ ID NO: 93), j) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR3 according to TGSRSNI-GADYDVH (SEQ ID NO: 45), ANNNRPS (SEQ ID NO: 65), and QSYDSSLSAWV (SEQ ID NO: 87), k) A VH CDR1, CDR2, and CDR3 according to SYAMS (SEQ ID NO: 46), AISGSGGSTYYADSVKG (SEQ ID NO: 66), IGRYSSSLGY (SEQ ID NO: 96), And a VL CDR1, CDR2, and CDR3 according to TGSSSNI-GRGYNVH (SEQ ID NO: 47), DNTNRPS (SEQ ID NO: 75), and QSYDSGLRWV (SEQ ID NO: 97), l) A VH CDR1, CDR2, and CDR3 according to SYAMS (SEQ ID NO: 46), AISGSGGSTYYADSVKG (SEQ ID NO: 66), YGDYGSLDY (SEQ ID NO: 98), And a VL CDR1, CDR2, and CDR3 according to TGSSSNI-GAGYDVH (SEQ ID NO: 48), ANNNRPS (SEQ ID NO: 65), and QSYDSSLRAWV (SEQ ID NO: 85), m) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR3 according to TGTSSNI-GAGYDVH (SEQ ID NO: 57), GNNNRPS (SEQ ID NO: 76), and QSYDKSLSWV (SEQ ID NO: 99), n) A VH CDR1, CDR2, and CDR3 according to SYAMS (SEQ ID NO: 46), AISGSGVSTYYADSVKG (SEQ ID NO: 77), YCSSTSCYRGMDV (SEQ ID NO: 100), And a VL CDR1, CDR2, and CDR3 according to TGSSSNIGAGYDVH (SEQ ID NO: 48), ANNNRPS (SEQ ID NO: 65), and QSYDSSLRAWV (SEQ ID NO: 85), o) A VH CDR1, CDR2, and CDR3 according to SYAMS (SEQ ID NO: 46), AISANGGTTYYADSVKG, (SEQ ID NO: 68), NGNYRGAFDI (SEQ ID NO: 88), And a VL CDR1, CDR2, and CDR3 according to TGSSSNI-GAGYDVH (SEQ ID NO: 48), GNNNRPS (SEQ ID NO: 76), and QSYDKSLTWV (SEQ ID NO: 101), p) A VH CDR1, CDR2, and CDR3 according to SYGMH (SEQ ID NO: 58), VISYDGSNKYYADSVKG (SEQ ID NO: 78), GRAARPPFDY (SEQ ID NO: 102), And a VL CDR1, CDR2, and CDR3 according to SGSSSNIGSNYVY (SEQ ID NO: 59), RNNQRPS (SEQ ID NO: 79), and AAWDDSLNGVV (SEQ ID NO: 103), q) A VH CDR1, CDR2, and CDR3 according to SYGMH (SEQ ID NO: 58), VISYDGSNKYYADSVKG (SEQ ID NO: 78), EAPYSSSLDAFDI (SEQ ID NO: 104), And a VL CDR1, CDR2, and CDR3 according to TGSSSNIGRGYNVH (SEQ ID NO: 47), GNSNRPS (SEQ ID NO: 69), and HSRDNNGHHI (SEQ ID NO: 105), r) A VH CDR1, CDR2, and CDR3 according to SYAMS (SEQ ID NO:); AISANGGTTYYADSVKG (SEQ ID NO: 68), NGNYRGAFDI (SEQ ID NO: 88), And a VL CDR1, CDR2, and CDR3 according to TGSSSNI-GAGYDVH (SEQ ID NO: 48), GNSNRPS (SEQ ID NO: 69), and QSYDSSLSAWV (SEQ ID NO: 87), s) A VH CDR1, CDR2, and CDR3 according to IYAMS (SEQ ID NO: 60), AISGSGGGTYHADSVKG (SEQ ID NO: 80), FSAYSGYDL (SEQ ID NO: 106), and a VL CDR1, CDR2, and CDR3 according to TGSSSNI-GRGYNVH (SEQ ID NO: 47), DNTNRPS (SEQ ID NO: 75), and QSYDSGLRWV (SEQ ID NO: 97), t) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR3 according to TGSSSNI-GAGFDVH (SEQ ID NO: 56), GNNNRPS (SEQ ID NO: 76), and QSYDSSLSAWV (SEQ ID NO: 87), u) A VH CDR1, CDR2, and CDR3 according to SYAMS (SEQ ID NO: 46), AISANGGTTYYADSVKG (SEQ ID NO: 68), NGNYRGAFDI (SEQ ID NO: 88), And a VL CDR1, CDR2, and CDR2 according to TGSSSNI-GAGYDVH (SEQ ID NO: 48), GNTNRPS (SEQ ID NO: 67), and QSYDSTLRVWM (SEQ ID NO: 107), v) A VH CDR1, CDR2, and CDR3 according to KYAMS (SEQ ID NO: 61), GISGSGGSTYYADSVKG (SEQ ID NO: 81), SSRSGYFLPLDY (SEQ ID NO: 108), And a VL CDR1, CDR2, and CDR3 according to QGNSLRYYYPS (SEQ ID NO: 62), GKNNRPS (SEQ ID NO: 82), and SSRDNTDNRVV (SEQ ID NO: 109), and w) A VH CDR1, CDR2, and CDR3 according to SYGMH (SEQ ID NO: 58), AISGSGGSTYYADSVKG (SEQ ID NO: 66), AAVTGGFDP (SEQ ID NO: 110), And a VL CDR1, CDR2, and CDR3 according to GGDNI-GRKSVH (SEQ ID NO: 63), DDRDRPS (SEQ ID NO: 83), and QVWDSSSKHYV (SEQ ID NO: 111), wherein the antigen binding domain specific for CD70 comprises a sequence consisting of a variable heavy chain (VH), comprising a CDR1, CDR2, and CDR3, and a variable light chain (VL) comprising a CDR1, CDR2, and CDR3, wherein the antigen binding domain specific for CD70 is selected from the group consisting of:

a) A VH CDR1, CDR2, and CDR3 according to GFTVSNYA (SEQ ID NO: 158), KSGSDGRT (SEQ ID NO: 167), AKGIYDVTGSSFDS (SEQ ID NO: 174), And a VL CDR1, CDR2, and CDR3 according to SGSIASNY (SEQ ID NO: 160), EDN, and QSYDSGNRRV (SEQ ID NO: 176), b) A VH CDR1, CDR2, and CDR3 according to GFTFSSYA (SEQ ID NO: 49), ISGSGGSR (SEQ ID NO: 165), ARGRGGHGMDV (SEQ ID NO:170), And a VL CDR1, CDR2, and CDR3 according to SSNIG-SNY (SEQ ID NO: 155), RNN, and AAWDDSLNGLV (SEQ ID NO: 171), c) A VH CDR1, CDR2, and CDR3 according to GGTFSSQA (SEQ ID NO: 156), IIPFFGVP (SEQ ID NO: 166), AVLKGRGNFDF (SEQ ID NO:172), And a VL CDR1, CDR2, and CDR3 according to YSVFHSPNNKNY (SEQ ID NO: 157), WAS, and QQRSNWPLT (SEQ ID NO:173), d) A VH CDR1, CDR2, and CDR3 according to GFTVSNYA (SEQ ID NO: 158), KSGSDGRT (SEQ ID NO: 167), AKGIYDVTGSSFDS (SEQ ID NO: 174), And a VL CDR1, CDR2, and CDR3 according to ALPKKY (SEQ ID NO: 159), EDS, and YSTDSSGNHKV (SEQ ID NO: 175), e) A VH CDR1, CDR2, and CDR3 according to GFTVSTSH (SEQ ID NO: 161), KDSGGKT (SEQ ID NO: 168), ARARPSDPYDGSGFDAFDI (SEQ ID NO: 177), And a VL CDR1, CDR2, and CDR3 according to SNNVGNQG (SEQ ID NO: 162), RNN, and SAWDSSLSAWV (SEQ ID NO: 178), and f) A VH CDR1, CDR2, and CDR3 according to GFIFSDYY (SEQ ID NO: 163), IRSRRGET (SEQ ID NO: 169), ARHRKSFTDLDAFDL (SEQ ID NO: 179), and And a VL CDR1, CDR2, and CDR3 according to QDIGTD (SEQ ID NO: 164), KAS, and QHFNNYPAT (SEQ ID NO: 180).

2. The engineered immune cell of claim 1, wherein the CAR further comprises a transmembrane polypeptide and an intracellular signaling domain.

3. The engineered immune cell of claim 2, wherein the CAR further comprises a co-stimulatory domain.

4. The engineered immune cell of claim 1, wherein the engineered immune cell is further engineered to express and secrete a recombinant polypeptide.

5. The engineered immune cell of claim 4, wherein the recombinant polypeptide comprises an antibody or fragment thereof, or a cytokine.

6. The engineered immune cell of claim 5, wherein the cytokine is selected from the group consisting interleukin-12 (IL-12), interleukin-15 (IL-15),—and interleukin-18 (IL-18).

7. The engineered immune cell of claim 1, wherein the cell is selected from the group consisting of comprises a T cell, a natural killer (NK) cell, and a natural killer T (NKT) cell.

8. The engineered immune cell of claim 7, wherein the T cell is selected from the group consisting of CD4+, CD8+, and CD3+ panT cells.

9. The engineered immune cell of claim 1, wherein the antibody, or antigen-binding fragment thereof, specific for CAIX is selected from the group consisting of:

a) a VH according to amino acid sequence QVQLQESGGGLVQPGGSLRLSCAASGFTFSS-YAMSWVRQAPGKGLEWVSAI SGSGGSTY YADSVKGRFTISRDNSKNTLYLQMNSLRAED-TAVY YCARSHSSG GFDYWGQGTLVTVSS (SEQ ID NO: 114), and a VL according to amino acid sequence QSVLTQPPSVSGAPGQRVTISCTGSSSNIGRGY-NVHWYQQLPGTAPKLLIYGN TNRPSGVPDRF-SGSKSGTSASLAITGLQAEDEGDY YCQSYDSSL-SAW VF GGG TKLTVLG (SEQ ID NO: 115);

b) a VH according to amino acid sequence EVQLVQSGGGVVQPGGSLRLSCAASGFPFSS YAMSWVRQAPGKGLEWVSAI SANGGTTY YADSVKGRFTISRDNSKNTLYLQMNSLRAED-TAVY YCANNGNY RGAFDIWGQGTMVTVSS (SEQ ID NO: 127), and a VL according to amino acid sequence QSVLTQPPSVSGAPGQRVTISCTGSSSNIGAG-FDVHWY QQLPGTAPKLLIYGN TNRPSGVPDR-FSGSKSGTSASLAITGLQAEDETDY YCQS YDSR-LSAW VF GGG TKLTVLG (SEQ ID NO: 128);

c) a VH according to amino acid sequence QVQOLVQOSGGGLVQPGGSLRLSCAASEFT-FGTY AMTWVRQAPGKGLEWVSA VSGSGGSTY YADSVKGRFTISRDNSRNTLYLQMNSLRADD-TAVYYCAR GPVLRYGFDI WGQGTMVIVSS (SEQ ID NO: 112), and a VL according to amino acid sequence QSVLTQPPSVSGAPGQRITISCTGSRSNIGADYD-VHW YQQLPGTAPKLLIY AN NNRPSGVPGRFS-ASKSGTSASLAISGLQAEDEADY YCQSYDSSL-RAW VFGGG TKLAVLG (SEQ ID NO: 113);

d) a VH according to amino acid sequence QVQOLVQOSGGGLVQPGGSLRLSCAASGFPFSS YAMSWVRQAPGKGLEWVSAI SANGGTTY YADSVKGRFTISRDNSKNTLYLQMNSLRAED-TAVY YCANNGNY RGAFDIWGQGTMVTVSS (SEQ ID NO: 116), and a VL according to amino acid sequence QSVLTQPPSVSGAPGQRVTISCTGSSSNIGAGYD-VHWYQQLPGTAPKLLIYGNSNRPSGVPDRFSG-SKSGS SASLAITGLQAEDEAHY YCQS YDRSLSW VFGGGT KLTVLG (SEQ ID NO: 117);

e) a VH according to amino acid sequence QVQOLVQOSGGGLVQPGGSLRLSCAASGFTF-SSYAMSW VRQAPGKGLEWVSAI SGSGGSTY YADSVKGRFTISRDNSKNTLYLQMNSLRAED-TAVYYCATYGDY GSLDY (SEQ ID NO: 118), and a VL according to amino acid sequence QSVLTQPPSVSGAPGQRVTISCTGSSSNIGAGYD-VHWYQQLPGTAPKLLIYANNNRPSGVPDRFSG-SKSGTS ASLAITGLQAEDEADY YCQSYDSSL-RAW VFGGG TKLAVLG (SEQ ID NO: 119);

f) a VH according to amino acid sequence QVQOLVQOSGGGLVQPGGSLRLSCAASGFTF-SSYAMSW VRQAPGKGLEWVSAI SGSGGSTY YADSVKGRFTISRDNSKNTLYLQMNSLRAED-TAVY YCARAAAG FDYWGQGTLVTVSS (SEQ ID NO: 120), and a VL according to amino acid sequence QSVLTQPPSVSGAPGQRVTISCTGSSSNIGRGY-NVHWYQQLPGTAPKLLIYDD INRPSGVPHRFS-GSKSGTSASLAITGLQAEDEADY YCQSYDSSL-RAW VFGGGT KLAVLG (SEQ ID NO: 121);

g) a VH according to amino acid sequence QVQLQESGGGLVQPGGSLRLSCAASGFTFS-SYAMSWVRQAPGKGLEWVSAI SGSGGSTY YADSVKGRFTISRDNSKNTLYLQMNSLRAED-TAVY YCARSHSSG GFDYWGQGTLVTVSS (SEQ ID NO: 114), and a VL according to amino acid sequence QSVLTQPPSVSGAPGQRVTISCTGSSSNIGRGY-NVHWYQQLPGTAPKLLIYGNTNRPSGVPD-RFSGSKSGTS ASLAITGLQAXDEGDY YCQSY-DSSLSAW VFGGG TKLTVLG (SEQ ID NO: 122);

h) a VH according to amino acid sequence QVTL-KESGGGVVQPGTSLRLSCAASGFTFSNYAMT-WVRQAPGKGLEWVGLI SYDGSVTHYTDSV-KGRFTISRDNAKNSLYLQMNTLRADDTAVY YCARGSGY QEHWGQGTLVTVSS (SEQ ID NO: 123), and a VL according to amino acid sequence LPVLTQPPSVSVAPGQTARITCGGNNIGSKSVEW YQQKPGQAPVLVIY YDSD RPSGIPERFSG-SNSGNTATLTISR VEAGDEADY YCQVWDSSS-DHHV VFGGGT KLTVLG (SEQ ID NO: 124);

i) a VH according to amino acid sequence QVTL-KESGGGVVQPGTSLRLSCAASGFTFSNY AMT-WVRQAPGKGLEWVGLI SYDGSVTHYTDS-VKGRFTISRDNAKNSLYLQMNTLRADDTAVY YCARGSGY QEH (SEQ ID NO: 125), and a VL according to amino acid sequence LPVLTQPPSVSVAPGQTARITCGGNNIGSKS VHW YQQKPGQAPVLVIY YDSD RPSGIPERFSG-SNSGNTATLTISR VEAGDEADY YCQVWDSSSDHHVV (SEQ ID NO: 126);

j) a VH according to amino acid sequence QVOELVOSGGGVVQPGGSLRLSCAASGFPFSS YAMSWVRQAPGKGLEWVSAI SANGGTTY YADSVKGRFTISRDNSKNTLYLQMNSLRAED-TAVY YCANNGNY RGAFDIWGQGTMVTVSS (SEQ ID NO: 129), and a VL according to amino acid sequence QSVLTQPPSVSGAPGQRITISCTGSRSNI-GADYDVHW YQQLPGTAPKLLIY AN NNRPSGVPDRFSGSKSGTSASLAITGLQAEDE-
TDYFCQSYDSSLSAW VFGGGT KVTVLG (SEQ
ID NO: 130);

k) a VH according to amino acid sequence
QVQLQESGGGLVQPGGSLRLSCAASGFTFSS-
YAMSWVRQAPGKGLEWVSAI SGSGGGSTY
YADSVKGRFTISRDNSKNTLYLQMNSLRAED-
TAVY YCAKIGRYS SSLGYWGQGTLVTVSS (SEQ
ID NO: 131), and a VL according to amino acid sequence
QSVLTQPPSVSGAPGQRVTISCTGSSSNIGRGY-
NVHWYQQLPGTAPKLLIYDN TNRPSGVPA-
RFSGSKSATSASLAITGLQADDEADY YCQSY-
DSGLRW VFGGGT KLTLLR (SEQ ID NO: 132);

l) a VH according to amino acid sequence
QVQOLVQOSGGGLVQPGGSLRLSCAASGFTF-
SSYAMSW VRQAPGKGLEWVSAI YADSVKGRF-
TISRDNSKNTLYLQMNSLRAEDTAVYY-
CATYGDY GSLDYWGQGTLVTVSS (SEQ ID NO:
133), and a VL according to amino acid sequence
QSVLTQPPSVSGAPGQRVTISCTGSSSNIGAGY-
DVHWYQQLPGTAPKLLIYAN NNRPSGVPD-
RFSGSKSGTSASLAITGLQAEDEADY YCQSY-
DSSLRAW VFGGG TKLAVLG (SEQ ID NO: 134);

m) a VH according to amino acid sequence
QVQOLVQOSGGGLVQPGGSLRLSCAASGFPFSS
YAMSWVRQAPGKGLEWVSAI SANGGTTY
YADSVKGRFTISRDNSKNTLYLQMNSLRAED-
TAVY YCANNGNY RGAFDIWGQGTMVTVSS
(SEQ ID NO: 116), and a VL according to amino acid sequence
QSVLTQPPSVSGAPGQRITISCTGTSSNIGAGYD-
VHW YQQLPGAAPRVLIYGN NNRPSGVPDRFSG-
SKSGTSASLAITGLQSEDEADY YCQSYDKS-
LSWVFGGGT KLTVLR (SEQ ID NO: 135);

n) a VH according to amino acid sequence
QVQOLVQOSGGGLVQPGGSLRLSCAASGFTFS-
SYAMSW VRQAPGKGLEWVSAI SGSGVSTYY-
ADSVKGRFTISRDNSKNTLYLQMNSLRAED-
TAVY YCAKYCSST SCYRGMDVWGKGTLVTVSS
(SEQ ID NO: 136), and a VL according to amino acid sequence
QSVLTQPPSVSGAPGQRVTISCTGSSSNIGAGY-
DVHWYQQLPGTAPKLLIYAN NNRPSGVPD-
RFSGSKSGTSASLAITGLQAEDEADY YCQSYD-
SSLRAW VFGGG TKLAVLG (SEQ ID NO: 134);

o) A VH according to amino acid sequence QVQL-
VQOSGGGLVRPGGSLRLSCAASGFPFSSYAM-
SWVRQAPGKGLEWVSAI SANGGTTY YADSV-
KGRFTISRDNSKNTLYLQMNSLRAEDTAVY
YCANNGNY RGAFDI WGQGTTVTVSS (SEQ ID
NO: 137), and a VL according to amino acid sequence
QSVLTQPPSVSGAPGQRITISCTGSSSNIGAG
YDVHW YQQVPGKAPKVVIYGN NNRPSGVP-
DRFSGSKSGASASLAITGLQTEDEADY YCQS
YDKSLTW VFGGGT KVTVLG (SEQ ID NO: 138);

p) a VH according to amino acid sequence QVQOL-
VQOSGGGVVQPGRSLRLSCAASGFTFSS YGMHW
VRQAPGKGLEWVAV ISYDGSNKYYADSVKG-
RFTISRDNSKNTLYLQMNSLRAEDTAVY YCAR-
GRAARPPFDYWGQGTLVTVSS (SEQ ID NO: 139), and a VL according to amino acid sequence QPVLTQPP-
SASGTPGQRVTISCSGSSSNIGSNY VYWY QQL-
PGTAPKLPIYRNN QRPSGVPDRFSGSKSGT-

SASLAISGLRSEDEADY YCAAWDDSLNGVVFG-
GGT KLTVLR (SEQ ID NO: 140);

q) a VH according to amino acid sequence QVQOL-
VOSGGGVVQPGRSLRLSCAASGFTFSS YGMHW
VRQAPGKGLEWVAV ISYDGSNKYYADSVKG-
RFTISRDNSKNTLYLQMNSLRAEDTAVY
YCAREAPY SSSLDAFDIWGQGTMVTVSS (SEQ
ID NO: 141), and a VL according to amino acid sequence
QSVLTQPPSVSGAPGQRVTISCTGSSSNIGRGY-
NVHWYQQLPGTAPKLLIYGN SNRPSGVPDRF-
SGSSSGNTASLTITGAQAEDEADY YCHSRDN-
NGHHIFGGGT KLTVLS (SEQ ID NO: 142);

r) a VH according to amino acid sequence
QVOELVOSGGGVVQPGGSLRLSCAASGFPFSS
YAMSWVRQAPGKGLEWVSAI SANGGTTY
YADSVKGRFTISRDNSKNTLYLQMNSLRAED-
TAVY YCANNGNY RGAFDIWGQGTMVTVSS
(SEQ ID NO: 143), and a VL according to amino acid sequence
QSVLTQPPSVSGAPGQRVTISCTGSSSNIGAGY-
DVHWY QHLPGTAPKLLIYGN SNRPSGVPDR-
FSGSKSGTSASLAITGLQAEDETDYFCQSYDSSL-
SAW VFGGGT KVTVLG (SEQ ID NO: 144);

s) a VH according to amino acid sequence
QVQLQESGGGLVQPGGSLRLSCAASGFTFSIY
AMSWVRQAPGKGLEWVSAIS GSGGGT YHAD-
SVKGRFTISRDNSKNTLYLQMNSLRAEDTAVY
YCAKFSAYS GYDLWGQGTLVTVSS (SEQ ID NO:
145), and a VL according to amino acid sequence
QSVLTQPPSVSGAPGQRVTISCTGSSSNIGRGY-
NVHWYQQLPGTAPKLLIYDN TNRPSGVPAR-
FSGSKSATSASLTITGLQADDEADY YCQSYDS-
GLRW VFGGGT KLTLLG (SEQ ID NO: 146);

t) a VH according to amino acid sequence EVQLVQSGG-
GLVQPGGSLRLSCAASGFTFSS YAMSW VRQA-
PGKGLEWVSAI SANGGTTY YADSVKGRFTIS-
RDNSKNTLYLQMNSLRAEDTAVY YCANNGNY
RGAFDIWGQGTTVTVSS (SEQ ID NO: 147), and a VL according to amino acid sequence
QSVLTQPPSVSGAPGQRVTISCTGSSSNIGAGFD
VHWY QQLPGTAPRLLIYGN NNRPSGVPDRFSG-
SKSGTSASLAITGLQAEDETDYFCQSYDSSLSAW
VFGGGT KVTVLR (SEQ ID NO: 148);

u) a VH according to amino acid sequence
QVQOLVQOSGGGLVQPGGSLRLSCAASGFPFSS
YAMSWVRQAPGKGLEWVSAI SANGGTTY
YADSVKGRFTISRDNSKNTLYLQMNSLRAED-
TAVY YCANNGNY RGAFDIWGQGTMVIVSS
(SEQ ID NO: 149), and a VL according to amino acid sequence
QSVLTQPPSVSGAPGQRVTISCTGSSSNIGAGY-
DVHWYQQLPGTAPKLLIYGN TNRPSGVP-
DRFSGSKSGTSASLAIIGLQADDEADY YCQS
YDSTLRVWMFGGG TKLTVLG (SEQ ID NO: 150);

v) a VH according to amino acid sequence QVQOL-
VQOSGGGLVQPGGSLRLSCAAPEFTFSK
YAMSW VRQAPGKGLEWVSGI SGSGGSTY
YADSVKGRFTISRDNSKNTLYLQMNSLRAED-
TAVY YCAKSSRSG YFLPLDYWGQGTLVTVSS
(SEQ ID NO: 151), and a VL according to amino acid sequence SSELTQD-
PAVSVALGQTVRITCQGNSLRY Y YPSW Y
QQKPGQAPVLVIYGKNN RPSGIPDRFSGSSSGN- TASLTITGTQAEDEADY YCSSRDNTDNRVVF-GGGTKL TVLG (SEQ ID NO: 152); and w) a VH according to amino acid sequence EVQLVES-GGGV VQPGRSLRLSCAASGFTFSS YGMHW VRQAPGKGLEWVSAI SGSGGSTY YADSVKGR-FTISRDNAKNTLYLQMNSLRAEDTAVY YCAR-AAVT GGFDPWGQGTLVTVSS (SEQ ID NO: 153), and a VL according to amino acid sequence QPGLTQPPSVSVAPGQTARITCGGDNIGRKS VHWY QQRPGQAPILVIRDDRD RPSGIPERF-SGSSSVNTATLIISR VEAGDEADY YCQVWDS-SSKHY VFGPGTKV TALG (SEQ ID NO: 154).

10. The engineered immune cell of claim 1, wherein the antibody, or antigen-binding fragment thereof, specific for CD70 is selected from the group consisting of:

a) a VH according to amino acid sequence QVQOLVQOSGGGLVQPRGSLRLSCAASGFTV-SNYAMSW VRQAPGKGLEWVAT KSGSDGRTY YADSVKGRFTIARDNSKNSLYLQMNSLRAAD-TAVYYCAKGIY DVTGSSFDS (SEQ ID NO: 185), and a VL according to amino acid sequence NFMLTQPHSVSESPGKTVTISCTRSSGSIASNY VQWY QQRPGSAPTTVIYEDN QRPSGVPDR-FSGSIDSSSNSASLTISGLKTEDEADY YCQS-YDSGNRRV (SEQ ID NO: 187);

b) a VH according to amino acid sequence QVQOLVQOSGGGLVQPGGSLRLSCAASGF-TFSSYAMSW VRQAPGKGLEWVSLI SGSGGSRY YADSVKGRFTISRDNSKNTLYLQMNNLRAED-TAVY YCARGRG GHGMDV (SEQ ID NO: 181), and a VL according to amino acid sequence QPGLTQPP-SASGTPGQRVTISCSGSSSNIGSNY VYWY QQLP-GTAPKLLIYRNN QRPSGVPDRFSGSKSGT-SASLAISGLQSEDEADY YCAAWDDSLNGLYV (SEQ ID NO: 182);

c) a VH according to amino acid sequence QVQLVQS-GAEVKKPGSSVK VSCRSSGGTFSSQAFSW VRQAPGQGLEWMG RUPFFGVPTY AQRFQGRV-TITADKSPTTAYMELTSLRSDDTAVY YCAVLKG RGNFDF (SEQ ID NO: 183), and a VL according to amino acid sequence DIVMTQSPDSLAVSLGERATINCKSS YS VFHSP-NNKNYLAW YQQRPGQPPK LLIYWAST-RGSGVPDRFSGSGSGTDFTLTISSLEPEDFAVY YCQQRSNWPLT (SEQ ID NO: 184);

d) a VH according to amino acid sequence QVQOL-VOQSGGGLVQPRGSLRLSCAASGFTVSNYAM-SWVRQAPGKGLEWV ATKSGSDGRTY YADS VKGRFTIARDNSKNSLYLQMNSLRAAD-TAVYYCA KGIYDVTGSSFDS (SEQ ID NO: 185), and a VL according to amino acid sequence SYELTQPPSVSVSPGQTARITCSGDALPKKYAY-WYQQKSGQAPVLVMFE DSKRPSGIPERFSGSS-SGTMAILTISGAQVEDEADY YCYSTDSSGNHKV (SEQ ID NO: 186);

e) a VH according to amino acid sequence EVOLVES-GGGV VQPGRSLRLSCAASGFT VSTSHMSW VRQAPGKGLEWLS GKDSGGKTYY ADS VRGRF-TIARDDSLNTVFLQMNNMRDEDSGVY YCAR ARPSDPYDGSGFDAFDI (SEQ ID NO: 188), and a VL according to amino acid sequence SYELTQPPSVSKGLRO-TATLTCTGNSNNVGNQGAAWLQQHQGHPPKLLS YRNNNRPSGISERFSASRSGNTASLTITGLQ-PEDEADY YCSAWDSSLSAW V (SEQ ID NO: 189); and f) a VH according to amino acid sequence QVQLVQSGGGLVKPRGSLRLSCAASGFIFSD Y YMSWIRQAPGKGLQWVA SIRSRRGETNY ADSVKGRFTIARDNAEKSLYLQMNSLRAE-DAAVYYCAR HRKSFTDLDAFDL (SEQ ID NO: 190), and a VL according to amino acid sequence DIVMTQSP-STLSASVGDRVTITCRASQDIGTDLSWY QQKPGKAPKLLIYK ASSLESGVPSRFSGSGS-GTDFTLTISSLQPDDFATY YCQHENNYPAT (SEQ ID NO: 191.

\* \* \* \* \*

```
                        SEQUENCE LISTING

<160> NUMBER OF SEQ ID NOS: 352

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000
```

-continued

```
<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16
```

```
<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Ala Ser Tyr Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Thr Phe Ala Ser Gln Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Thr Phe Ala Ser Ser Trp
1               5

<210> SEQ ID NO 24
<211> LENGTH: 8
<212> TYPE: PRT
```

<213> ORGANISM: Artificial Sequence
<220> FEATURE:
<223> OTHER INFORMATION: Description of Artificial Sequence: Synthetic
     peptide

<400> SEQUENCE: 24

Gly Tyr Thr Phe Ala Ser Gln Tyr
1                5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 25

Gly Tyr Thr Phe Ala Ser Ala Trp
1                5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 26

Gln Ser Ile Leu Tyr Ser Ser Asn Gln Lys Asn Tyr
1                5               10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 27

Ile Asn Pro Gly Asn Val Asn Thr
1                5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 28

Trp Ala Ser Thr Arg Glu
1                5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 29

Ser Thr Tyr Tyr Arg Pro Leu Asp Tyr
1                5

```
<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Thr Trp Tyr Arg Pro Leu Asp Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Thr Trp Tyr Arg Pro Asn Asp Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Thr Arg Tyr Arg Pro Leu Asp Tyr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Thr Tyr Tyr Arg Pro Pro Asp Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Gln Tyr Leu Ser Ser Tyr Thr
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 35

His Gln Tyr Ile Ser Ser Tyr Thr
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His Gln Tyr Lys Ser Ser Tyr Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Gln Tyr Arg Ser Ser Tyr Thr
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Gln Tyr Tyr Ser Ser Tyr Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Gln Tyr Met Ser Ser Tyr Thr
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Ser
1

<210> SEQ ID NO 41
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Gly Ser Ser Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Gly Gly Ser Ser Ser Ser Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Glu Asp Leu Pro Glu
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Tyr Ala Met Thr
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Gly Ser Arg Ser Asn Ile Gly Ala Asp Tyr Asp Val His
1               5                   10

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Tyr Ala Met Ser
```

-continued
```
1               5

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Gly Ser Ser Ser Asn Ile Gly Arg Gly Tyr Asn Val His
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Gly Ser Ser Ser Asn Ile Gly Ala Gly Tyr Asp Val His
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Ser Ser Tyr Ala
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ser Asn Ile Gly Ala Gly Tyr Asp
1               5

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Gly Ser Ser Ser Asn Ile Gly Arg Gly Thr His Thr Val His
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 52

Asn Tyr Ala Met Thr
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 53

Gly Gly Asn Asn Ile Gly Ser Lys Ser Val Glu
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 54

Gly Phe Thr Phe Ser Asn Tyr Ala
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 55

Asn Ile Gly Ser Lys Ser
1               5

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 56

Thr Gly Ser Ser Ser Asn Ile Gly Ala Gly Phe Asp Val His
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 57

Thr Gly Thr Ser Ser Asn Ile Gly Ala Gly Tyr Asp Val His
1               5                   10

<210> SEQ ID NO 58
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Tyr Gly Met His
1               5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Ser Ser Ser Asn Ile Gly Ser Asn Tyr Val Tyr
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Tyr Ala Met Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Tyr Ala Met Ser
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gly Asn Ser Leu Arg Tyr Tyr Tyr Pro Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

```
Gly Gly Asp Asn Ile Gly Arg Lys Ser Val His
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Val Ser Gly Ser Gly Gly Ser Thr Tyr Tyr Ala Asp Ser Val Lys
1               5                   10                  15

Gly

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Asn Asn Asn Arg Pro Ser
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Ile Ser Gly Ser Gly Gly Ser Thr Tyr Tyr Ala Asp Ser Val Lys
1               5                   10                  15

Gly

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Asn Thr Asn Arg Pro Ser
1               5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ile Ser Ala Asn Gly Gly Thr Thr Tyr Tyr Ala Asp Ser Val Lys
1               5                   10                  15

Gly
```

```
<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Asn Ser Asn Arg Pro Ser
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ser Gly Ser Gly Gly Ser Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Asp Ile Asn Arg Pro Ser
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ile Ser Tyr Asp Gly Ser Val Thr His Tyr Thr Asp Ser Val Lys
1               5                   10                  15

Gly

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Asp Ser Asp Arg Pro Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued

```
              peptide

<400> SEQUENCE: 74

Ile Ser Tyr Asp Gly Ser Val Thr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asn Thr Asn Arg Pro Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Asn Asn Asn Arg Pro Ser
1               5

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ile Ser Gly Ser Gly Val Ser Thr Tyr Tyr Ala Asp Ser Val Lys
1               5                   10                  15

Gly

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Val Ile Ser Tyr Asp Gly Ser Asn Lys Tyr Tyr Ala Asp Ser Val Lys
1               5                   10                  15

Gly

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Asn Asn Gln Arg Pro Ser
```

```
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ile Ser Gly Ser Gly Gly Gly Thr Tyr His Ala Asp Ser Val Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ile Ser Gly Ser Gly Gly Ser Thr Tyr Tyr Ala Asp Ser Val Lys
1               5                   10                  15

Gly

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Lys Asn Asn Arg Pro Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Asp Arg Asp Arg Pro Ser
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Pro Val Leu Arg Tyr Gly Phe Asp Ile
1               5                   10

<210> SEQ ID NO 85
<211> LENGTH: 11
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Ser Tyr Asp Ser Ser Leu Arg Ala Trp Val
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser His Ser Ser Gly Gly Phe Asp Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Ser Tyr Asp Ser Ser Leu Ser Ala Trp Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Gly Asn Tyr Arg Gly Ala Phe Asp Ile
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Tyr Asp Arg Ser Leu Ser Trp Val
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Thr Tyr Gly Asp Tyr Gly Ser Leu Asp Tyr
```

-continued

```
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ala Ala Gly Phe Asp Tyr
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Tyr Gln Glu
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Val Trp Asp Ser Ser Ser Asp His His Val Val
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Arg Gly Ser Gly Tyr Gln Glu His
1               5

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Ser Tyr Asp Ser Arg Leu Ser Ala Trp Val
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 96

Ile Gly Arg Tyr Ser Ser Ser Leu Gly Tyr
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 97

Gln Ser Tyr Asp Ser Gly Leu Arg Trp Val
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 98

Tyr Gly Asp Tyr Gly Ser Leu Asp Tyr
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 99

Gln Ser Tyr Asp Lys Ser Leu Ser Trp Val
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 100

Tyr Cys Ser Ser Thr Ser Cys Tyr Arg Gly Met Asp Val
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 101

Gln Ser Tyr Asp Lys Ser Leu Thr Trp Val
1               5                   10

<210> SEQ ID NO 102
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Arg Ala Ala Arg Pro Pro Phe Asp Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ala Trp Asp Asp Ser Leu Asn Gly Val Val
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ala Pro Tyr Ser Ser Ser Leu Asp Ala Phe Asp Ile
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

His Ser Arg Asp Asn Asn Gly His His Ile
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Ser Ala Tyr Ser Gly Tyr Asp Leu
1               5

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

-continued

```
Gln Ser Tyr Asp Ser Thr Leu Arg Val Trp Met
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ser Arg Ser Gly Tyr Phe Leu Pro Leu Asp Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Ser Arg Asp Asn Thr Asp Asn Arg Val Val
1               5                   10

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Ala Val Thr Gly Gly Phe Asp Pro
1               5

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Val Trp Asp Ser Ser Ser Lys His Tyr Val
1               5                   10

<210> SEQ ID NO 112
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Val Gln Ser Gly Gly Gly Leu Val Gln Pro Gly Gly
1               5                   10                  15

Ser Leu Arg Leu Ser Cys Ala Ala Ser Glu Phe Thr Phe Gly Thr Tyr
            20                  25                  30

Ala Met Thr Trp Val Arg Gln Ala Pro Gly Lys Gly Leu Glu Trp Val
        35                  40                  45
```

-continued

```
Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Pro Val Leu Arg Tyr Gly Phe Asp Ile Trp Gly Gln Gly
            100                 105                 110

Thr Met Val Ile Val Ser Ser
        115
```

```
<210> SEQ ID NO 113
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113
```

```
Gln Ser Val Leu Thr Gln Pro Pro Ser Val Ser Gly Ala Pro Gly Gln
1               5                   10                  15

Arg Ile Thr Ile Ser Cys Thr Gly Ser Arg Ser Asn Ile Gly Ala Asp
                20                  25                  30

Tyr Asp Val His Trp Tyr Gln Gln Leu Pro Gly Thr Ala Pro Lys Leu
            35                  40                  45

Leu Ile Tyr Ala Asn Asn Asn Arg Pro Ser Gly Val Pro Gly Arg Phe
    50                  55                  60

Ser Ala Ser Lys Ser Gly Thr Ser Ala Ser Leu Ala Ile Ser Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
            100                 105                 110
```

```
<210> SEQ ID NO 114
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114
```

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser His Ser Ser Gly Gly Phe Asp Tyr Trp Gly Gln Gly Thr
            100                 105                 110
```

-continued

Leu Val Thr Val Ser Ser
        115

<210> SEQ ID NO 115
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Gly Asp Tyr Tyr Cys Gln Ser Tyr Asp Ser Ser
                85                  90                  95

Leu Ser Ala Trp Val Phe Gly Gly Gly Thr Lys Leu Thr Val Leu Gly
            100                 105                 110

<210> SEQ ID NO 116
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 117
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 117

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Ser Ser Ala Ser Leu Ala Ile Thr Gly Leu
65                  70                  75                  80

Gln Ala Glu Asp Glu Ala His Tyr Tyr Cys Gln Ser Tyr Asp Arg Ser
                85                  90                  95

Leu Ser Trp Val Phe Gly Gly Gly Thr Lys Leu Thr Val Leu Gly
            100                 105                 110
```

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Tyr Gly Asp Tyr Gly Ser Leu Asp Tyr
            100                 105
```

<210> SEQ ID NO 119
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
```

```
65                  70                  75                  80

Gln Ala Glu Asp Glu Ala Asp Tyr Tyr Cys Gln Ser Tyr Asp Ser Ser
                85                  90                  95

Leu Arg Ala Trp Val
            100

<210> SEQ ID NO 120
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Ala Gly Phe Asp Tyr Trp Gly Gln Gly Thr Leu Val
            100                 105                 110

Thr Val Ser Ser
        115

<210> SEQ ID NO 121
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
            20                  25                  30

Tyr Asn Val His Trp Tyr Gln Gln Leu Pro Gly Thr Ala Pro Lys Leu
        35                  40                  45

Leu Ile Tyr Asp Asp Ile Asn Arg Pro Ser Gly Val Pro His Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
            100                 105                 110

<210> SEQ ID NO 122
<211> LENGTH: 112
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (83)..(83)
<223> OTHER INFORMATION: Any amino acid

<400> SEQUENCE: 122

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Xaa Asp Glu Gly Asp Tyr Tyr Cys Gln Ser Tyr Asp Ser Ser
                85                  90                  95

Leu Ser Ala Trp Val Phe Gly Gly Gly Thr Lys Leu Thr Val Leu Gly
            100                 105                 110

<210> SEQ ID NO 123
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Val Thr Leu Lys Glu Ser Gly Gly Gly Val Val Gln Pro Gly Thr
1               5                   10                  15

Ser Leu Arg Leu Ser Cys Ala Ala Ser Gly Phe Thr Phe Ser Asn Tyr
                20                  25                  30

Ala Met Thr Trp Val Arg Gln Ala Pro Gly Lys Gly Leu Glu Trp Val
            35                  40                  45

Gly Leu Ile Ser Tyr Asp Gly Ser Val Thr His Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Asp Asp Thr Ala Val Tyr Tyr Cys
                85                  90                  95

Ala Arg Gly Ser Gly Tyr Gln Glu His Trp Gly Gln Gly Thr Leu Val
            100                 105                 110

Thr Val Ser Ser
        115

<210> SEQ ID NO 124
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Pro Val Leu Thr Gln Pro Pro Ser Val Ser Val Ala Pro Gly Gln

-continued

```
1             5                    10                   15

Thr Ala Arg Ile Thr Cys Gly Gly Asn Asn Ile Gly Ser Lys Ser Val
            20                   25                   30

Glu Trp Tyr Gln Gln Lys Pro Gly Gln Ala Pro Val Leu Val Ile Tyr
            35                   40                   45

Tyr Asp Ser Asp Arg Pro Ser Gly Ile Pro Glu Arg Phe Ser Gly Ser
        50                   55                   60

Asn Ser Gly Asn Thr Ala Thr Leu Thr Ile Ser Arg Val Glu Ala Gly
65                   70                   75                   80

Asp Glu Ala Asp Tyr Tyr Cys Gln Val Trp Asp Ser Ser Ser Asp His
                85                   90                   95

His Val Val Phe Gly Gly Gly Thr Lys Leu Thr Val Leu Gly
            100                  105                  110
```

<210> SEQ ID NO 125
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gln Val Thr Leu Lys Glu Ser Gly Gly Gly Val Val Gln Pro Gly Thr
1             5                    10                   15

Ser Leu Arg Leu Ser Cys Ala Ala Ser Gly Phe Thr Phe Ser Asn Tyr
            20                   25                   30

Ala Met Thr Trp Val Arg Gln Ala Pro Gly Lys Gly Leu Glu Trp Val
            35                   40                   45

Gly Leu Ile Ser Tyr Asp Gly Ser Val Thr His Tyr Thr Asp Ser Val
        50                   55                   60

Lys Gly Arg Phe Thr Ile Ser Arg Asp Asn Ala Lys Asn Ser Leu Tyr
65                   70                   75                   80

Leu Gln Met Asn Thr Leu Arg Ala Asp Asp Thr Ala Val Tyr Tyr Cys
                85                   90                   95

Ala Arg Gly Ser Gly Tyr Gln Glu His
            100                  105
```

<210> SEQ ID NO 126
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Leu Pro Val Leu Thr Gln Pro Pro Ser Val Ser Val Ala Pro Gly Gln
1             5                    10                   15

Thr Ala Arg Ile Thr Cys Gly Gly Asn Asn Ile Gly Ser Lys Ser Val
            20                   25                   30

His Trp Tyr Gln Gln Lys Pro Gly Gln Ala Pro Val Leu Val Ile Tyr
            35                   40                   45

Tyr Asp Ser Asp Arg Pro Ser Gly Ile Pro Glu Arg Phe Ser Gly Ser
        50                   55                   60

Asn Ser Gly Asn Thr Ala Thr Leu Thr Ile Ser Arg Val Glu Ala Gly
65                   70                   75                   80

Asp Glu Ala Asp Tyr Tyr Cys Gln Val Trp Asp Ser Ser Ser Asp His
```

-continued

```
                 85                    90                    95
His Val Val

<210> SEQ ID NO 127
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Ala Asn Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 128
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Tyr Cys Gln Ser Tyr Asp Ser Arg
                85                  90                  95

Leu Ser Ala Trp Val Phe Gly Gly Gly Thr Lys Leu Thr Val Leu Gly
            100                 105                 110

<210> SEQ ID NO 129
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 129

```
Gln Val Gln Leu Val Gln Ser Gly Gly Gly Val Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115
```

<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Ser Val Leu Thr Gln Pro Pro Ser Val Ser Gly Ala Pro Gly Gln
1               5                   10                  15

Arg Ile Thr Ile Ser Cys Thr Gly Ser Arg Ser Asn Ile Gly Ala Asp
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Gly
            100                 105                 110
```

<210> SEQ ID NO 131
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Arg Tyr Ser Ser Ser Leu Gly Tyr Trp Gly Gln Gly
                100                 105                 110

Thr Leu Val Thr Val Ser Ser
        115

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
        35                  40                  45

Leu Ile Tyr Asp Asn Thr Asn Arg Pro Ser Gly Val Pro Ala Arg Phe
    50                  55                  60

Ser Gly Ser Lys Ser Ala Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Gly
                85                  90                  95

Leu Arg Trp Val Phe Gly Gly Gly Thr Lys Leu Thr Leu Leu Arg
                100                 105                 110

<210> SEQ ID NO 133
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Tyr Gly Asp Tyr Gly Ser Leu Asp Tyr Trp Gly Gln Gly Thr
                100                 105                 110
```

-continued

Leu Val Thr Val Ser Ser
        115

<210> SEQ ID NO 134
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
            100                 105                 110

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Ser Val Leu Thr Gln Pro Pro Ser Val Ser Gly Ala Pro Gly Gln
1               5                   10                  15

Arg Ile Thr Ile Ser Cys Thr Gly Thr Ser Ser Asn Ile Gly Ala Gly
            20                  25                  30

Tyr Asp Val His Trp Tyr Gln Gln Leu Pro Gly Ala Ala Pro Arg Val
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Gln Ser Tyr Asp Lys Ser
                85                  90                  95

Leu Ser Trp Val Phe Gly Gly Gly Thr Lys Leu Thr Val Leu Arg
            100                 105                 110

<210> SEQ ID NO 136
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Val Gln Ser Gly Gly Gly Leu Val Gln Pro Gly Gly

-continued

```
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Val Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Cys Ser Ser Thr Ser Cys Tyr Arg Gly Met Asp Val Trp
            100                 105                 110

Gly Lys Gly Thr Leu Val Thr Val Ser Ser
        115                 120
```

```
<210> SEQ ID NO 137
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Gln Ser Gly Gly Gly Leu Val Arg Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Ala Asn Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Thr Val Thr Val Ser Ser
        115
```

```
<210> SEQ ID NO 138
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ser Val Leu Thr Gln Pro Pro Ser Val Ser Gly Ala Pro Gly Gln
1               5                   10                  15

Arg Ile Thr Ile Ser Cys Thr Gly Ser Ser Ser Asn Ile Gly Ala Gly
            20                  25                  30

Tyr Asp Val His Trp Tyr Gln Gln Val Pro Gly Lys Ala Pro Lys Val
        35                  40                  45

Val Ile Tyr Gly Asn Asn Asn Arg Pro Ser Gly Val Pro Asp Arg Phe
```

-continued

```
        50              55              60

Ser Gly Ser Lys Ser Gly Ala Ser Ala Ser Leu Ala Ile Thr Gly Leu
65              70              75              80

Gln Thr Glu Asp Glu Ala Asp Tyr Tyr Cys Gln Ser Tyr Asp Lys Ser
                85              90              95

Leu Thr Trp Val Phe Gly Gly Gly Thr Lys Val Thr Val Leu Gly
            100             105             110

<210> SEQ ID NO 139
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Gln Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Gly Met His Trp Val Arg Gln Ala Pro Gly Lys Gly Leu Glu Trp Val
        35              40              45

Ala Val Ile Ser Tyr Asp Gly Ser Asn Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Gly Arg Ala Ala Arg Pro Pro Phe Asp Tyr Trp Gly Gln Gly
            100             105             110

Thr Leu Val Thr Val Ser Ser
        115

<210> SEQ ID NO 140
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Pro Val Leu Thr Gln Pro Pro Ser Ala Ser Gly Thr Pro Gly Gln
1               5               10              15

Arg Val Thr Ile Ser Cys Ser Gly Ser Ser Ser Asn Ile Gly Ser Asn
            20              25              30

Tyr Val Tyr Trp Tyr Gln Gln Leu Pro Gly Thr Ala Pro Lys Leu Pro
        35              40              45

Ile Tyr Arg Asn Asn Gln Arg Pro Ser Gly Val Pro Asp Arg Phe Ser
    50              55              60

Gly Ser Lys Ser Gly Thr Ser Ala Ser Leu Ala Ile Ser Gly Leu Arg
65              70              75              80

Ser Glu Asp Glu Ala Asp Tyr Tyr Cys Ala Ala Trp Asp Asp Ser Leu
                85              90              95

Asn Gly Val Val Phe Gly Gly Gly Thr Lys Leu Thr Val Leu Arg
            100             105             110
```

```
<210> SEQ ID NO 141
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Tyr Ser Ser Ser Leu Asp Ala Phe Asp Ile Trp
                100                 105                 110

Gly Gln Gly Thr Met Val Thr Val Ser Ser
            115                 120

<210> SEQ ID NO 142
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Ser Ser Gly Asn Thr Ala Ser Leu Thr Ile Thr Gly Ala
65                  70                  75                  80

Gln Ala Glu Asp Glu Ala Asp Tyr Tyr Cys His Ser Arg Asp Asn Asn
                85                  90                  95

Gly His His Ile Phe Gly Gly Gly Thr Lys Leu Thr Val Leu Ser
            100                 105                 110

<210> SEQ ID NO 143
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Gln Ser Gly Gly Gly Val Val Gln Pro Gly Gly
1               5                   10                  15
```

Ser Leu Arg Leu Ser Cys Ala Ala Ser Gly Phe Pro Phe Ser Ser Tyr
        20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Thr Val Ser Ser
        115

<210> SEQ ID NO 144
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln His Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Gly
            100                 105                 110

<210> SEQ ID NO 145
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
        20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Phe Ser Ala Tyr Ser Gly Tyr Asp Leu Trp Gly Gln Gly Thr
                100                 105                 110

Leu Val Thr Val Ser Ser
        115

<210> SEQ ID NO 146
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
        35                  40                  45

Leu Ile Tyr Asp Asn Thr Asn Arg Pro Ser Gly Val Pro Ala Arg Phe
    50                  55                  60

Ser Gly Ser Lys Ser Ala Thr Ser Ala Ser Leu Thr Ile Thr Gly Leu
65                  70                  75                  80

Gln Ala Asp Asp Glu Ala Asp Tyr Tyr Cys Gln Ser Tyr Asp Ser Gly
                85                  90                  95

Leu Arg Trp Val Phe Gly Gly Gly Thr Lys Leu Thr Leu Leu Gly
                100                 105                 110

<210> SEQ ID NO 147
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Ala Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
                100                 105                 110

Thr Thr Val Thr Val Ser Ser
        115

<210> SEQ ID NO 148
```

<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Phe Asp Val His Trp Tyr Gln Gln Leu Pro Gly Thr Ala Pro Arg Leu
            35                  40                  45

Leu Ile Tyr Gly Asn Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Thr Asp Tyr Phe Cys Gln Ser Tyr Asp Ser Ser
                85                  90                  95

Leu Ser Ala Trp Val Phe Gly Gly Gly Thr Lys Val Thr Val Leu Arg
            100                 105                 110

<210> SEQ ID NO 149
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Ala Asn Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Asn Tyr Arg Gly Ala Phe Asp Ile Trp Gly Gln Gly
            100                 105                 110

Thr Met Val Ile Val Ser Ser
        115

<210> SEQ ID NO 150
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ser Val Leu Thr Gln Pro Pro Ser Val Ser Gly Ala Pro Gly Gln
1               5                   10                  15

-continued

```
Arg Val Thr Ile Ser Cys Thr Gly Ser Ser Ser Asn Ile Gly Ala Gly
              20                  25                  30

Tyr Asp Val His Trp Tyr Gln Gln Leu Pro Gly Thr Ala Pro Lys Leu
          35                  40                  45

Leu Ile Tyr Gly Asn Thr Asn Arg Pro Ser Gly Val Pro Asp Arg Phe
      50                  55                  60

Ser Gly Ser Lys Ser Gly Thr Ser Ala Ser Leu Ala Ile Ile Gly Leu
65                  70                  75                  80

Gln Ala Asp Asp Glu Ala Asp Tyr Tyr Cys Gln Ser Tyr Asp Ser Thr
                  85                  90                  95

Leu Arg Val Trp Met Phe Gly Gly Gly Thr Lys Leu Thr Val Leu Gly
              100                 105                 110
```

<210> SEQ ID NO 151
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
Gln Val Gln Leu Val Gln Ser Gly Gly Gly Leu Val Gln Pro Gly Gly
1               5                   10                  15

Ser Leu Arg Leu Ser Cys Ala Ala Pro Glu Phe Thr Phe Ser Lys Tyr
              20                  25                  30

Ala Met Ser Trp Val Arg Gln Ala Pro Gly Lys Gly Leu Glu Trp Val
          35                  40                  45

Ser Gly Ile Ser Gly Ser Gly Gly Ser Thr Tyr Tyr Ala Asp Ser Val
      50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                  85                  90                  95

Ala Lys Ser Ser Arg Ser Gly Tyr Phe Leu Pro Leu Asp Tyr Trp Gly
              100                 105                 110

Gln Gly Thr Leu Val Thr Val Ser Ser
          115                 120
```

<210> SEQ ID NO 152
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Ser Ser Glu Leu Thr Gln Asp Pro Ala Val Ser Val Ala Leu Gly Gln
1               5                   10                  15

Thr Val Arg Ile Thr Cys Gln Gly Asn Ser Leu Arg Tyr Tyr Tyr Pro
              20                  25                  30

Ser Trp Tyr Gln Gln Lys Pro Gly Gln Ala Pro Val Leu Val Ile Tyr
          35                  40                  45

Gly Lys Asn Asn Arg Pro Ser Gly Ile Pro Asp Arg Phe Ser Gly Ser
      50                  55                  60

Ser Ser Gly Asn Thr Ala Ser Leu Thr Ile Thr Gly Thr Gln Ala Glu
65                  70                  75                  80
```

Asp Glu Ala Asp Tyr Tyr Cys Ser Ser Arg Asp Asn Thr Asp Asn Arg
                85                  90                  95

Val Val Phe Gly Gly Gly Thr Lys Leu Thr Val Leu Gly
            100                 105

<210> SEQ ID NO 153
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Val Thr Gly Gly Phe Asp Pro Trp Gly Gln Gly Thr
            100                 105                 110

Leu Val Thr Val Ser Ser
        115

<210> SEQ ID NO 154
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Pro Gly Leu Thr Gln Pro Pro Ser Val Ser Val Ala Pro Gly Gln
1               5                   10                  15

Thr Ala Arg Ile Thr Cys Gly Gly Asp Asn Ile Gly Arg Lys Ser Val
            20                  25                  30

His Trp Tyr Gln Gln Arg Pro Gly Gln Ala Pro Ile Leu Val Ile Arg
        35                  40                  45

Asp Asp Arg Asp Arg Pro Ser Gly Ile Pro Glu Arg Phe Ser Gly Ser
    50                  55                  60

Ser Ser Val Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Lys His
                85                  90                  95

Tyr Val Phe Gly Pro Gly Thr Lys Val Thr Ala Leu Gly
            100                 105

<210> SEQ ID NO 155
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 155

Ser Ser Asn Ile Gly Ser Asn Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Gly Thr Phe Ser Ser Gln Ala
1               5

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Ser Val Phe His Ser Pro Asn Asn Lys Asn Tyr
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Phe Thr Val Ser Asn Tyr Ala
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Leu Pro Lys Lys Tyr
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Gly Ser Ile Ala Ser Asn Tyr
1               5

-continued

```
<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Phe Thr Val Ser Thr Ser His
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Asn Asn Val Gly Asn Gln Gly
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Phe Ile Phe Ser Asp Tyr Tyr
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Asp Ile Gly Thr Asp
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Ser Gly Ser Gly Gly Ser Arg
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166
```

-continued

```
Ile Ile Pro Phe Phe Gly Val Pro
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Ser Gly Ser Asp Gly Arg Thr
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Asp Ser Gly Gly Lys Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ile Arg Ser Arg Arg Gly Glu Thr
1               5

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Arg Gly Arg Gly Gly His Gly Met Asp Val
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Ala Trp Asp Asp Ser Leu Asn Gly Leu Val
1               5                   10

<210> SEQ ID NO 172
<211> LENGTH: 11
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 172

Ala Val Leu Lys Gly Arg Gly Asn Phe Asp Phe
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Gln Arg Ser Asn Trp Pro Leu Thr
1               5

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Lys Gly Ile Tyr Asp Val Thr Gly Ser Ser Phe Asp Ser
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Tyr Ser Thr Asp Ser Ser Gly Asn His Lys Val
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gln Ser Tyr Asp Ser Gly Asn Arg Arg Val
1               5                   10

<210> SEQ ID NO 177
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Arg Ala Arg Pro Ser Asp Pro Tyr Asp Gly Ser Gly Phe Asp Ala
1               5                   10                  15
```

-continued

Phe Asp Ile

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Ala Trp Asp Ser Ser Leu Ser Ala Trp Val
1               5                   10

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Arg His Arg Lys Ser Phe Thr Asp Leu Asp Ala Phe Asp Leu
1               5                   10                  15

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln His Phe Asn Asn Tyr Pro Ala Thr
1               5

<210> SEQ ID NO 181
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile Ser Gly Ser Gly Gly Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Gly Arg Gly Gly His Gly Met Asp Val
            100                 105

<210> SEQ ID NO 182
<211> LENGTH: 100

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Leu Val
            100

<210> SEQ ID NO 183
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Gln Ser Gly Ala Glu Val Lys Lys Pro Gly Ser
1               5                   10                  15

Ser Val Lys Val Ser Cys Arg Ser Ser Gly Gly Thr Phe Ser Ser Gln
                20                  25                  30

Ala Phe Ser Trp Val Arg Gln Ala Pro Gly Gln Gly Leu Glu Trp Met
            35                  40                  45

Gly Arg Ile Ile Pro Phe Phe Gly Val Pro Thr Tyr Ala Gln Arg Phe
        50                  55                  60

Gln Gly Arg Val Thr Ile Thr Ala Asp Lys Ser Pro Thr Thr Ala Tyr
65                  70                  75                  80

Met Glu Leu Thr Ser Leu Arg Ser Asp Asp Thr Ala Val Tyr Tyr Cys
                85                  90                  95

Ala Val Leu Lys Gly Arg Gly Asn Phe Asp Phe
            100                 105

<210> SEQ ID NO 184
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asp Ile Val Met Thr Gln Ser Pro Asp Ser Leu Ala Val Ser Leu Gly
1               5                   10                  15

Glu Arg Ala Thr Ile Asn Cys Lys Ser Ser Tyr Ser Val Phe His Ser
                20                  25                  30

Pro Asn Asn Lys Asn Tyr Leu Ala Trp Tyr Gln Gln Arg Pro Gly Gln
```

```
        35                  40                  45

Pro Pro Lys Leu Leu Ile Tyr Trp Ala Ser Thr Arg Gly Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Gln Gln
                85                  90                  95

Arg Ser Asn Trp Pro Leu Thr
                100
```

<210> SEQ ID NO 185
<211> LENGTH: 110
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 185

```
Gln Val Gln Leu Val Gln Ser Gly Gly Gly Leu Val Gln Pro Arg Gly
1                   5                   10                  15

Ser Leu Arg Leu Ser Cys Ala Ala Ser Gly Phe Thr Val Ser Asn Tyr
                20                  25                  30

Ala Met Ser Trp Val Arg Gln Ala Pro Gly Lys Gly Leu Glu Trp Val
            35                  40                  45

Ala Thr Lys Ser Gly Ser Asp Gly Arg Thr Tyr Tyr Ala Asp Ser Val
    50                  55                  60

Lys Gly Arg Phe Thr Ile Ala Arg Asp Asn Ser Lys Asn Ser Leu Tyr
65                  70                  75                  80

Leu Gln Met Asn Ser Leu Arg Ala Ala Asp Thr Ala Val Tyr Tyr Cys
                85                  90                  95

Ala Lys Gly Ile Tyr Asp Val Thr Gly Ser Ser Phe Asp Ser
            100                 105                 110
```

<210> SEQ ID NO 186
<211> LENGTH: 98
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 186

```
Ser Tyr Glu Leu Thr Gln Pro Pro Ser Val Ser Val Ser Pro Gly Gln
1                   5                   10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Met Phe
            35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Lys Val
```

<210> SEQ ID NO 187

<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Gly Asn Arg Arg Val
            100

<210> SEQ ID NO 188
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Val Ser Thr Ser
            20                  25                  30

His Met Ser Trp Val Arg Gln Ala Pro Gly Lys Gly Leu Glu Trp Leu
        35                  40                  45

Ser Gly Lys Asp Ser Gly Gly Lys Thr Tyr Tyr Ala Asp Ser Val Arg
    50                  55                  60

Gly Arg Phe Thr Ile Ala Arg Asp Asp Ser Leu Asn Thr Val Phe Leu
65                  70                  75                  80

Gln Met Asn Asn Met Arg Asp Glu Asp Ser Gly Val Tyr Tyr Cys Ala
                85                  90                  95

Arg Ala Arg Pro Ser Asp Pro Tyr Asp Gly Ser Gly Phe Asp Ala Phe
            100                 105                 110

Asp Ile

<210> SEQ ID NO 189
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Ser Tyr Glu Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln

-continued

```
                20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Trp Val
            100

<210> SEQ ID NO 190
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Gly Gly Leu Val Lys Pro Arg Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Gln Trp Val
            35                  40                  45

Ala Ser Ile Arg Ser Arg Arg Gly Glu Thr Asn Tyr Ala Asp Ser Val
    50                  55                  60

Lys Gly Arg Phe Thr Ile Ala Arg Asp Asn Ala Glu Lys Ser Leu Tyr
65                  70                  75                  80

Leu Gln Met Asn Ser Leu Arg Ala Glu Asp Ala Ala Val Tyr Tyr Cys
                85                  90                  95

Ala Arg His Arg Lys Ser Phe Thr Asp Leu Asp Ala Phe Asp Leu
            100                 105                 110

<210> SEQ ID NO 191
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Asp Ile Gly Thr Asp
            20                  25                  30

Leu Ser Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln His Phe Asn Asn Tyr Pro Ala
                85                  90                  95

Thr
```

```
<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Tyr Thr Phe Thr Ser Tyr Gly
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Ser Ala Tyr Asn Gly Asn Thr
1               5

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Arg Asp Pro Gly Leu Trp Phe Gly Leu Thr His Asp Tyr Tyr Phe
1               5                   10                  15

Asp Tyr

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Ser Asn Ile Gly Ser Asn Thr
1               5

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Ala Trp Asp Asp Ser Arg Ser Gly Pro Val
1               5                   10

<210> SEQ ID NO 197
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 197

Gly Phe Thr Phe Ser Asp Tyr Ser
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Asn Ser Asp Gly Ser Arg Thr
1               5

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Arg Gly Pro Gly Phe Phe Gly Phe Asp Ile
1               5                   10

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ser Asn Ile Gly Arg Asn Ser
1               5

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Ala Trp Asp Ala Arg Leu Thr Gly Pro Leu
1               5                   10

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Tyr Ser Phe Thr Asn Tyr Trp
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Asn Pro Val Asn Ser Arg Thr
1               5

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Arg Tyr Tyr Tyr Tyr Ala Met Glu Val
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Ala Trp Asp Asp Ser Leu Asn Gly Pro Val
1               5                   10

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Thr Phe Thr Asn Tyr Gly
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Val Asp Asn Asn Asn Gly Asn Ile
1               5

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

-continued

```
Ala Arg Gly Leu Phe Ser Ser Arg Trp Tyr Leu Trp Phe Asp Pro
1               5                   10                  15

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Ser Asp Val Gly Gly Tyr Asn Tyr
1               5

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Ser Tyr Thr Arg Ser Ser Thr Ser Tyr Val Val
1               5                   10

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Thr Phe Ser Ser Tyr Ala
1               5

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ile Leu Pro Met Phe Gly Ser Thr
1               5

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Arg Gly Arg Asp Ile Val Ala Pro Ser Asn Ser Gly Phe Asp Val
1               5                   10                  15

<210> SEQ ID NO 214
<211> LENGTH: 11
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 214

Ser Ala Tyr Asp Arg Ser Leu Asn Ala Trp Val
1               5                   10

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Ile Pro Ile Phe Gly Thr Ala
1               5

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Arg Gly Arg Gln Met Phe Gly Ala Gly Ile Asp Phe
1               5                   10

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Tyr Thr Leu Ser Ser His Gly
1               5

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ile Ser Ala His Asn Gly His Ala
1               5

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Arg Val His Ala Ala Leu Tyr Tyr Gly Met Asp Val
1               5                   10
```

-continued

```
<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Gly Ser Ile Asp Ser Asn Tyr
1               5

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Ser Tyr Asp Ser Asn Asn Arg His Val Ile
1               5                   10

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asn Ile Gly Ser Lys Gly
1               5

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Val Trp Asp Ser Gly Ser Asp His Trp Val
1               5                   10

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Asn Ile Gly Asp Lys Gly
1               5

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 225

Gln Val Trp Asp Ser Ser Ser Asp His Trp Val
1               5                   10

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asn Ile Gly Asn Lys Gly
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asn Ile Gly Gly Lys Gly
1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Phe Thr Phe Asp Asp Tyr Ala
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ile Ser Trp Asn Ser Gly Ser Ile
1               5

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ser Asp Tyr Gly Asp Lys Tyr Tyr Tyr Gly Met Asp Val
1               5                   10                  15

<210> SEQ ID NO 231
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 231

Gly Tyr Thr Phe Thr Thr Tyr Trp
1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ile Tyr Pro Asp Asp Ser Asp Thr
1               5

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Phe Trp Gly Ala Ser Gly Ala Pro Val Asn Gly Phe Asp Ile
1               5                   10                  15

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Asp Ser Val Ser Ser Asp Asn Tyr Phe
1               5                   10

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Val Tyr Tyr Asn Gly Asn Thr
1               5

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Thr Glu Thr Pro Pro Thr Ser Tyr Phe Asn Ser Gly Pro Phe Asp
1               5                   10                  15
```

Ser

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Tyr Thr Phe Asn Arg Phe Gly
1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Thr Asn Pro Tyr Asn Gly Asn Thr
1               5

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Arg Val Val Ala Val Asn Gly Met Asp Val
1               5                   10

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ile Ser Tyr Asp Gly Ser Asn Lys
1               5

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Ser Gln Thr Val Ala Gly Ser Asp Tyr
1               5                   10

<210> SEQ ID NO 242
<211> LENGTH: 15
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 242

Ala Ser Asp Tyr Gly Asp Lys Tyr Ser Tyr Tyr Gly Met Asp Val
1               5                   10                  15

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Phe Thr Phe Asp Asp Phe Ala
1               5

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Ala Trp Asp Gly Gly Leu Asn Gly Arg Gly Val
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Ser Asn Ile Gly Ala Gly Tyr Val
1               5

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Ala Trp Asp Asp Ser Leu Asn Ala Pro Val
1               5                   10

<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ser Asn Asn Val Gly Ala His Gly
1               5

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Ser Trp Asp Ser Ser Leu Ser Gly Tyr Val
1               5                   10

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Gly Ser Ile Ala Ala Tyr Tyr
1               5

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gln Ser Tyr Asp Ser Ser Asn Leu Trp Val
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Val Trp His Ser Val Ser Asp Gln Gly Val
1               5                   10

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Ile Asn Pro Gly Asn Val Asn Thr Lys Tyr Asn Glu Lys Phe Lys
1               5                   10                  15

Gly

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Lys Ser Ser Gln Ser Ile Leu Tyr Ser Ser Asn Gln Lys Asn Tyr Leu
1               5                   10                  15

Ala

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Ala Ser Thr Arg Glu Ser
1               5

<210> SEQ ID NO 255
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
                20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
                100                 105                 110

Leu Val Thr Val Ser Ser
        115

<210> SEQ ID NO 256
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
            100                 105                 110

<210> SEQ ID NO 257
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Ala Ser Gln
                20                  25                  30

Trp Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
        50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Trp Tyr Arg Pro Leu Asp Tyr Trp Gly Gln Gly Thr
            100                 105                 110

Leu Val Thr Val Ser Ser
        115

<210> SEQ ID NO 258
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Ile Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Ile Ser Ser Tyr Thr Phe Gly Gln Gly Thr Lys Leu Glu Ile Lys
            100                 105                 110

<210> SEQ ID NO 259
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Trp Tyr Arg Pro Asn Asp Tyr Trp Gly Gln Gly Thr
            100                 105                 110

Leu Val Thr Val Ser Ser
        115

<210> SEQ ID NO 260
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Lys Ser Ser Tyr Thr Phe Gly Gln Gly Thr Lys Leu Glu Ile Lys
            100                 105                 110

<210> SEQ ID NO 261
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Gln Leu Val Gln Ser Gly Ala Glu Val Lys Lys Pro Gly Ala
1               5                   10                  15
```

-continued

_____

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Thr Arg Tyr Arg Pro Leu Asp Tyr Trp Gly Gln Gly Thr
            100                 105                 110

Leu Val Thr Val Ser Ser
        115

<210> SEQ ID NO 262
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Arg Ser Ser Tyr Thr Phe Gly Gln Gly Thr Lys Leu Glu Ile Lys
            100                 105                 110

<210> SEQ ID NO 263
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Gln
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Arg Leu Thr Tyr Tyr Arg Pro Pro Asp Tyr Trp Gly Gln Gly Thr
            100                 105                 110

Leu Val Thr Val Ser Ser
        115
```

```
<210> SEQ ID NO 264
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Tyr Thr Phe Gly Gln Gly Thr Lys Leu Glu Ile Lys
            100                 105                 110
```

```
<210> SEQ ID NO 265
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ala
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser
        115
```

```
<210> SEQ ID NO 266
<211> LENGTH: 112
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Met Ser Ser Tyr Thr Phe Gly Gln Gly Thr Lys Leu Glu Ile Lys
                100                 105                 110

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Gly Gly Gly Ser
1               5

<210> SEQ ID NO 268
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Asn Tyr Arg Gly Ser Leu Ala Phe Asp Ile Trp Gly
                100                 105                 110

Gln Gly Thr Leu Val Thr Val Ser Ser
        115                 120

-continued

```
<210> SEQ ID NO 269
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gln Val Gln Leu Val Gln Ser Gly Gly Gly Leu Val Gln Pro Gly Gly
1               5                   10                  15

Ser Leu Arg Leu Ser Cys Ala Ala Ser Glu Phe Thr Phe Gly Thr Tyr
            20                  25                  30

Ala Met Thr Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Pro Val Leu Arg Tyr Gly Phe Asp Ile Trp Gly Gln Gly
            100                 105                 110

Thr Met Val Thr Val Ser Ser
        115

<210> SEQ ID NO 270
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gln Ser Val Leu Thr Leu Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Trp Val Val Phe Gly Gly Gly Thr Lys Leu Thr Val Leu
            100                 105                 110

Gly

<210> SEQ ID NO 271
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271
```

-continued

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Arg Gly
                20                  25                  30

Tyr Asn Val His Trp Tyr Gln Gln Leu Pro Gly Thr Ala Pro Lys Leu
            35                  40                  45

Leu Ile Tyr Asp Asp Thr Asn Arg Pro Ser Gly Val Pro His Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Arg Ala Trp Val Phe Gly Gly Gly Thr Lys Leu Ala Val Leu Gly
                100                 105                 110
```

<210> SEQ ID NO 272
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

```
Leu Pro Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

His Val Val Phe Gly Gly Gly Thr Lys Leu Thr Val Leu Gly
                100                 105                 110
```

<210> SEQ ID NO 273
<211> LENGTH: 459
<212> TYPE: PRT
<213> ORGANISM: Homo sapiens

<400> SEQUENCE: 273

```
Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
                20                  25                  30

Met Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
        50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95
```

```
Glu Val Lys Pro Lys Ser Glu Glu Glu Gly Ser Leu Lys Leu Glu Asp
          100                 105                 110

Leu Pro Thr Val Glu Ala Pro Gly Asp Pro Gln Glu Pro Gln Asn Asn
          115                 120                 125

Ala His Arg Asp Lys Glu Gly Asp Asp Gln Ser His Trp Arg Tyr Gly
          130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
          180                 185                 190

Leu Arg Leu Arg Asn Asn Gly His Ser Val Gln Leu Thr Leu Pro Pro
          195                 200                 205

Gly Leu Glu Met Ala Leu Gly Pro Gly Arg Glu Tyr Arg Ala Leu Gln
          210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
                260                 265                 270

Ala Val Leu Ala Ala Phe Leu Glu Glu Gly Pro Glu Glu Asn Ser Ala
          275                 280                 285

Tyr Glu Gln Leu Leu Ser Arg Leu Glu Glu Ile Ala Glu Glu Gly Ser
          290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
          340                 345                 350

Ala Lys Gln Leu His Thr Leu Ser Asp Thr Leu Trp Gly Pro Gly Asp
          355                 360                 365

Ser Arg Leu Gln Leu Asn Phe Arg Ala Thr Gln Pro Leu Asn Gly Arg
          370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
                420                 425                 430

Val Gln Met Arg Arg Gln His Arg Arg Gly Thr Lys Gly Gly Val Ser
          435                 440                 445

Tyr Arg Pro Ala Glu Val Ala Glu Thr Gly Ala
          450                 455

<210> SEQ ID NO 274
<211> LENGTH: 437
<212> TYPE: PRT
<213> ORGANISM: Mus sp.

<400> SEQUENCE: 274

Met Ala Ser Leu Gly Pro Ser Pro Trp Ala Pro Leu Ser Thr Pro Ala
1                 5                   10                  15
```

```
Pro Thr Ala Gln Leu Leu Leu Phe Leu Leu Leu Gln Val Ser Ala Gln
            20                  25                  30

Pro Gln Gly Leu Ser Gly Met Gln Gly Glu Pro Ser Leu Gly Asp Ser
            35                  40                  45

Ser Ser Gly Glu Asp Glu Leu Gly Val Asp Val Leu Pro Ser Glu Glu
            50                  55                  60

Asp Ala Pro Glu Glu Ala Asp Pro Pro Asp Gly Glu Asp Pro Pro Glu
65                  70                  75                  80

Val Asn Ser Glu Asp Arg Met Glu Glu Ser Leu Gly Leu Glu Asp Leu
            85                  90                  95

Ser Thr Pro Glu Ala Pro Glu His Ser Gln Gly Ser His Gly Asp Glu
            100                 105                 110

Lys Gly Gly Gly His Ser His Trp Ser Tyr Gly Gly Thr Leu Leu Trp
            115                 120                 125

Pro Gln Val Ser Pro Ala Cys Ala Gly Arg Phe Gln Ser Pro Val Asp
            130                 135                 140

Ile Arg Leu Glu Arg Thr Ala Phe Cys Arg Thr Leu Gln Pro Leu Glu
145                 150                 155                 160

Leu Leu Gly Tyr Glu Leu Gln Pro Leu Pro Glu Leu Ser Leu Ser Asn
            165                 170                 175

Asn Gly His Thr Val Gln Leu Thr Leu Pro Pro Gly Leu Lys Met Ala
            180                 185                 190

Leu Gly Pro Gly Gln Glu Tyr Arg Ala Leu Gln Leu His Leu His Trp
            195                 200                 205

Gly Thr Ser Asp His Pro Gly Ser Glu His Thr Val Asn Gly His Arg
            210                 215                 220

Phe Pro Ala Glu Ile His Val Val His Leu Ser Thr Ala Phe Ser Glu
225                 230                 235                 240

Leu His Glu Ala Leu Gly Arg Pro Gly Gly Leu Ala Val Leu Ala Ala
            245                 250                 255

Phe Leu Gln Glu Ser Pro Glu Glu Asn Ser Ala Tyr Glu Gln Leu Leu
            260                 265                 270

Ser His Leu Glu Glu Ile Ser Glu Glu Gly Ser Lys Ile Glu Ile Pro
            275                 280                 285

Gly Leu Asp Val Ser Ala Leu Leu Pro Ser Asp Phe Ser Arg Tyr Tyr
            290                 295                 300

Arg Tyr Glu Gly Ser Leu Thr Thr Pro Pro Cys Ser Gln Gly Val Ile
305                 310                 315                 320

Trp Thr Val Phe Asn Glu Thr Val Lys Leu Ser Ala Lys Gln Leu His
            325                 330                 335

Thr Leu Ser Val Ser Leu Trp Gly Pro Arg Asp Ser Arg Leu Gln Leu
            340                 345                 350

Asn Phe Arg Ala Thr Gln Pro Leu Asn Gly Arg Thr Ile Glu Ala Ser
            355                 360                 365

Phe Pro Ala Ala Glu Asp Ser Ser Pro Glu Pro Val His Val Asn Ser
            370                 375                 380

Cys Phe Thr Ala Gly Asp Ile Leu Ala Leu Val Phe Gly Leu Leu Phe
385                 390                 395                 400

Ala Val Thr Ser Ile Ala Phe Leu Leu Gln Leu Arg Arg Gln His Arg
            405                 410                 415

His Arg Ser Gly Thr Lys Asp Arg Val Ser Tyr Ser Pro Ala Glu Met
            420                 425                 430
```

-continued

```
Thr Glu Thr Gly Ala
        435

<210> SEQ ID NO 275
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 276
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 277
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 278
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 279
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 280
```

```
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 281
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly

<210> SEQ ID NO 282
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
```

-continued

```
              35               40                45

Glu Asp Ser Lys Arg Pro Ser Gly Ile Pro Glu Arg Phe Ser Gly Ser
    50               55                60

Ser Ser Gly Thr Met Ala Thr Leu Thr Ile Ser Gly Ala Gln Val Glu
65               70                75                80

Asp Glu Ala Asp Tyr Tyr Cys Tyr Ser Thr Asp Ser Ser Gly Asn His
                85                90                95

<210> SEQ ID NO 283
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Glu Val Gln Leu Val Glu Ser Gly Gly Gly Leu Val Gln Pro Gly Gly
1               5                10                15

Ser Leu Arg Leu Ser Cys Ala Ala Ser Gly Phe Thr Val Ser Ser Asn
            20                25                30

Tyr Met Ser Trp Val Arg Gln Ala Pro Gly Lys Gly Leu Glu Trp Val
        35                40                45

Ser Val Ile Tyr Ser Gly Gly Ser Thr Tyr Tyr Ala Asp Ser Val Lys
    50                55                60

Gly Arg Phe Thr Ile Ser Arg Asp Asn Ser Lys Asn Thr Leu Tyr Leu
65                70                75                80

Gln Met Asn Ser Leu Arg Ala Glu Asp Thr Ala Val Tyr Tyr Cys Ala
                85                90                95

Arg

<210> SEQ ID NO 284
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gln Ala Gly Leu Thr Gln Pro Pro Ser Val Ser Lys Gly Leu Arg Gln
1               5                10                15

Thr Ala Thr Leu Thr Cys Thr Gly Asn Ser Asn Asn Val Gly Asn Gln
            20                25                30

Gly Ala Ala Trp Leu Gln Gln His Gln Gly His Pro Pro Lys Leu Leu
        35                40                45

Ser Tyr Arg Asn Asn Asn Arg Pro Ser Gly Ile Ser Glu Arg Leu Ser
    50                55                60

Ala Ser Arg Ser Gly Asn Thr Ala Ser Leu Thr Ile Thr Gly Leu Gln
65                70                75                80

Pro Glu Asp Glu Ala Asp Tyr Tyr Cys Ser Ala Trp Asp Ser Ser Leu
                85                90                95

Ser Ala

<210> SEQ ID NO 285
<211> LENGTH: 109
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe
            100                 105

<210> SEQ ID NO 286
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
                20                  25                  30

Tyr Val Gln Trp Tyr Gln Gln Arg Pro Gly Ser Ala Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 287
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Asn
                20                  25                  30

Tyr Val Gln Trp Tyr Gln Gln Arg Pro Gly Ser Ala Pro Thr Thr Val
            35                  40                  45

Ile Tyr Glu Asp Asn Gln Arg Pro Ser Gly Val Pro Asp Arg Phe Ser
        50                  55                  60

-continued

```
Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Arg His Val Ile
            100

<210> SEQ ID NO 288
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 289
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Phe
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Gly Asp Lys Tyr Ser Tyr Tyr Gly Met Asp Val
            100                 105                 110

<210> SEQ ID NO 290
<211> LENGTH: 98
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 290

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 291
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Phe Pro Gly Lys Ala Pro Lys Leu Leu
        35                  40                  45

Ile Phe Asp Asp Asn Gln Arg Pro Ser Gly Val Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Gly Leu
                85                  90                  95

Asn Gly Arg Gly Val
            100

<210> SEQ ID NO 292
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

-continued

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 293
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 294
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 295
<211> LENGTH: 98
<212> TYPE: PRT
<213> ORGANISM: Homo sapiens

<400> SEQUENCE: 295

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg
```

```
<210> SEQ ID NO 296
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Gly Leu Trp Phe Gly Leu Thr His Asp Tyr Tyr Phe
            100                 105                 110

Asp Tyr Trp Gly Gln Gly Thr Leu Val Thr Val Ser Ser
            115                 120                 125
```

```
<210> SEQ ID NO 297
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297
```

```
Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Ser Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Asn Gly Leu Gln
65                  70                  75                  80
```

```
Ser Glu Asp Glu Ala Asp Tyr Tyr Cys Ala Ala Trp Asp Asp Ser Arg
                85                  90                  95

Ser Gly Pro Val Phe Gly Gly Gly Thr Arg Leu Thr Val Leu
            100             105             110

<210> SEQ ID NO 298
<211> LENGTH: 98
<212> TYPE: PRT
<213> ORGANISM: Homo sapiens

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 299
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Glu Val Gln Leu Val Gln Ser Gly Gly Gly Leu Val Lys Pro Gly Gly
1               5                   10                  15

Ser Leu Arg Leu Ser Cys Glu Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Arg Ile Asn Ser Asp Gly Ser Arg Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Gly Pro Gly Phe Phe Gly Phe Asp Ile Trp Gly Gln Gly Thr
            100             105             110

Leu Val Thr Val Ser Ser
        115

<210> SEQ ID NO 300
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300
```

-continued

```
Ser Tyr Glu Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Arg Asn
            20                  25                  30

Ser Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Gly Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Thr Asp Tyr Tyr Cys Ala Ala Trp Asp Ala Arg Leu
                85                  90                  95

Thr Gly Pro Leu Phe Gly Gly Gly Thr Lys Leu Ser Val Leu
            100                 105                 110
```

```
<210> SEQ ID NO 301
<211> LENGTH: 98
<212> TYPE: PRT
<213> ORGANISM: Homo sapiens

<400> SEQUENCE: 301
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

```
<210> SEQ ID NO 302
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Asn Pro Val Asn Ser Arg Thr Ile Tyr Ser Pro Ser Phe
    50                  55                  60

Gln Gly Gln Val Thr Ile Ser Val Asp Lys Ser Val Thr Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Tyr Tyr Tyr Tyr Ala Met Glu Val Trp Gly Arg Gly Thr Leu
            100                 105                 110

Val Thr Val Ser Ser
        115

<210> SEQ ID NO 303
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Thr Ser Gly Thr Ser Ala Ser Leu Ala Ile Ser Gly Leu Gln
65                  70                  75                  80

Ser Glu Asp Glu Ala Asp Tyr Tyr Cys Glu Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 304
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gly Leu Glu Trp Met
        35                  40                  45

Gly Trp Val Asp Asn Asn Asn Gly Asn Ile Asn Tyr Ala Gln Lys Phe
    50                  55                  60

Leu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Leu Phe Ser Ser Arg Trp Tyr Leu Trp Phe Asp Pro Trp
            100                 105                 110

Gly Gln Gly Thr Leu Val Thr Val Ser Ser
        115                 120

<210> SEQ ID NO 305
<211> LENGTH: 99
<212> TYPE: PRT
<213> ORGANISM: Homo sapiens
```

```
<400> SEQUENCE: 305

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 306
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Thr Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Thr Arg Ser
                85                  90                  95

Ser Thr Ser Tyr Val Val Phe Gly Gly Gly Thr Lys Val Thr Val Leu
            100                 105                 110

<210> SEQ ID NO 307
<211> LENGTH: 98
<212> TYPE: PRT
<213> ORGANISM: Homo sapiens

<400> SEQUENCE: 307

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

Ala Arg

```
<210> SEQ ID NO 308
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Leu Pro Met Phe Gly Ser Thr Asn Tyr Ala Gln Lys Phe
    50                  55                  60

Gln Gly Arg Leu Thr Leu Ile Ala Asp Glu Ser Thr Arg Thr Val Tyr
65                  70                  75                  80

Leu Glu Leu Asn Ser Leu Thr Ser Glu Asp Thr Ala Val Tyr Tyr Cys
                85                  90                  95

Ala Arg Gly Arg Asp Ile Val Ala Pro Ser Asn Ser Gly Phe Asp Val
            100                 105                 110

Trp Gly Gln Gly Thr Thr Val Thr Val Ser Ser
        115                 120

<210> SEQ ID NO 309
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Ser Tyr Glu Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asp Asn Arg Pro Ser Gly Ile Ser Glu Arg Phe Ser
    50                  55                  60

Ala Ser Arg Ser Gly Asn Thr Ala Ser Leu Thr Ile Ser Gly Leu Gln
65                  70                  75                  80

Pro Glu Asp Glu Ala Asp Tyr Tyr Cys Ser Ala Tyr Asp Arg Ser Leu
                85                  90                  95

Asn Ala Trp Val Phe Gly Gly Gly Thr Lys Leu Thr Val Leu
            100                 105                 110

<210> SEQ ID NO 310
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 310

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Pro
            100                 105                 110

Gly Thr Leu Val Thr Val Ser Ser
        115                 120

<210> SEQ ID NO 311
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Leu Ser Ser His
                20                  25                  30

Gly Ile Thr Trp Val Arg Gln Ala Pro Gly Gln Gly Leu Glu Trp Met
            35                  40                  45

Gly Trp Ile Ser Ala His Asn Gly His Ala Ser Asn Ala Gln Lys Val
        50                  55                  60

Glu Asp Arg Val Thr Met Thr Thr Asp Thr Ser Thr Asn Thr Ala Tyr
65                  70                  75                  80

Met Glu Leu Arg Ser Leu Thr Ala Asp Asp Thr Ala Val Tyr Tyr Cys
                85                  90                  95

Ala Arg Val His Ala Ala Leu Tyr Tyr Gly Met Asp Val Trp Gly Gln
            100                 105                 110

Gly Thr Leu Val Thr Val Ser Ser
        115                 120

<210> SEQ ID NO 312
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Asn
                20                  25                  30

Tyr Val Gln Trp Tyr Gln Gln Arg Pro Gly Ser Ala Pro Thr Thr Val
```

-continued

```
            35                    40                    45

Ile Tyr Glu Asp Asn Gln Arg Pro Ser Gly Val Pro Asp Arg Phe Ser
    50                    55                    60

Gly Ser Ile Asp Ser Ser Ser Asn Ser Ala Ser Leu Thr Ile Ser Gly
65                    70                    75                    80

Leu Lys Thr Glu Asp Glu Ala Asp Tyr Tyr Cys Gln Ser Tyr Asp Ser
                85                    90                    95

Asn Asn Arg His Val Ile Phe Gly Gly Gly Thr Lys Leu Thr Val Leu
            100                   105                   110
```

```
<210> SEQ ID NO 313
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Ser Tyr Glu Leu Thr Gln Pro Pro Ser Val Ser Leu Ala Pro Gly Gln
1               5                   10                  15

Ser Ala Arg Ile Ser Cys Gly Gly Asp Asn Ile Gly Ser Lys Gly Val
            20                  25                  30

His Trp Tyr Gln Gln Lys Pro Gly Gln Ala Pro Val Val Val Val Tyr
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Asp His
                85                  90                  95

Trp Val Phe Gly Gly Gly Thr Lys Leu Thr Val Leu
            100                 105
```

```
<210> SEQ ID NO 314
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Leu Pro Val Leu Thr Gln Pro Pro Ser Val Ser Ala Ala Pro Gly Gln
1               5                   10                  15

Thr Ala Arg Ile Ser Cys Gly Gly Ser Asn Ile Gly Asp Lys Gly Val
            20                  25                  30

His Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105
```

-continued

```
<210> SEQ ID NO 315
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Asn Lys Gly Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 316
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Leu Pro Val Leu Thr Gln Pro Pro Ser Val Ser Val Ala Leu Gly Gln
1               5                   10                  15

Thr Ala Arg Ile Thr Cys Arg Gly Asn Asn Ile Gly Gly Lys Gly Val
                20                  25                  30

His Trp Tyr Gln Gln Lys Pro Gly Gln Ala Pro Val Leu Val Val Tyr
            35                  40                  45

Asp Asp Tyr Ser Arg Arg Ser Gly Ile Pro Glu Arg Phe Ser Gly Ser
        50                  55                  60

His Ser Gly Ser Ala Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 317
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 317
caggtgcagc tggtgcagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
```

-continued

```
gcggactctg tgaagggccg attcaccgtc tccagagaca acgccaagaa ctcactgtat        240
ctgcaaatga acagcctgag agccgaggac acggctgtgt attactgtgc gagtgactac        300
ggtgacaaat actactacta cggtatggac gtctggggca aagggaccac ggtcaccgtc        360
tcctca                                                                   366
```

```
<210> SEQ ID NO 318
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318
cagcctgggc tgactcagcc accctcagcg tctgggaccc ccgggcagag ggtcaccatc         60
tcttgttctg gaagcagctc caacatcgga agtaatactg tcaactggta tcagcaattc        120
cccggaaagg cccccaaact cctcatcttt aatgataatc agcggccctc aggggtccct        180
gaccgcttct ctgcttccaa gtctggcacc tcagcctccc tggccattag tggcctccag        240
tctgaggatg aggctgacta ttactgtgcg gcatgggatg gcggtctgaa tggtcgaggg        300
gtgttcggcg gagggaccaa actgaccgtc cta                                     333
```

```
<210> SEQ ID NO 319
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Tyr Gly Asp Lys Tyr Tyr Tyr Tyr Gly Met Asp Val Trp
            100                 105                 110

Gly Lys Gly Thr Thr Val Thr Val Ser Ser
        115                 120
```

```
<210> SEQ ID NO 320
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Gln Pro Gly Leu Thr Gln Pro Pro Ser Ala Ser Gly Thr Pro Gly Gln
```

-continued

```
1                5                10               15
Arg Val Thr Ile Ser Cys Ser Gly Ser Ser Asn Ile Gly Ser Asn
            20               25               30

Thr Val Asn Trp Tyr Gln Gln Phe Pro Gly Lys Ala Pro Lys Leu Leu
            35               40               45

Ile Phe Asn Asp Asn Gln Arg Pro Ser Gly Val Pro Asp Arg Phe Ser
        50               55               60

Ala Ser Lys Ser Gly Thr Ser Ala Ser Leu Ala Ile Ser Gly Leu Gln
65               70               75               80

Ser Glu Asp Glu Ala Asp Tyr Tyr Cys Ala Ala Trp Asp Gly Gly Leu
                85               90               95

Asn Gly Arg Gly Val Phe Gly Gly Gly Thr Lys Leu Thr Val Leu
            100              105              110
```

```
<210> SEQ ID NO 321
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
accaagggcc catcggtctt cccctggca ccctcctcca agagcacctc tgggggcaca       60
gcggccctgg gctgcctggt caaggactac ttccccgaac cggtgacggt gtcgtggaac      120
tcaggcgccc tgaccagcgg cgtgcacacc ttcccggctg tcctacagtc ctcaggactc      180
tactccctca gcagcgtggt gaccgtgccc tccagcagct tgggcaccca gacctacatc      240
tgcaacgtga atcacaagcc cagcaacacc aaggtggaca gaaaa                      285
```

```
<210> SEQ ID NO 322
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gcagagccca aatcttgtga caaaactcac acatgcccac cgtgccca                    48
```

```
<210> SEQ ID NO 323
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323
gcacctgaac tcctgggggg accgtcagtc ttcctcttcc ccccaaaacc caaggacacc       60
ctcatgatct cccggacccc tgaggtcaca tgcgtggtgg tggacgtgag ccacgaagac      120
cctgaggtca agttcaactg gtacgtggac ggcgtggagg tgcataatgc caagacaaag      180
ccgcgggagg agcagtacaa cagcacgtac cgtgtggtca gcgtcctcac cgtcctgcac      240
caggactggc tgaatggcaa ggagtacaag tgcaaggtct ccaacaaagc cctcccagcc      300
cccatcgaga aaaccatctc caaagccaaa                                       330
```

```
<210> SEQ ID NO 324
```

```
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 324
gggcagcccc gagaaccaca ggtgtacacc ctgcccccat cccgggatga gctgaccaag      60
aaccaggtca gcctgacctg cctggtcaaa ggcttctatc ccagcgacat cgccgtggag     120
tgggagagca atgggcagcc ggagaacaac tacaagacca cgcctcccgt gctggactcc     180
gacggctcct tcttcctcta cagcaagctc accgtggaca gagcaggtg gcagcagggg      240 aacgtcttct catgctccgt gatgcatgag gctctgcaca accactacac gcagaagagc     300
ctctccctgt ctccgggtaa atga                                            324

<210> SEQ ID NO 325
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatggcag ccccgtcaag gcgggagtgg agaccaccac accctccaaa     180
caaagcaaca caagtacgc ggccagcagc tatctgagcc tgacgcctga gcagtggaag      240
tcccacagaa gctacagctg ccaggtcacg catgaaggga gcaccgtgga agacagtg       300 gcccctacag aatgttcatg a                                              321

<210> SEQ ID NO 326
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys

<210> SEQ ID NO 327
<211> LENGTH: 16
<212> TYPE: PRT
```

<213> ORGANISM: Artificial Sequence
<220> FEATURE:
<223> OTHER INFORMATION: Description of Artificial Sequence: Synthetic
     peptide

<400> SEQUENCE: 327

Ala Glu Pro Lys Ser Cys Asp Lys Thr His Thr Cys Pro Pro Cys Pro
1               5                   10                  15

<210> SEQ ID NO 328
<211> LENGTH: 110
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 328

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 329
<211> LENGTH: 107
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 329

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 330
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 331
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331
caggtgcagc tggtgcagtc tggagcagag gtgaagaagc ccgggggagtc tctgaagatc      60 tcctgtaagg attctggata cacctttacc acctactgga tcggctgggt gcgccagctg     120
cccgggaaag gcctggagtt gatggggatc atctatcctg atgactctga taccacatac     180
agcccgtcct tccaaggcca tgtcaccatc tcagccgaca gtccatcaa caccgcctac      240 ctgcagtgga gcagcctgaa ggcctcggac accgccatgt attactgtgc gttttggggt     300
gcgagtggag cgccagtgaa tggttttgat atctggggcc aaggcaccct ggtcaccgtc     360
tcctca                                                                 366

<210> SEQ ID NO 332
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332
ctgcctgtgc tgactcagcc accctcagcg tctgggaccc ccgggcagag ggtcaccatc      60
tcctgcactg ggagcagctc caacatcggg gcaggttatg ttgtacactg gtaccagcag     120
ctcccaggaa cggccccaa actcctcatc tatagtaata tcagcggcc ctcaggggtc        180 cctgaccgat tctctggctc caagtctggc acctcagcct ccctggccat cagtgggctc     240
cagtctgagg atgaggctga ttattactgt gcagcatggg atgacagcct gaatgctccg     300
gtgttcggcg gagggaccaa gctgaccgtc cta                                   333

<210> SEQ ID NO 333
<211> LENGTH: 122
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 333

Gln Val Gln Leu Val Gln Ser Gly Ala Glu Val Lys Lys Pro Gly Glu
1               5                   10                  15

Ser Leu Lys Ile Ser Cys Lys Asp Ser Gly Tyr Thr Phe Thr Thr Tyr
            20                  25                  30

Trp Ile Gly Trp Val Arg Gln Leu Pro Gly Lys Gly Leu Glu Leu Met
        35                  40                  45

Gly Ile Ile Tyr Pro Asp Asp Ser Asp Thr Thr Tyr Ser Pro Ser Phe
    50                  55                  60

Gln Gly His Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Phe Trp Gly Ala Ser Gly Ala Pro Val Asn Gly Phe Asp Ile Trp
            100                 105                 110

Gly Gln Gly Thr Leu Val Thr Val Ser Ser
        115                 120

<210> SEQ ID NO 334
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Leu Pro Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Ala Pro Val Phe Gly Gly Gly Thr Lys Leu Thr Val Leu Leu
            100                 105                 110

<210> SEQ ID NO 335
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 335
caggtacagc tgcagcagtc aggcccagga ctggtgaggc cttcggcgac cctgtccctc      60
acctgcactg tctctggtga ctccgtcagc agtgataatt acttctggag ttggattcgg     120
cagcccccag ggaagccact ggagtggatt ggctatgtct attacaatgg gaacaccaac     180
```

-continued tacaacccct ccttcaacag tcgagtcacc atgtcacttg acacgtccaa gaaccagttc          240
tccttgaagc tgaggtctgt gaccgccgcg gacacggcct tttattactg tgcgacagag          300
acgcccccaa ccagctattt taatagtgga cccctttgact cctggggcca gggcaccctg          360
gtcaccgtct cctcg                                                           375

<210> SEQ ID NO 336
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336
cagcctgggc tgactcagcc accctcggtg tccaagggct tgagacagac cgccacactc           60
acctgcactg ggagcagcaa caatgtaggc gcccacggag cagcttggct gcagcagcac          120
cagggccacc ctcccaaact ccttgcctac aggaataaca accggccctc agggatctca          180
gagagattct ctgcatccag gtcaggaaac acagcctccc tgaccattat tggactccag          240
cctgaggacg agggtgacta ttactgctca tcatgggaca gcagcctcag tggttatgtc          300
ttcggacctg ggaccaaagt caccgtccta                                           330

<210> SEQ ID NO 337
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gln Val Gln Leu Gln Gln Ser Gly Pro Gly Leu Val Arg Pro Ser Ala
1               5                   10                  15

Thr Leu Ser Leu Thr Cys Thr Val Ser Gly Asp Ser Val Ser Ser Asp
            20                  25                  30

Asn Tyr Phe Trp Ser Trp Ile Arg Gln Pro Pro Gly Lys Pro Leu Glu
        35                  40                  45

Trp Ile Gly Tyr Val Tyr Tyr Asn Gly Asn Thr Asn Tyr Asn Pro Ser
    50                  55                  60

Phe Asn Ser Arg Val Thr Met Ser Leu Asp Thr Ser Lys Asn Gln Phe
65                  70                  75                  80

Ser Leu Lys Leu Arg Ser Val Thr Ala Ala Asp Thr Ala Phe Tyr Tyr
                85                  90                  95

Cys Ala Thr Glu Thr Pro Pro Thr Ser Tyr Phe Asn Ser Gly Pro Phe
            100                 105                 110

Asp Ser Trp Gly Gln Gly Thr Leu Val Thr Val Ser Ser
        115                 120                 125

<210> SEQ ID NO 338
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gln Pro Gly Leu Thr Gln Pro Pro Ser Val Ser Lys Gly Leu Arg Gln

-continued

```
1               5                   10                  15

Thr Ala Thr Leu Thr Cys Thr Gly Ser Ser Asn Asn Val Gly Ala His
            20                  25                  30

Gly Ala Ala Trp Leu Gln Gln His Gln Gly His Pro Pro Lys Leu Leu
        35                  40                  45

Ala Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Ile Gly Leu Gln
65                  70                  75                  80

Pro Glu Asp Glu Gly Asp Tyr Tyr Cys Ser Ser Trp Asp Ser Ser Leu
            85                  90                  95

Ser Gly Tyr Val Phe Gly Pro Gly Thr Lys Val Thr Val Leu
            100                 105                 110
```

```
<210> SEQ ID NO 339
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 339
caggtgcagc tggtgcagtc tggggctgag gtgaagaagc ctgggtcctc agtgaaggtc      60
tcctgcaaga cttctggcta cacctttaac aggtttggtc tcacctgggt gcgacaggcc     120
cctggacaag ggcttgagtg gatgggatgg accaaccctt acaatggtaa cacaaggtat     180
gcacagaagt tccagggcag agtcaccatg accacagaca catccacgag cacagcctac     240
atggagctga ggagcctgag atctgacgac acggccatgt atttctgtgc gagagtcgta     300
gccgtaaacg gtatggacgt ctgggggccaa gggaccacgg tcaccgtctc ctca          354
```

```
<210> SEQ ID NO 340
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340
aattttatgc tgactcagcc ccactctgtg tcggagtctc cggggaagac ggttaccatc      60
tcctgcaccc gcaacagtgg cagcattgcc gcctactatg tgcagtggta ccagcagcgc     120
ccgggcagtt cccccaccac tgtgatctat gaagataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatctttgg     300
gtgttcggcg gagggaccaa gctgaccgtc cta                                   333
```

```
<210> SEQ ID NO 341
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Val Gln Ser Gly Ala Glu Val Lys Lys Pro Gly Ser
1               5                   10                  15
```

```
Ser Val Lys Val Ser Cys Lys Thr Ser Gly Tyr Thr Phe Asn Arg Phe
            20                  25                  30

Gly Leu Thr Trp Val Arg Gln Ala Pro Gly Gln Gly Leu Glu Trp Met
            35                  40                  45

Gly Trp Thr Asn Pro Tyr Asn Gly Asn Thr Arg Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Met Tyr Phe Cys
                85                  90                  95

Ala Arg Val Val Ala Val Asn Gly Met Asp Val Trp Gly Gln Gly Thr
            100                 105                 110

Thr Val Thr Val Ser Ser
        115
```

```
<210> SEQ ID NO 342
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342
```

```
Asn Phe Met Leu Thr Gln Pro His Ser Val Ser Glu Ser Pro Gly Lys
1               5                   10                  15

Thr Val Thr Ile Ser Cys Thr Arg Asn Ser Gly Ser Ile Ala Ala Tyr
            20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Leu Trp Val Phe Gly Gly Gly Thr Lys Leu Thr Val Leu
            100                 105                 110
```

```
<210> SEQ ID NO 343
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 343
```

```
gaggtgcagc tggtgcagtc tgggggaggc gtggtccagc ctgggaggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagccaaaca     300
gtggctggaa gtgactactg gggccagggc accctggtca ccgtctcctc a              351
```

```
<210> SEQ ID NO 344
```

-continued

```
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 344
cagcctgggc tgactcagcc accctcggtg ccagtggccc caggacagac ggccaggatt        60
acctgtgggg gaaacaacat tggaagtaaa agtgtgcact ggtaccagca gaagccaggc       120
caggcccctg tgctggtcgt ctatgatgat agcgaccggc cctcaggat ccctgagcga        180 ttctctggct ccaactctgg gaacacggcc accctgacca tcagcagggt cgaagccggg       240
gatgaggccg actattactg tcaggtgtgg catagtgtta gtgatcaagg ggtcttcgga       300
actgggacca aagtcaccgt ccta                                              324

<210> SEQ ID NO 345
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln Thr Val Ala Gly Ser Asp Tyr Trp Gly Gln Gly Thr Leu
            100                 105                 110

Val Thr Val Ser Ser
        115

<210> SEQ ID NO 346
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Gln Pro Gly Leu Thr Gln Pro Pro Ser Val Pro Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60
```

-continued

```
Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp His Ser Val Ser Asp Gln
                85                  90                  95

Gly Val Phe Gly Thr Gly Thr Lys Val Thr Val Leu
                100                 105

<210> SEQ ID NO 347
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Gln Val Gln Leu Gln Gln Ser Gly Pro Gly Leu Val Arg Pro Ser Ala
1               5                   10                  15

Thr Leu Ser Leu Thr Cys Thr Val Ser Gly Asp Ser Val Ser Ser Asp
                20                  25                  30

Asn Tyr Phe Trp Ser Trp Arg Gln Pro Pro Gly Lys Pro Leu Glu Trp
            35                  40                  45

Ile Gly Tyr Val Tyr Tyr Asn Gly Asn Thr Asn Tyr Asn Pro Ser Phe
        50                  55                  60

Asn Ser Arg Val Thr Met Ser Leu Asp Thr Ser Lys Asn Gln Phe Ser
65                  70                  75                  80

Leu Lys Leu Arg Ser Val Thr Ala Ala Asp Thr Ala Phe Tyr Tyr Cys
                85                  90                  95

Ala Thr Glu Thr Pro Pro Thr Ser Tyr Phe Asn Ser Gly Pro Phe Asp
                100                 105                 110

Ser Trp Gly Gln Gly Thr Leu Val Thr Val Ser Ser
        115                 120

<210> SEQ ID NO 348
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Leu Pro Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Ala Pro Val Phe Gly Gly Gly Thr Lys Leu Thr Val Leu
                100                 105                 110

<210> SEQ ID NO 349
<211> LENGTH: 109
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Gln Pro Gly Leu Thr Gln Pro Pro Ser Val Ser Lys Gly Leu Arg Gln
1               5                   10                  15

Thr Ala Thr Leu Thr Cys Thr Gly Ser Ser Asn Asn Val Gly Ala His
                20                  25                  30

Gly Ala Ala Trp Leu Gln Gln His Gln Gly His Pro Pro Lys Leu Leu
            35                  40                  45

Ala Tyr Arg Asn Asn Asn Arg Pro Ser Gly Ile Ser Glu Arg Phe Ser
        50                  55                  60

Ala Ser Arg Ser Gly Asn Thr Ala Ser Leu Thr Ile Gly Leu Gln Pro
65                  70                  75                  80

Glu Asp Glu Gly Asp Tyr Tyr Cys Ser Ser Trp Asp Ser Ser Leu Ser
                85                  90                  95

Gly Tyr Val Phe Gly Pro Gly Thr Lys Val Thr Val Leu
            100                 105

<210> SEQ ID NO 350
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Gln Pro Gly Leu Thr Gln Pro Pro Ser Val Pro Val Ala Pro Gly Gln
1               5                   10                  15

Thr Ala Arg Ile Thr Gly Gly Gly Asn Asn Ile Gln Ser Lys Ser Val
                20                  25                  30

His Trp Tyr Gln Gln Lys Pro Gly Gln Ala Pro Val Leu Tyr Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ser Arg Val Glu Ala Gly Asp
65                  70                  75                  80

Glu Ala Asp Tyr Tyr Cys Gln Val Trp His Ser Val Ser Asp Gln Gly
                85                  90                  95

Val Phe Gly Thr Gly Thr Lys Val Thr Val Leu
            100                 105

<210> SEQ ID NO 351
<211> LENGTH: 98
<212> TYPE: PRT
<213> ORGANISM: Homo sapiens

<400> SEQUENCE: 351

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser

-continued

```
         50               55               60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 352
<211> LENGTH: 98
<212> TYPE: PRT
<213> ORGANISM: Homo sapiens

<400> SEQUENCE: 352

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
        50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala
```